(12) United States Patent
Blanchard et al.

(10) Patent No.: US 9,441,263 B2
(45) Date of Patent: Sep. 13, 2016

(54) RIBOSOMAL TARGETS FOR ANTIBIOTIC DRUG DISCOVERY

(75) Inventors: Scott C. Blanchard, New York, NY (US); Michael Brian Feldman, Setauket, NY (US); Leyi Wang, New York, NY (US); James H. Doudna Cate, Berkeley, CA (US); Arto Pulk, Berkeley, CA (US); Roger B. Altman, New York, NY (US); Michael R. Wasserman, New York, NY (US)

(73) Assignees: Cornell University, Ithaca, NY (US); The Regents of the University of California, Oakland, CA (US)

( * ) Notice: Subject to any disclaimer, the term of this patent is extended or adjusted under 35 U.S.C. 154(b) by 6 days.

(21) Appl. No.: 14/111,947

(22) PCT Filed: Apr. 14, 2012

(86) PCT No.: PCT/US2012/033699
§ 371 (c)(1),
(2), (4) Date: Oct. 15, 2013

(87) PCT Pub. No.: WO2012/142542
PCT Pub. Date: Oct. 18, 2012

(65) Prior Publication Data
US 2014/0127682 A1 May 8, 2014

Related U.S. Application Data

(60) Provisional application No. 61/476,102, filed on Apr. 15, 2011, provisional application No. 61/603,023, filed on Feb. 24, 2012.

(51) Int. Cl.
*C12Q 1/68* (2006.01)
*G01N 33/542* (2006.01)
*G01N 33/94* (2006.01)

(52) U.S. Cl.
CPC .............. *C12Q 1/68* (2013.01); *G01N 33/542* (2013.01); *G01N 33/9446* (2013.01); *G01N 2333/245* (2013.01)

(58) Field of Classification Search
None
See application file for complete search history.

(56) References Cited

U.S. PATENT DOCUMENTS

2002/0188108 A1 12/2002 Noller et al.

FOREIGN PATENT DOCUMENTS

WO WO 2008/148054 A1 12/2008
WO WO 2010/096720 A2 8/2010

OTHER PUBLICATIONS

Song et al., "cDNA, genomic sequence cloning and overexpression of the ribosomal protein S13 gene in the giant panda (Ailuropoda melanoleuca)", Genetics and Molecular Research, Jan. 2011, 10 (1): 121-132.*
Blanchard, S.C. et al., Probing Translation with Small-Molecule Inhibitors, Chemistry & Biology, (Jun. 25, 2010), vol. 17, pp. 633-645.
Blanchard, S.C. et al., tRNA dynamics on the ribosome during translation, PNAS, (Aug. 31, 2004), vol. 101, No. 35, pp. 12893-12898.
Borovinskaya, M.A. et al., Structural basis for aminoglycoside inhibition of bacterial ribosome recycling, Nature Structural & Molecular Biology, (Aug. 2007), vol. 14, No. 8, pp. 727-732.
Brandt, F. et al., The Native 3D Organization of Bacterial Polysomes, Cell, (Jan. 23, 2009), vol. 136, pp. 261-271.
Cornish, P.V. et al., Spontaneous Intersubunit Rotation in Single Ribosomes, Molecular Cell, (Jun. 6, 2008), vol. 30, pp. 578-588.
Cukras, A.R. et a., Multiple Effects of S13 in Modulating the Strength of Intersubunit Interactions in the Ribosome During Translation, J. Mol. Biol., (2005), vol. 349, pp. 47-59.
David-Eden, H. et al., Structural signatures of antibiotic binding sites on the ribosome, Nucleic Acids Research, (2010), vol. 38, No. 18, pp. 5982-5994.
Dunkle, J.A. et al., Structures of the Bacterial Ribosome in Classical and Hybrid States of tRNA Binding, Science, (May 20, 2011), vol. 332, pp. 981-984.
Dunkle, J.A. et al., Ribosome Structure and Dynamics During Translocation and Termination, Annu. Rev. Biophys., (2010), vol. 39, pp. 227-244.
Ermolenko, D.N. et al., The antibiotic viomycin traps the ribosome in an intermediate state of translocation, Nature Structural & Molecular Biology, (Jun. 2007), vol. 14, No. 6, pp. 493-497.

(Continued)

*Primary Examiner* — Suzanne M Noakes
(74) *Attorney, Agent, or Firm* — Scully, Scott, Murphy & Presser, P.C.

(57) ABSTRACT

The present invention relates to methods to identify molecules that binds in the neomycin binding pocket of a bacterial ribosome using structures of an intact bacterial ribosome that reveal how the ribosome binds tRNA in two functionally distinct states, determined by x-ray crystallography. One state positions tRNA in the peptidyl-tRNA binding site. The second, a fully rotated state, is stabilized by ribosome recycling factor (RRF) and binds tRNA in a highly bent conformation in a hybrid peptidyl/exit (P/E) site. Additionally, the invention relates to various assays, including single-molecule assay for ribosome recycling, and methods to identify compounds that interfere with ribosomal function by detecting newly identified intermediate FRET states using known and novel FRET pairs on the ribosome. The invention also provides vectors and compositions with an N-terminally tagged S13 protein.

7 Claims, 29 Drawing Sheets
(7 of 29 Drawing Sheet(s) Filed in Color)

(56) References Cited

OTHER PUBLICATIONS

Feldman, M.B. et al., Aminoglycoside activity observed on single pre-translocation ribosome complexes, Nature Chemical Biology, (Jan. 2010), vol. 6, pp. 54-63.

Gao, Y. et al., The Structure of the Ribosome with Elongation Factor G Trapped in the Posttranslocational State, Science, (Oct. 30, 2009), vol. 326, pp. 694-699.

Geggier, P. et al., Conformational Sampling of Aminoacyl-tRNA during Selection on the Bacterial Ribosome, J. Mol. Biol., (2010), vol. 399, pp. 576-595.

Jin, H. et al., Crystal structure of the hybrid state of ribosome in complex with the guanosine triphosphatase release factor 3, PNAS, (Sep. 20, 2011), vol. 108, No. 38, pp. 15798-15803.

Komoda, T. et al., The A-site Finger in 23 S rRNA Acts as a Functional Attenuator for Translocation, Journal of Biological Chemistry, (Oct. 27, 2006), vol. 281, No. 43, pp. 32303-32309.

Laurberg, M. et al., Structural basis for translation termination on the 70S ribosome, nature, (Aug. 14, 2008), vol. 454, pp. 852-857.

Li, W. et al., Transfer RNA in the hybrid P/E state: Correlating molecular dynamics simulations with cryo-EM data, PNAS, (Oct. 16, 2007), vol. 104, No. 42, pp. 16540-16545.

Lill, R. et al., Binding of the 3' terminus of tRNA to 23S rRNA in the ribosomal exit site actively promotes translocation, The EMBO Journal, (1989), vol. 8, No. 12, pp. 3933-3938.

Llano-Sotelo, B. et al., Fluorescently labeled ribosomes as a tool for analyzing antibiotic binding, RNA, (2009), vol. 15, pp. 1597-1604.

Munro, J.B. et al., A fast dynamic mode of the EF-G-bound ribosome, The EMBO Journal, (2010), vol. 29, No. 4, pp. 770-781.

Munro, J.B. et al., Identification of Two Distinct Hybrid State Intermediates on the Ribosome, Molecular Cell, (Feb. 23, 2007), vol. 25, pp. 505-517.

Munro, J.B. et al., Spontaneous formation of the unlocked state of the ribosome is a multistep process, PNAS, (Jan. 12, 2010), vol. 107, No. 2, pp. 709-714.

Ogle, J.M. et al., Structural Insights Into Translational Fidelity, Annu. Rev. Biochem., (2005), vol. 74, pp. 129-177.

Peske, F. et al., Sequence of Steps in Ribosome Recycling as Defined by Kinetic Analysis, Molecular Cell, (May 13, 2005), vol. 18, pp. 403-412.

Pulk, A. et al., Identification of nucleotides in E. coli 16S rRNA essential for ribosome subunit association, RNA, (2006), vol. 12, pp. 790-796.

Recht, M.I. et al., Basis for prokaryotic specificity of action of aminoglycoside antibiotics, The EMBO Journal, (1999), vol. 18, No. 11, pp. 3133-3138.

Schmeing, T.M. et al., Structures of deacylated tRNA mimics bound to the E site of the large ribosomal subunit, RNA, (2003), vol. 9, 1345-1352.

Schmeing, T.M. et al., The Crystal Structure of the Ribosome Bound to EF-Tu and Aminoacyl-tRNA, Science, (Oct. 30, 2009), vol. 326, pp. 688-694.

Schuwirth, B.S. et al., Structures of the Bacterial Ribosome at 3.5 A Resolution, Science, (Nov. 4, 2005), vol. 310, pp. 827-834.

Selmer, M. et al., Structure of the 70S Ribosome Complexed with mRNA and tRNA, Science, (Sep. 29, 2006), vol. 313, pp. 1935-1942.

Valle, M. et al., Locking and Unlocking of Ribosomal Motions, Cell, (Jul. 11, 2003), vol. 114, pp. 123-134.

Valle, M. et al., Cryo-EM reveals an active role for aminoacyl-tRNA in the accommodation process, The EMBO Journal, (2002), vol. 21, No. 13, pp. 3557-3567.

Voorhees, R.M. et al., The Mechanism for Activation of GTP Hydrolysis on the Ribosome, Science, (Nov. 5, 2010), vol. 330, pp. 835-838.

Wang, L. et al., Insights into the molecular determinants of EF-G catalyzed translocation, RNA, (2011), vol. 17, pp. 2189-2200.

Zhang, W. et al., Structures of the Ribosome in Intermediate States of Ratcheting, Science, (Aug. 31, 2009), vol. 325, pp. 1014-1017.

Munro, J.B. et al., Correlated conformational events if EF-G and the ribosome regulate translocation, Nature Structural & Molecular Biology, (Dec. 2010), vol. 17, No. 12, pp. 1470-1478.

Munro, J.B. et al., Navigating the ribosome's metastable energy landscape, Trends in Biochemical Sciences, (Aug. 2009), vol. 34, No. 8, pp. 390-400.

Ratje, A.H. et al., Head swivel on the ribosome facilitates translocation by means of intra-subunit tRNA hybrid sites, Nature, (Dec. 2, 2010), vol. 468, pp. 713-719.

Schmeing, T.M. et al., What recent ribosome structures have revealed about the mechanism of translation, nature, (Oct. 29, 2009), vol. 461, pp. 1234-1242.

Stanley, R.E. et al., The structures of the anti-tuberculosis antibiotics viomycin and capreomycin bound to the 70S ribosome, Nature Structural & Molecular Biology, (Mar. 2010), vol. 17, No. 3, pp. 289-294.

Valle, M. et al., Incorporation of aminoacyl-tRNA into the ribosome as seen by cryo-electron microscopy, Nature Structural Biology, (Nov. 2003), vol. 10, No. 11, pp. 899-907.

Weixlbaumer, A. et al., Crystal structure of the ribosome recycling factor bound to the ribosome, Nature Structural & Molecular Biology, (Aug. 2007), vol. 14, No. 8, pp. 733-737.

International Search Report dated Oct. 25, 2012 issued in PCT/US2012/033699 previously submitted on Oct. 15, 2013.

Wang L. et al., "Allosteric Control of the Ribosome by Small-Molecule Antibiotics", Nature Structural & Molecular Biology 19(9):957-963, Supplementary Information (Sep. 2012).

* cited by examiner

C

D

A  Unrotated, L1 open, P/P tRNA

B  Partially rotated, L1 closed, P/pe tRNA

C  Fully rotated, L1 closed, P/E tRNA

RIBOSOMAL TARGETS FOR ANTIBIOTIC DRUG DISCOVERY

CROSS-REFERENCE TO RELATED APPLICATIONS

This application claims priority from U.S. Provisional Application No. 61/476,102, filed Apr. 15, 2011, and U.S. Provisional Application No. 61/603,023, filed Feb. 24, 2012 which are herein incorporated by reference in their entirety.

GOVERNMENT FUNDING

This invention was made with Government support under Grant Number 2R01GM079238, 1R01GM65050 awarded by National Institute of Health; National Cancer Institute grant CA92584; U.S. Department of Energy DE-AC0376SF00098; National Institutes of Health Medical Scientist Training Program grant GM07739; National Institute of Health NRSA fellowship 1F31DC012026-01. The United States Government has certain rights in the invention.

FIELD OF THE INVENTION

During protein synthesis, the ribosome controls the movement of transfer RNA (tRNA) and messenger RNA (mRNA) by means of large-scale structural rearrangements. The present invention describes structures of the intact bacterial ribosome from *Escherichia coli* that reveal how the ribosome binds tRNA in two functionally distinct states, determined by x-ray crystallography. One state positions tRNA in the peptidyl-tRNA binding site. The second, a fully rotated state, is stabilized by ribosome recycling factor (RRF) and binds tRNA in a highly bent conformation in a hybrid peptidyl/exit (P/E) site. The structures help to explain how the ratchet-like motion of the two ribosomal subunits contributes to the mechanisms of translocation, termination, and ribosome recycling

INCORPORATION BY REFERENCE OF SEQUENCE LISTING

The Sequence Listing in an ASCII text file, named 28553_5468_02_SequenceListing.txt of 1 KB, created on Dec. 18, 2013, and submitted to the United States Patent and Trademark Office via EFS-Web, is incorporated herein by reference.

BACKGROUND OF THE INVENTION

Protein biosynthesis by the ribosome proceeds in defined phases of initiation, protein elongation, termination, and ribosome recycling (Schmeing 2009a). Understanding the molecular mechanism of translation requires high-resolution descriptions of the motions in the ribosome that enable key translational events (Munro 2009; Schmeing 2009a; Dunkle 2010). A ratchet-like rotation of the small ribosomal subunit relative to the large ribosomal subunit (Frank 2000) is crucial to the positioning of tRNAs in intermediate—or hybrid—binding sites, in which the 3'-CCA termini and acceptor stems of tRNA advance by one site on the large subunit while the anticodon elements of tRNA remain fixed on the small subunit (Moazed 1989). Binding of tRNAs in hybrid sites is central to mRNA and tRNA movements on the ribosome when they are translocated after each peptide bond is formed, during termination, and during ribosome recycling (Semenkov 2000; Zavialov 2003). However, the molecular basis for ribosome positioning of tRNAs in hybrid sites has been unclear.

Atomic resolution x-ray crystal structures of the bacterial ribosome with ligands bound have revealed molecular details of conformational rearrangements taking place in the unratcheted ribosome (Schmeing 2009a). The first molecular descriptions of intermediate states of ribosome ratchet-like rotation at atomic resolution were provided by x-ray crystal structures of the *Escherichia coli* 70S ribosome (Zhang 2009), with additional sub-steps proposed based on cryo-EM reconstructions (Fischer 2010). A post-translocation rotated state of the ribosome was recently identified by cryo-EM (Ratje 2010), in a conformation similar to that of the *Saccharomyces cerevisiae* 80S ribosome in the absence of bound substrates (Ben-Shem 2010).

After the termination of protein synthesis, ribosome recycling is required to free ribosomes from the mRNA transcript to enable further rounds of translation. In bacteria and organelles, ribosome recycling factor (RRF) binds in the tRNA binding cleft of the 70S ribosome at the interface of the large (50S) and small (30S) subunits and interacts with the 50S subunit peptidyl transferase center (PTC) (Lancaster 2002; Agrawal. 2004). In so doing, RRF sterically occludes deacylated tRNA binding in the peptidyl-tRNA site (P site, P/P configuration) to favor tRNA positioning in the hybrid peptidyl/exit tRNA binding site (P/E configuration) (FIG. 1A) (Gao 2005; Sternberg 2009). In the P/E configuration, tRNA is bound simultaneously to the P site of the small (30S) subunit and to the E site of the large (50S) subunit (Moazed 1989). Binding of the GTPase elongation factor-G (EF-G) to the RRF-ribosome complex and subsequent GTP hydrolysis lead to the dissociation of ribosomal subunits (Savelsbergh 2009).

Using single-molecule fluorescence resonance energy transfer (smFRET) techniques to interrogate the conformational states of the ribosome, conditions were found that favored positioning the tRNA in the hybrid P/E configuration for longer periods and allowed crystallization of the ribosome with tRNA bound in the P/E hybrid site. From these crystals, the structure of the intact *E. coli* 70S ribosome at a resolution of ~3.2 Å was determined and showed that the crystals contain two independent copies of the ribosome per asymmetric unit in a "top-top" polysome configuration (Brandt 2009), with one ribosome in an unrotated state with the classic positioning of the tRNA at the P/P site and, as heretofore never crytallographically observed at this resolution, with the second ribosome in a fully-rotated state and having the tRNA bound in the hybrid P/E configuration, revealing new targets on the ribosome for drug discovery.

Many antibiotic agents in clinical use target bacterial protein synthesis. The majority of these chemically diverse compounds inhibit translation by targeting functional centers in the ribosome (Blanchard 2010). Despite the enormous size and complexity of the 2.5 Megadalton ribosome particle, only a few target sites have been identified: near the Peptidyl- (P) tRNA binding and messenger RNA (mRNA) decoding sites of the small ribosomal subunit, and near the peptidyl transferase and GTPase centers of the large ribosomal subunit (Poehlsgaard 2005; Tenson 2006). The ability to identify new target sites within this dynamic macromolecular machine depends on sensitive methods for their identification and validation (Llano-Sotelo 2009; David-Eden, 2010).

Aminoglycoside antibiotics in the 2-deoxystreptamine family are broad spectrum bacteriocidal agents used to treat gram-negative bacterial infections. In vivo, these compounds are thought to act by altering the mechanism of aminoacyl-tRNA (aa-tRNA) selection during mRNA decoding on the ribosome (Fourmy 1996; Rodnina 2000; Schmeing 2009a). Aminoglycosides do so by inducing local rearrangements in ribosomal RNA (rRNA) within the highly conserved helix 44 (h44) decoding site of the small (30S) subunit that allow near- and non-cognate tRNAs to be inappropriately recognized and incorporated into the Aminoacyl- (A) tRNA binding site. Increased levels of aa-tRNA mis-incorporation eventually exceed the cell's capacity to cope with the reductions in translational fidelity, ultimately leading to cell death (Zaher 2009). However, in vitro, these aminoglycosides inhibit a range of steps in the translation mechanism. This includes mRNA and tRNA translocation, the directional movement of substrates with respect to both subunits of the intact (70S) ribosome (Gale 1981; Feldman 2010), and ribosome recycling, the process of subunit separation following the termination phase of protein synthesis (Hirokawa 2002). The physical origins of these aminoglycoside-induced effects are not known.

Early biochemical studies demonstrated that aminoglycosides can bind to regions of the ribosome outside the canonical decoding region (Davies 1968; Dahlberg 1978). Recently, the aminoglycoside neomycin was shown crystallographically, on classic ribosomal structures, to bind to the bacterial ribosome within Helix 69 (H69) of 23S ribosomal RNA (rRNA) in the large (50S) subunit (Borovinskaya 2007). While binding at this site was proposed to be responsible for inhibition of ribosome recycling and possibly translocation, the structural refinement at the time was insufficient to identify the points of contact and interaction (Feldman 2010; Borovinskaya 2007). Notably, neomycin concentrations higher than 100 nM inhibit translocation as potently as the most effective translocation inhibitor known, viomycin (Feldman 2010). Ribosome complexes bearing the well-established A1408G neomycin-resistance mutation in the small subunit ribosomal RNA (rRNA) which disrupts neomycin binding to the h44 decoding site (Recht 1999) exhibit a similar translocation inhibition profile at the higher (micromolar) neomycin concentrations, suggesting that strong inhibitory effects arise from the binding of neomycin outside of the canonical h44 decoding region (Feldman 2010).

Using the crystals reported herein with a combination of smFRET and further detailed x-ray crystallographic methods, the molecular basis of neomycin-induced inhibition of translation processes specific to its interactions with H69 of the large subunit have been determined and reveal the complete structural extent of a neomycin-binding pocket on the ribosome when neomycin stabilizes an inactive configuration of the ribosome. This site is termed the H69 neomycin-binding site or pocket and provides a powerful starting point for rational drug design.

SUMMARY OF THE INVENTION

The present invention is directed to methods of identifying candidate molecules, and in some embodiments candidate antibiotics, that bind in the H69 neomycin-binding pocket of a bacterial ribosome. These methods can be accomplished by providing a molecular model comprising the neomycin-binding pocket prepared from the atomic coordinates for an *E. coli* ribosome and from the neomycin binding pocket having the atomic coordinates in any one of Tables 6 to 9, or from atomic coordinates that may be derived from those of the ribosome or the tables using molecular modeling. Chemical structures are then docked to or fit to the molecular model to identify a candidate molecule that can bind to the neomycin binding pocket.

In one embodiment, the method comprises (a) providing a molecular model comprising of the neomycin binding pocket prepared from the atomic coordinates for an *E. coli* ribosome in a fully-rotated or intermediately-rotated state along with the neomycin binding pocket atomic coordinates in Table 6 or 8, respectively, (or atomic coordinates derived by molecular modeling any of those coordinates) and (b) docking or fitting chemical structures to the molecular model to identify a candidate molecule that can bind to the neomycin binding pocket.

In further embodiments, once a candidate molecule is identified, it can be produced for testing identified and determining whether it is capable of modulating ribosomal activity. All of the foregoing can be iteratively repeated to identify and produce a modified candidate molecule having higher binding specificity, higher binding affinity or higher potency relative to the candidate molecule.

In the above modeling candidate molecule can have a chemical structure suitable for binding/docking to the region defined by the residues from about 1905 to about 1931 in helix 69 (H69) in 23S ribosomal RNA, and in addition or in alternative to, can have a chemical structure suitable for binding/docking to a region defined by residues from about 1402 to about 1412 and residues from about 1488 to about 1500 in helix 44 (h44) in 16S ribosomal RNA.

Another aspect of the invention provides a crystal of a fully rotated or an intermediately-rotated ribosome having the three-dimensional structures (atomic coordinates) of the ribosomal crystals described in Examples 3 and 4.

Still another aspect of the invention relates to a single-molecule assay for ribosome recycling which comprises surface-immobilizing a ribosome labeled on the 50S subunit in the presence of tRNA, RRF and EF-G under translation conditions; and monitoring changes in the signal from the label, wherein a change in the signal indicates recycling or lack thereof. For example, this assay can be conducted in solution or using smFRET like imaging techniques (following fluorescence decay), with the label on the ribosome being a fluorophore. Further, if a test compound is added, then the presence of a signal indicates that recycling has been altered.

Further still, the invention is directed to an expression vector comprising a nucleic acid encoding ribosomal protein S13 having an N-terminal tag for attachment of a fluorophore. In some embodiments, the N-terminal tag is an SFP tag or an AcpS tag.

The invention also provides compositions comprising isolated N-terminal tagged S13. In some embodiments, the tagged S13 has a fluorophore linked via the tag to produce labeled S13 which in certain embodiments, is useful to assess ribosome structural states, for example, when incorporated into translationally competent ribosomes, especially when used as a FRET pair in conjunction with fluorophore-labeled L1. Any of these compositions can additionally include the components for in vitro translation.

Yet another aspect of the instant invention relates to methods to identify a compound that interferes with ribosomal function by assessing test compounds which cause the ribosome to alter, form adopt, change rate of formation into or out of, or otherwise be in, an intermediate FRET state. This method comprises (a) surface-immobilizing a ribosome having a FRET pair sensitive to transitioning between low FRET and high FRET states under translation competent conditions; (b) adding a test compound to the immobilized ribosome; and (c) monitoring or detecting changes in FRET states using smFRET imaging techniques to identify a test compound capable of (i) stabilizing the ribosome in an intermediate FRET state, (ii) changing the ribosome's distribution into or out of an intermediate FRET state, or (iii) changing the ribosome's rate of transition into or out of an intermediate FRET state. This method can be conducted with a FRET pair formed by a fluorophore on ribosomal protein L1 and a fluorophore on ribosomal protein S13.

Yet still a further method of the invention provides methods to identify a compound that interferes with ribosomal function using a FRET pair which has a fluorophore on ribosomal protein L1 and a fluorophore on ribosomal protein S13. This method comprises (a) surface-immobilizing a ribosome having a FRET pair sensitive to transitioning between a low FRET state and a high FRET state under translation competent conditions, wherein the FRET pair is formed with a fluorophore on ribosomal protein L1 and a fluorophore on ribosomal protein S13; (b) adding a test compound to the immobilized ribosome; and (c) monitoring or detecting changes in FRET states using smFRET imaging techniques to identify a test compound capable of (i) stabilizing the ribosome in a low FRET state, an intermediate FRET state or in a high FRET state, (ii) changing the ribosome's distribution among low, intermediate and high FRET states, (iii) changing the ribosome's rate of transition among low, intermediate and high FRET states, or (iv) abolishing FRET signals.

For either of the two foregoing methods, in certain embodiments, the L1 fluorophore is at (T202C) L1 and the fluorophore on S13 is at or near the amino terminus of S13. FRET pairs that are a donor-acceptor fluorophore pair or a donor-quencher fluorophore pair are useful.

Similarly, the two foregoing methods can be used in certain embodiments to identify candidate antibiotics. For example, a test compound is considered a candidate antibiotic when the test compound (i) stabilizes the ribosome in an intermediate FRET state or in a high FRET state, (ii) increases the ribosome's distribution in intermediate or high FRET states, (iii) increases the ribosome's rate of transition into intermediate or high FRET states, or abolishes FRET. Such candidate antibiotics can be tested to establish whether they inhibit function of a bacterial ribosome of pathological interest. The intermediate FRET state includes ribosomes having a structure assumed when the tRNA is present at the P/pe tRNA binding state (see Example 4).

BRIEF DESCRIPTION OF THE DRAWINGS

The patent or application file contains at least one drawing executed in color. Copies of this patent or patent application publication with color drawing(s) will be provided by the Patent and Trademark Office upon request and payment of the necessary fee.

DETAILED DESCRIPTION OF THE INVENTION

Figure 1:
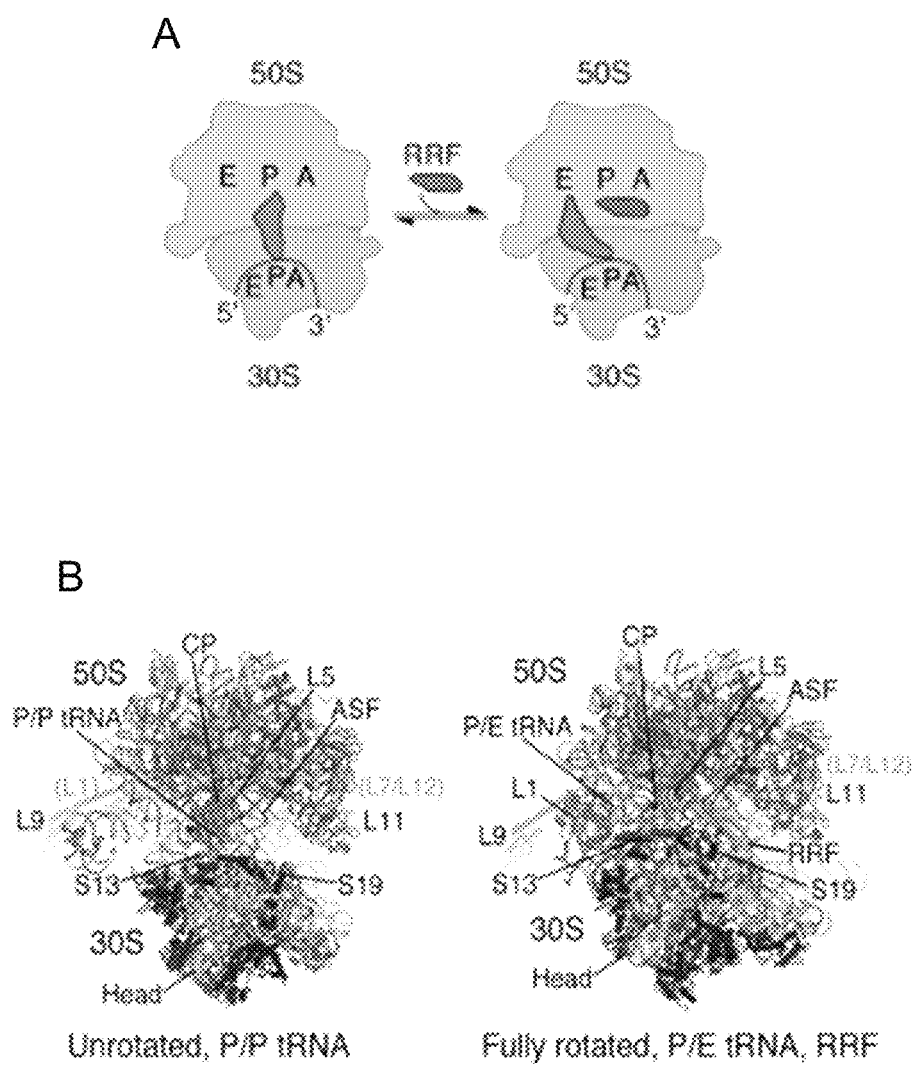
FIG. 1A and FIG. 1B illustrate ribosome recycling in bacteria and organelles. Panel A is a schematic drawing showing the steps of ribosome recycling. After termination, ribosomes with deacylated tRNA in the P site undergo a structural rearrangement to a fully rotated state in which tRNA adopts a P/E hybrid state of binding and RRF is bound in the 50S P site. EF-G then catalyzes subunit dissociation (not shown). Panel B shows a global view of the ribosome in an unrotated, post-termination state (left) and in a fully rotated, intermediate state of recycling (right). The small subunit rRNA and proteins at the bottom of the complex are colored lighter and darker, respectively, with the large subunit rRNA and proteins at the top of the complex colored lighter and darker, respectively. Bound tRNA (dark form in center of image A), mRNA (dark grey at top of complexes shown in D), and RRF are also shown.
FIG. 1C illustrates the dependence of subunit release on RRF, EF-G and GTP under crystallographic buffer conditions. Release was monitored by the loss of Cy5-labeled L1 fluorescence in 50S subunits from surface-immobilized ribosome complexes carrying Cy3-labeled tRNA$^{Phe}$ in the P site. Complexes imaged in the absence of factors (diamonds) or in the presence of 10 µM RRF (circles); 20 µM EF-G and 2 mM GTP (inverted triangles); 10 µM RRF, 20 µM EF-G and 2 mM GDPNP (triangles); or 10 µM RRF, 20 µM EF-G and 2 mM GTP (squares). Data reflect the mean±SD of normalized Cy5 fluorescence intensity as a function of time from three experimental replicates.
FIG. 1D shows the conformational changes in the 70S ribosome during ratcheting with a view of the 30S subunit from the perspective of the 50S subunit (inset). Shifts between equivalent RNA phosphorus atoms and protein Cα atoms in the unrotated (R0) and fully rotated (RF) states are color coded as indicated by the scale. Ribosomes were superimposed using the 50S subunit as the frame of reference (Frank, Gao et al. 2007). Difference vectors between equivalent phosphorus or Cα atoms of the 30S subunits in the unrotated and fully rotated ribosome structures are shown on the right.
Figure 1:
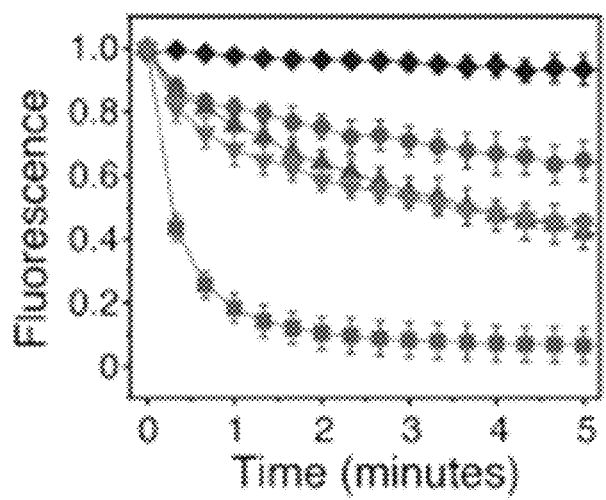
Figure 1:
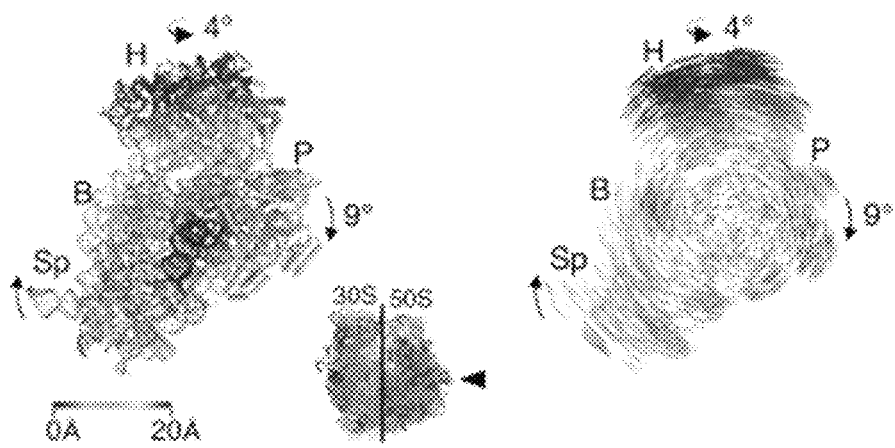

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that logical changes may be made without departing from the scope of the present invention. The following description of example embodiments is, therefore, not to be taken in a limited sense, and the scope of the present invention is defined by the appended claims.

1. Definitions

"Single-molecule fluorescence resonance energy transfer" (or "smFRET") is the application of FRET techniques to study a single molecule with at least two fluorescent labels, or the interaction of at least two molecules, each with a label. Fluorescence Resonance Energy Transfer (FRET) is a non-radiative pathway by which a molecule in an electronic excited state may relax back to the more stable ground state. The transfer of energy occurs through space via dipole-dipole interaction: energy from the excited state molecule (the donor fluorophore) may transfer to a neighboring molecule (the acceptor fluorophore) given significant degree of spectral overlap between donor emission and acceptor absorption, properly oriented dipole moments of the interacting dye molecules, and the appropriate distance between the two fluorophores. The Förster relationship defining the efficiency of FRET as a function of distance is unique for each dye pair. In smFRET the donor and receptor fluorophores are on the same molecule, or are on different molecules that interact, bringing the two fluorophores into proximity. The detection of FRET at the single-molecule scale enables the direct measurement of conformational events and/or binding processes on biologically-relevant time scales. Methods to perform smFRET imaging are known in the art, and are described, for example, in Blanchard 2004. Methods to attach translationally competent ribosomes to a surface are described, for example, in U.S. Pat. No. 7,297,532.

Dynamic smFRET refers to the use of smFRET techniques to interrogate biological samples of interest over extended periods of time in order to quantify changes in the amount of time that the sample spends in its various conformational states. By measuring time-dependent conformational dynamics in a biomolecule, insights into the physical parameters of motion are obtained that relate to regulation and function.

The labels used herein will generally comprise fluorophores. A "fluorophore" is a component of a molecule which causes a molecule to be fluorescent. It is a functional group in a molecule which will absorb energy of a specific wavelength and re-emit energy at a specific wavelength. The amount and wavelength of the emitted energy depend on both the fluorophore and the chemical environment of the fluorophore. Fluorescein isothiocyanate (FITC), a reactive derivative of fluorescein, has been one of the most common fluorophores chemically attached to other, non-fluorescent molecules to create new fluorescent molecules for a variety of applications. Other common fluorophores are derivatives of rhodamine (TRITC), coumarin, and cyanine Newer generations of fluorophores such as the CF dyes, Cyanin (Cy) dyes, the FluoProbes dyes, the DyLight Fluors, the Oyester dyes, the Atto dyes, the HiLyte Fluors, and the Alexa Fluors are claimed to be perform better (more photostable, brighter, and/or less pH-sensitive) than other standard dyes of comparable excitation and emission. Fluorophores especially useful for practicing the instant invention are described in PCT application PCT/US10/24824 which is incorporated herein in its entirety by reference.

The fluorophore may incorporate or be located proximally to a "protective agent" (or "quencher" or "triplet state quencher" or "fluorescence modifier", in particular embodiments), which is a molecule or a moiety (i.e., chemical group) that has the ability to alter the photophysical properties of a fluorophore, particularly by altering the light state-dark state (i.e., singlet-triplet) occupancy distribution or relaxation pathway of excited and relaxing electrons. The ability of a molecule to function as a protective agent is often evidenced by its ability to alter the blinking and/or photobleaching characteristics of a fluorophore.

Those of skill in the art can readily select appropriate donor-acceptor pairs for FRET in accordance with the invention as well as modify the biomolecules of the invention to attach the donor and acceptor fluorophores in site-specific manner without substantially altering functionality of the biomolecule.

As used herein, "h44" is helix 44 (h44) decoding site of the small (30S) subunit.

As used herein, H69 is Helix 69 (H69) of 23S ribosomal RNA (rRNA) in the large (50S) subunit.

As used herein, "H69 neomycin-binding site" or "H69 neomycin-binding pocket" and neomycin-binding site refers to the location of neomycin binding or interaction at H69 on any one of the crystal structures described in Examples 3 and 4 herein. This term is used as a general shorthand to refer and to identify the contact points between neomycin and the ribosome at this site and embraces points of contact at this site or pocket to other parts of the ribosome in addition to those found on H69. These terms are also used to refer to the equivalent sites as found in the structures known in the art for other bacterial ribosomes.

Figure 13:
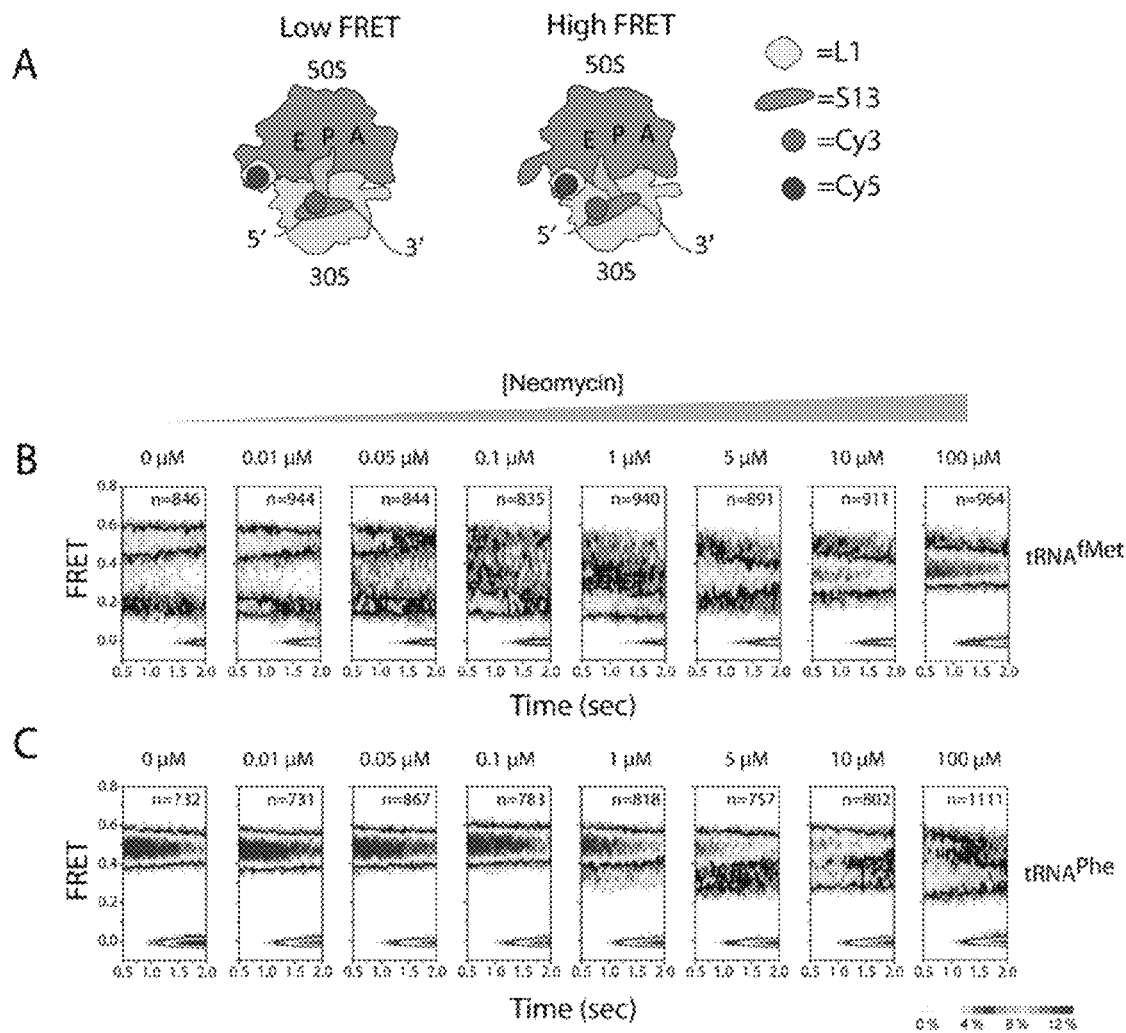
FIG. 13 illustrates that neomycin stabilizes an intermediate conformation of the ribosome. (A) Cartoon depicting the low FRET and High FRET states of the ribosome. (B, C) Single-molecule FRET trajectories, as shown in FIG. 14, were summed into population FRET histograms to reveal the population behaviors of Cy3-labeled S13 (N-terminus) and Cy5-labeled L1 (T202C) ribosome complexes bearing (B) deacylated tRNA$^{fMet}$ or (C) deacylated tRNA$^{Phe}$ in the P site.

The FRET states described herein depend upon the selected FRET pair used to interrogate structural transitions. The top panel of FIG. 13 shows a particularly useful example with its schematic diagram of the low FRET and High FRET states using an L1 with S13 pair. The general locations of L1, S13, their respective fluorophores and tRNA relative to the E, P and A sites on the ribosome are indicated. The intermediate FRET state of the present invention is one in which the ribosome has the structure assumed when the tRNA is present at the P/pe tRNA binding state (see Example 4). This intermediate state is stabilized by at least neomycin.

2. Overview

A combination of smFRET techniques and x-ray crystallographic methods were used to probe the molecular basis of neomycin-induced inhibition of translation processes specific to its interactions with H69 of the large subunit.

3. Ribosome Structure in Unrotated (classic P/P tRNA Bound) and Rotated (hybrid P/E tRNA Bound) States without Neomycin The structures were determined for the intact E. coli 70S ribosomes at a resolution of ~3.2 Å (Table 1, 2), based on crystals that contain two independent copies of the ribosome per asymmetric unit in a "top-top" polysome configuration (Brand 2009). Prior to this work, a rotated x-ray crystal structure had never before been obtained for any ribosome.

One ribosome adopts an unrotated state, with tRNA$^{Phe}$ bound in the "classical" peptidyl-tRNA (P/P) binding site (FIG. 1B) (Selmer 2006) that mimics a post-termination state of the translation cycle. The second ribosome adopts a fully rotated conformation that contains tRNA$^{Phe}$ bound in the hybrid P/E binding site and RRF bound at the ribosomal subunit interface (FIG. 1B). This structure is thought to represent an early intermediate in bacterial ribosome recycling (FIG. 1A; Gao 2005). A similar hybrid P-site tRNA configuration may also be found in other functionally relevant configurations of the ribosome (e.g., the intermediate, "unlocked state" prior to translocation; Munro 2010a, b, c; Munro 2010).

When compared to the post-termination ribosome complex, the 30S subunit of the RRF-bound ribosome is rotated ~9° relative to the 50S subunit. An approximately orthogonal rotation of the head domain of the 30S subunit of ~4° swivels the head domain in the direction of the ribosomal E site on the 50S subunit. These motions of the 30S subunit into the rotated state result in shifts at the periphery of the ribosome of more than 20 Å (FIG. 1D) that direct deacylated P-site tRNA into the P/E hybrid site. The tRNA anticodon stem-loop (ASL) and mRNA move laterally by ~6 Å relative to the 50S subunit, coupled to the motion of the 30S subunit platform domain (FIG. 1D, FIG. 2A). When tRNA moves into the P/E site from the P/P site, ASL of the tRNA remains in contact with the 30S subunit head and platform domains (FIG. 2B, FIG. 3A), but breaks its interactions with 23S ribosomal RNA (rRNA) helix H69 in the large subunit (Selmer 2006) (FIG. 2B).

Bound in the hybrid P/E site, tRNA$^{Phe}$ is severely kinked at the junction between the ASL and D stem when compared to tRNA$^{Phe}$ bound in the P/P site. Although the conformation of the anticodon and two closing base pairs of the ASL region remain essentially unchanged, the major groove widens by ~4 Å at the junction of the ASL and D stem (FIG. 2C, FIG. 3). The kink between the ASL and D stems allows the acceptor stem of P/E tRNA to swing by ~37° into the 50S E site (FIG. 2D). This abrupt kink contrasts with the more distributed bend that occurs in mRNA decoding complexes bound to elongation factor EF-Tu (A/T state, (Schmeing 2009b; Voorhees 2010), in which tRNA bends in the opposite direction. Comparing P/E tRNA to A/T tRNA, the total extent of tRNA bending at the ASL/D-stem junction amounts to ~70° (FIG. 2D).

Figure 2:
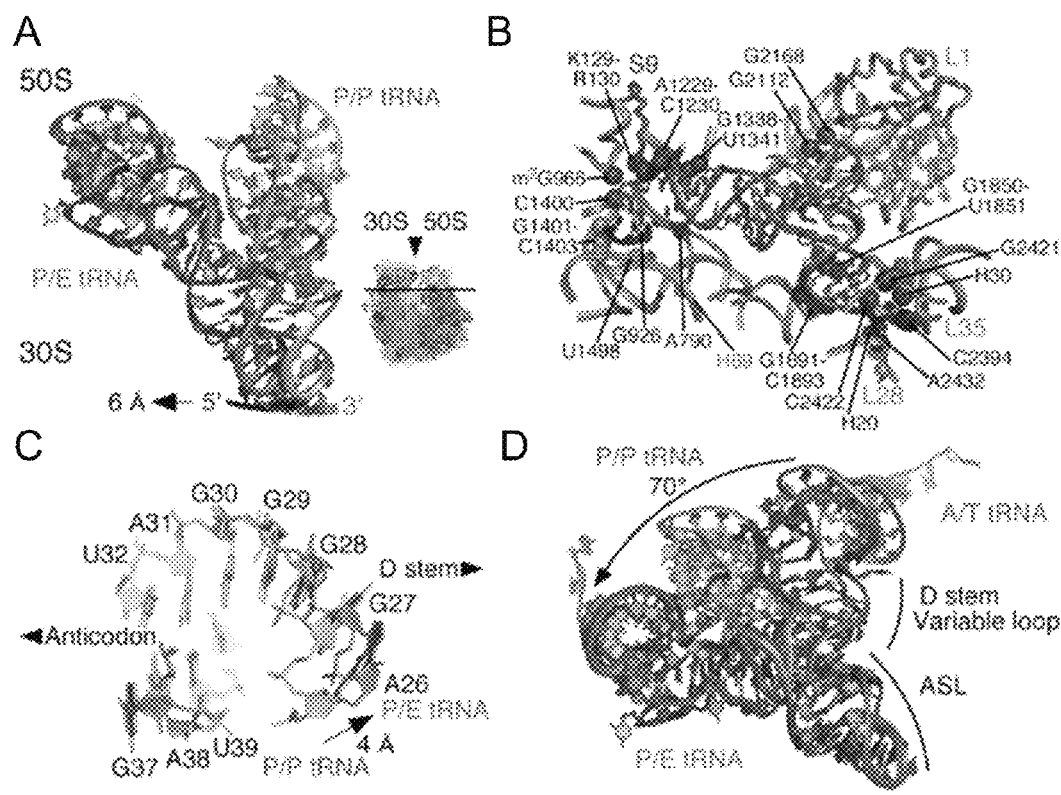
FIG. 2 depicts models of the conformation of tRNA in the P/E hybrid state. (A) Movement of P/E tRNA and mRNA towards the E site when compared to P/P tRNA and mRNA. The direction of view is shown to the right. (B) View of mRNA and P/E tRNA interactions with the 30S subunit P site and 50S subunit E site. Residues that contact mRNA (darker) and P/E tRNA (darkest) are shown. Colors for the ribosome, mRNA and tRNA as in FIG. 1. (C) View of the P/E tRNA ASL/D stem junction (darkest grey). P/P tRNA (lighter grey) is shown for comparison, with an arrow indicating the widening of the helix major groove. (D) Comparison of ASL/D stem junctions between P/E tRNA (darkest grey at bottom left), P/P tRNA (light grey in center), and A/T tRNA (darker grey toward upper right part of complex). A/T tRNA structure is a homology model adapted from Voorhees 2010. The bending angle for the A/T to P/E conformational change (70°) is shown.
Figure 3:
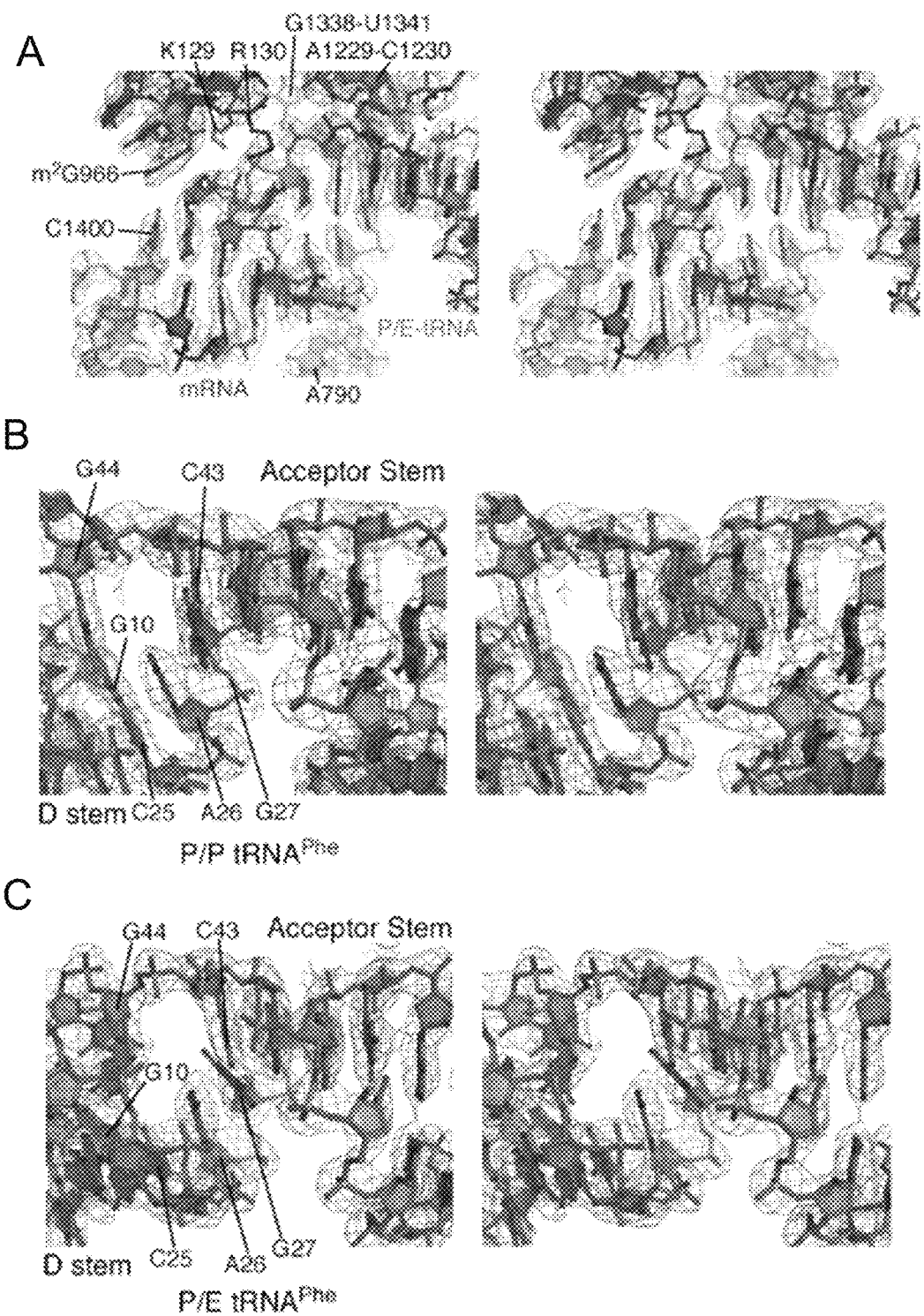
FIG. 3 shows stereo views of electron density maps for P/P tRNA and P/E tRNA. (A) Electron density map for the anticodon stem-loop region of P/E tRNA. Shown is a (2F$_{obs}$−F$_{calc}$) electron density map, calculated using sharpened amplitudes and Pirate density-modified structure factor phases and contoured at 0.7 standard deviations from the mean. (B) Electron density map for P/P tRNA. Shown is a (2F$_{obs}$−F$_{calc}$) electron density map, calculated in Phenix and contoured at 1.1 standard deviations from the mean. The region shown is the junction between the anticodon stem, variable loop, and D stem. (C) Electron density map for P/E tRNA, as in B. In B and C, the base triple between G10, C25, and G44 in tRNA$^{Phe}$ in these structures is marked.
Figure 4:
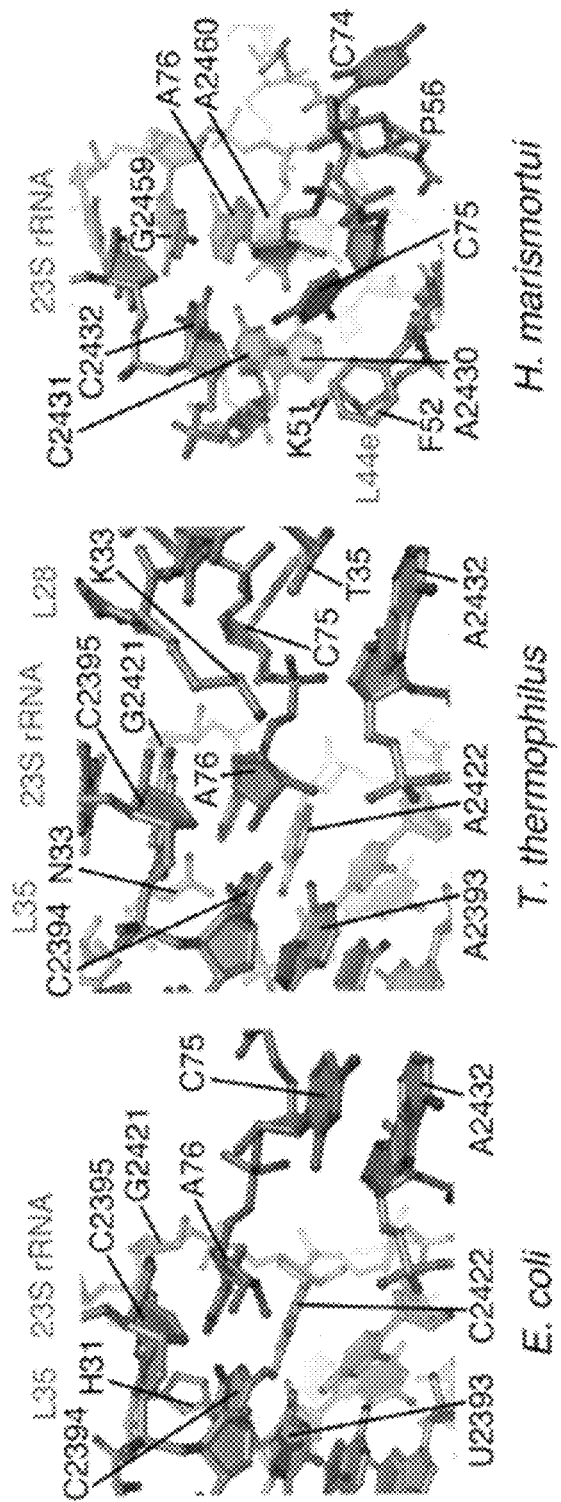
FIG. 4 illustrates the interactions of the 3'-CCA end of P/E tRNA with the 50S subunit E site. Elements of 23S rRNA (lighter grey), tRNA (darkest grey) and ribosomal proteins (medium grey) are shown. E. coli numbering is used for nucleotides and amino acids for the left and middle panels. Numbering for H. marismortui is used in the right panel. The positions of proteins L35, L28, and L44e are marked.
Figure 5:
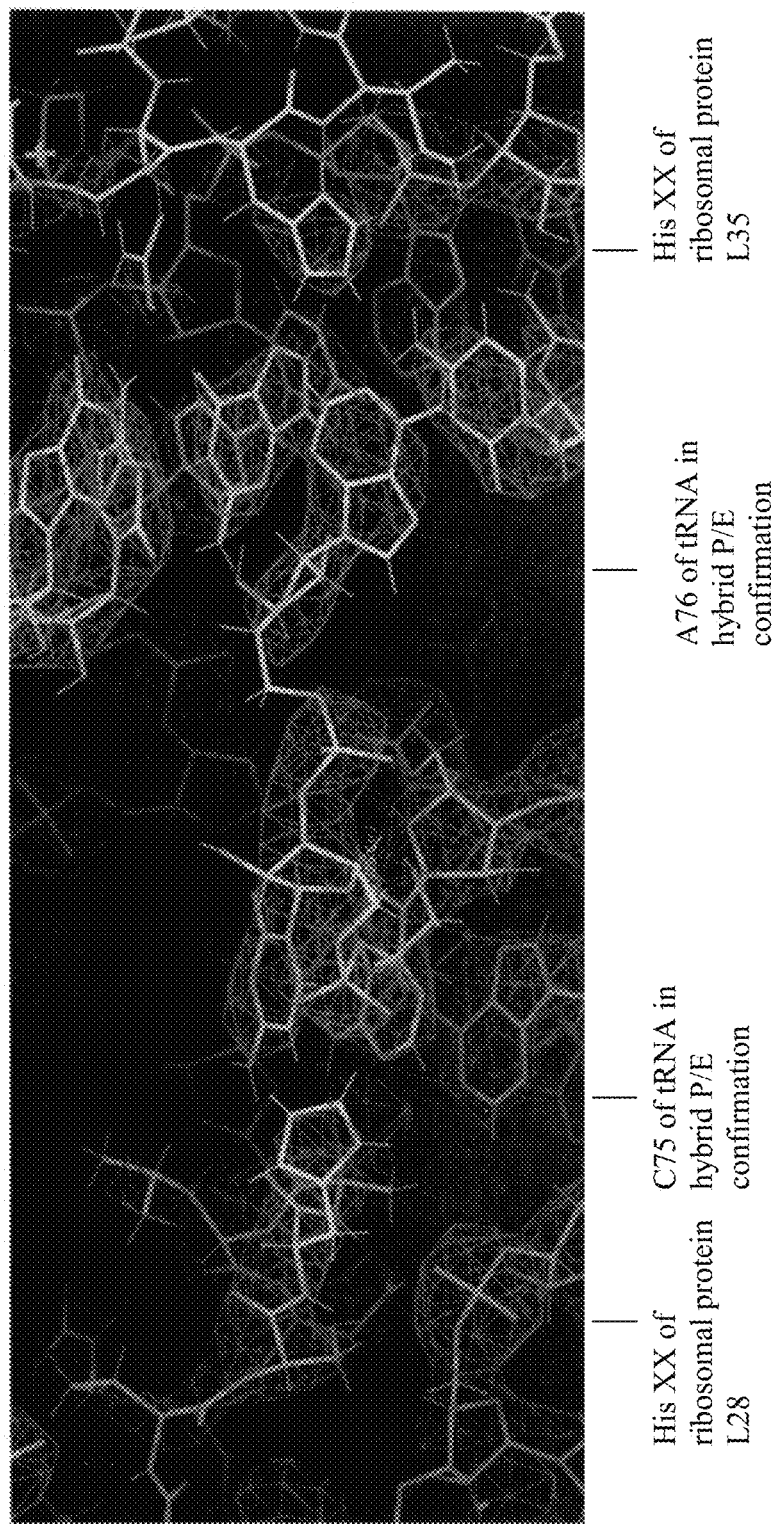
FIG. 5 is an expanded view of FIG. 4 showing the interactions of the 3'-CCA end of P/E tRNA with the 50S subunit E site in E. coli.

In the large subunit E site, P/E tRNA contacts the ribosome in a similar manner to tRNA bound in the E/E site (FIG. 2B; Selmer 2006). Nucleotides G2112 and G2168 in 23S rRNA, part of the protein L1-containing arm of the 50S subunit, stack on the D-loop and T-loop of P/E tRNA (FIG. 1C, FIG. 2B). Consistent with biochemical studies of the mechanism of translocation (Lill 1989), nucleotide A76 at the acceptor end of P/E tRNA stacks between nucleotides in helix H88 of 23S rRNA (FIG. 2B, FIG. 4, FIG. 5), where the terminal ribose engages the Watson-Crick face of nucleotide C2394 (Schmeing 2003; Selmer 2006). In contrast to the positioning of C75 in E-site tRNA in the bacterium T. thermophilus (Selmer 2006) and in the archaeal large subunit (Schmeing 2003), in E. coli, nucleotide C75 in P/E tRNA stacks on nucleotide A2432 in 23S rRNA, away from the tRNA acceptor stem (FIG. 4, FIG. 5). The striking divergence of the 50S E site contacts contrasts with the high level of conservation in the peptidyl transferase center, supporting the notion that the ribosomal E site evolved relatively late, and has continued to diverge (Selmer 2006; Bokov 2009).

The divergence among species shown in FIG. 4 (see also, FIG. 5) indicates that this is a site that may be targeted for drug discovery efforts in order to generate compounds that will bind this region to preferentially stabilize or inhibit formation of the P/E hybrid configuration in a target cell (e.g. pathogenic organism or cancerous cell) while not negatively affecting the performance of normal mammalian ribosome functions in an unwanted manner.

The molecular contacts between the two ribosomal subunits are composed of both rRNA and ribosomal proteins, with the central contacts, or bridges, conserved across kingdoms (Schuwirth 2005; Ben-Shem 2010). In the fully-rotated state, the pivot point for inter-subunit ratcheting occurs at bridge B3 (FIG. 6A, FIG. 7), which maintains the same conformation and contacts when compared to the unrotated ribosome (Schuwirth 2005). Bridge B3 is composed of a cross-strand adenosine stacking motif (Cate 1996a,b) in which residues A1418 and A1483 within helix 44 (h44) of 16S rRNA in the 30S subunit dock into the minor groove of helix 71 (H71) in 23S rRNA of the 50S subunit. Residues A1418 and A1483 lie within adjacent sheared G-A base pairs that coordinate an inner-sphere magnesium ion that possibly contributes to subunit association in all organisms (Schuwirth 2005; Shenvi 2005) (FIG. 6B).

Figure 8:
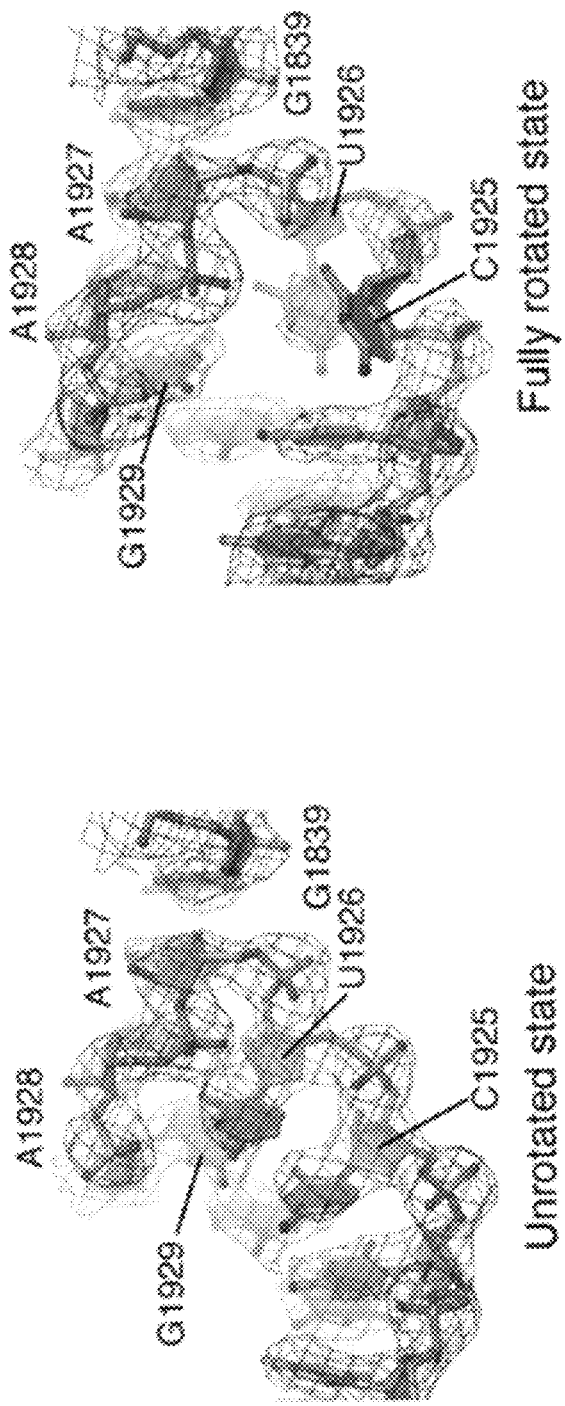
FIG. 8 illustrates the extrusion of C1925 and U1926 due to helix H69 compression. The $(2F_{Obs}-F_{Calc})$ electron density map contoured at 1.3 standard deviations from the mean is also shown.

In the aminoacyl-tRNA (A) and P sites, bridge B2a involves contacts between 23S rRNA helix H69 in the 50S subunit and 16S rRNA residues at the end of helix h44 in the 30S subunit, and is preserved in both the unrotated and fully-rotated states of the ribosome (FIG. 6A). In both states, residue A1913 of H69 penetrates the minor groove of the h44 mRNA decoding site. However, in going from the unrotated to fully-rotated state, the P-site tRNA anticodon and mRNA (FIG. 2A) and the end of helix h44 move laterally by ~6 Å towards the E site (FIG. 6C). Remarkably, the interactions between H69 and h44 are maintained during this movement due to a ~5 Å compression of H69 (FIG. 6C). In part, this compression is enabled by disruption of the terminal base pair (C1925-G1929) of H69 and extrusion of the nearly universally conserved uridine U1926 (Cannone 2002) from the tight U-turn motif at the base of H69 (Schuwirth 2005) (FIG. 8).

The observed conformational rearrangements in bridge B2a may help explain how antibiotics such as viomycin that target translocation stabilize the fully rotated state of the ribosome (Ermolenko 2007; Cornish 2008). Viomycin and the related antibiotic capreomycin bind to the unrotated state of the ribosome in the vicinity of nt A1913 in 23S rRNA (Stanley 2010), the only nucleotide whose contacts with h44 change appreciably during inter-subunit rotation. Aminoglycosides such as neomycin, which bind to two sites in bridge B2a (Borovinskaya 2007; Feldman 2010), may favor the fully rotated state of the ribosome by stabilizing the compressed conformation of helix H69.

On the opposite end of the tRNA binding cleft, bridge B7a is disrupted due to the rotation of the 30S platform domain (FIG. 1D). In the unrotated state, nucleotide A702 in 16S rRNA stacks on an A-A dinucleotide platform near the end of helix H68 of 23S rRNA (Cate 1996a,b). This interaction involves a hydrogen bond between N1 of A702 and G1846 in 23S rRNA (Schuwirth 2005). Consistent with chemical probing data used to identify hybrid tRNA binding sites (Moazed 1989), rotation of the 30S platform domain into the fully rotated position results in a ~13 Å displacement of A702 away from H68 that exposes the base pairing face of A702 to solvent (FIG. 6D). Consistent with biochemical observations (Feinberg 2001), H68 moves in the opposite direction by 2-3 Å to pack in the minor groove of the acceptor stem of P/E tRNA (FIG. 6D) likely helping to stabilize tRNA in the P/E hybrid site.

The absence of bridge B7a in the fully rotated state appears to be partially compensated for by new contacts between protein L2 in the large subunit and helices h23 and h24 in 16S rRNA (Bridges B7b, B7c; FIG. 6A). However, the most significant stabilizing contact to the 30S platform region in both the unrotated and fully rotated ribosome configurations remains bridge B4, which in bacteria involves intimate contacts between the hairpin loop at the end of helix H34 in 23S rRNA of the large subunit and protein S15 in the small subunit. Helix H34 bends by ~7 Å, or 12°, due to inter-subunit rotation and slightly adjusts how nucleotide A715 packs on the hydrophobic surface of protein S15 (Schuwirth 2005; FIG. 6E). Compensation for the loss of bridge B7a in the fully rotated state may also result from the formation of more extensive interactions between the 30S subunit body domain and the 50S subunit near bridge B8. In bridge B8, large subunit proteins L14 and L19 interact more strongly with helices h8 and h14 in the 30S subunit (FIG. 6A).

As the mechanism of translation hinges on bridge B7a remodeling during the normal process of translation, this site, encompassing the AA platform at the base of helix 68 in the 23S rRNA and residues from about A650—to about A750 of 16s rRNA (in *E. coli* numbering) may also be considered a key target for drug discovery as small molecules affecting the stability of this bridge interaction are expected to strongly inhibit translation performance.

In the fully rotated state, the head domain of the 30S subunit swivels as a rigid body in the direction of tRNA movement, rearranging bridge B1b to place the central alpha helix of protein S13 directly across from protein L5 in the 50S subunit (FIG. 1C) (Valle 2003a,b). This lateral change in protein S13 position correlates with tRNA binding in the hybrid P/E site and may help control the position of tRNAs on the ribosome (Frank 2007). Thus, the contacts between protein S13 and protein L5 probably play an important role in the ribosome ratcheting mechanism. Consistent with this view, deletions in protein S13 result in more rapid and lower fidelity translocation of mRNA and tRNA (Cukras 2005). Mutations in the other major contact between the 30S subunit head domain and helix H38 in the 50S subunit, bridge B1a, have a similar effect (Komoda 2006).

As head swivel is understood to play a key role in the translation mechanism (e.g. translocation), the two structures reported here also provide insights into means to regulate the observed motions of the head domain using small molecule compounds to either stabilize or disrupt the key points of contact between the small subunit head domain via small subunit ribosomal proteins S13, and the central protuberance (via large subunit ribosomal protein L5) and/or H38 (the so-called A-site finger helix) of the large subunit as well as points of contact between the small subunit head domain and tRNA substrates.

Figure 9:
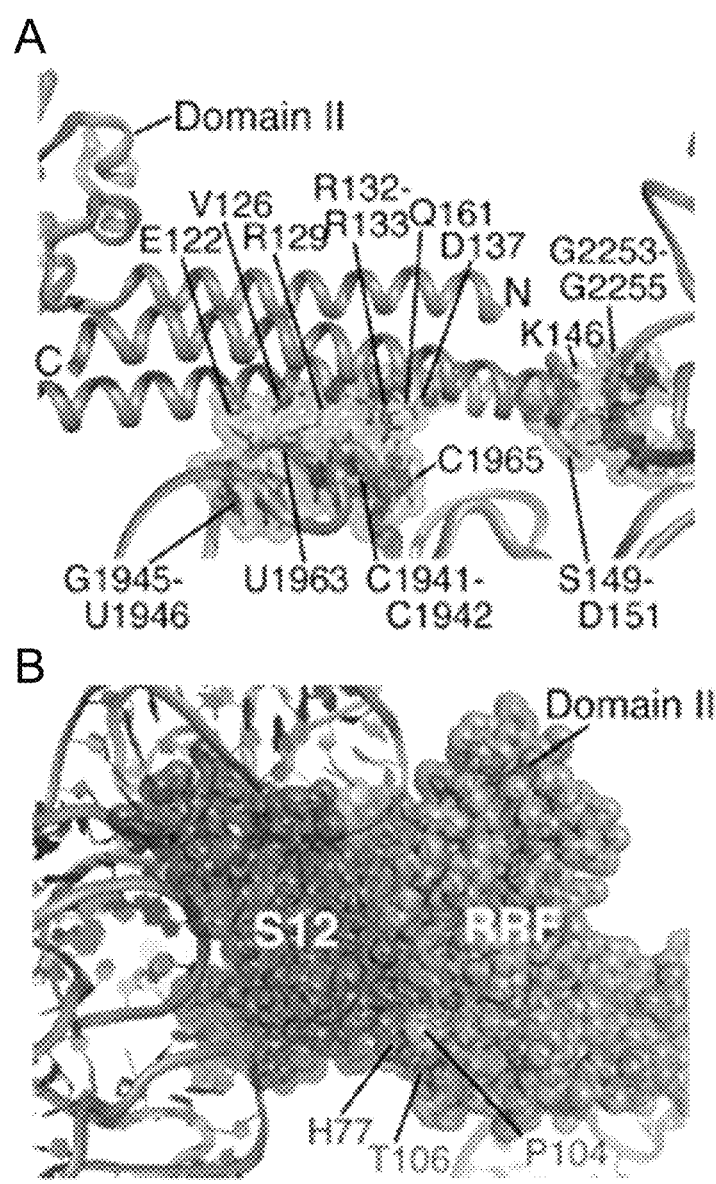
FIG. 9 shows the RRF interactions with the ribosome in the fully rotated state. (A) Contacts between RRF domain I and the P and A sites of the 50S subunit. Amino acids in RRF (grey helix across top of figure) and nucleotides in 23S rRNA (grey) in direct contact are shown. Helix H69 and the 30S subunit are behind the view shown. (B) Contacts between RRF and protein S12 in the 30S subunit. Amino acids at the junction of RRF domains I and II that interact closely with S12 are indicated. RRF, S12 and rRNAs colored as in FIG. 1.

In the fully rotated ribosome, RRF binds in the P-site and A-site cleft of the 50S subunit, precluding tRNA binding in either site. Its 3-helix bundle domain (domain I) runs nearly parallel to the subunit interface, with alpha helix 3 packed tightly against helix H71 in 23S rRNA (FIG. 9A). Mutations in this region result in lethal or temperature-sensitive phenotypes (Janosi 2000). In addition, conserved amino acids within the tip of RRF domain I (Ashkenazy 2010) interact with rRNA nucleotides of the universally conserved P loop element of the peptidyl transferase center (FIG. 9A). These sets of interactions appear to be the same in both the unrotated and fully rotated states of the ribosome (Borovinskaya 2007; Weixlbaumer 2007), suggesting that they are necessary but not sufficient for the recycling mechanism.

Figure 10:
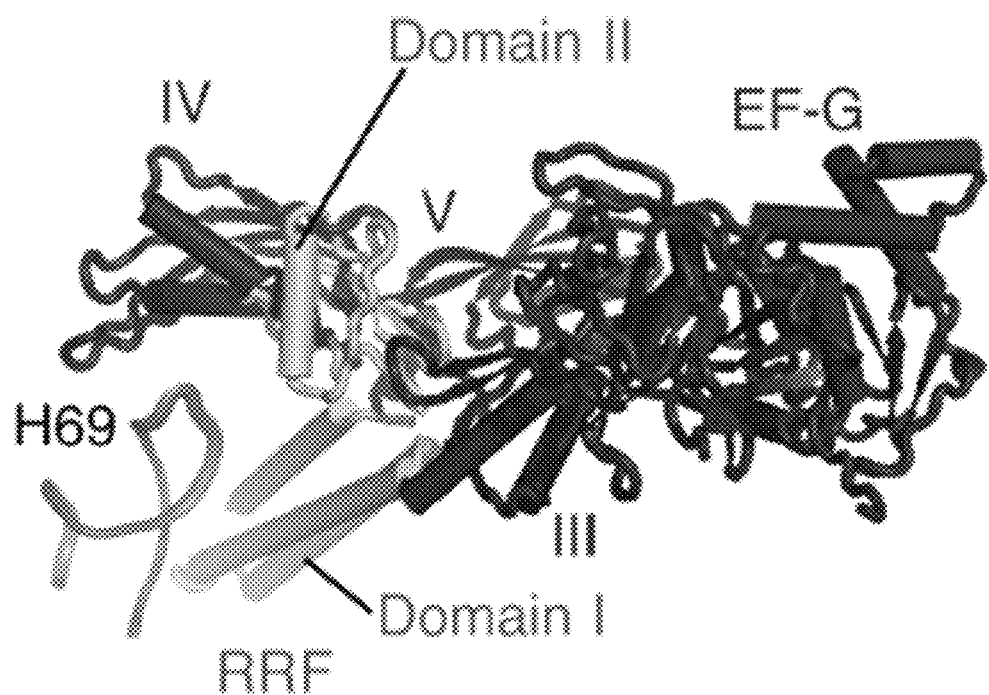
FIG. 10 depicts the superposition of a fully rotated ribosome in a pre-translocation complex mimic (Ratje 2010) with the recycling intermediate structure. Domains IV and V of EF-G (darkest grey) and domain II of RRF (lightest grey) significantly overlap, with some overlap of domain III in EF-G and hinge region of RRF. H69 in the recycling complex is also shown for reference. Superposition used the 50S subunit as a frame of reference (Frank 2007).

Additional points of contact between RRF and the fully rotated ribosome occur between conserved amino acids near the junction of domains I and II in RRF and ribosomal protein S12 of the small subunit (FIG. 9B) (Ashkenazy 2010). Domain II of RRF is more constrained in its position in the ratcheted state compared to its location in the unratcheted ribosome (Borovinskaya 2007; Weixlbaumer 2007). As suggested by cryo-EM reconstructions of the ribosome in complexes with RRF (Agrawal 2004; Gao, 2005), RRF domain II likely serves a steric function in ribosome recycling. Docking of EF-G from a cryo-EM reconstruction of the ribosome in a rotated conformation related to translocation (Ratje 2010) onto the ratcheted 70S ribosome structure determined here shows significant overlap between domain II of RRF and domains IV and V of EF-G (FIG. 10). Thus, EF-G binding to the RRF-bound ribosome likely entails large-scale rearrangements in RRF, EF-G, and the ribosome (Gao 2005), the precise energetics of which may be altered by small-molecule compounds to alter or inhibit the mechanism of recycling.

When compared to other structures of the ribosome, the structure of the fully rotated state of the ribosome provides critical insights into the molecular description of the ratcheting mechanism in translation. As simple mRNAs can be translated in the absence of exogenous factors like EF-G (Gavrilova 1976), the ribosome itself serves as a Brownian ratchet (Munro 2009a; Spirin 2009a,b), with tRNA substrates likely serving as the "teeth". A notable feature of the ratcheting mechanism is the use of RNA secondary structural elements to control large-scale conformational rearrangements in the ribosome. These include RNA stem-loops in bridges B2a and B4 that adjust as the 30S subunit rotates relative to the 50S subunit (Spahn 2004; Gao, 2005; Connell 2007; Zhang 2009; Ben-Shem 2010), helix H68 in 23S rRNA adjacent to bridge B7a and P/E tRNA, RNA helices H76 and H42 in the L1 and L11 arms of the large subunit, respectively (Valle 2003a,b; Munro 2009a; Schmeing 2009a; Ben-Shem 2010), and helix h28 in 16S rRNA which directs swiveling of the 30S subunit head domain (Schuwirth 2005). Helix h28 likely serves as the "spring" in the ratcheting process, helping to position the "pawl" between the small subunit P and E sites (Schuwirth 2005; Spirin 2009a,b; Dunkle 2010; Ratje 2010). The hinge-like motion in P/E tRNA observed here, when compared to P/P tRNA, suggests that the conserved tertiary structure of tRNA is required not only for mRNA decoding (Valle 2002; Schmeing 2009b; Voorhees 2010), but also for translocation, termination, and ribosome recycling (Li 2007; Ratje 2010). Intact P-site tRNA is required for translocation (Joseph 1998), a requirement that may in part be due to need for a large distortion of tRNA in the P/E binding site. This distortion may be used to tune the energetics of the transition between the pre-translocation state and post-translocation state of the ribosome. Future structural studies of ribosome complexes with EF-G will be required to explain how this factor controls the conformational events described here to accelerate translocation and ribosome recycling.

As mentioned above, aminoglycosides such as neomycin, which binds to two sites in bridge B2a (Borovinskaya 2007; Feldman 2010), likely favor the fully rotated state of the ribosome by stabilizing the compressed conformation of helix H69. In the aminoglycoside-stabilized rotated state, the normal mechanism of EF-G binding and translocation (Munro 2010c) is markedly more inhibited than observed for aminoglycoside binding to the h44 decoding site of the small subunit and the ribosome, by virtue of being unable to return to the classical unrotated state, is also no longer competent for the process of aminoacyl-tRNA selection mediated by Elongation Factor-Tu. Further, the ribosome is prevented from recycling. These are previously unknown mechanisms of action for antibiotics.

The nature of the secondary aminoglycoside binding site on the ribosome and its central importance to the translation mechanism was not clear until before this structure. It was previously known that loss of the tlyA gene, which encodes a 2'-O-methyltransferase that is specific for ribose methylation at C1409 (helix 44) of 16S rRNA and C1920 (H69) of 23S rRNA, confers ribosome resistance to the viomycin class of antibiotics (Johansen 2006), and it has been reported that viomycin binds the ribosome near the intersubunit bridge B2a (formed between 16S rRNA helix 44 and 23S rRNA H69), stabilizing the translocational intermediate conformation of the ribosome, in which the 30S subunit is rotated counter-clockwise relative to the 50S subunit and the tRNAs are bound in hybrid states (Ermolenko 2007)—this provides evidence that H69 is an antibiotic target and identifies a key residue on H69, but does not identify the boundaries of the location on H69. We previously defined residues C1920-C1925 and G1906 in H69 as well as G1929 in H69 as a neomycin and gentamicin binding site (Borovinskaya 2007) and determined the crystal structure, albeit in the ribosome's classic state. Our work makes it clear that the pocket is the circled region in FIG. 6C, which resides from about residue 1905 to about 1931 of H69 while the ribosome is in the rotated state; in the rotated state this new site is proximal to the canonical binding site for neomycin and other aminoglycosides, namely the residues from about 1402 to about 1412 and the residues from about 1488 to about 1500 in helix 44, in $E.\ coli$ numbering. The identification of these sites provides rationale for applying in silico and in vitro drug discovery methods (both traditional and/or new (e.g. the proposed use a single-molecule methods described herein or in our previous work)) to identify compounds that bind to one or both sites to inhibit a specified translation activity and/or alter the conformation and/or energetics of the ribosome.

4. smFRET Studies

Figure 11:
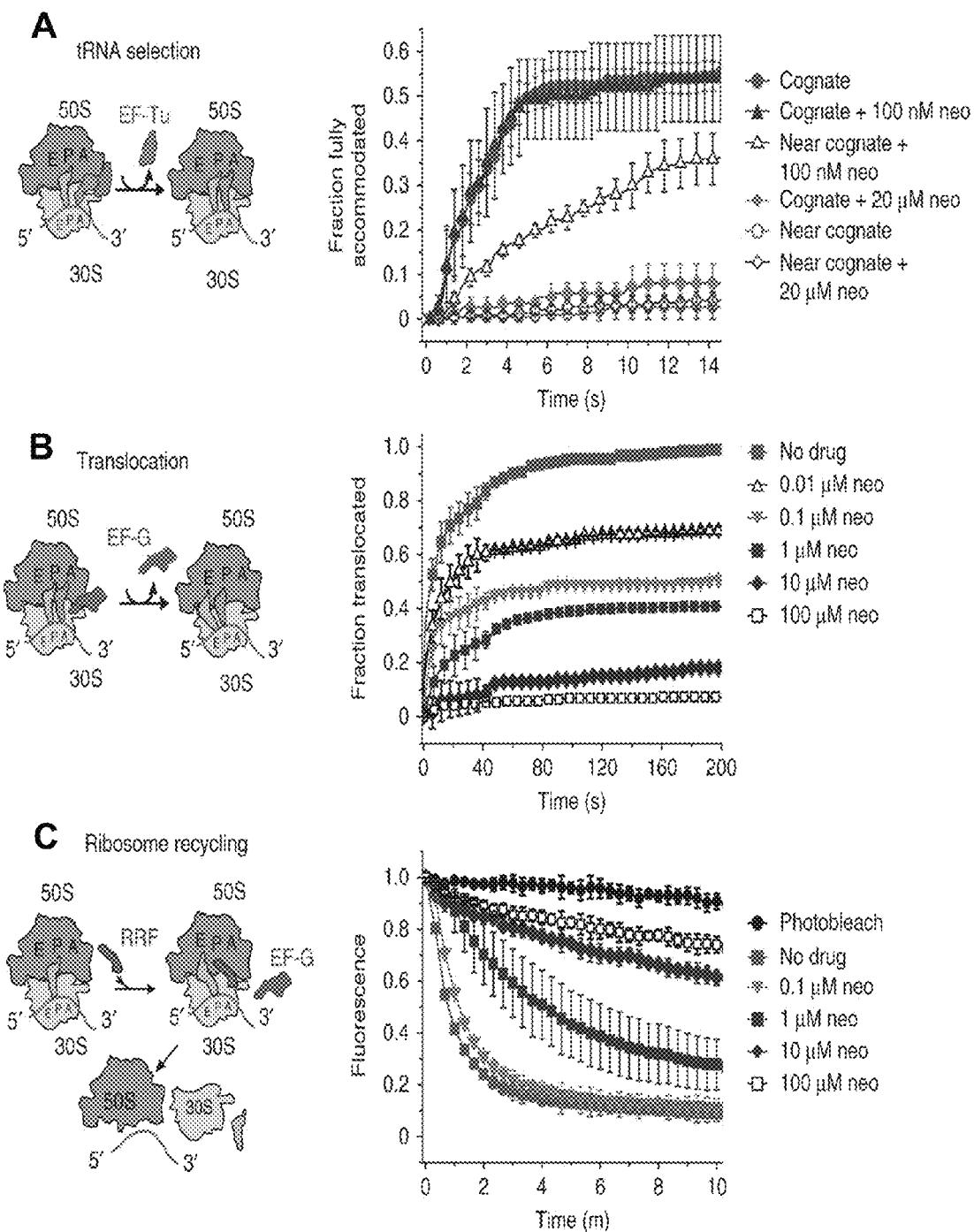
FIG. 11 illustrates that neomycin inhibits ribosome functions in vitro. (A) EF-Tu(GTP)-catalyzed accommodation of Phe-tRNA$^{Phe}$ at the A site of wild-type ribosomes programmed with cognate (UUC) and near-cognate (UCU) codons was monitored via FRET. The incorporation of cognate (Cog) tRNA (closed circles) and near-cognate (NC) tRNA (open circles) in the absence of antibiotics is shown. The incorporation of cognate tRNA (grey triangles) and of near-cognate tRNA (open triangles) in the presence of 100 nM neomycin, and the incorporation of cognate and near cognate tRNAs (grey closed diamond and open diamond, respectively) in the presence of 20 µM neomycin are also shown. (B) EF-G catalyzed translocation, monitored by smFRET, was normalized to the no drug case. The fractions of translocated molecules observed at neomycin concentrations of 0 µM (red squares), 0.01 µM (open triangles), 0.1 µM (inverted grey triangles), 1 µM (dark grey squares), 10 µM (diamonds) and 100 µM (open squares) are shown. (C) Recycling of wild-type 70S ribosome complexes was monitored by the disappearance of Cy5-labeled L1 fluorescence in 50S subunits from surface-immobilized wild-type ribosome complexes. Ribosome recycling at neomycin concentrations of 0 µM (squares), 0.1 µM (inverted grey triangles), 1 µM (dark grey squares), 10 µM (blue diamonds) and 100 µM (open squares) are shown. Under identical conditions, photobleaching was negligible (black circles).
Figure 12:
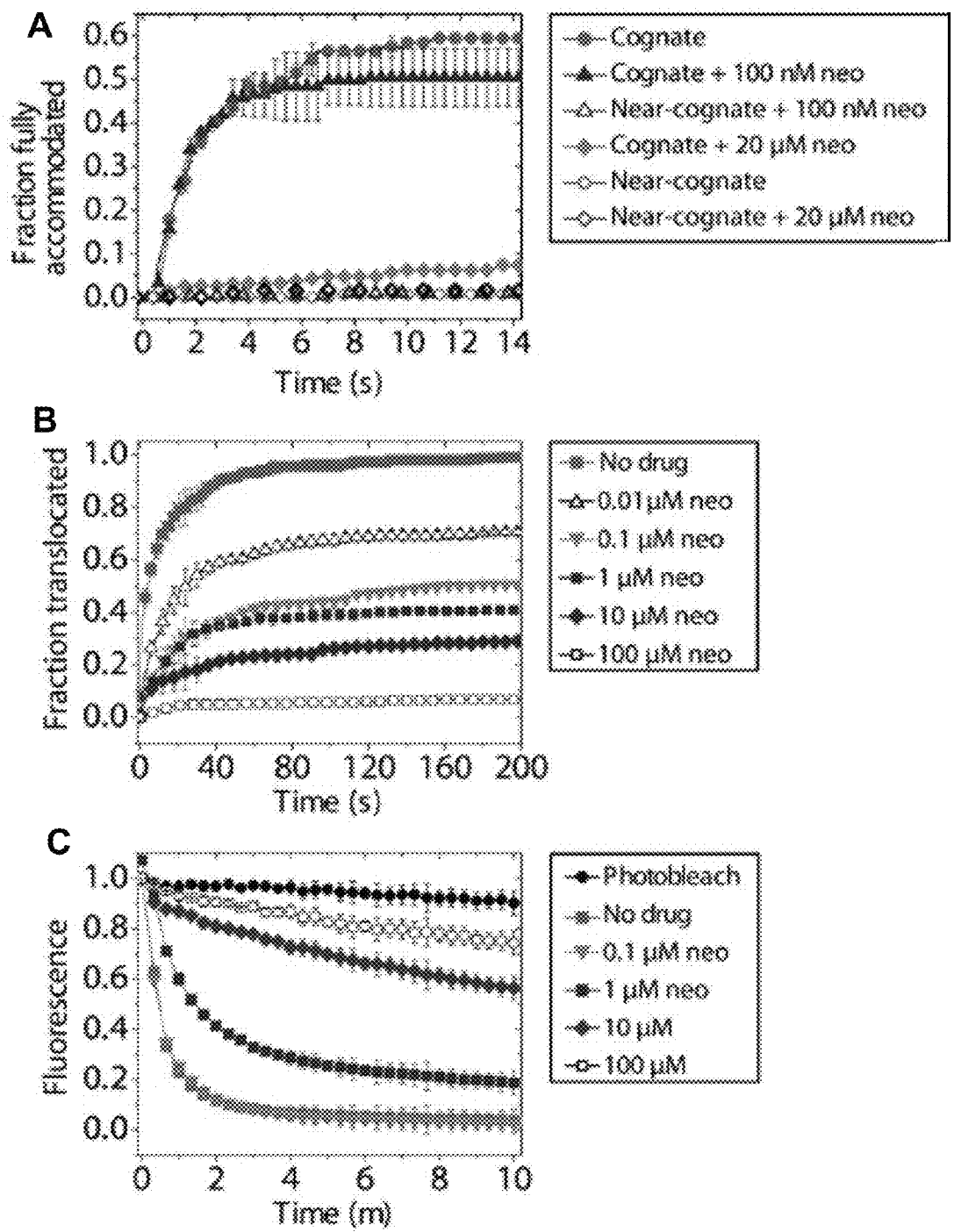
FIG. 12 illustrates that neomycin inhibits ribosomal functions in A1408G mutant ribosomes. (A) The process of EF-Tu(GTP)-catalyzed accommodation of Phe-tRNA$^{Phe}$ aa-tRNA at the A site of A1408G mutant ribosomes programmed with cognate (UUC) and near-cognate (UCU) codons were monitored via smFRET. In the absence of antibiotic, the incorporation of cognate (Cog) tRNA into A1408G ribosomes (closed circles) was similar to that of the wild-type system (FIG. 11). The incorporation of near-cognate (NC) tRNA (open circles) was minimal, similar to the wild-type system (FIG. 11). In the presence of 100 nM neomycin, the incorporation of cognate (dark grey triangles) was similar to that of the wild-type system while the incorporation of near-cognate (grey open triangles) tRNAs was reduced. At a neomycin concentration of 20 µM, the incorporation of cognate (grey closed diamond) and near-cognate (open black diamond) tRNAs were both reduced. (B) Neomycin inhibits EF-G catalyzed translocation in a concentration dependent manner in the A1408G mutant background. The fraction of molecules that translocated under each neomycin concentration was normalized to the no drug case. Neomycin concentrations of 0 µM (red squares, at top), 0.01 µM (open black triangles), 0.1 µM (inverted grey triangles), 1 µM (dark grey squares), 10 µM (blue squares, in middle) and 100 µM (black open squares) were tested. (C) Neomycin inhibits the process of ribosome recycling catalyzed by RRF, EF-G and GTP in a concentration-dependent manner in the A1408G mutant background. Neomycin concentrations of 0 µM (red squares, at bottom), 0.1 µM (inverted grey triangles), 1 µM (dark grey squares), 10 µM (blue squares, in lower middle) and 100 µM (black open squares) were tested. Under identical conditions, photobleaching was minimal (black circles).

Consistent with earlier findings (David-Eden 2010); Ogle 2005), pre-steady state smFRET measurements of aa-tRNA selection showed that low concentrations of neomycin (100 nM) substantially increased the rates of near-cognate aa-tRNA accommodation, while having negligible effects on the selection of cognate tRNA (FIG. 11B). These miscoding effects were almost entirely suppressed by the A1408G resistance mutation in the h44 decoding site (FIG. 12A). However, when identical experiments were performed at a higher neomycin concentration (20 µM), the selection of both cognate and near-cognate tRNA was significantly attenuated (FIG. 11B) Inhibition persisted in the A1408G context, suggesting that neomycin binding outside of the h44 decoding region alters the selection mechanism (FIG. 12A). In line with previous investigations (Feldman 2010), neomycin blocked substrate translocation on both wild-type and A1408G ribosomes at concentrations above 1 µM (FIG. 11C and FIG. 12B). Neomycin also inhibited ribosome recycling—mediated by ribosome recycling factor (RRF) and EF-G—on both wild-type and A1408G ribosomes, with similar concentration dependence (FIG. 11D and FIG. 12C). Together, these findings argue that neomycin binding outside the canonical h44 decoding site prevents one or more central aspects of the translation mechanism.

In order to probe neomycin-induced inhibition of these three key translation steps, a new smFRET approach was developed to examine global conformational changes in the ribosome related to subunit rotation and distinct from tRNA motions. A FRET pair with acceptor fluorophore attached to protein L1 in the large subunit (Munro 2010b) and donor fluorophore conjugated to the N-terminus of protein S13, located within the small subunit head domain (FIG. 13A) was designed to report on formation of "unlocked state" configurations achieved prior to translocation and ribosome recycling (Valle 2003b); Munro 2010c); Munro 2010a).

Unlocked state formation entails the repositioning of deacylated tRNA bound in the Peptidyl-tRNA (P) site into the Exit (E) site on the large ribosomal subunit, termed the P/E hybrid state. Formation of the unlocked state also involves closure of the L1 stalk towards the subunit interface and an approximately 9° rotation of the small subunit with respect to the large (Example 3); Valle 2003b). Here, we probed ribosomes lacking A-site tRNA and bearing either deacylated P-site tRNA$^{fMet}$ (FIG. 13B) or tRNA$^{Phe}$ (FIG. 13C), similar to the substrates in the above tRNA selection and recycling studies, respectively.

Figure 14:
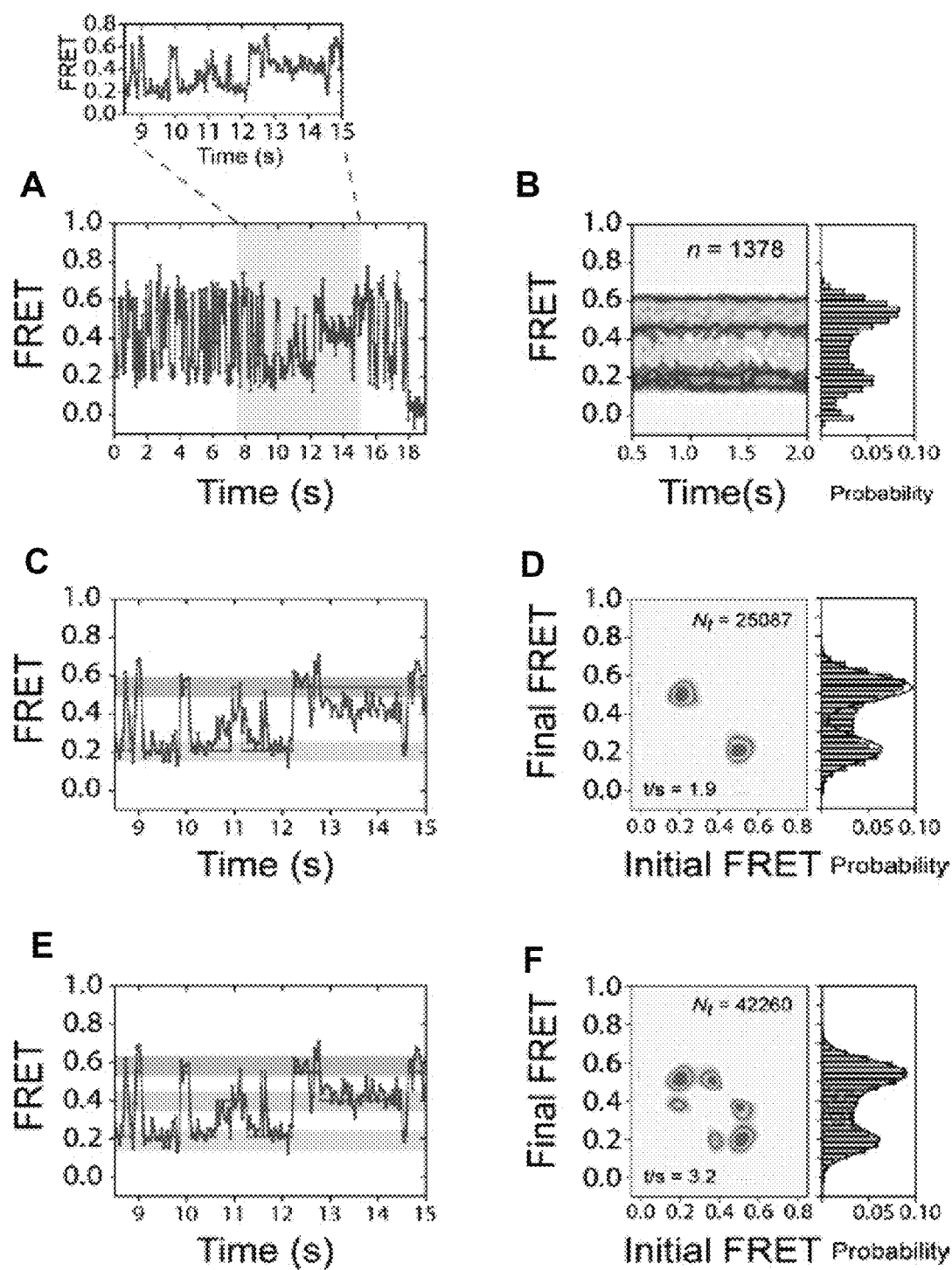
FIG. 14 illustrates the dynamics between S13 and L1 in the absence of neomycin. (A) A representative smFRET trajectory from a ribosome complex labeled with Cy3-S13 and Cy5-L1 imaged at 40 ms time resolution in the absence of drug. FRET efficiency (FRET=$I_{Cy5}/[I_{Cy3}+I_{Cy5}]$) is shown in blue. The inset reveals short-lived dwells in multiple FRET states. (B) A population FRET histogram, composed of >1500 smFRET trajectories, reveals the existence of multiple, FRET states. The representative smFRET trajectory shown in the inset of FIG. 14A is idealized using the segmental k-means algorithm in QuB (Qin 1996) to (C) 2- and (E) 3-state models. Transition density plots (Munro 2007), obtained by the idealization of individual smFRET trajectories to the (D) 2- and (F) 3-state model, suggest the existence of at least one short-lived intermediate-FRET state. Population FRET histograms fit using Gaussian distributions to the sum (black) of (D) two or (F) three non-zero FRET states (red).
Figure 15:
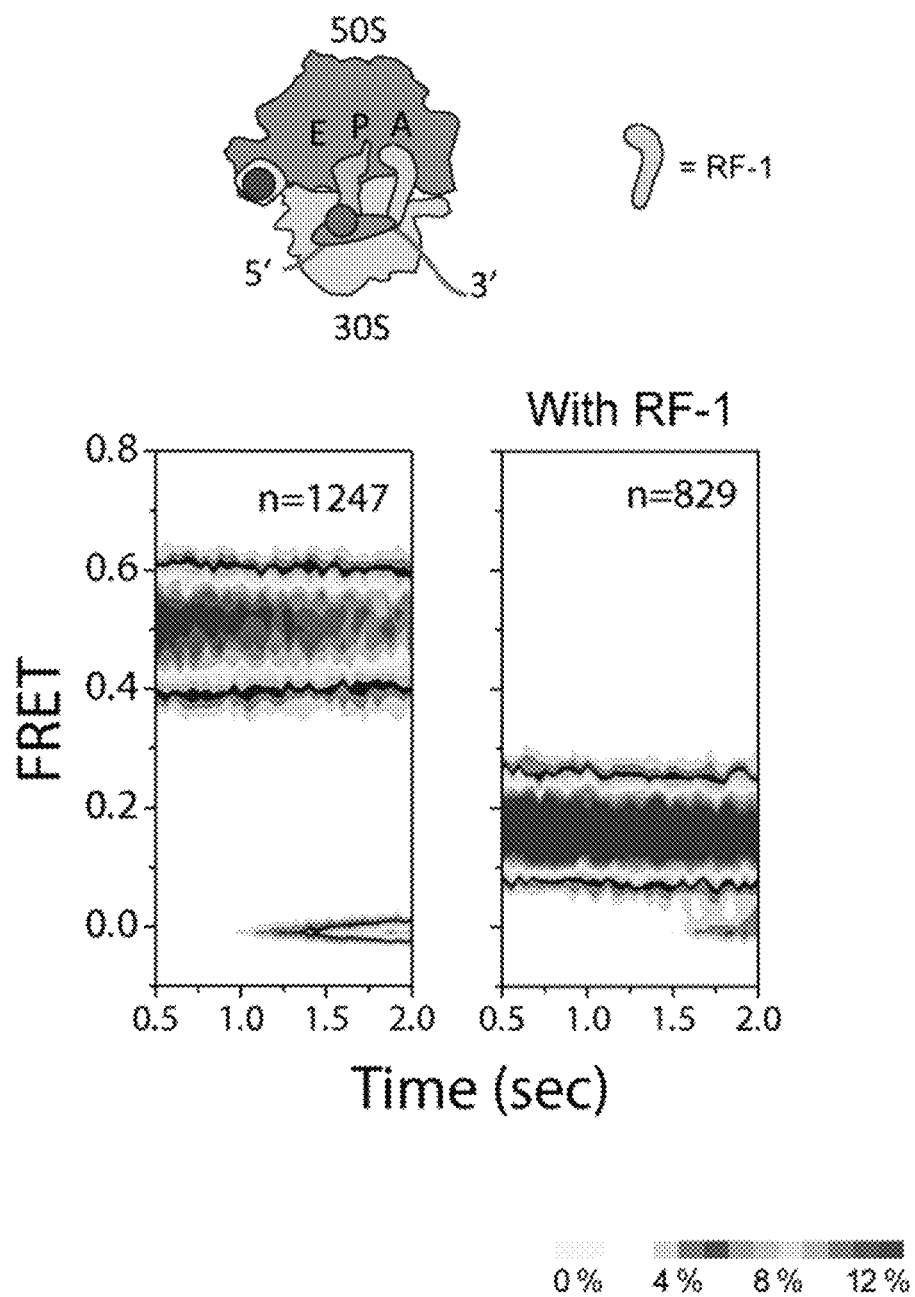
FIG. 15 shows that ribosome release factor (RF)-1 stabilizes the post-termination ribosome complex bearing deacylated tRNA$^{Phe}$ in the P site in a high-FRET, unrotated state. Top panel, cartoon depicting binding sites. Bottom panel, population FRET histograms, generated as described in FIG. 14, reveal the population behavior in the absence (left) and presence (right) of 10 μM RF-1.
Figure 16:
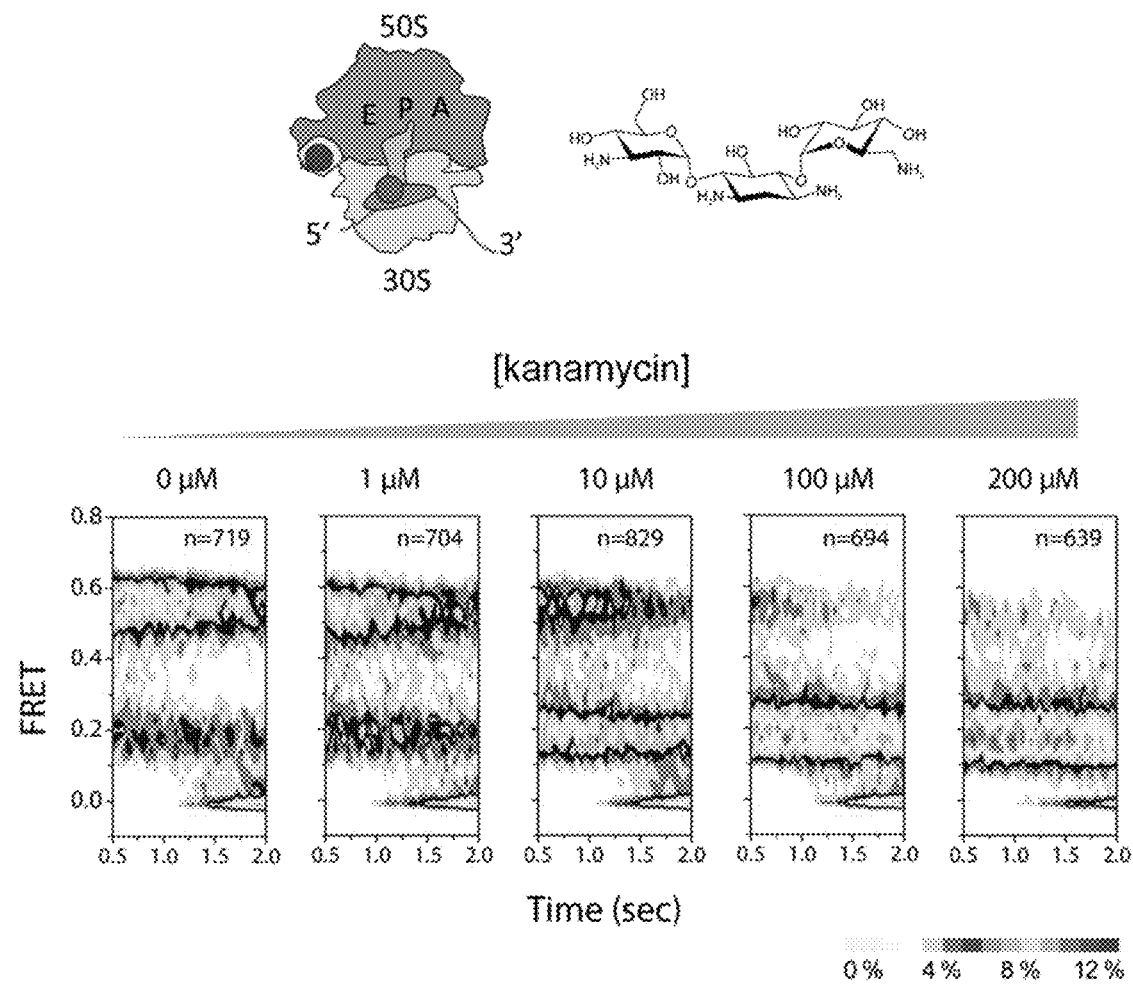
FIG. 16 shows that kanamycin stabilizes ribosome complexes bearing deacylated tRNA$^{fMet}$ in the P site in a low-FRET, unrotated state. Top panel, cartoon depicting binding sites and kanamycin structure. Bottom panel, population FRET histograms, generated as described in FIG. 14, reveal the kanamycin concentration dependence of low-FRET, unrotated, state stabilization.
Figure 17:
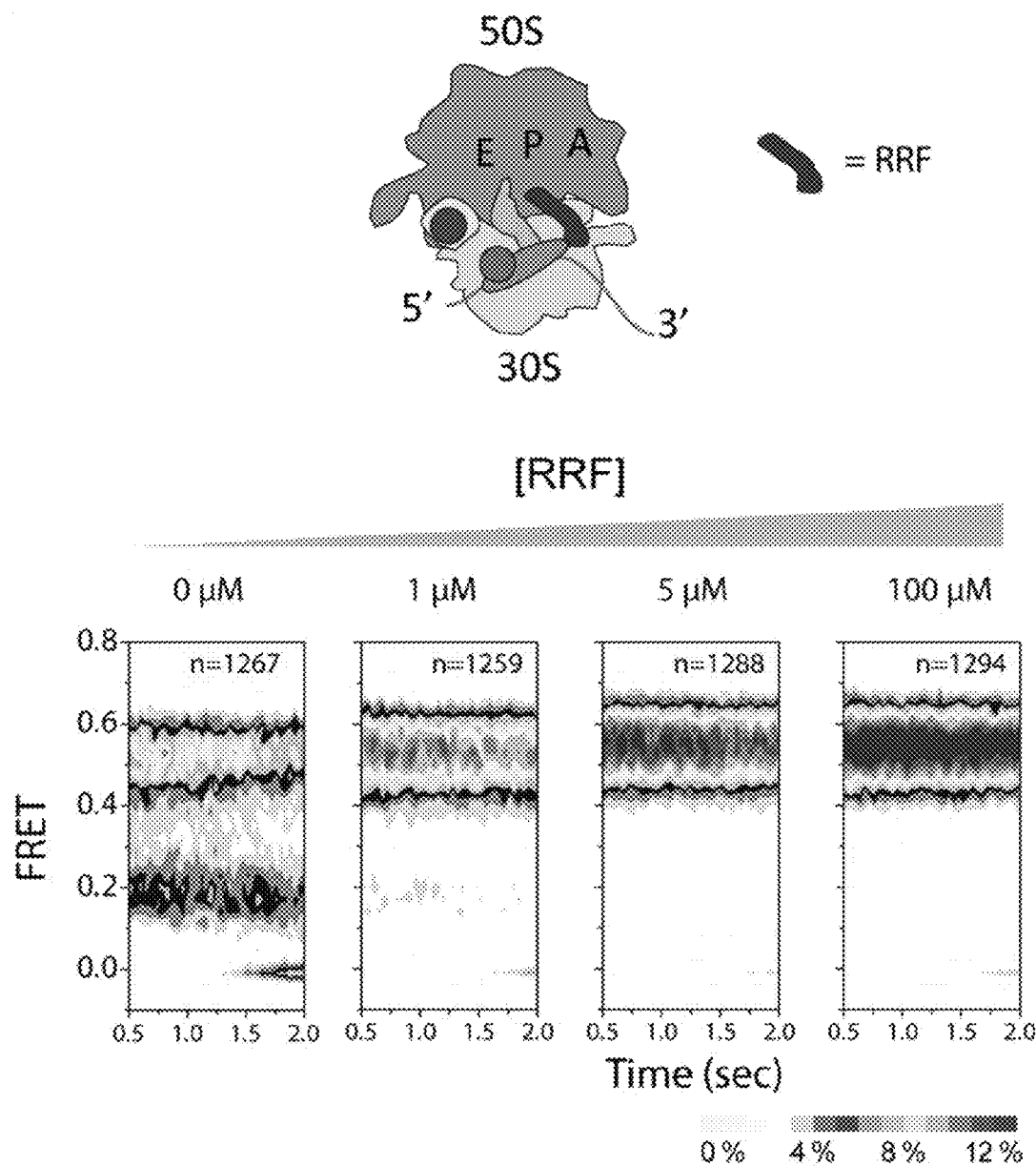
FIG. 17 shows that ribosome recycling factor (RRF) stabilizes ribosome complexes bearing deacylated tRNA$^{fMet}$ in the P site in a high-FRET rotated state. Top panel, cartoon depicting binding sites. Bottom panel, population FRET histograms, generated as described in FIG. 14, reveal the RRF concentration dependence of high-FRET, rotated, state stabilization.
Figure 18:
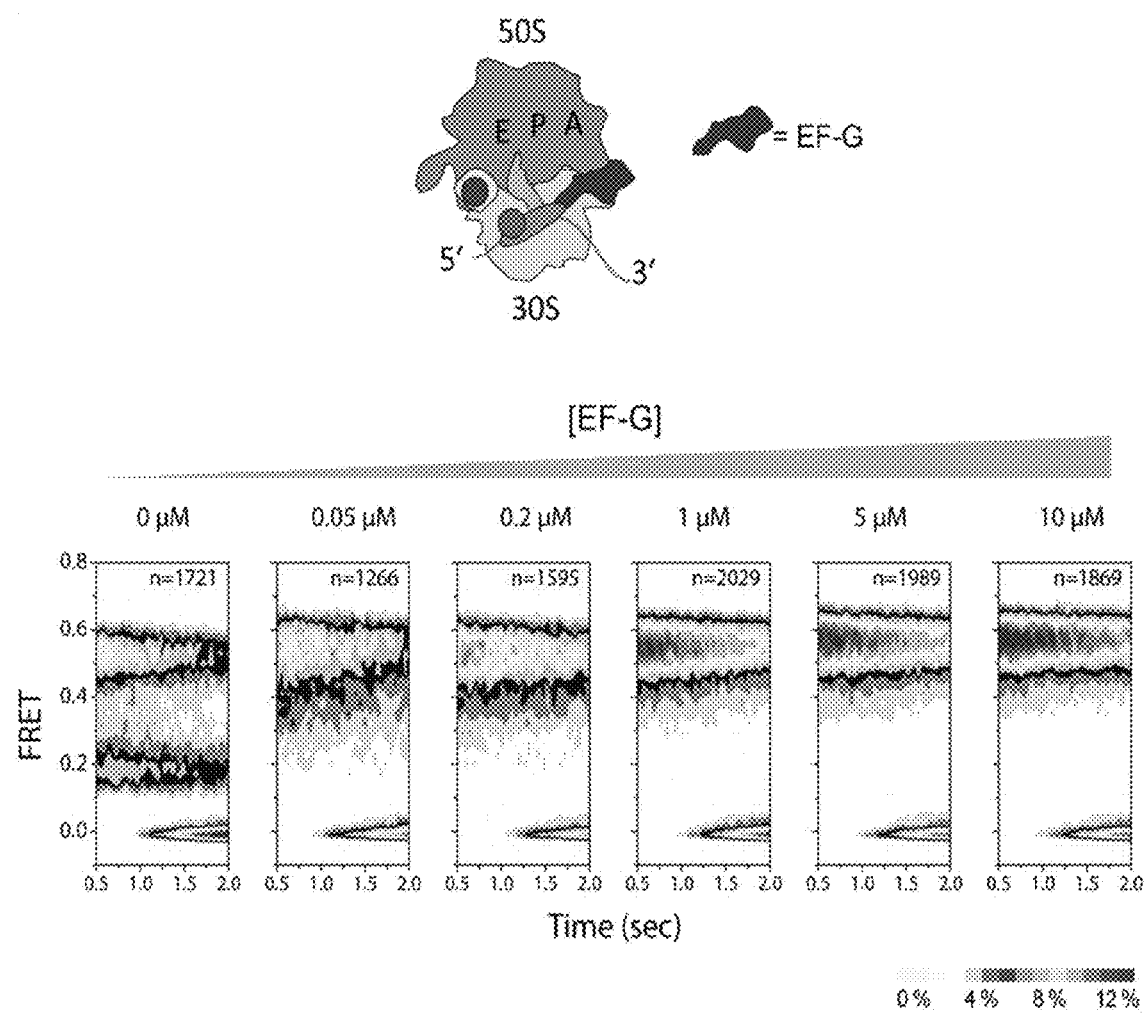
FIG. 18 shows that elongation factor (EF)-G stabilizes ribosome complexes bearing deacylated tRNA$^{fMet}$ in the P site in a high-FRET, rotated state. Top panel, cartoon depicting binding sites. Bottom panel, population FRET histograms, generated as described in FIG. 14, reveal the EF-G concentration dependence of high-FRET, rotated, state stabilization.
Figure 19:
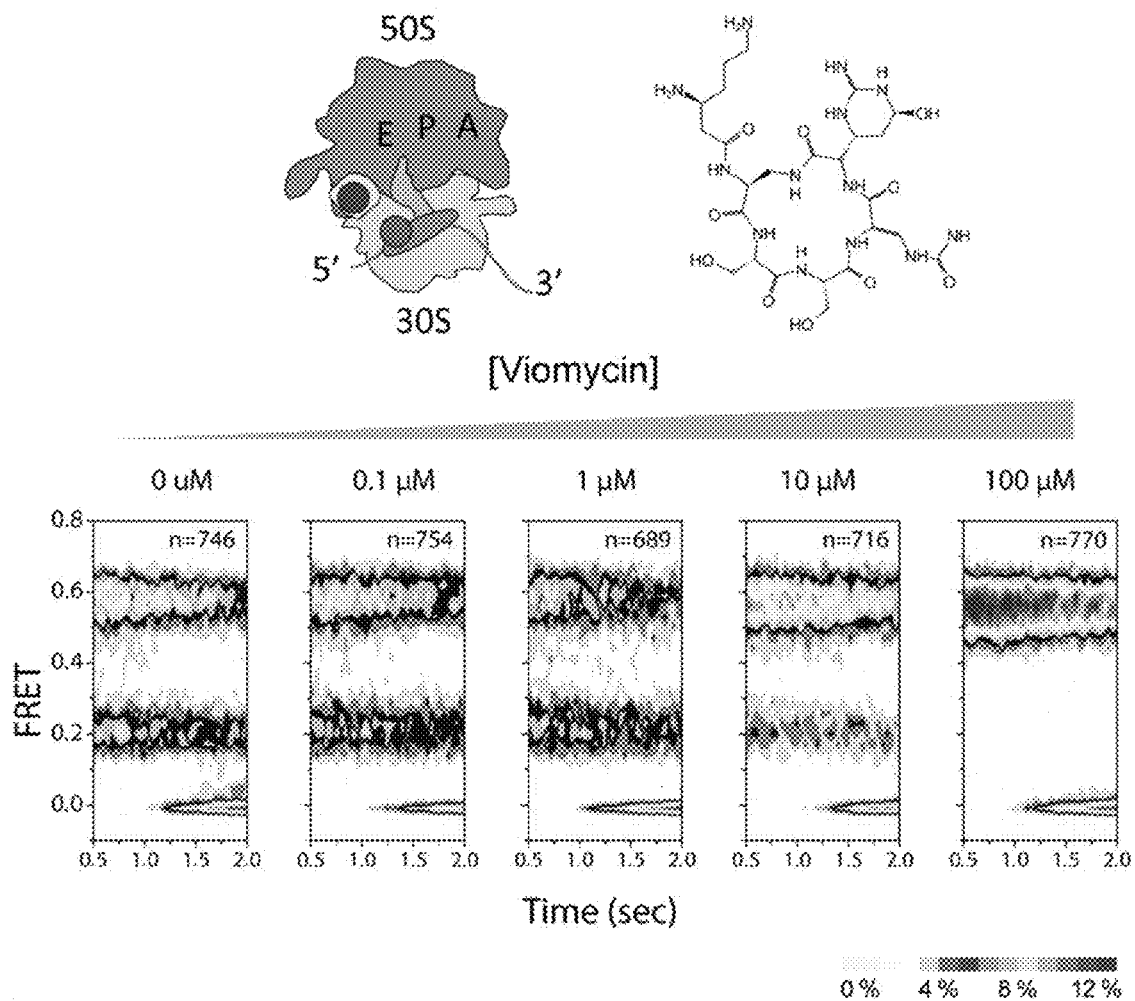
FIG. 19 shows that viomycin stabilizes ribosome complexes bearing deacylated tRNA$^{fMet}$ in the P site in a rotated state. Top panel, cartoon depicting binding sites and viomycin structure. Bottom panel, population FRET histograms, generated as described in FIG. 14, reveal the viomycin concentration dependence of high-FRET, rotated, state stabilization.

In the absence of antibiotic, both complexes populated two, dominant FRET states that dynamically exchanged on a sub-second time scale (FIG. 14A-B), as well as one or more short-lived intermediate configurations (FIG. 14C-F) (Munro 2010b; Zhang 2009). The structural origins of these FRET states were probed using translation factors and antibiotics known to stabilize distinct ribosome conformations. In saturating concentration of release factor 1 (RF-1), known to stabilize a "locked" ribosome configuration with P-site tRNA bound in the P site of both ribosomal subunits (P/P site) and the L1 stalk in an "open" state (Sternberg 2009); Laurberg 2008; Petry 2008), the ribosome adopts the low-FRET state (FIG. 15). The addition of the 4,5-linked deoxystreptamine antibiotic kanamycin also stabilized the low-FRET state (FIG. 16). This observation is consistent with kanamycin's ability to stabilize peptidyl-tRNA in the A site of both ribosomal subunits (A/A site) within pre-translocation ribosome complexes by binding to helix h44 in the mRNA decoding site (Feldman 2010). Notably, the present complexes lack peptidyl-tRNA in the A site, indicating that kanamycin stabilizes the unrotated configuration of the ribosome directly—a finding consistent with the notion that the helix h44 decoding site changes conformation in its transition to the rotated ribosome configuration (Feldman 2010; Example 3). The high-FRET state was stabilized by binding of either RRF or EF-G (in the presence of the nonhydrolyzable GTP analog, GDPNP), factors that stabilize the ribosome in a rotated and unlocked state (FIGS. 17 and 18) (Valle 2003b). The high-FRET state was also favored in the presence of viomycin (FIG. 19), an antibiotic previously shown to stabilize a hybrid P/E tRNA position and a rotated state of the ribosome (Cornish 2008; Ermolenko 2007).

By contrast, neomycin exerted a bimodal effect on the dynamics and FRET distributions of ribosomes containing tRNA$^{fMet}$ in the P site (FIG. 13B). At low concentrations of neomycin (<100 nM), the low-FRET state was favored, as expected for ground state stabilization of classical tRNA positions by binding to h44 in the decoding site (Feldman 2010; Peske 2005). At higher concentrations (>1 µM), neomycin surprisingly stabilized a ribosome configuration exhibiting an intermediate FRET value, falling between those assigned above to unrotated (locked) and rotated (unlocked) states. At high neomycin concentrations, a similar intermediate-FRET configuration was also observed for complexes containing tRNA$^{Phe}$ in the P site (FIG. 13C). Taken together, these data suggest that neomycin may stabilize an otherwise transient intermediate in the transition of the ribosome that exists between locked and unlocked states (Munro 2010b) and that this configuration is incompatible with tRNA selection, translocation and ribosome recycling (FIG. 11).

5. Ribosome Structures for Unrotated and Rotated States with Bound Neomycin

Crystals containing 70S ribosomes in both the unrotated and fully rotated states, with bound P/P or P/E deacylated tRNA$^{Phe}$, respectively, as described in Section 2 above, were soaked with neomycin. These crystals were used to measure diffraction data to a resolution of 3.5 Å (Tables 4 and 5).

Figure 20:
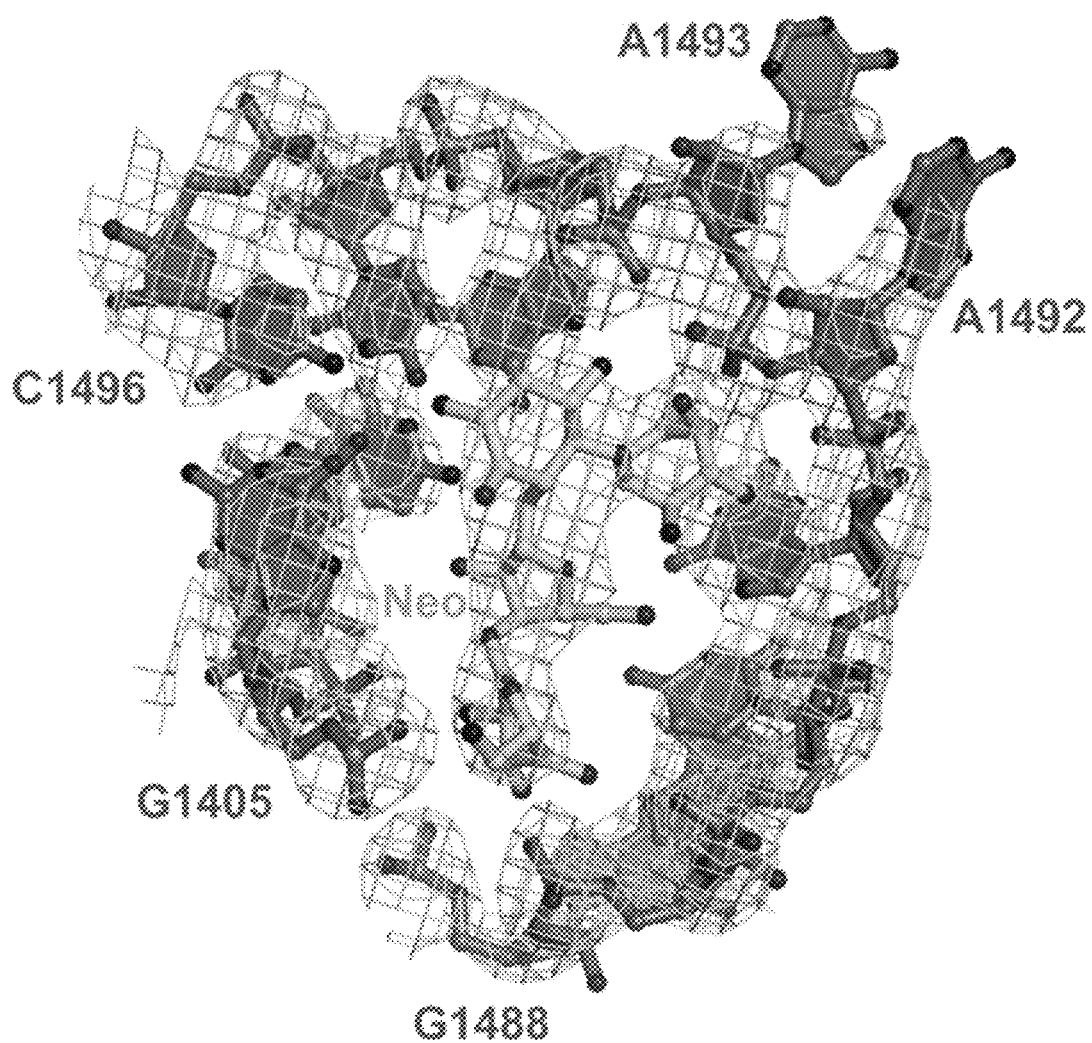
FIG. 20 provides a $2F_{obs}-F_{calc}$ electron density difference map of neomycin bound in the h44 decoding site of the intermediate-rotated ribosome, contoured at 1.7 standard deviations from the mean. Colors for 16S rRNA and neomycin are as in FIG. 23A. The 16S rRNA residues A1492 and A1493 are extruded from h44 as previously reported Borovinskaya 2007).
Figure 21:
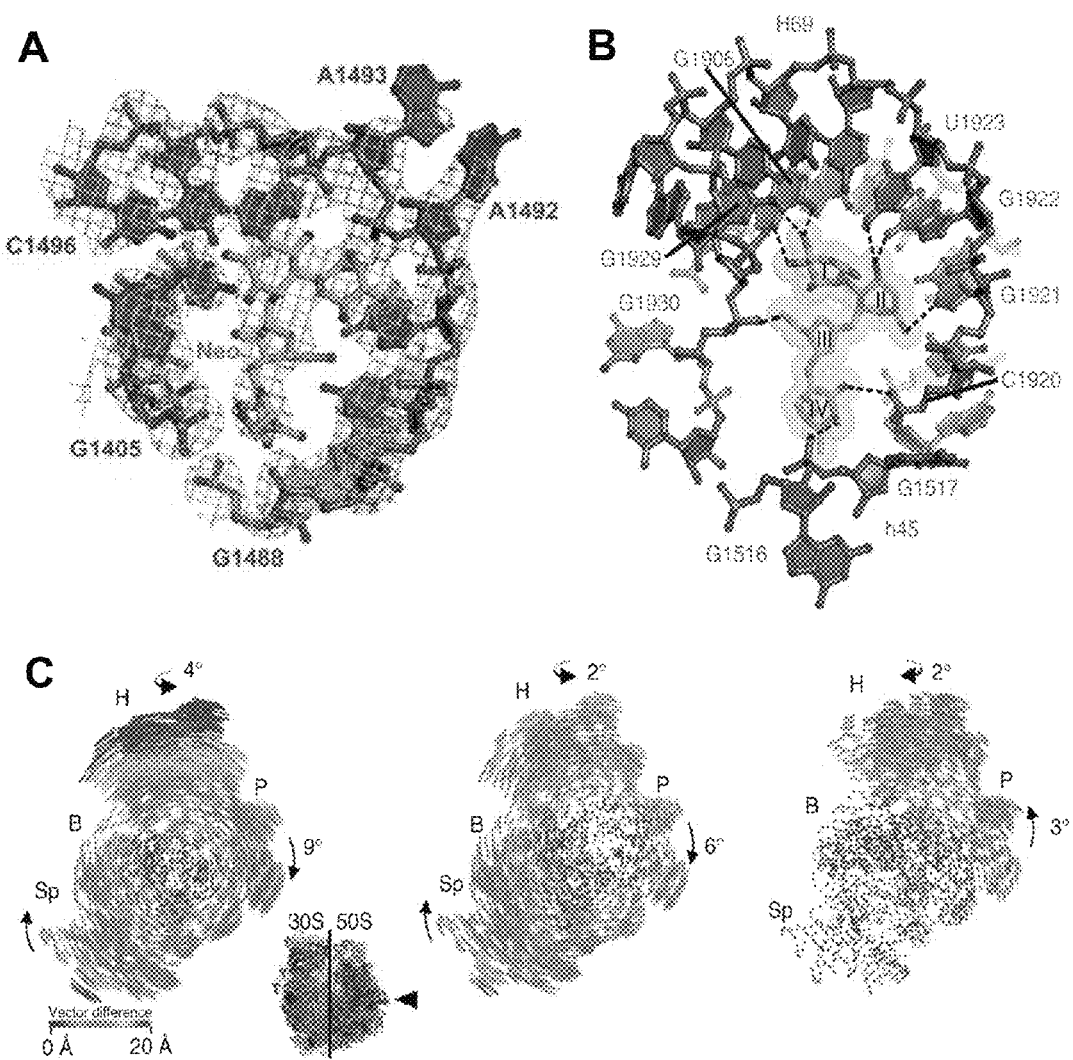
FIG. 21 shows that the neomycin contacts within H69 of 23S rRNA and its bridging interactions with h45 of 16S rRNA induce global rearrangements in the 70S ribosome. (A) Electron density map for neomycin within the H69 binding site. The 23S rRNA helix H69 (grey), 16S rRNA helix h45 (blue) and neomycin (light blue) are shown, along with a $(2F_{obs}-F_{calc})$ electron density map, calculated in Phenix and contoured at 1.4 standard deviations from the mean. (B) Neomycin interactions with the H69 binding site showing points of contacts with the major groove and bridging interactions with the backbone of rRNA helix h45 of the small subunit. Neomycin and rRNA contacts <3.5 Å are shown as dashed lines. Ring II of neomycin packs against the major groove face of residues G1921, G1922 and U1923, while rings I, III and IV largely participate in backbone contacts. (C) Effects of neomycin binding to H69 on inter-subunit rotation in the ribosome. (Inset) View of the 30S subunit from the perspective of the 50S subunit. Difference vector shifts between equivalent RNA phosphorus atoms and protein Cα atoms in the unrotated ($R_0$) vs. fully rotated ($R_F$) states on the left; unrotated ($R_0$) vs. intermediate-rotated ($R_I$) state with neomycin bound to H69 in the middle; fully rotated ($R_F$) state vs. intermediate-rotated ($R_I$) state with neomycin bound to H69 on the right. Vectors are color coded as indicated by the scale. Ribosomes were superimposed using the 50S subunit as the frame of reference as described in the Example 4.

After refinement of the 70S ribosome structures with tRNA removed from the models, $F_{Obs}-F_{Calc}$ difference electron density maps contained clear, positive electron density for neomycin. In the unrotated ribosome, neomycin was bound in its canonical h44 decoding site (FIG. 20). In the rotated ribosome, neomycin was present in the h44 site as well as a site at the base of helix H69 in the large subunit, near its site of interaction with elements h24 and h45 of the small subunit rRNA in intersubunit bridge B2b (FIG. 21A). In this site, rings I-III of neomycin make specific contacts with residues within the H69 major groove, while ring IV contacts h45 of the small subunit (FIG. 21B).

Figure 22:
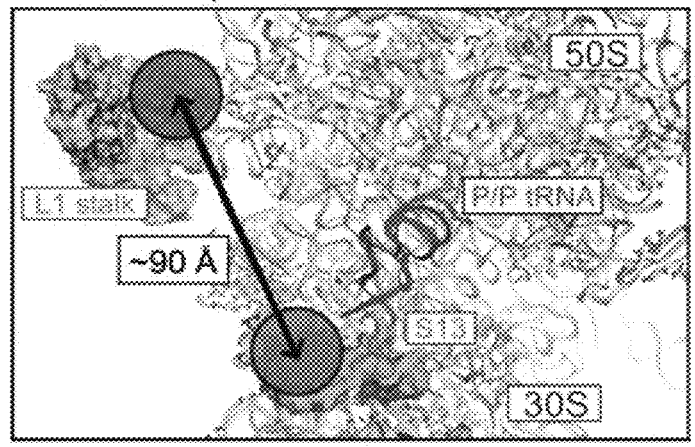
FIG. 22 depicts structural models of ribosome complexes with fluorescence components in (A) the unrotated, (B) partially rotated and (C) fully rotated configurations. The unrotated and fully rotated models were constructed using coordinates from Example 3. The partially rotated model was obtained by superimposing the neomycin-bound, partially rotated structure reported here onto the fully rotated structure (Example 3) using PyMOL (see Examples). The various components are marked and in a color version of this figure, the L1 stalk (L1 protein and 23S rRNA helices 76-78) is shown in pink. Ribosomal protein S13 of the small subunit is shown in cyan. Classically configured (P/P) P-site tRNA is shown in red; P/pe tRNA in green and P/E tRNA in blue. RRF is shown in orange. Approximate positions of Cy3 and Cy5 are shown as green and red circles, respectively; and distances between them in each model were estimated using PyMOL.
Figure 22:
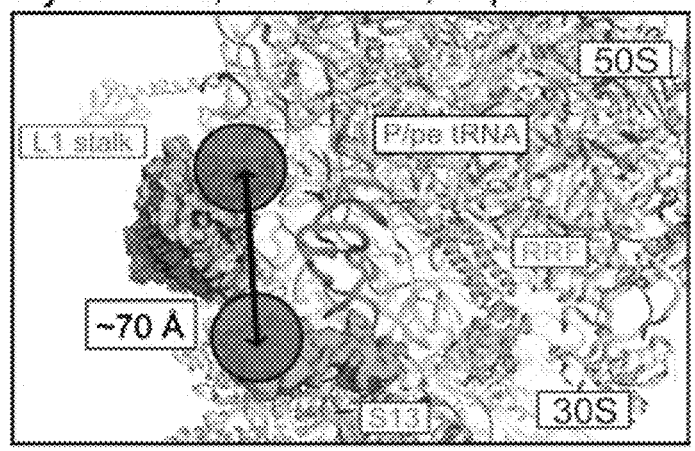
Figure 22:
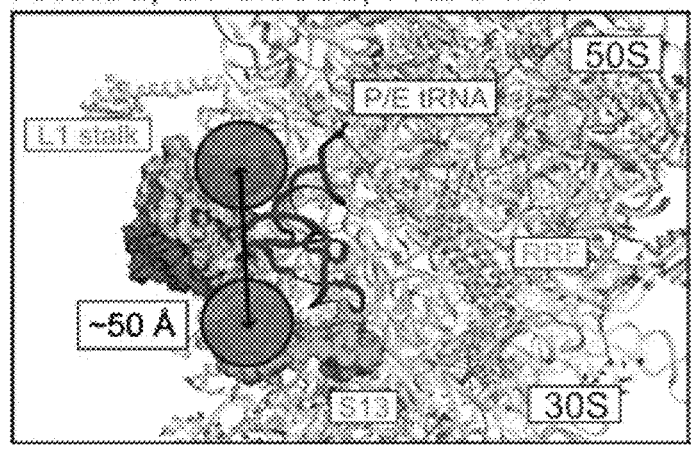

Notably, neomycin binding within helix H69 was accompanied by a large rearrangement of the rotated configuration of the ribosome. In contrast to the fully rotated state, the overall extent of small subunit rotation was markedly attenuated (FIG. 21C). In addition, motions of the small subunit body along the subunit rotation trajectory were partially uncoupled from those of the platform and head domains. Correspondingly, while the small subunit spur region moved to the same extent as in the fully rotated structure (approximately 20 Å), the small subunit platform domain rotated to a lesser extent (approximately 6° vs. 9°). Lateral motions of the small subunit head domain were also less than observed in the fully rotated state (approximately 15 Å vs. 20 Å). The swivel-like rotation of the small subunit head domain in the direction of translocation was likewise reduced (approximately 2° vs. 4°). These structural rearrangements agree well with the apparent distance between L1 and S13 observed by smFRET in the neomycin-stabilized intermediate (FIG. 13 and FIG. 22).

Figure 23:
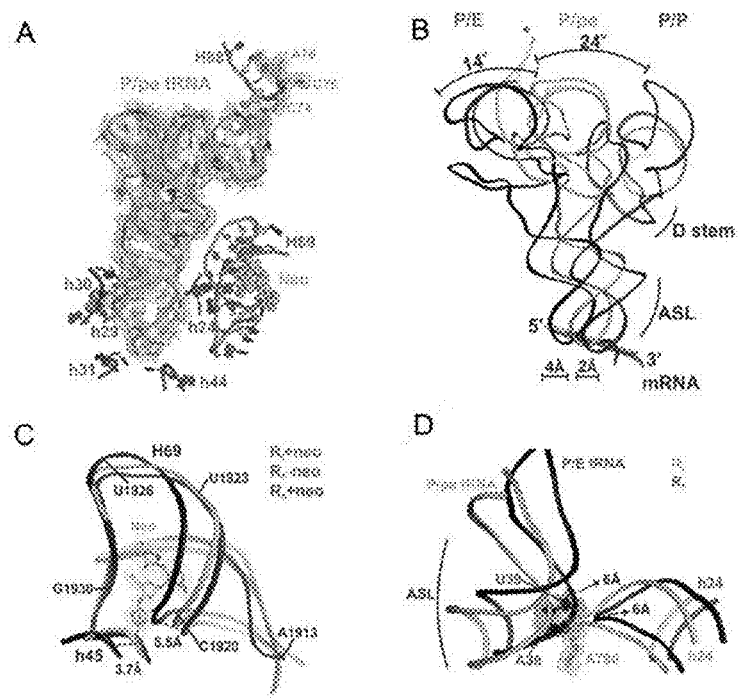
FIG. 23 shows the position of tRNA$^{Phe}$ in the intermediate-rotated and neomycin-bound ribosome. (A) $F_{obs}-F_{calc}$ difference electron density map for P/pe tRNA in the neomycin-bound, intermediate-rotated ribosome configuration with its position relative to rRNA elements h24, h29, h30, h31 and h44 of the small subunit and rRNA elements H69 and H88 (grey) of the large subunit and neomycin bound to H69. Shown is a ($F_{obs}-F_{calc}$) electron density map, calculated in Phenix and contoured at 2.5 standard deviations from the mean. (B) The position of P-site tRNA observed (P/pe in pale grey) is intermediate between classical (P/P, right) and hybrid (P/E, left) configurations showing the relative angle of T stem displacement towards the large subunit E site and the extent of anticodon movement towards the small subunit E site. The D stem corresponds to the dihydrouridine loop (residues 14-21) of P-site tRNA; ASL refers to its anticodon stem loop; the 3' CCA end is denoted with an asterisk. The tRNA anticodon stem loops move 2 and 4 Ångstroms from P/P to P/pe, and P/pe to P/E, respectively. (C) Superposition of unrotated $R_0$ (classical, P/P tRNA), fully rotated $R_F$ (P/E tRNA) and intermediate $R_I$ (P/pe tRNA) ribosome configurations showing the change in major groove width of H69 of the large subunit rRNA, the relative positions of H69 and h45 of the small subunit rRNA, as well as the observed position of neomycin (Neo) in the $R_I$ structure. The helix conformation of H69 in the unrotated state is essentially unchanged by neomycin binding. (D) In the intermediate-rotated configuration, helix h24 near position A790 in the small ribosomal subunit sterically blocks the transition of P-site tRNA (near position U39) into the P/E hybrid configuration. The P/E tRNA (dark grey), and P/pe tRNA (light grey) anticodon stem loop region, and 16S rRNA helix 24 of fully rotated ($R_F$, dark) or intermediate-rotated ($R_I$, light) conformations are shown. Directional arrows indicate movements of tRNA or h24, and the extent of the movement is shown in Ångstroms.
Figure 24:
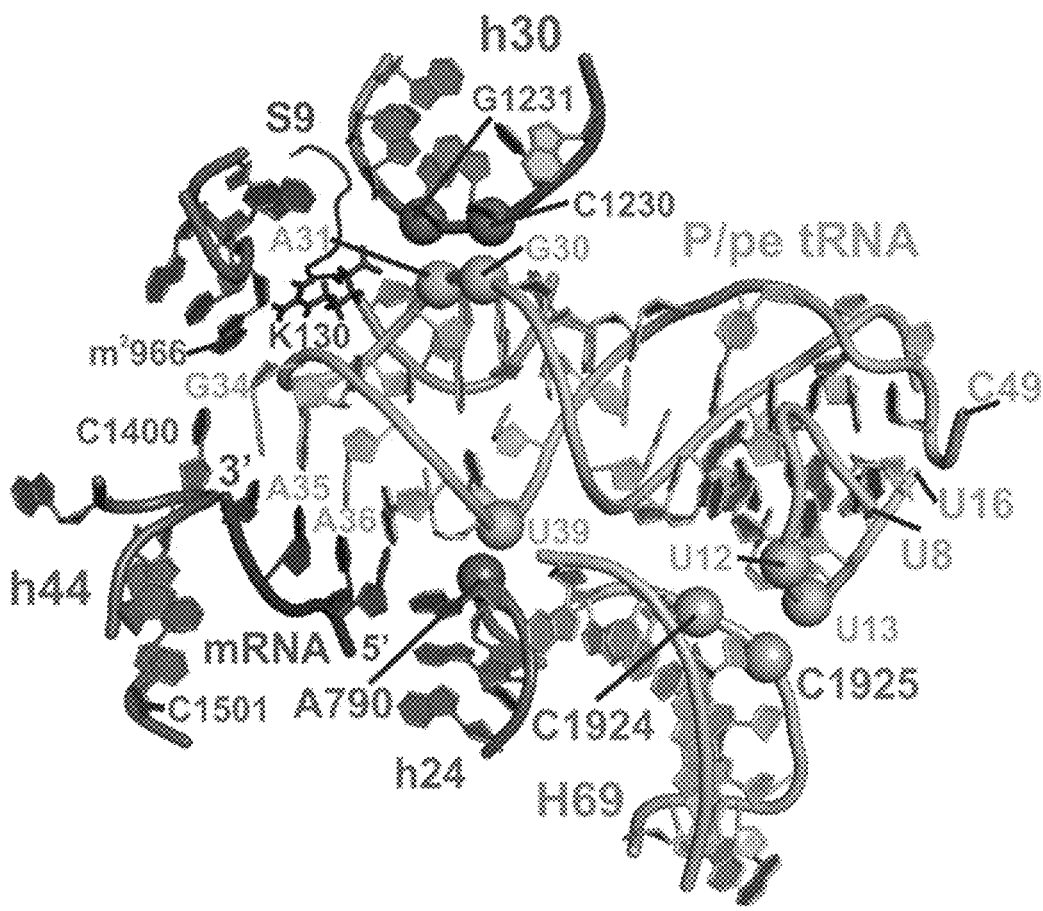
FIG. 24 shows a view of mRNA and Pipe tRNA interactions with the 30S subunit P site. Residues that contact P/pe tRNA (spheres) are shown. Colors for the ribosome and tRNA are as in FIG. 23A. Additionally, mRNA and small subunit protein S9 are shown. The key contacts between P-site tRNA and the small subunit are maintained in the neomycin-bound, intermediate-rotated ribosome configuration, as are the contacts between the tRNA ASL-D-stem junction and the minor groove of H69.
Figure 25:
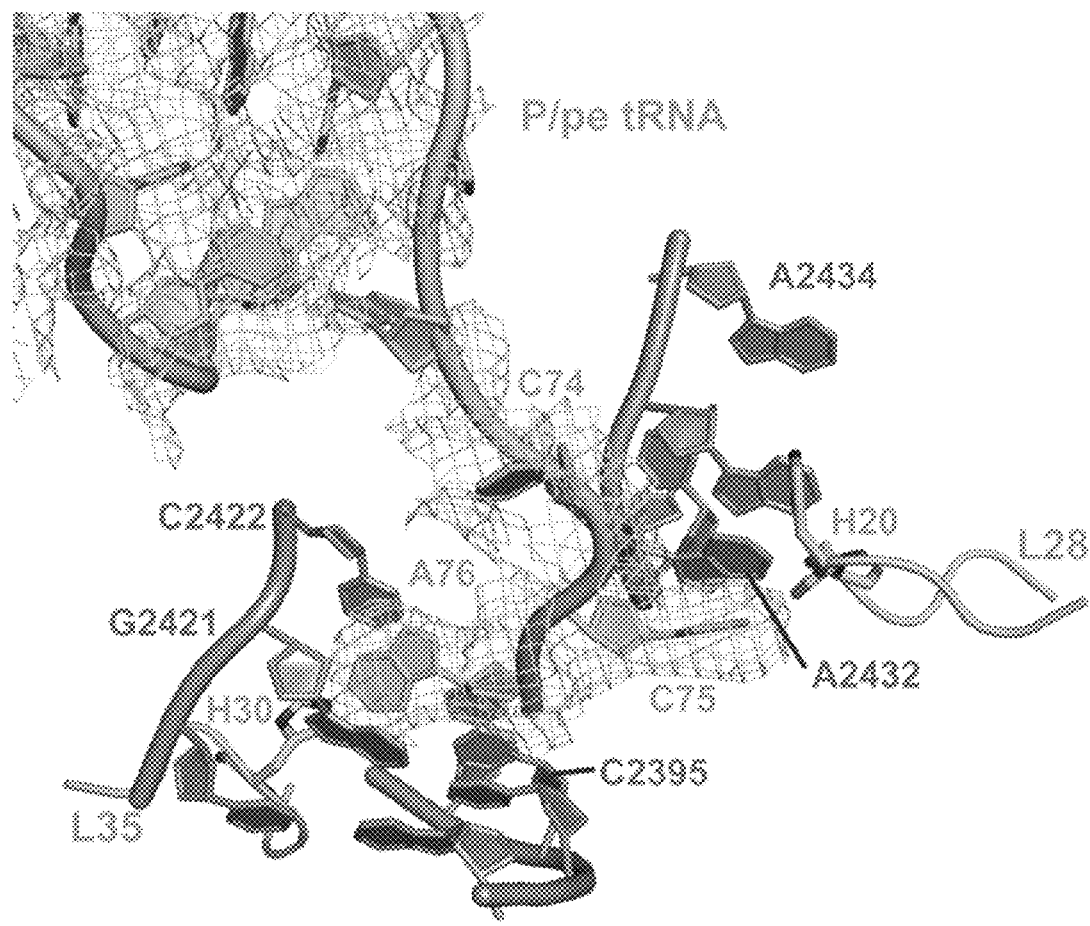
FIG. 25 illustrates that the CCA-end of P/pe tRNA occupies the large subunit E site. Shown is a ($F_{obs}$–$F_{calc}$) difference electron density map, calculated in Phenix and contoured at 2.5 standard deviations from the mean. P/pe tRNA CCA-end contacts are similar to the P/E tRNA CCA-end in Example 3. P/pe tRNA position A76 interacts with H88 near positions G2421 and C2395, and to ribosomal protein L35 H is 30. C75 of P/pe tRNA is close to 23S rRNA position A2432, and to L28 H is 20.

Strikingly, $F_{Obs}-F_{Calc}$ difference electron density maps also placed P-site tRNA in a position intermediate between classical (P/P) and hybrid (P/E) configurations (Example 3; Jin 2011) (FIG. 23A-B). In this new configuration, the tRNA anticodon stem-loop maintains its key interactions within the small subunit P site that are observed in both unrotated and fully rotated ribosome structures (FIG. 24). The 3'-CCA terminus of the tRNA also occupies the large subunit E site, as previously observed for tRNA in its P/E hybrid position (above); Jin, 2011) (FIG. 25). However, correlating with the intermediate rotation of the small subunit (FIG. 21C), the tRNA anticodon is only partially displaced in the direction of translocation (approximately 2 Å vs. 6 Å observed in the fully rotated state) (FIG. 23B). Furthermore, the P-site tRNA elbow domain is clearly located in a position that is intermediate between classical (P/P) and hybrid (P/E) configurations (above). In this position, the elbow domain of the tRNA does not physically interact with the L1 stalk (FIG. 22B). In keeping with nomenclature previously established for other intersubunit hybrid tRNA positions (Ratje 2010), we define this state as a P/pe hybrid configuration.

Figure 26:
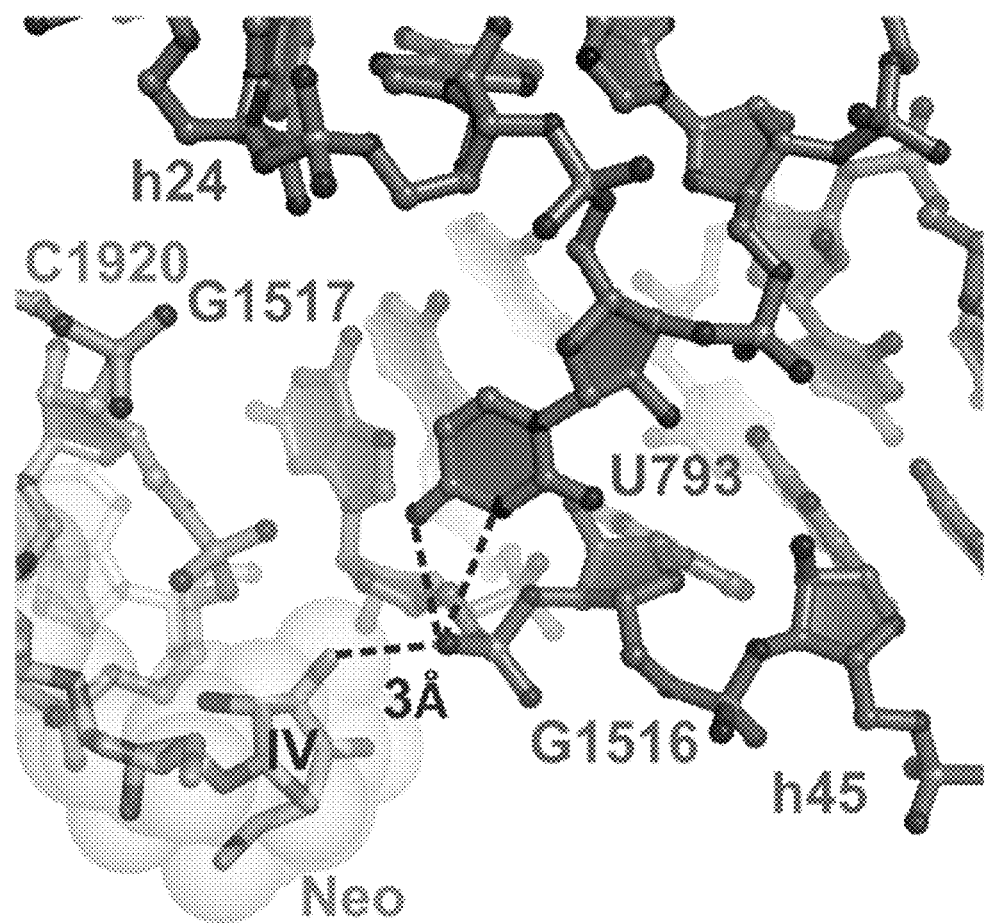
FIG. 26 shows that neomycin binding to H69 stabilizes the small subunit platform conformation through interactions with neomycin ring IV, h45 position G1517 backbone, and h24 position U793 N3 or O4 group. Shown is neomycin ring IV, 16S RNA helix h45 and h24 and 23S rRNA H69. Dashed lines indicate possible hydrogen-bond contacts between neomycin ring IV, G1517 backbone phosphate oxygen, and U793 N3 or O4 position.

The attenuated degree of small subunit rotation and the corresponding positioning of P/E tRNA into the intermediate P/pe site seen in neomycin-soaked crystals can be explained by neomycin's position within H69. In the fully rotated state, compression of the major groove of H69 is required for intersubunit rotation (above). However, neomycin's specific interactions in the major groove of H69 prevent helix compression and enable bridging interactions between ring IV of neomycin and the phosphate of G1517 within h45 and the Watson-Crick face of U793 of h24 (FIG. 26), a residue previously shown to be important for subunit association (Pulk 2006). By altering bridge B2b rearrangements and sterically preventing H69 compression (FIG. 23C) accompanying the unrotated-to-rotated transition, neomycin alters the normal mechanism of 30S subunit rotation such that helix h24 of 16S rRNA sterically blocks P-site tRNA movement into its P/E hybrid position (FIG. 23D).

6. Structural Summary

Taken together, the smFRET and crystallographic data reveal that neomycin binding to the base of H69 can globally inhibit the mechanism of translation by preventing the full extent of H69 compression, thereby interrupting complete subunit rotation and P/E hybrid state formation. Correspondingly, the ribosome is unable to adopt the fully unlocked configuration that precedes both translocation and ribosome recycling (above; Munro 2010b). Neomycin-induced stabilization of this intermediate configuration also inhibits the process of tRNA selection, which occurs on the unrotated state. These inhibitory effects can be rationalized by the partially overlapping EF-G and EF-Tu binding sites. (Ratje 2010; Gao 2009; Schmeing 2009b).

Figure 27:
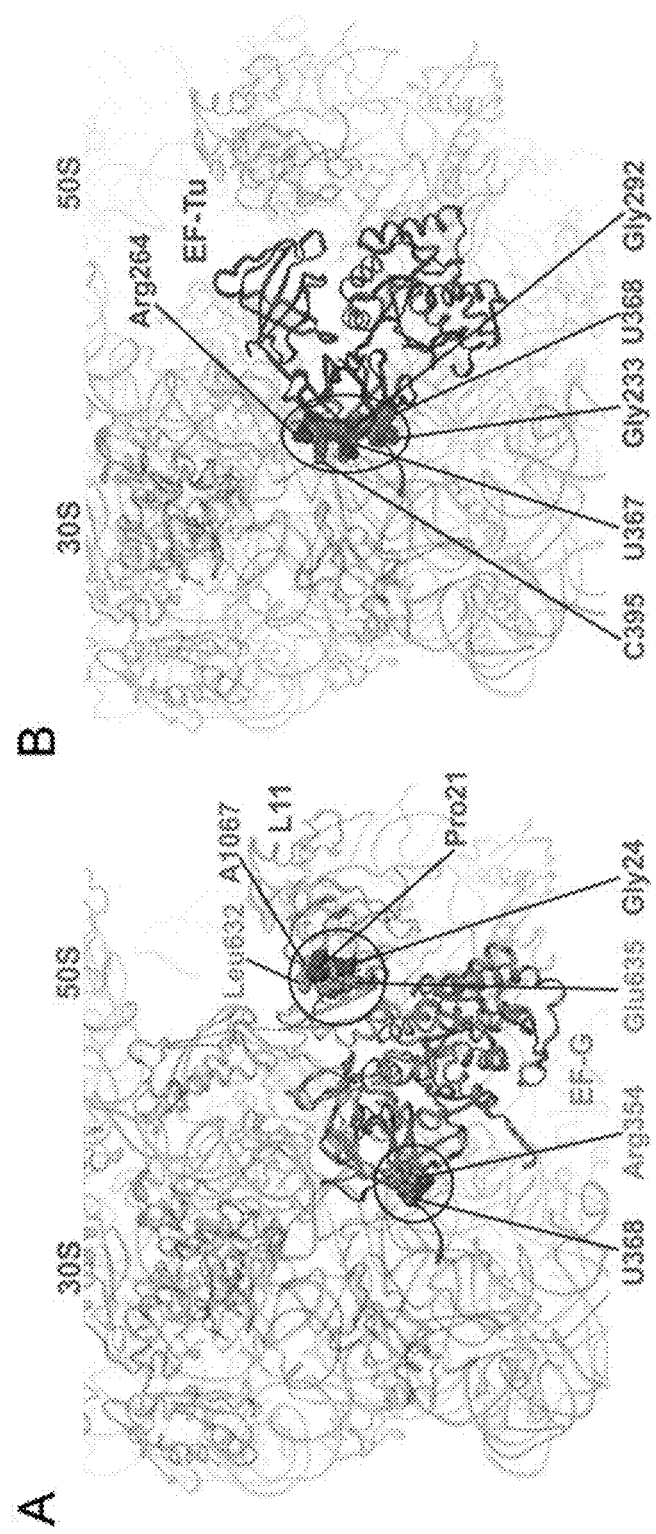
FIG. 27 shows that EF-G and EF-Tu clash with the neomycin stabilized intermediate ribosome conformation. (A) Intermediate ($R_I$) ribosome structure was superimposed to the *T. thermophilus* ribosome structure containing EF-G (dark; Ratje 2010). EF-G domain II clashes with the 30S body near helix h15 (spheres), and EF-G domain V clashes with L7/L12 stalk protein L11 (spheres) and 23S rRNA H43 (grey). (B) Superposition of the intermediate structure with the EF-Tu (darkd) bound *T. thermophilus* ribosome structure (Schmeing 2009b). Domain II of EF-Tu sterically clashes with 30S body of the intermediate conformation. Superpositions were carried out by using the Pymol pairfit function.

When docked in the intermediate ribosome configuration, both EF-G and EF-Tu would clash sterically with the small subunit (FIG. 27). Furthermore, these results provide structural evidence that translation proceeds through cycles of conformational selection to allow both translation factors to bind overlapping regions of the ribosome without inhibiting translation (Feldman 2010); Munro 2010c; Chan, 2008; Whitford 2011; Wang 2011).

Figure 28:
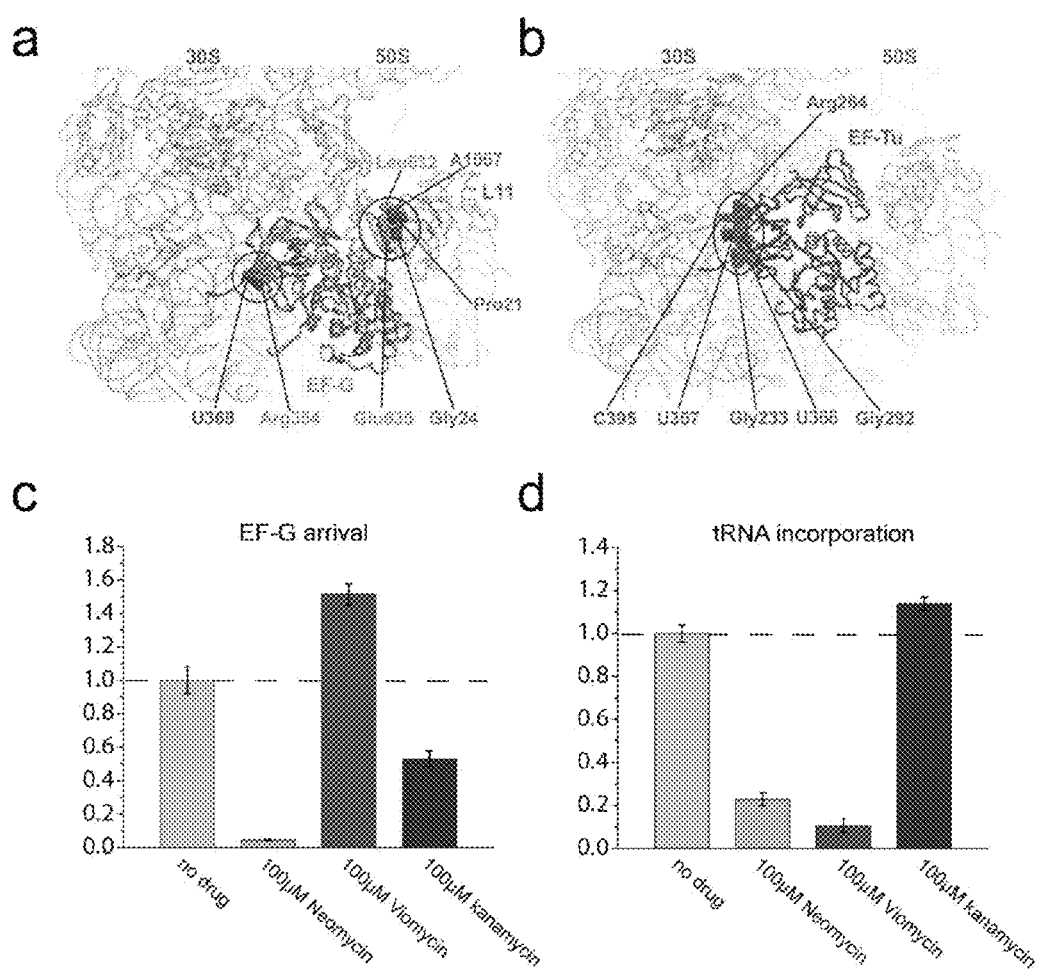
FIG. 28 shows the results from an smFRET tRNA incorporation assay. (A, B) Repeat of the structures depicted in FIG. 27. (C, D) In these bar graphs, all selected traces were manually inspected for the appearance of stable 0.15-0.2 FRET state, which indicated Cy5-tRNAPhe incorporation into the A site. The ratio of the number of molecules showing A-site tRNA incorporation to the total number of molecules inspected for all experiments (no drug, 100 µM neomycin, 100 µM viomycin and 100 µM kanamycin) were normalized to that of the no drug case and are shown.

The unrotated ribosome configuration is competent to productively engage EF-Tu in ternary complex with tRNA and GTP; the fully rotated, P/E hybrid ribosome configuration is competent to productively engage EF-G; intermediate configurations of subunit rotation fail to productively bind either factor. This model is supported by direct measurements of elongation factor binding to the A site (FIG. 28).

The present findings further argue that the intrinsically dynamic nature of the ribosome and tRNA motions within the translating particle contribute to each step in the translation process. The capacity of aminoglycosides to alter the global conformation of the ribosome through two distinct sites (small subunit helix h44 and large subunit helix H69) sheds new light on the observed pleiotropic activities of aminoglycosides in translation. Neomycin-induced stabilization of the intermediate state observed here further supports a central role for H69 in the translation mechanism. Future efforts exploring whether ribosome dynamics and conformation can be manipulated through this site in a species-specific manner may offer important new means for therapeutic control of translation.

7. Rational Drug Design

The atomic coordinates for the ribosomal structures described herein and in particular, the coordinates defining the H69 neomycin-binding pocket, whether derived from one or more of X-ray crystallography structures herein, or from molecular modeling, homology modeling or molecular replacement, are used in rational drug design (RDD) to design a novel molecules of interest, and preferably novel antibiotics. The atomic coordinates for the H69 neomycin-binding pocket are provided, with and without bound neomycin as set forth in Tables 6-9.

It is contemplated that, by using the principles disclosed herein, the skilled artisan can design, make, test, refine and use novel protein synthesis inhibitors specifically engineered to reduce, disrupt, or otherwise or inhibit ribosomal function in an organism or species of interest. For example, by using the principles discussed herein, the skilled artisan can engineer new molecules that specifically target and inhibit ribosomal function in a pathogen, for example, a particular prokaryotic, organism, while preserving ribosomal function in a host, for example, a eukaryotic organism, specifically a mammal, and more specifically, a human. As a result, the atomic coordinates provided and discussed herein permit the skilled artisan to design new antibiotics that can kill certain pathogenic organisms while having little or no toxicity in the intended recipient, for example, a human.

It is contemplated that RDD using atomic co-ordinates of the large ribosomal subunit can be facilitated most readily via computer-assisted drug design (CADD) using conventional computer hardware and software known and used in the art. The candidate molecules may be designed de novo or may be designed as a modified version of an already existing molecule, for example, a pre-existing antibiotic, using conventional methodologies. Once designed, candidate molecules can be synthesized using standard methodologies known and used in the art. Following synthesis, the candidate molecules can be screened for bioactivity, for example, by their ability to reduce or inhibit ribosome function, their ability to interact with or bind a ribosome or a ribosomal subunit. Based in part upon these results, the candidate molecules may be refined iteratively using one or more of the foregoing steps to produce a more desirable molecule with a desired biological activity. The resulting molecules can be useful in treating, inhibiting or preventing the biological activities of target organisms, thereby killing the organism or impeding its growth. Alternatively, the resulting molecules can be useful for treating, inhibiting or preventing microbial infections in any organism, particularly animals, more particularly humans.

The tools and methodologies provided by the present invention may be used to identify and/or design molecules which bind and/or interact in desirable ways in with ribosomes and ribosomal subunits, and in particular with the neomucin-binding pocket.

Molecular modeling can be most readily facilitated by using computers to build realistic models of a ribosome, ribosomal subunit, or a portion thereof. Molecular modeling also permits the modeling of new smaller molecules, for example ligands, agents and other molecules, that can bind to a ribosome, ribosomal subunit, or a portion therein. The methods utilized in molecular modeling range from molecular graphics i.e., three-dimensional representations) to computational chemistry (i.e., calculations of the physical and chemical properties) to make predictions about the binding of the smaller molecules or their activities; to design new molecules; and to predict novel molecules, including ligands such as drugs, for chemical synthesis.

For basic information on molecular modeling, see, for example, Schlecht, 1998; Gans 1996; Cohen 1996; and Smith 1996. U.S. patents which provide detailed information on molecular modeling include, for example: U.S. Pat. Nos. 6,093,573; 6,080,576; 6,075,014; 6,075,123; 6,071, 700; 5,994,503; 5,884,230; 5,612,894; 5,583,973; 5,030, 103; 4,906,122; and 4,812,12.

Three-dimensional modeling can include, but is not limited to, making three-dimensional representations of structures, drawing pictures of structures, building physical models of structures, and determining the structures of related ribosomes, ribosomal subunits and ribosome/ligand and ribosomal subunit/ligand complexes using the known coordinates. The appropriate co-ordinates are entered into one or more computer programs for molecular modeling, as known in the art.

One approach to RDD is to search for known molecular structures that bind to the H69 neomycin-binding pocket. Using molecular modeling, RDD programs can look at a range of different molecular structures of molecules that may fit into this site, and by moving them on the computer screen or via computation it can be decided which structures actually fit the site well (Bains 1998). Examples of modeling software include, but are not limited to, InsightII, Discovery studio and Cerius by Accelrys; Sybyl by Tripos; Molecular Operating Environment (MOE) by Chemical Computing Group; Glide, Prime, and Maestro by Schrödinger Inc.; Bio-Suite by Tata Consultancy Services Ltd; Sanjeevini by Indian Institute of Technology, New Delhi; MoDeST (Molecular Design Software Toolkit) by SimBioSys; ICM-Pro and ICM-VLS by molsoft; VLifeMDS by Vlife Sciences Technologies To facilitate molecular modeling and/or RDD the skilled artisan may use some or all of the atomic co-ordinates deposited at the RCSB Protein Data Bank under the numbers PDB ID: 3R8N, 3R8O, 3R8S, 3R8T (for structures without neomycin; and incorporated herein by reference), and/or those atomic co-ordinates for the H69 neomycin-binding pocket provided in Tables 6-9.

8. S13 Constructs and Assays

The present invention also provides a tagged S13 protein labeled with a fluorophore. While a tag can be introduced in any number of solvent accessible regions of the protein that do not disrupt its function or binding to the ribosome, a preferred site for introducing a tag is at the N terminus. It has been found that positioning an N-terminal fluorophore provides a FRET pair with labeled L1 (as described herein) that is a sensitive reporter of the transition of the ribosome from an unrotated to fully rotated stated as described herein.

The tag can be an SFP tag as generally described by Yin 2006. Other tags can be used as well including the 12 amino acid acyl carrier protein tag (AcpS) and a shorter, 8 amino acid tag derived therefrom, both of which are described in Zhou 2008.

Further tags for enzymatic labeling include ACP, Q-tag (for example Q3: NH2-GQQQLG-COOH) transglutaminase-catalyzed site-specific conjugation of small-molecule probes to proteins in vitro and on the surface of living cells and FGE-tag (for example: LCTPSR (wild-type), LCTASR, and LCTASA) (Rush 2008). Peptidyl affinity tags can also be present for purification, and include, but are not limited to, Sumo, Glutathione S-transferase (GST), His6, His10 and Flag. These purification tags can be used with a protease cleavage site and when located upstream from the labeling tag obtain the tagged protein. provide a way to fish They also can also serve as purification tag for pulling out tagged ribosomes from mixed populations of ribosomes. Hence, if both wild-type S13 protein and tagged S13 are incorporated into the ribosome and affinity purification can be used to isolate the "tagged" subpopulation. This is achieved by placing, for example, a His6-10 tag upstream of the SFP tag and using a NTA or cobalt resin to "fish out" the tagged subpopulation.

Further still, the invention is directed to an expression vector comprising a nucleic acid encoding ribosomal protein S13 having an N-terminal tag for attachment of a fluorophore. In some embodiments, the N-terminal tag is an SFP tag or an AcpS tag.

Hence, the instant invention relates to a variety of compositions, including compositions comprising isolated N-terminal tagged S13 with or without a label. Fluorophore labeled S13 is particularly useful when incorporated into translationally competent ribosomes and used as part of a FRET pair. When the FRET partner is a fluorophore-labeled L1 as described herein, this composition is useful for interrogating ribosome conformations and dynamics via changes in FRET states in accordance with this invention. Any of these compositions can additionally include the components for in vitro translation.

9. Other Aspects of the Invention

As described in the examples, this invention provides single-molecule assays for ribosome recycling which comprises surface-immobilizing a ribosome labeled on the 50S subunit in the presence of tRNA, RRF and EF-G under translation conditions; and monitoring changes in the signal from the label, wherein a change in the signal indicates recycling or lack thereof. For example, this assay can be conducted in solution or using smFRET like imaging techniques (following fluorescence decay), with the label on the ribosome being a fluorophore. Further, if a test compound is added, then the presence of a signal indicates that recycling has been altered.

Yet another aspect of the instant invention relates to methods to identify a compound that interferes with ribosomal function by assessing test compounds which cause the ribosome to alter, form adopt, change rate of formation into or out of, or otherwise be in, an intermediate FRET state. This method comprises (a) surface-immobilizing a ribosome having a FRET pair sensitive to transitioning between low FRET and high FRET states under translation competent conditions; (b) adding a test compound to the immobilized ribosome; and (c) monitoring or detecting changes in FRET states using smFRET imaging techniques to identify a test compound capable of (i) stabilizing the ribosome in an intermediate FRET state, (ii) changing the ribosome's distribution into or out of an intermediate FRET state, or (iii) changing the ribosome's rate of transition into or out of an intermediate FRET state. This method can be conducted with a FRET pair formed by a fluorophore on ribosomal protein L1 and a fluorophore on ribosomal protein S13.

Yet still a further method of the invention provides methods to identify a compound that interferes with ribosomal function using a FRET pair which has a fluorophore on ribosomal protein L1 and a fluorophore on ribosomal protein S13. This method comprises (a) surface-immobilizing a ribosome having a FRET pair sensitive to transitioning between a low FRET state and a high FRET state under translation competent conditions, wherein the FRET pair is formed with a fluorophore on ribosomal protein L1 and a fluorophore on ribosomal protein S13; (b) adding a test compound to the immobilized ribosome; and (c) monitoring or detecting changes in FRET states using smFRET imaging techniques to identify a test compound capable of (i) stabilizing the ribosome in a low FRET state, an intermediate FRET state or in a high FRET state, (ii) changing the ribosome's distribution among low, intermediate and high FRET states, (iii) changing the ribosome's rate of transition among low, intermediate and high FRET states, or (iv) abolishing FRET signals.

The conditions and smFRET techniques for conducting the foregoing methods can be readily determined by those of skill in the art, are known in the art or are described in the Examples hereof. The methods can be used with any source of bacterial ribosomes as well as with any mutant forms thereof. When testing for antibiotic candidates, one preferably uses ribosomes from a bacterial pathogen.

For either of the two foregoing methods, in certain embodiments, the L1 fluorophore is at (T202C) L1 and the fluorophore on S13 is at or near the amino terminus of S13. FRET pairs that are a donor-acceptor fluorophore pair or a donor-quencher fluorophore pair are useful.

Similarly, the two foregoing methods can be used in certain embodiments to identify candidate antibiotics. For example, a test compound is considered a candidate antibiotic when the test compound (I) stabilizes the ribosome in an intermediate FRET state or in a high FRET state, (ii) increases the ribosome's distribution in intermediate or high FRET states, (iii) increases the ribosome's rate of transition into intermediate or high FRET states, or abolishes FRET. Such candidate antibiotics can be tested to establish whether they inhibit function of a bacterial ribosome of pathological interest. The intermediate FRET state includes ribosomes having a structure assumed when the tRNA is present at the P/pe tRNA binding state (see Example 4).

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention. All references patents, patent applications, PDB data or other documents cited are herein incorporated by reference in their entirety.

EXAMPLE 1

General Methods and Materials

Purification of Native E. coli tRNA$^{Phe}$.

The purification protocol for tRNA$^{Phe}$ was adapted from a published protocol (Cayama 2000). Briefly, E. coli cells (strain MRE600) harboring plasmid pBS-tRNA$^{Phe}$, which overexpresses E. coli tRNA$^{Phe}$, were cultured and harvested as previously described (Junemann 1996). The cell pellets were lysed by sonication in 20 mM Tris HCl, pH 7.5, 50 mM MgCl$_2$ and 20 mM β-mercaptoethanol. The cell lysate was clarified by centrifugation at 35000 rpm in a Beckman Ti-70 rotor at 4° C. for 2 hours. Total cellular RNA was extracted from the supernatant by phenol extraction and ethanol precipitation. High molecular weight RNAs were removed by isopropanol precipitation (von Ehrenstein 1967). The soluble RNA fraction was then incubated for 15 min at 37° C. after adjusting the pH to 8 by addition of 0.5 M Tris HCl, pH 8.8 to deacylate tRNAs. As previously described (Blanchard 2004), tRNA$^{Phe}$ was specifically aminoacylated following brief incubation with phenylalanine, ATP and phenylalanyl-tRNA synthase. The reaction mixture was phenol extracted and the nucleic acid fraction was obtained by ethanol precipitation. After resuspending the pellet in 10 mM ammonium acetate pH 6.3, the sample was applied to a TSK Phenyl 5PW hydrophobic interaction column (Tosoh Bioscience) and Phe-tRNA$^{Phe}$ was purified by fractionation as previously described (Blanchard 2004). The isolated peak was desalted, deacylated by brief incubation at elevated pH and repurified using analogous methods.

Preparation of Dye-Labeled Ribosome Complexes.

The labeling of L1 protein (Cy5-S55C) and tRNA$^{Phe}$ (Cy3-s$^4$U8) for smFRET experiment were performed as previously described (Munro 2010a,b). 70S ribosomes were reconstituted with dye-labeled L1 and non-enzymatically initiated with mRNA and (Cy3-s$^4$U8) tRNA$^{Phe}$ by incubating with 1.5 molar excess of each over ribosomes at 37° C. for 10 minutes. The mRNA used has the same sequence as the one used in crystallization except for biotin modification at 5' end to enable surface immobilization.

Purification of A1408G Ribosomes.

Wild-type ribosomes and ribosomes bearing A1408G mutation were purified from a Δ7prrn E. coli MG1655 strain (RecA-) for single-molecule translocation and recycling experiments. The A1408G neomycin resistance mutation was introduced into a NT102 (KanR, SpecR) plasmid containing an rrnB operon (Komoda 2006) using Quickchange II site-directed mutagenesis (Stratagene). Wild-type and A1408G containing pRB102 plasmids (Komoda 2006) were then swapped into a Δ7prrn E. coli MG1655 (pKK3535, AmpR; ptRNA67, SpecR) strain. Tightly-coupled 70S ribosomes were purified from these strains in Tris-polymix buffer as previously described (Munro 2007).

Single-Molecule FRET tRNA Incorporation Assay.

The process of tRNA selection on the ribosome was monitored using single-molecule FRET by stopped-flow injection of a 10 nM solution of ternary complex (EF-Tu (GTP)·aa-tRNA) containing Phe-tRNA$^{Phe}$ (Cy5-acp$^3$U47) to surface-immobilized ribosome complexes containing deacylated tRNA$^{fMet}$ (Cy3-s$^4$U8) in the P site as previously described (Geggier 2010). Fluorescence and FRET traces were extracted from video and selected for analysis using automated analysis software implemented in MATLAB (MathWorks) using the segmental k-means algorithm (Qin, 1996). Complete accommodation of Phe-tRNA$^{Phe}$ into the A site was marked by the first observation of a 400 ms dwell in a high (0.55±0.61) FRET state, structurally assigned to the "classical" pre-translocation complex configuration through previous investigations (Geggier 2010). Individual experiments, in which approximately 100 accommodation events were obtained, were performed in triplicate. The mean extent of accommodation and standard deviations are plotted as a function of time. Wild type and mutant ribosomes for these experiments were purified as previously described (Feldman 2010).

Single-Molecule Translocation Assay.

Fluorescence-based, single-molecule translocation assays were carried out as previously described (Munro 2010c) on either wild-type or A1408G mutant pre-translocation ribosome complexes. Experiments were performed in Trispolymix buffer (pH 7.5, 5 mM Mg(OAc)$_2$) and analyzed as previously described (Munro 2010c; Wang 2011), plotting the fraction of translocating molecules as a function of time.

EXAMPLE 1A

Ribosome Recycling Assays

Ribosome Recycling Factor Purification.

RRF was purified from E. coli strain BL21 Star cells (Invitrogen) expressing a C-terminal hexa-histidine tagged version of the protein. Cells were lysed by sonication in lysis buffer (50 mM HEPES, pH 7.6, 1 M NH$_4$Cl, 10 mM MgCl$_2$, 200 μM PMSF, 7 mM β-mercaptoethanol, 0.1% Triton-X11, and Roche EDTA-free protease inhibitor cocktail). After the lysate was clarified by centrifugation, it was applied to a HisTrap column (GE Healthcare). The column was washed with buffer containing 50 mM HEPES, 1 M NH$_4$Cl, 10 mM MgCl$_2$, 7 mM β-mercaptoethanol, and 20 mM imidizole; RRF was eluted in the same buffer containing 400 mM imidazole. The protein was concentrated by ultrafiltration and applied to Sephacryl $^{16}$/$_{60}$ size exclusion column (GE Healthcare). The RRF containing fractions were concentrated to 550 μM and stored at −80° C.

Single-Molecule Fluorescence Experiments.

All single-molecule fluorescence experiments were performed at room temperature in an MES-Polymix buffer that resembled the crystallization condition (50 mM MES, pH 6.5, 5.0 mM MgCl$_2$, 350 mM NH$_4$Cl, 5.0 mM putrescine, 5.0 mM spermidine, 5 mM (3-mercaptoethanol and 0.5 mM EDTA). Oxygen scavenging and triplet-state quenching systems used were as previously described (Dave 2009). The smFRET data were acquired with Metamorph (Molecular Device), and analyzed in MATLAB (Mathwork) and QuB (www.qub.buffalo.edu) as previously described (Munro 2010a,b). Subunit release was monitored by directly exciting the Cy5 fluorophore within surface-immobilized ribosome complexes (Coherent) at 10 mW laser power. Time lapse imaging of the recycling reaction was performed by acquiring snapshot images (40 millisecond integration time) every 20 seconds over the course of 20 minutes. Changes in fluorescence intensity were analyzed and plotted in Origin (OriginLab).

Single-Molecule FRET tRNA Incorporation Assay.

The process of tRNA selection on the ribosome was monitored using single-molecule FRET by stopped-flow injection of a 10 nM solution of ternary complex (EF-Tu (GTP)·aa-tRNA) containing Phe-tRNAPhe (Cy5-acp3U47) to surface-immobilized ribosome complexes containing Cy3-labeled S13 and deacylated tRNAfMet in the P site as generally described in PCT/US12/32602, filed Apr. 6, 2012. After 30 seconds incubation, ternary complex was washed out with Tris-polymix Mg2+ buffer. The smFRET data were acquired by directly exciting the Cy3 fluorophore at 532 nm (LaserQuantum) while simultaneously recording Cy3 and Cy5 intensities in Metamorph (Molecular Devices) with 100 ms integration time. Fluorescence and FRET traces were extracted from video and traces from each movie were selected according to the criteria: signal-to-noise>5, background intensity<1500 and Cy3 blinking<1. All selected traces were then manually inspected for the appearance of stable 0.15-0.2 FRET state, which indicated Cy5-tRNAPhe incorporation into the A site. The ratio of the number of molecules showing A-site tRNA incorporation to the total number of molecules inspected for all experiments (no drug, 100 µM neomycin, 100 µM viomycin and 100 µM kanamycin) were normalized to that of the no drug case. Three independent experiments were performed under each condition and the mean with standard deviation were plotted using Origin (OriginLab). The results are shown in FIG. 28.

EXAMPLE 2

Tagged S13 and Its Uses
Generation of Site-Specifically Labeled 30S Subunits and 50S Subunits.

Ribosomal protein S13 was PCR-cloned from *E. coli* strain K12 genomic DNA into the pPROEX HTb vector with a TEV-cleavable His$_6$-tag and a 12-residue peptide encoding the S6 epitope for the Sfp phosphopantetheinyl transferase reaction (Yin 2006), fused at the N terminus. Following transformation of this plasmid into an *E. coli* ΔS13 knockout strain (Cukras 2005), cells were cultured and ribosomes were harvested as previously described (Wang 2011). Pure 30S subunits were isolated via sucrose gradient centrifugation in a low magnesium buffer (20 mM HEPES pH 7.5, 50 mM KCl, 10 mM NH$_4$Cl, 0.5 mM EDTA, 6 mM BME, 1 mM MgCl$_2$). 30S subunits containing Sfp-tagged S13 were isolated from this population by cobalt affinity chromatography (Clontech). Subsequently, the Sfp tag was enzymatically labeled and the His$_6$-tag was enzymatically removed in a buffer containing 20 mM HEPES, pH 7.5, 100 mM KCl, 10 mM MgCl, and 6 mM BME. 20 µM N-Sfp-S13 30S subunits, 5 µM TEV protease, 250 µM Cy3-CoA and 25 µM Sfp were incubated for 24 h at 18° C. Sfp enzyme, TEV protease and unbound Cy3-CoA were then removed by filtration over a 100K membrane (Millipore). Prior to 70S complex formation, ribosomes were buffer exchanged into Tris-polymix buffer (Munro 2010c). 50S subunits labeled with Cy5-L1 (T202C) were prepared and purified as previously described (Munro 2010b).
Preparation of L1-S13 FRET Ribosome Complexes with tRNA$^{fMet}$ or tRNA$^{Phe}$ in the P Site.

Cy3-S13 30S and Cy5-L1 50S subunits were heat activated at 42° C. for 10 min in Tris-polymix Mg$^{2+}$ buffer and ribosomes were then initiated with fMet-tRNA$^{fMet}$ or NAc-Phe-tRNA$^{Phe}$ as previously described (Munro 2010c).
Single-Molecule L1-S13 FRET Assay.

All single-molecule FRET experiments were performed at room temperature in Tris-Polymix with 5 mM Mg$^{2+}$ buffer as previously described (Wang 2011), where oxygen scavenging and triplet-state quenching systems were employed (Dave 2009). Following surface immobilization (Munro 2007), the ribosome-bound, P-site tRNA was deacylated by incubation with 2 mM puromycin for 10 min at room temperature. The smFRET data were acquired by directly exciting the Cy3 fluorophore at 532 nm (LaserQuantum) while Cy3 and Cy5 intensities were simultaneously recorded in Metamorph (Molecular Devices) with 40 ms integration time. The data were analyzed in MATLAB (MathWorks) and plotted in Origin (OriginLab) as previously described (Munro 2007).
Monitoring FRET Between Elongation Factors and the Ribosome During Translocation and tRNA Selection.

To monitor EF-G productively engaging the pre-translocation complex, EF-G was labeled with Cy5 fluorophore and stop-flow delivered to surface-immobilized ribosome complexes bearing deacylated tRNA$^{fMet}$ in the P site and Cy3-labeled dipeptidyl fMet-Phe-tRNA$^{Phe}$ (Cy3-acp$^3$U47) in the A site, as previously described (Munro 2010c; Wang 2011). Pre-steady state smFRET measurements of this kind were taken in the absence and presence of 20 µM neomycin at 100 ms time resolution. Fluorescent traces were analyzed with MATLAB (MathWorks). All molecules with signal/noise>3 were inspected individually. Productive EF-G binding events were marked by the appearance of FRET (≥0.2), indicative of EF-G's domain IV entering the A site (Munro 2010c). The interaction of ternary complex (EF-Tu(GTP)·aa-tRNA) with the ribosome was similarly monitored in pre-steady state experiments collected at 15 ms time resolution in the absence and presence of 20 µM neomycin. Here, productive binding was marked by the appearance of FRET (>0.15) between the ternary complex containing Phe-tRNA$^{Phe}$ (Cy5-acp$^3$U47) and deacylated tRNA$^{fMet}$ (Cy3-S$^4$U8) within the P site of surface-immobilized 70S ribosome complexes (Geggier 2010). Complete accommodation was marked by the appearance of a relatively stable (>200 ms) high-FRET state (0.55±0.61). Fluorescent traces were analyzed with MATLAB (MathWorks). All molecules with signal/noise>3 were inspected individually. Each tRNA selection and translocation experiment were performed in triplicate and the average number and standard deviation of each event type were calculated and plotted in Origin (OriginLab).

EXAMPLE 3

Structural Analysis of Unrotated and Rotated Ribosome without Neomycin

Ribosome Purification and Crystallization.

Ribosomes lacking protein S1 were purified from *E. coli* strain MRE600 using sucrose gradient centrifugation, as described (Blaha 2000). Ribosomes were crystallized at 18° C. using microbatch 96-well plates and buffers containing 4.0-6.0% 2-methyl-2,4-pentanediol (MPD), 4.1-4.5% PEG 8000, 4.0 mM MgCl$_2$, 380 mM NH$_4$Cl, 5.7 mM putrescine, 5.0 mM spermidine, 10 mM Tris plus 40 mM MES, pH 6.5-7.0, and 0.25 mM EDTA. Ribosome complexes were formed by incubating 4 µM deacylated tRNA$^{Phe}$ and 8 µM mRNA of sequence 5'-GGCAAG GAGGUAAAAUUCUA-CAAA-3' (SEQ ID NO: 1; Dharmacon) with 2 µM ribosomes at 37° C. for 15 minutes. 8 µM RRF was then added and the samples were incubated for an additional 15 minutes at 37° C. Prior to crystallization, samples were subjected to ultrafiltration to remove excess ligands.
Data Collection and Processing.

Ribosome crystals were stabilized with crystallization buffer containing 7.0% MPD, 7.0% PEG 8000 and 24% PEG 400, pH 4.8, to allow cryocooling of the crystals to liquid nitrogen temperatures. Diffraction data were measured from crystals cooled to 100° K using 0.1-0.3° oscillations at beamlines 24ID-C at the Advanced Photon Source or at the Advanced Light Source (SIBYLS and 8.3.1 beamlines), each of which is equipped with an ADSC Q315 area detector. Data were reduced using XDS (Kabsch 1993), yielding the statistics shown in Table 1.

TABLE 1

X-ray crystallographic statistics

| Space group | $P2_12_12_1$ |
|---|---|
| unit cell (a, b, c in Å) | 211.67, 438.07, 613.42 |
| Resolution (Å) | 70-3.0 |
| (high-resolution shell)* | (3.35-3.16) |
| $R_{merge}^†$ | 19.4 (57.7) |
| I/σ (I) | 7.4 (1.8) |
| Completeness (%) | 83.5 (66.1) |
| Measurement redundancy | 5.3 (3.3) |
| Unique reflections | 938,380 (101,586) |
| No. crystals used | 10 |

*Data beyond the high-resolution shell in parenthesis was used for refinement and map calculation, and extend to an I/σ (I) of about 1. Data are 92.5% complete in the 3.9 Å-3.6 Å resolution shell, and 99% complete in lower-resolution shells.
†All statistics not in parentheses include data over the whole reported resolution range.

Molecular Replacement and Structure Refinement.

The two copies of the 70S ribosome in the crystallographic asymmetric unit were located using rigid-body refinement in Phenix (Adams 2010) of the well-ordered *E. coli* ribosome from a recent atomic-resolution structure determination (Zhang 2009). That starting model had previously been improved by diagnosing problems with stereochemistry, all-atom sterics, and conformations using MolProbity (Chen 2010) and correcting them using a variety of protein and RNA remodeling tools. RNA corrections were carried out with the automated RNABC software (Wang 2008), and were accepted if the fixes of all-atom clashes (Word 1999a,b), ribose pucker outliers or backbone conformer outliers (Richardson 2008) survived in refinement without compromising model geometry or R-factors. Protein corrections first included automated correction of Asn/Gln/His 180° "flips" (Word 1999a,b) in MolProbity or Phenix. More extensive corrections were carried out in Coot (Emsley 2010) or with the backrub (Davis 2006) and sidechain-rotator tools in KiNG (Chen 2009). Refinement was carried out in Phenix, including the use of pucker-specific target parameters. Corrections made prior to this new structure included rebuilds of 20 RNA suites with RNABC, plus pucker corrections in refinement, and numerous improvements to 50S proteins (Chen 2010), including sequence register-shifts, peptide flips in β-strands, and rotamer repairs of H-bonding at protein/RNA interfaces, to produce the model used in molecular replacement.

The resulting structural models were then refined using rounds of manual rebuilding in O (Jones 1991), Coot, or KiNG as well as positional refinement in Phenix, including use of a new functionality for automatic assignment of H-bond restraints using the Saenger base-pair types (Saenger 1984). Electron density maps were generated from the Phenix output directly, or using the program Pirate (Cowtan 2000). RNA rebuilding concentrated on the tRNAs and mRNAs, using the RNArotator tool in KiNG to make changes that improved both steric clashes and ribose pucker outliers in those regions to 80-90$^{th}$ percentile levels for this resolution. Protein corrections concentrated on RRF, L5, L27, and S12, in some cases making dramatic improvements such as taking L27 from a 0$^{th}$ percentile MolProbity score (combined clash, Ramachandran, and rotamer criteria) to 53$^{rd}$ percentile for the $R_O$ molecule and 88$^{th}$ percentile for the $R_F$ molecule. While the overall sterics, geometry, and RNA conformations are all well above median quality (high percentile scores in Tables 2, 3), future rebuilding and refinements will be used to further improve protein and RNA sterics and geometry. In contrast to the earlier *E. coli* 70S structure determination (Zhang 2009), in which one of the two molecules was partially disordered, both ribosomes in the present structure are well ordered, with similar B-factors, validation statistics, and electron density quality.

The structures are deposited under PDB ID codes (searchable, e.g., at www.rcsb.org/pdb and www.wwpdb.org) as follows:

Fully rotated state: 3R8N, 3R8S
Unrotated state: 3R8O, 3R8T (the letter O, not zero)

TABLE 2

X-ray structure refinement

| Resolution (Å) | 40-3.0 | |
|---|---|---|
| No. Reflections | 938,304 | |
| $R_{free}$ Set | 19,021 | |
| R/$R_{free}$ (%)* | 20.2/26.1 | |
| No. non-H Atoms | 293,365 | |
| R.m.s. deviations | Bond lengths (Å) | 0.013 |
|  | Bond angles (°) | 1.39 |
| Mean ADP values (Å²)† | State $R_O$ 70S | 29.0 |
|  | State $R_F$ 70S | 24.6 |

*Refinement in Phenix (Adams 2010) with riding H atoms.
†Atomic displacement parameter values are reported as isotropic B-factors. B-factor model is 2 per residue, wxu weight set to 1.66.

TABLE 3

Validation statistics**

| | State $R_O$ 70S | State $R_F$ 70S |
|---|---|---|
| All-atom clashscore | 44.1 56$^{th}$ percentile | 38.5 68$^{th}$ percentile |
| Ramachandran outliers | 9.2% 10$^{th}$ percentile | 8.4% 12$^{th}$ percentile |
| Ribose pucker outliers | 1.6% 73$^{rd}$ percentile | 1.9% 70$^{th}$ percentile |
| Bond + angle outliers | 0.63% | 1.77% |

**From MolProbity (Chen 2010).
**From MolProbity (Chen 2010).

Comparisons to atomic-resolution structures of the ribosome, and to structural models of the intact ribosome refined against cryo-EM density maps, were carried out by least-squares superposition in the program O (Jones 1991), using ribose C1' positions or phosphorous atoms in nucleotides. Superpositions to identify the relative position of the small and large subunits in the ribosome used the large subunit as the frame of reference (Frank 2007). The angles of rotation of the 30S subunit domains were calculated essentially as described in (Zhang 2009). Angles given for the rotation of the head domain were calculated from 30S subunit structures superimposed by means of their platform domains. A rotation of 0° is defined as centering the head domain over the 30S P site, as seen in the structure of the unratcheted ribosome presented here. The bending angle of helix H34 in 23S rRNA, part of bridge B4, was determined from the shift in position of A715 relative to G725 at the based of the helix. Superpositions of P/E, P/P and A/T tRNAs utilized the C1' atoms of nucleotides 31-39 in the anticodon stem-loop. Comparisons of tRNA bending angles used the glycosidic bond of position 31 near the end of the anticodon stem-loop and the glycosidic bond of nucleotide 63 in the superimposed tRNAs. The bending angles calculated in this way are 37° for A/T tRNA compared to P/P tRNA, 37° for P/P tRNA compared to P/E tRNA, and 70° for A/T tRNA compared to P/E tRNA.

Structurally conserved nucleotides in the yeast 80S ribosome were used for superpositions of the two yeast 80S ribosome structures (Ben-Shem 2010) with the bacterial 30S and 50S subunits (Dunkle 2011, Table S3). One of the yeast 80S ribosomes most closely aligns with the post-translocation state recently identified (Ratje 2010). The body and platform domains are not fully rotated, and the small subunit head domain is rotated towards the E site by ~16°. In the yeast 80S ribosome, H69 is extended, as seen in the unrotated state $R_0$ and the ratcheting intermediate $R_2$ (Zhang 2009), and is not compressed, as seen in the present structure of the fully rotated state $R_F$.

Intersubunit Contacts.

Figure 6:
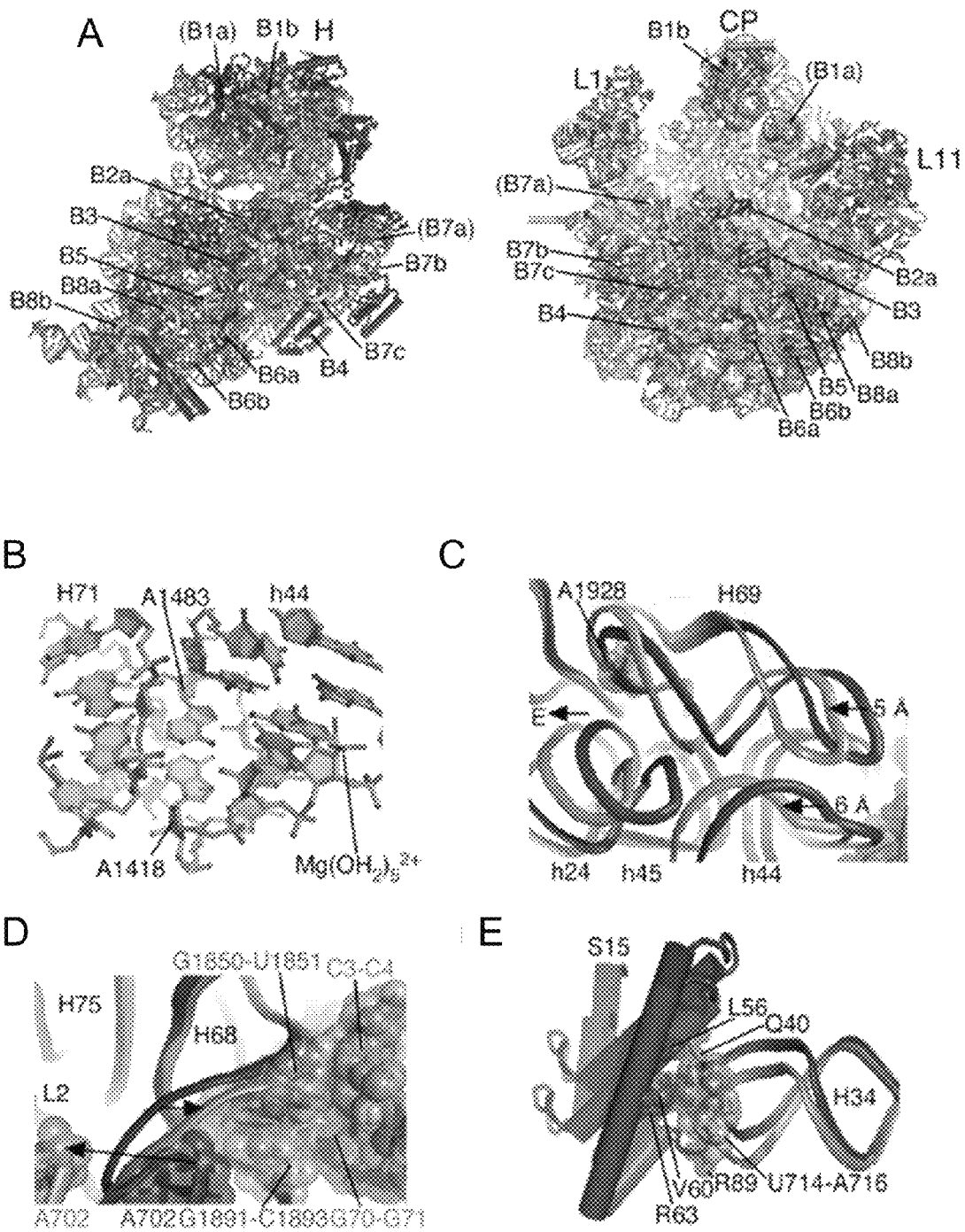
FIG. 6 depicts the inter-subunit contacts in the fully rotated state. (A) Global view of inter-subunit contacts of the fully rotated state. Ribosomal RNAs and proteins are colored as in FIG. 1. Bridge numbering is adapted from (Schuwirth 2005; Ben-Shem 2010). The tip of helix H38 in bridge B1a is disordered in the present structures. (B) Bridge B3 serves as the pivot of inter-subunit rotation. The Mg2+ ion involved in inner-sphere coordination to the tandem sheared GA pairs in 16S rRNA and a fully hydrated Mg2+ ion in 23S rRNA are also shown. Ribosomal RNA colored as in FIG. 1. (C) Compression of helix H69 in 23S rRNA due to inter-subunit rotation. The direction of view is similar to FIG. 1. Color coding of the fully rotated ribosome (R) as in FIG. 1, with unrotated ribosome (U) in darkest grey. Nucleotide A1928 in 23S rRNA, nearly invariant in position, is shown for reference. Dashed circle shows the novel neomycin binding pocket. (D) Movement of H68 due to disruption of A702 interactions and packing with P/E tRNA. Nucleotides involved in H68 packing with P/E tRNA are indicated. Elements of the fully rotated ribosome are colored as in FIG. 1. Elements of the unrotated ribosome are shown in darkest grey. Arrows indicate movement from the unrotated to fully rotated state. (E) Bridge B4 in the fully rotated state compared to that in state R0 (darkest grey). Residues involved in direct contact in the fully rotated state are shown. Coloring for the fully rotated state as in FIG. 1.
Figure 7:
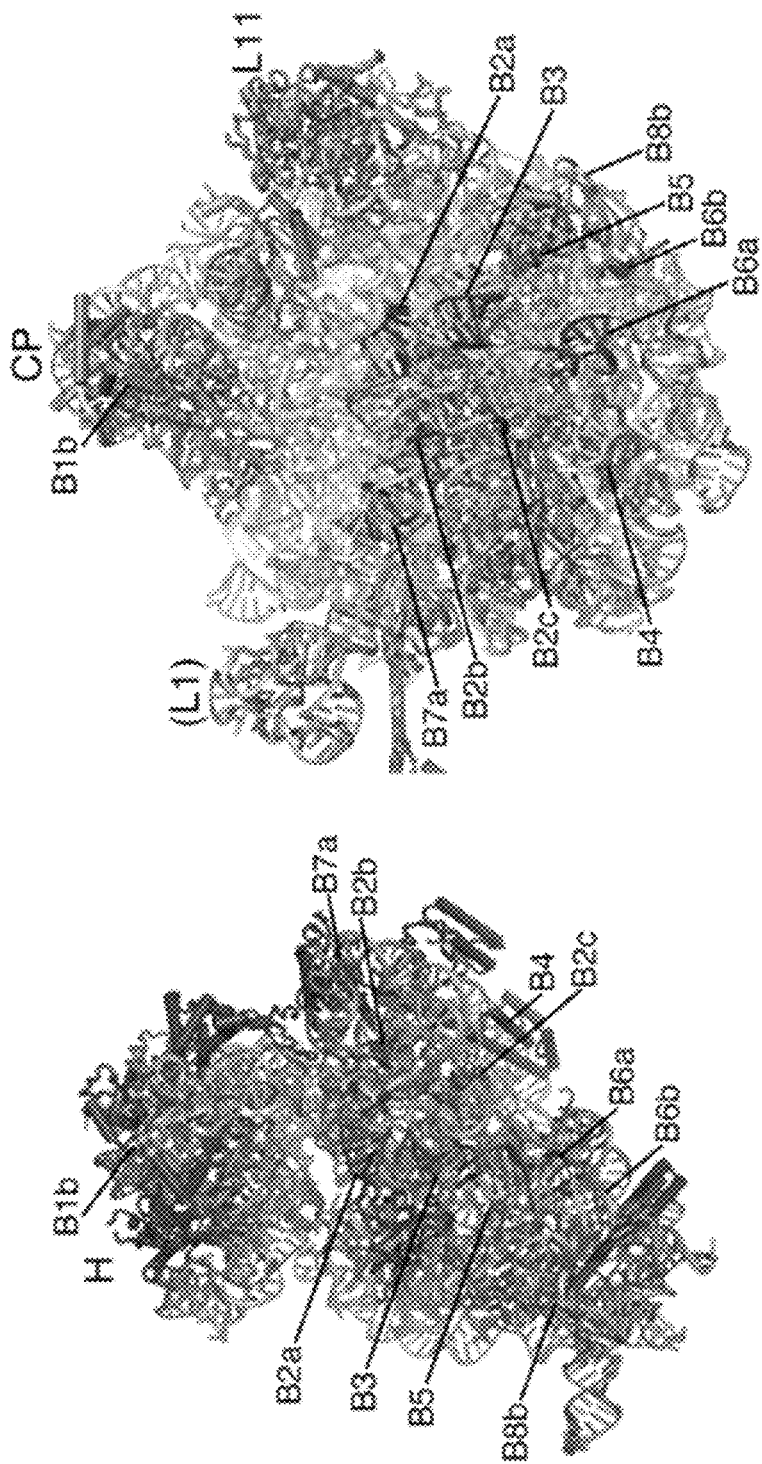
FIG. 7 identifies the bridges between the two ribosomal subunits in the unrotated state. The small subunit rRNA and proteins are colored lighter and darker, respectively, with the large subunit rRNA and proteins colored lighter and darker, respectively. The tip of helix H38 in bridge B1a is disordered in the present structures.

Contacts, or bridges, between the ribosomal subunits were determined using the program Probe (Word 1999a,b). Identified contacts were manually examined by comparison to difference electron density maps, calculated either in Phenix or using Pirate density modified phases, to discount disordered side chains. Only direct contacts are shown in FIGS. 6 and 7. Nomenclature for bridges adapted from (Yusupov 2001; Schuwirth 2005; Ben-Shem 2010). The dinucleotide platform formed by nucleotides A1847-A1848 in 23S rRNA differs from prior structural models of the 70S ribosome 2006; Laurberg 2008; Jenner 2010a,b), although in *Haloarcula marismortui* the motif is conserved as a U-A dinucleotide platform (nts U1888-A1889)(Klein 2004).

Figure Preparation.

Figures for Examples 3 and 4 were made using the program Pymol (Delano 2002). Numbering for ribosomal proteins follows that in the UniProt database (http://www.uniprot.org) (Uniprot 2010). Morphing movies were made using interpolation scripts written for CNS (Brünger 1998; Echols 2003) and were rendered in Pymol (Delano 2002).

EXAMPLE 4

Structural Analysis of Unrotated and Rotated Ribosome with Neomycin

Ribosome Purification and Crystallization.

Ribosomes were purified and crystallized as described in Example 3. Ribosome crystals were stabilized with crystallization buffer containing 7.0% MPD, 7.0% PEG 8000, 24% PEG 400, pH 4.8, to allow cryo-cooling of the crystals to liquid nitrogen temperatures. During the last cryo-cooling step (PEG 400 24%), neomycin (Sigma-Aldrich) was added at 100 μM concentration to the cryo-protection buffer, and crystals were incubated at 4° C. with neomycin containing cryo-protection buffer. After two hours of incubation, the concentration of neomycin was reduced to 2 μM by cryo-protection buffer exchange, and crystals were frozen with liquid nitrogen after 1-4 days of incubation at 4° C.

Data Collection and Processing.

Diffraction data were measured from crystals cooled to 100° K using 0.1-0.3° oscillations at the Advanced Light Source (beamlines 8.3.1 and 12.3.1), each of which is equipped with an ADSC Q315 area detector. Data were reduced using XDS (Kabsch 1993), yielding the statistics shown in Tables 4 and 5.

TABLE 4

X-ray crystallographic statistics

| | |
|---|---|
| Space group | $P\,2_1 2_1 2_1$ |
| Unit cell (a, b, c in Å) | 212.18 433.90 608.83 |
| Resolution (Å) | 70-3.3 |

TABLE 4-continued

X-ray crystallographic statistics

| | |
|---|---|
| (high-resolution shell)* | (3.58-3.48) |
| $R_{merge}$† | 23.1 (77.8) |
| I/σ (I) | 5.76 (1.64) |
| Completeness (%) | 95.2 (89.2) |
| Measurement redundancy | 5.6 (3.4) |
| Unique reflections | 793808 (51869) |
| No. crystals used | 1 |

*Data beyond the high-resolution shell in parentheses were used for refinement and map calculation, and extend to an I/σ (I) of about 1.12. Data are 96% complete in the 4.09-3.94 Å resolution shell, and 99% complete in lower-resolution shells.
†All statistics not in parentheses include data over the whole reported resolution range.

TABLE 5

X-ray structure refinement

| | |
|---|---|
| Resolution (Å) | 70-3.3 |
| No. reflections | 792715 |
| $R_{free}$ set | 1997 |
| $R/R_{free}$ (%)* | 0.22/0.27 |
| No. non-H atoms | 293687 |
| R.m.s. deviations | |
| | |
| Bond lengths (Å) | 0.006 |
| Bond angles (°) | 0.98 |
| Molprobity statistics | |
| | |
| All-atom clashscore | 24.53 |
| Ramachandran plot | |
| Outliers | 12.25% |
| Allowed | 19.1% |
| Favored | 68.65% |
| Rotamer outliers | 22.1% |

*Refinement in Phenix (Adams 2010) with riding H atoms.

Molecular Replacement and Structure Refinement.

The two copies of the 70S ribosome in the crystallographic asymmetric unit were located using rigid-body refinement in Phenix (Adams et al. 2010) of the well-ordered *E. coli* ribosome from a the atomic-resolution structure determination in Example 3. More extensive corrections were carried out in Coot (Emsley 2010) and sidechain-rotator tools in KiNG (Chen 2009a,b). Refinement was carried out in Phenix, including the use of pucker-specific target parameters. The resulting structural models were then refined using rounds of manual rebuilding in Coot, or KiNG as well as positional refinement in Phenix, including the use of a new functionality for automatic assignment of H-bond restraints using the Saenger base-pair types (Saenger 1984). Electron density maps were generated from the Phenix output directly. RNA rebuilding concentrated on the tRNAs, H69 and h44 (neomycin binding sites) and neomycin structure was inserted and fitted by using the Coot and Phenix.

Superpositions.

Comparisons to atomic-resolution structures of the ribosome were carried out by the "pair_fit" command in PyMOL that fits a set of atom pairs between two models. From the chosen atom pairs, disordered or moving regions of 23S rRNA were not used (e.g. L1 stalk, L7/L12 stalk, H38, H69) in the superpositions. Superpositions were performed using ribose C1' positions or phosphorus atoms in nucleotides. The angles of rotation of the 30S subunit domains were calculated essentially as described in (Zhang 2009). Angles given for the rotation of the head domain were calculated from 30S subunit structures superimposed by means of their platform domains. A rotation of 0° is defined as centering the head domain over the 30S P site, as seen in the structure of the unratcheted ribosome (Example 3). Superpositions of P/P, P/pe and P/E tRNAs utilized the C1' atoms of nucleotides 31-39 in the anticodon stem-loop (Example 3). Comparisons of tRNA bending angles used the glycosidic bond of position 31 near the end of the anticodon stem-loop and the glycosidic bond of nucleotide 63 in the superimposed tRNAs (Example 3). The bending angles calculated in this way are 24° for P/P tRNA compared to P/pe tRNA, 14° for P/pe tRNA compared to P/E tRNA.

EXAMPLE 5

Atomic Coordinates of H69Neomycin-Binding Pocket

The atomic coordinates for the H69 neomycin-binding pocket are provided in Tables 6-9. These tables contain the data from PDB files for the crystals described in Example 3 (Tables 6 and 7) and for the crystals described in Example 4 (Tables 8 and 9).

Table 6 provides the ribosomal coordinates for the residues involved in neormycin binding at the H69 site for the fully-rotated ribosome with the compressed H69 neomycin-binding site. Table 7 provides the same coordinates for the unrotated ribosome but the binding site is open (uncompressed).

Since the crystals from Example 4 were solved with neomycin bound, Table 8 provides the H69 neomycin-binding pocket coordinates for both neomycin and the ribosome in an intermediate-rotated state. Table 9 provides the same information as in Table 8 but for the ribosome in an unrotated state. These two latter sets of coordinates can be used for molecular modeling with or without the neomycin coordinates.

The tables are set forth after the References section.

REFERENCES

Adams et al. (2010) Acta Crystallogr D Biol Crystallogr 66(Pt 2): 213-21.
Agrawal et al. (2004. Proc Natl Acad Sci USA 101(24): 8900-5.
Ashkenazy et al. (2010) Nucleic Acids Res 38(Web Server issue): W529-33.
Bains (1998) Biotechnology from A to Z, 2nd ed., Oxford University Press, p. 259.
Ben-Shem, et al. (2010) Science 330(6008): 1203-9.
Blaha et al. (2000). Methods Enzymol 317: 292-309.
Blanchard et al. (2010) Chem Biol 17, 633.
Blanchard et al. (2004 Proc Natl Acad Sci USA 101(35): 12893-8.
Bokov et al. 2009). Nature 457(7232): 977-80.
Borovinskaya et al. (2007) Nat Struct Mol Biol 14(8): 727-32.
Brandt et al. (2009) Cell 136(2): 261-71.
Brünger et al. (1998) Acta Crystallogr. D Biol. Crystallogr. 54(Pt 5): 905-21.
Cannone et al. (2002) BMC Bioinformatics 3: 2.
Cate et al. (1996) Science 273(5282): 1678-85.
Cate et al. (1996) Science 273(5282): 1696-9.
Cayama et al. (2000) Nucleic Acids Res 28(12): E64.
Chan et al. (2008) J Mol Biol 378, 12.
Chen, V. B. (2010). Building Better Backbones: Visualizations, Analyses, and Tools for Higher Quality Macromolecular Structure Models. Biochemistry. Durham, N.C., Duke University. Ph.D.: 272.
Chen et al. (2009) Protein Sci 18(11): 2403-9.
Chen et al. (2010) Acta Crystallogr D Biol Crystallogr 66(Pt 1): 12-21.
Cohen, ed. (1996) Guidebook on Molecular Modeling in Drug Design, Academic Press.
Connell et al. (2007) Mol Cell 25(5): 751-64.
Cornish et al. (2008). Mol Cell 30(5): 578-88.
Cowtan (2000) Acta Crystallogr D Biol Crystallogr 56 Pt 12: 1612-21.
Cukras et al. (2005) J Mol Biol 349(1): 47-59.
Dahlberg et al. (1978) Antimicrob Agents Chemother 13, 331.
Dave, et al. (2009) Biophys J 96(6): 2371-81.
David-Eden et al. (2010) Nucleic Acids Res 38, 5982.
Davies et al. (1968) J Biol Chem 243, 3312.
Davis et al. (2006). Structure 14(2): 265-74.
Delano, W. L. (2002) The PyMOL User's Manual. San Carlos, Calif., USA., Delano Scientific.
Dunkle et al. (2011) Science 332, 981.
Dunkle et al. (2010) Annu Rev Biophys 39: 227-44.
Echols et al. (2003) Nucleic Acids Res 31(1): 478-82.
Emsley et al. (2010) Acta Crystallogr D Biol Crystallogr 66(Pt 4): 486-501.
Ermolenko et al. (2007) Nat Struct Mol Biol 14(6): 493-7.
Feinberg and Joseph (2001) Proc Natl Acad Sci USA 98(20): 11120-5.
Feldman et al. (2010) Nat Chem Biol 6(1): 54-62.
Fischer et al. (2010) Nature 466(7304): 329-33.
Fourmy et al. (1996) Science 274, 1367.
Frank, J. et al. (2000) Nature 406(6793): 318-22.
Frank et al. (2007) Proc Natl Acad Sci USA 104(50): 19671-8.
Gale et al. (1981) The Molecular Basis of Antibiotic Action. (John Wiley & Sons Ltd, ed. 2nd.
Gans et al. (1996) Fundamental Principals of Molecular Modeling, Plenum Pub. Corp. Gao et al. (2009) Science 326, 694.
Gao (2005) Mol Cell 18(6): 663-74.
Gavrilova et al. (1976) J Mol Biol 101(4): 537-52.
Geggier et al. (2010) J Mol Biol 399, 576.
Hirokawa et al. (2002) EMBO J 21, 2272.
Janosi, L et al. (2000) J Mol Biol 295(4): 815-29.
Jenner et al. (2010) Nat Struct Mol Biol 17(5): 555-60.
Jenner et al. (2010) Nat Struct Mol Biol 17(9): 1072-8.
Jin et al (2011) Proc Natl Acad Sci USA 108, 15798.
Johansen et al. (2006) Mol. Cell 23, 173-182
Joseph et al. (1998) EMBO J 17(12): 3478-83.
Jones et al. (1991) Acta Crystallogr. A 47: 110-9.
Junemann et al. (1996) Nucleic Acids Res 24(5): 907-13.
Kabsch, (1993) J. Appl. Cryst. 26: 795-800.
Klein et al. (2004) J Mol Biol 340(1): 141-77.
Komoda et al. (2006) J Biol Chem 281(43): 32303-9.
Lancaster et al. (2002) Cell 111(1): 129-40.
Laurberg et al. (2008) Nature 454, 852.
Laurberg et al. (2008) Nature 454(7206): 852-7.
Li, W. et al. (2007) Proc Natl Acad Sci USA 104(42): 16540-5.
Lill et al. (1989) EMBO J 8(12): 3933-8.
Llano-Sotelo et al. (2009) RNA 15, 1597.
Moazed et al. (1989). Nature 342(6246): 142-8.
Munro et al. (2007) Mol Cell 25, 505.
Munro (2009) Trends Biochem Sci 34(8): 390-400.
Munro (2010a) EMBO J 29(4): 770-81.
Munro et al. (2010b) Proc Natl Acad Sci USA 107(2): 709-14.
Munro et al. (2010c) Nat Struct Mol Biol. 2010 December; 17(12):1470-7.
Ogle et al. (2005) Annu Rev Biochem 74, 129.

Peske et al. (2005) Mol Cell 18, 403.
Petry et al. (2008) Curr Opin Struct Biol 18, 70.
Poehlsgaard et al. (2005) Nat Rev Microbiol 3, 870.
Pulk et al. (2006) RNA 12, 790.
Qin et al. (1996) Biophys J 70, 264.
Ratje et al. (2010) Nature 468(7324): 713-6.
Recht et al. (1999) EMBO J 18, 3133.
Richardson et al. (2008) RNA 14(3): 465-81.
Rodnina et al. (2000) Biol Chem 381, 377.
Rush et al. (2008) J. Am. Chem. Soc. 2008, 130, 12240-12241.
Saenger, W. (1984). Principles of Nucleic Acid Structure. New York, Springer-Verlag.
Savelsbergh et al. (2009) RNA 15(5): 772-80.
Schlecht (1998) Molecular Modeling on the PC, John Wiley & Sons.
Schmeing et al. (2009) Nature 461(7268): 1234-42.
Schmeing et al. (2003) RNA 9(11): 1345-52.
Schmeing et al. (2009) Science 326(5953): 688-94.
Schuwirth et al. (2005) Science 310(5749): 827-34.
Selmer et al. (2006) Science 313(5795): 1935-42.
Semenkov et al. (2000). Nat Struct Biol 7(11): 1027-31.
Shenvi et al. (2005) RNA 11(12): 1898-908.
Smith (1996) Introduction to Theoretical Organic Chemistry and Molecular Modeling.
Spahn et al. (2004) EMBO J 23(5): 1008-19.
Spirin (2009a) Biochemistry 48(45): 10688-92.
Spirin. (2009b) J Biol Chem 284(32): 21103-19.
Stanley et al. (2010) Nat Struct Mol Biol 17(3): 289-93.
Sternberg et al. (2009) Nat Struct Mol Biol 16(8): 861-8.
Tenson et al. (2006) Mol Microbiol 59, 1664.
Uniprot (2010). "The Universal Protein Resource (UniProt) in 2010." Nucleic Acids Res 38(Database issue): D142-8.
Valle et al. (2003a) Nat Struct Biol 10(11): 899-906.
Valle et al. (2003b) Cell 114(1): 123-34.
Valle et al. (2002) EMBO J 21(13): 3557-67.
von Ehrenstein et al. (1967). Isolation of sRNA from intact *Escherichia coli* cells. Methods in Enzymology, Academic Press. Volume 12, Part 1: 588-596.
Voorhees et al. (2010) Science 330(6005): 835-8.
Wang et al. (2011) RNA 17, 2189.
Wan et al. (2008). J Math Biol 56(1-2): 253-78.
Weixlbaumer et al. (2007) Nat Struct Mol Biol 14(8): 733-7.
Whitford et al. (2011) Proc Natl Acad Sci USA 108, 18943.
Word et al. (1999a) J Mol Biol 285(4): 1735-47.
Word et al. (1999b) J Mol Biol 285(4): 1711-33.
Yin et al. (2006) Nat Protoc 1, 280-5.
Yusupov et al. (2001) Science 292(5518): 883-96.
Zaher et al. (2009) Cell 136, 746.
Zavialov et al. (2003) Cell 114(1): 113-22.
Zhang et al. (2009) Science 325(5943): 1014-7.
Zhou et al. (2008) J. Am. Chem. Soc. 130, 9925-9930.

TABLE 6

H69 Neomycin Binding Site for Fully-Rotated Ribosome

| ATOM | 32464 | P | G A1515 | −73.805 | 5.885 | 3.472 | 1.00 | 0.65 | P |
|---|---|---|---|---|---|---|---|---|---|
| ATOM | 32465 | OP1 | G A1515 | −73.359 | 4.506 | 3.851 | 1.00 | 0.65 | O |
| ATOM | 32466 | OP2 | G A1515 | −73.520 | 6.372 | 2.097 | 1.00 | 0.65 | O |
| ATOM | 32467 | O5' | G A1515 | −75.359 | 6.088 | 3.818 | 1.00 | 0.65 | O |
| ATOM | 32468 | C5' | G A1515 | −75.847 | 5.853 | 5.130 | 1.00 | 0.65 | C |
| ATOM | 32469 | C4' | G A1515 | −77.109 | 6.620 | 5.398 | 1.00 | 0.65 | C |
| ATOM | 32470 | O4' | G A1515 | −76.909 | 8.001 | 5.036 | 1.00 | 0.65 | O |
| ATOM | 32471 | C3' | G A1515 | −78.307 | 6.235 | 4.567 | 1.00 | 0.65 | C |
| ATOM | 32472 | O3' | G A1515 | −78.923 | 5.028 | 4.972 | 1.00 | 0.65 | O |
| ATOM | 32473 | C2' | G A1515 | −79.186 | 7.468 | 4.687 | 1.00 | 0.65 | C |
| ATOM | 32474 | O2' | G A1515 | −79.792 | 7.536 | 5.965 | 1.00 | 0.65 | O |
| ATOM | 32475 | C1' | G A1515 | −78.129 | 8.565 | 4.592 | 1.00 | 0.65 | C |
| ATOM | 32476 | N9 | G A1515 | −77.952 | 9.050 | 3.209 | 1.00 | 0.68 | N |
| ATOM | 32477 | C8 | G A1515 | −76.918 | 8.758 | 2.353 | 1.00 | 0.68 | C |
| ATOM | 32478 | N7 | G A1515 | −77.047 | 9.322 | 1.175 | 1.00 | 0.68 | N |
| ATOM | 32479 | C5 | G A1515 | −78.234 | 10.039 | 1.274 | 1.00 | 0.68 | C |
| ATOM | 32480 | C6 | G A1515 | −78.906 | 10.852 | 0.326 | 1.00 | 0.68 | C |
| ATOM | 32481 | O6 | G A1515 | −78.520 | 11.071 | −0.819 | 1.00 | 0.68 | O |
| ATOM | 32482 | N1 | G A1515 | −80.087 | 11.410 | 0.799 | 1.00 | 0.68 | N |
| ATOM | 32483 | C2 | G A1515 | −80.547 | 11.190 | 2.054 | 1.00 | 0.68 | C |
| ATOM | 32484 | N2 | G A1515 | −81.693 | 11.769 | 2.400 | 1.00 | 0.68 | N |
| ATOM | 32485 | N3 | G A1515 | −79.937 | 10.441 | 2.950 | 1.00 | 0.68 | N |
| ATOM | 32486 | C4 | G A1515 | −78.793 | 9.889 | 2.514 | 1.00 | 0.68 | C |
| ATOM | 32487 | P | G A1516 | −79.407 | 3.970 | 3.847 | 1.00 | 5.61 | P |
| ATOM | 32488 | OP1 | G A1516 | −79.551 | 2.635 | 4.515 | 1.00 | 5.61 | O |
| ATOM | 32489 | OP2 | G A1516 | −78.484 | 4.104 | 2.693 | 1.00 | 5.61 | O |
| ATOM | 32490 | O5' | G A1516 | −80.827 | 4.536 | 3.464 | 1.00 | 5.61 | O |
| ATOM | 32491 | C5' | G A1516 | −81.759 | 4.843 | 4.477 | 1.00 | 5.61 | C |
| ATOM | 32492 | C4' | G A1516 | −82.904 | 5.610 | 3.921 | 1.00 | 5.61 | C |
| ATOM | 32493 | O4' | G A1516 | −82.485 | 6.974 | 3.662 | 1.00 | 5.61 | O |
| ATOM | 32494 | C3' | G A1516 | −83.414 | 5.136 | 2.573 | 1.00 | 5.61 | C |
| ATOM | 32495 | O3' | G A1516 | −84.238 | 3.987 | 2.648 | 1.00 | 5.61 | O |
| ATOM | 32496 | C2' | G A1516 | −84.124 | 6.371 | 2.060 | 1.00 | 5.61 | C |
| ATOM | 32497 | O2' | G A1516 | −85.380 | 6.519 | 2.693 | 1.00 | 5.61 | O |
| ATOM | 32498 | C1' | G A1516 | −83.185 | 7.482 | 2.550 | 1.00 | 5.61 | C |
| ATOM | 32499 | N9 | G A1516 | −82.218 | 7.834 | 1.516 | 1.00 | 5.64 | N |
| ATOM | 32500 | C8 | G A1516 | −80.895 | 7.517 | 1.408 | 1.00 | 5.64 | C |
| ATOM | 32501 | N7 | G A1516 | −80.369 | 7.946 | 0.287 | 1.00 | 5.64 | N |
| ATOM | 32502 | C5 | G A1516 | −81.436 | 8.535 | −0.366 | 1.00 | 5.64 | C |
| ATOM | 32503 | C6 | G A1516 | −81.514 | 9.151 | −1.614 | 1.00 | 5.64 | C |
| ATOM | 32504 | O6 | G A1516 | −80.569 | 9.310 | −2.403 | 1.00 | 5.64 | O |
| ATOM | 32505 | N1 | G A1516 | −82.796 | 9.606 | −1.902 | 1.00 | 5.64 | N |
| ATOM | 32506 | C2 | G A1516 | −83.868 | 9.479 | −1.090 | 1.00 | 5.64 | C |
| ATOM | 32507 | N2 | G A1516 | −85.040 | 9.958 | −1.478 | 1.00 | 5.64 | N |
| ATOM | 32508 | N3 | G A1516 | −83.804 | 8.910 | 0.074 | 1.00 | 5.64 | N |

TABLE 6-continued

H69 Neomycin Binding Site for Fully-Rotated Ribosome

| ATOM | 32509 | C4 | G A1516 | −82.571 | 8.467 | 0.369 | 1.00 | 5.64 | C |
|------|-------|-----|---------|---------|-------|-------|------|------|---|
| ATOM | 32510 | P | G A1517 | −84.128 | 2.853 | 1.506 | 1.00 | 8.95 | P |
| ATOM | 32511 | OP1 | G A1517 | −84.956 | 1.700 | 1.947 | 1.00 | 8.95 | O |
| ATOM | 32512 | OP2 | G A1517 | −82.680 | 2.627 | 1.226 | 1.00 | 8.95 | O |
| ATOM | 32513 | O5' | G A1517 | −84.820 | 3.557 | 0.270 | 1.00 | 8.95 | O |
| ATOM | 32514 | C5' | G A1517 | −86.228 | 3.744 | 0.253 | 1.00 | 8.95 | C |
| ATOM | 32515 | C4' | G A1517 | −86.790 | 3.530 | −1.123 | 1.00 | 8.95 | C |
| ATOM | 32516 | O4' | G A1517 | −88.194 | 3.199 | −1.023 | 1.00 | 8.95 | O |
| ATOM | 32517 | C3' | G A1517 | −86.761 | 4.739 | −2.032 | 1.00 | 8.95 | C |
| ATOM | 32518 | O3' | G A1517 | −85.521 | 4.917 | −2.667 | 1.00 | 8.95 | O |
| ATOM | 32519 | C2' | G A1517 | −87.896 | 4.462 | −2.985 | 1.00 | 8.95 | C |
| ATOM | 32520 | O2' | G A1517 | −87.522 | 3.473 | −3.933 | 1.00 | 8.95 | O |
| ATOM | 32521 | C1' | G A1517 | −88.913 | 3.857 | −2.037 | 1.00 | 8.95 | C |
| ATOM | 32522 | N9 | G A1517 | −89.758 | 4.879 | −1.401 | 1.00 | 8.51 | N |
| ATOM | 32523 | C8 | G A1517 | −89.727 | 5.231 | −0.072 | 1.00 | 8.51 | C |
| ATOM | 32524 | N7 | G A1517 | −90.600 | 6.159 | 0.250 | 1.00 | 8.51 | N |
| ATOM | 32525 | C5 | G A1517 | −91.241 | 6.408 | −0.944 | 1.00 | 8.51 | C |
| ATOM | 32526 | C6 | G A1517 | −92.272 | 7.302 | −1.224 | 1.00 | 8.51 | C |
| ATOM | 32527 | O6 | G A1517 | −92.831 | 8.057 | −0.466 | 1.00 | 8.51 | O |
| ATOM | 32528 | N1 | G A1517 | −92.656 | 7.272 | −2.528 | 1.00 | 8.51 | N |
| ATOM | 32529 | C2 | G A1517 | −92.085 | 6.475 | −3.457 | 1.00 | 8.51 | C |
| ATOM | 32530 | N2 | G A1517 | −92.588 | 6.601 | −4.681 | 1.00 | 8.51 | N |
| ATOM | 32531 | N3 | G A1517 | −91.109 | 5.626 | −3.234 | 1.00 | 8.51 | N |
| ATOM | 32532 | C4 | G A1517 | −90.741 | 5.638 | −1.962 | 1.00 | 8.51 | C |
| ATOM | 32533 | P | A A1518 | −84.783 | 6.329 | −2.553 | 1.00 | 8.03 | P |
| ATOM | 32534 | OP1 | A A1518 | −83.411 | 6.148 | −3.107 | 1.00 | 8.03 | O |
| ATOM | 32535 | OP2 | A A1518 | −84.952 | 6.797 | −1.157 | 1.00 | 8.03 | O |
| ATOM | 32536 | O5' | A A1518 | −85.626 | 7.247 | −3.506 | 1.00 | 8.03 | O |
| ATOM | 32537 | C5' | A A1518 | −85.517 | 7.125 | −4.890 | 1.00 | 8.03 | C |
| ATOM | 32538 | C4' | A A1518 | −86.576 | 7.930 | −5.535 | 1.00 | 8.03 | C |
| ATOM | 32539 | O4' | A A1518 | −87.850 | 7.546 | −4.975 | 1.00 | 8.03 | O |
| ATOM | 32540 | C3' | A A1518 | −86.488 | 9.412 | −5.267 | 1.00 | 8.03 | C |
| ATOM | 32541 | O3' | A A1518 | −85.581 | 10.062 | −6.140 | 1.00 | 8.03 | O |
| ATOM | 32542 | C2' | A A1518 | −87.930 | 9.857 | −5.421 | 1.00 | 8.03 | C |
| ATOM | 32543 | O2' | A A1518 | −88.283 | 9.923 | −6.795 | 1.00 | 8.03 | O |
| ATOM | 32544 | C1' | A A1518 | −88.662 | 8.676 | −4.798 | 1.00 | 8.03 | C |
| ATOM | 32545 | N9 | A A1518 | −88.891 | 8.837 | −3.354 | 1.00 | 8.10 | N |
| ATOM | 32546 | C8 | A A1518 | −88.133 | 8.263 | −2.353 | 1.00 | 8.10 | C |
| ATOM | 32547 | N7 | A A1518 | −88.576 | 8.547 | −1.141 | 1.00 | 8.10 | N |
| ATOM | 32548 | C5 | A A1518 | −89.722 | 9.325 | −1.361 | 1.00 | 8.10 | C |
| ATOM | 32549 | C6 | A A1518 | −90.650 | 9.937 | −0.485 | 1.00 | 8.10 | C |
| ATOM | 32550 | N6 | A A1518 | −90.594 | 9.867 | 0.847 | 1.00 | 8.10 | N |
| ATOM | 32551 | N1 | A A1518 | −91.657 | 10.642 | −1.054 | 1.00 | 8.10 | N |
| ATOM | 32552 | C2 | A A1518 | −91.731 | 10.715 | −2.390 | 1.00 | 8.10 | C |
| ATOM | 32553 | N3 | A A1518 | −90.925 | 10.189 | −3.310 | 1.00 | 8.10 | N |
| ATOM | 32554 | C4 | A A1518 | −89.930 | 9.500 | −2.730 | 1.00 | 8.10 | C |
| TER | | | | | | | | | |
| ATOM | 40759 | P | G A1903 | −77.149 | −18.965 | 16.920 | 1.00 | 1.59 | P |
| ATOM | 40760 | OP1 | G A1903 | −77.353 | −20.402 | 16.624 | 1.00 | 1.59 | O |
| ATOM | 40761 | OP2 | G A1903 | −76.245 | −18.169 | 16.052 | 1.00 | 1.59 | O |
| ATOM | 40762 | O5' | G A1903 | −78.554 | −18.232 | 17.082 | 1.00 | 1.59 | O |
| ATOM | 40763 | C5' | G A1903 | −79.415 | −17.998 | 15.987 | 1.00 | 1.59 | C |
| ATOM | 40764 | C4' | G A1903 | −80.810 | −17.639 | 16.459 | 1.00 | 1.59 | C |
| ATOM | 40765 | O4' | G A1903 | −80.749 | −16.623 | 17.512 | 1.00 | 1.59 | O |
| ATOM | 40766 | C3' | G A1903 | −81.733 | −17.049 | 15.404 | 1.00 | 1.59 | C |
| ATOM | 40767 | O3' | G A1903 | −82.405 | −18.042 | 14.682 | 1.00 | 1.59 | O |
| ATOM | 40768 | C2' | G A1903 | −82.668 | −16.173 | 16.217 | 1.00 | 1.59 | C |
| ATOM | 40769 | O2' | G A1903 | −83.662 | −16.958 | 16.836 | 1.00 | 1.59 | O |
| ATOM | 40770 | C1' | G A1903 | −81.730 | −15.634 | 17.291 | 1.00 | 1.59 | C |
| ATOM | 40771 | N9 | G A1903 | −81.042 | −14.423 | 16.829 | 1.00 | 1.70 | N |
| ATOM | 40772 | C8 | G A1903 | −79.720 | −14.396 | 16.503 | 1.00 | 1.70 | C |
| ATOM | 40773 | N7 | G A1903 | −79.323 | −13.244 | 16.069 | 1.00 | 1.70 | N |
| ATOM | 40774 | C5 | G A1903 | −80.457 | −12.458 | 16.092 | 1.00 | 1.70 | C |
| ATOM | 40775 | C6 | G A1903 | −80.617 | −11.092 | 15.729 | 1.00 | 1.70 | C |
| ATOM | 40776 | O6 | G A1903 | −79.777 | −10.285 | 15.301 | 1.00 | 1.70 | O |
| ATOM | 40777 | N1 | G A1903 | −81.917 | −10.686 | 15.887 | 1.00 | 1.70 | N |
| ATOM | 40778 | C2 | G A1903 | −82.903 | −11.490 | 16.333 | 1.00 | 1.70 | C |
| ATOM | 40779 | N2 | G A1903 | −84.074 | −10.873 | 16.392 | 1.00 | 1.70 | N |
| ATOM | 40780 | N3 | G A1903 | −82.785 | −12.761 | 16.696 | 1.00 | 1.70 | N |
| ATOM | 40781 | C4 | G A1903 | −81.530 | −13.184 | 16.545 | 1.00 | 1.70 | C |
| ATOM | 40782 | P | G A1904 | −82.389 | −18.034 | 13.095 | 1.00 | 15.24 | P |
| ATOM | 40783 | OP1 | G A1904 | −82.621 | −19.429 | 12.662 | 1.00 | 15.24 | O |
| ATOM | 40784 | OP2 | G A1904 | −81.167 | −17.351 | 12.660 | 1.00 | 15.24 | O |
| ATOM | 40785 | O5' | G A1904 | −83.649 | −17.153 | 12.758 | 1.00 | 15.24 | O |
| ATOM | 40786 | C5' | G A1904 | −84.894 | −17.439 | 13.376 | 1.00 | 15.24 | C |
| ATOM | 40787 | C4' | G A1904 | −85.865 | −16.304 | 13.217 | 1.00 | 15.24 | C |
| ATOM | 40788 | O4' | G A1904 | −85.530 | −15.238 | 14.129 | 1.00 | 15.24 | O |
| ATOM | 40789 | C3' | G A1904 | −85.875 | −15.627 | 11.865 | 1.00 | 15.24 | C |

TABLE 6-continued

H69 Neomycin Binding Site for Fully-Rotated Ribosome

| ATOM | 40790 | O3' | G A1904 | −86.607 | −16.337 | 10.904 | 1.00 | 15.24 | O |
|------|-------|-----|---------|---------|---------|--------|------|-------|---|
| ATOM | 40791 | C2' | G A1904 | −86.494 | −14.317 | 12.206 | 1.00 | 15.24 | C |
| ATOM | 40792 | O2' | G A1904 | −87.866 | −14.517 | 12.497 | 1.00 | 15.24 | O |
| ATOM | 40793 | C1' | G A1904 | −85.780 | −14.009 | 13.510 | 1.00 | 15.24 | C |
| ATOM | 40794 | N9  | G A1904 | −84.486 | −13.322 | 13.298 | 1.00 | 15.28 | N |
| ATOM | 40795 | C8  | G A1904 | −83.250 | −13.814 | 13.634 | 1.00 | 15.28 | C |
| ATOM | 40796 | N7  | G A1904 | −82.284 | −12.988 | 13.375 | 1.00 | 15.28 | N |
| ATOM | 40797 | C5  | G A1904 | −82.914 | −11.868 | 12.848 | 1.00 | 15.28 | C |
| ATOM | 40798 | C6  | G A1904 | −82.387 | −10.645 | 12.367 | 1.00 | 15.28 | C |
| ATOM | 40799 | O6  | G A1904 | −81.236 | −10.247 | 12.291 | 1.00 | 15.28 | O |
| ATOM | 40800 | N1  | G A1904 | −83.336 | −9.785  | 11.915 | 1.00 | 15.28 | N |
| ATOM | 40801 | C2  | G A1904 | −84.656 | −10.056 | 11.921 | 1.00 | 15.28 | C |
| ATOM | 40802 | N2  | G A1904 | −85.404 | −9.057  | 11.424 | 1.00 | 15.28 | N |
| ATOM | 40803 | N3  | G A1904 | −85.190 | −11.187 | 12.357 | 1.00 | 15.28 | N |
| ATOM | 40804 | C4  | G A1904 | −84.264 | −12.051 | 12.805 | 1.00 | 15.28 | C |
| ATOM | 40805 | P   | C A1905 | −86.064 | −16.416 | 9.417  | 1.00 | 12.32 | P |
| ATOM | 40806 | OP1 | C A1905 | −86.932 | −17.354 | 8.669  | 1.00 | 12.32 | O |
| ATOM | 40807 | OP2 | C A1905 | −84.602 | −16.700 | 9.498  | 1.00 | 12.32 | O |
| ATOM | 40808 | O5' | C A1905 | −86.301 | −14.940 | 8.906  | 1.00 | 12.32 | O |
| ATOM | 40809 | C5' | C A1905 | −87.558 | −14.325 | 9.064  | 1.00 | 12.32 | C |
| ATOM | 40810 | C4' | C A1905 | −87.505 | −12.908 | 8.616  | 1.00 | 12.32 | C |
| ATOM | 40811 | O4' | C A1905 | −86.525 | −12.205 | 9.397  | 1.00 | 12.32 | O |
| ATOM | 40812 | C3' | C A1905 | −87.066 | −12.702 | 7.190  | 1.00 | 12.32 | C |
| ATOM | 40813 | O3' | C A1905 | −88.132 | −12.865 | 6.287  | 1.00 | 12.32 | O |
| ATOM | 40814 | C2' | C A1905 | −86.505 | −11.297 | 7.208  | 1.00 | 12.32 | C |
| ATOM | 40815 | O2' | C A1905 | −87.548 | −10.354 | 7.078  | 1.00 | 12.32 | O |
| ATOM | 40816 | C1' | C A1905 | −85.942 | −11.194 | 8.627  | 1.00 | 12.32 | C |
| ATOM | 40817 | N1  | C A1905 | −84.468 | −11.341 | 8.696  | 1.00 | 13.11 | N |
| ATOM | 40818 | C2  | C A1905 | −83.623 | −10.390 | 8.109  | 1.00 | 13.11 | C |
| ATOM | 40819 | O2  | C A1905 | −84.161 | −9.480  | 7.460  | 1.00 | 13.11 | O |
| ATOM | 40820 | N3  | C A1905 | −82.272 | −10.491 | 8.213  | 1.00 | 13.11 | N |
| ATOM | 40821 | C4  | C A1905 | −81.760 | −11.491 | 8.909  | 1.00 | 13.11 | C |
| ATOM | 40822 | N4  | C A1905 | −80.430 | −11.593 | 9.012  | 1.00 | 13.11 | N |
| ATOM | 40823 | C5  | C A1905 | −82.600 | −12.449 | 9.549  | 1.00 | 13.11 | C |
| ATOM | 40824 | C6  | C A1905 | −83.927 | −12.341 | 9.429  | 1.00 | 13.11 | C |
| ATOM | 40825 | P   | G A1906 | −87.983 | −13.826 | 5.008  | 1.00 | 33.88 | P |
| ATOM | 40826 | OP1 | G A1906 | −86.784 | −14.680 | 5.212  | 1.00 | 33.88 | O |
| ATOM | 40827 | OP2 | G A1906 | −88.039 | −12.965 | 3.818  | 1.00 | 33.88 | O |
| ATOM | 40828 | O5' | G A1906 | −89.283 | −14.724 | 5.089  | 1.00 | 33.88 | O |
| ATOM | 40829 | C5' | G A1906 | −90.556 | −14.187 | 4.805  | 1.00 | 33.88 | C |
| ATOM | 40830 | C4' | G A1906 | −91.611 | −14.868 | 5.623  | 1.00 | 33.88 | C |
| ATOM | 40831 | O4' | G A1906 | −91.809 | −14.152 | 6.869  | 1.00 | 33.88 | O |
| ATOM | 40832 | C3' | G A1906 | −92.988 | −14.927 | 5.006  | 1.00 | 33.88 | C |
| ATOM | 40833 | O3' | G A1906 | −93.118 | −15.984 | 4.081  | 1.00 | 33.88 | O |
| ATOM | 40834 | C2' | G A1906 | −93.889 | −15.059 | 6.229  | 1.00 | 33.88 | C |
| ATOM | 40835 | O2' | G A1906 | −93.874 | −16.386 | 6.741  | 1.00 | 33.88 | O |
| ATOM | 40836 | C1' | G A1906 | −93.171 | −14.161 | 7.220  | 1.00 | 33.88 | C |
| ATOM | 40837 | N9  | G A1906 | −93.666 | −12.780 | 7.175  | 1.00 | 33.83 | N |
| ATOM | 40838 | C8  | G A1906 | −93.015 | −11.685 | 6.689  | 1.00 | 33.83 | C |
| ATOM | 40839 | N7  | G A1906 | −93.699 | −10.589 | 6.816  | 1.00 | 33.83 | N |
| ATOM | 40840 | C5  | G A1906 | −94.870 | −10.989 | 7.432  | 1.00 | 33.83 | C |
| ATOM | 40841 | C6  | G A1906 | −96.016 | −10.252 | 7.833  | 1.00 | 33.83 | C |
| ATOM | 40842 | O6  | G A1906 | −96.273 | −9.037  | 7.734  | 1.00 | 33.83 | O |
| ATOM | 40843 | N1  | G A1906 | −96.956 | −11.082 | 8.416  | 1.00 | 33.83 | N |
| ATOM | 40844 | C2  | G A1906 | −96.818 | −12.423 | 8.586  | 1.00 | 33.83 | C |
| ATOM | 40845 | N2  | G A1906 | −97.845 | −13.047 | 9.172  | 1.00 | 33.83 | N |
| ATOM | 40846 | N3  | G A1906 | −95.765 | −13.109 | 8.212  | 1.00 | 33.83 | N |
| ATOM | 40847 | C4  | G A1906 | −94.846 | −12.334 | 7.655  | 1.00 | 33.83 | C |
| ATOM | 40848 | P   | G A1907 | −93.834 | −15.733 | 2.668  | 1.00 | 44.42 | P |
| ATOM | 40849 | OP1 | G A1907 | −94.331 | −17.051 | 2.204  | 1.00 | 44.42 | O |
| ATOM | 40850 | OP2 | G A1907 | −92.878 | −14.979 | 1.809  | 1.00 | 44.42 | O |
| ATOM | 40851 | O5' | G A1907 | −95.058 | −14.809 | 3.051  | 1.00 | 44.42 | O |
| ATOM | 40852 | C5' | G A1907 | −96.350 | −15.115 | 2.581  | 1.00 | 44.42 | C |
| ATOM | 40853 | C4' | G A1907 | −97.194 | −15.712 | 3.665  | 1.00 | 44.42 | C |
| ATOM | 40854 | O4' | G A1907 | −96.841 | −15.100 | 4.932  | 1.00 | 44.42 | O |
| ATOM | 40855 | C3' | G A1907 | −98.690 | −15.469 | 3.526  | 1.00 | 44.42 | C |
| ATOM | 40856 | O3' | G A1907 | −99.331 | −16.425 | 2.708  | 1.00 | 44.42 | O |
| ATOM | 40857 | C2' | G A1907 | −99.167 | −15.451 | 4.965  | 1.00 | 44.42 | C |
| ATOM | 40858 | O2' | G A1907 | −99.225 | −16.764 | 5.493  | 1.00 | 44.42 | O |
| ATOM | 40859 | C1' | G A1907 | −98.008 | −14.716 | 5.626  | 1.00 | 44.42 | C |
| ATOM | 40860 | N9  | G A1907 | −98.152 | −13.240 | 5.510  | 1.00 | 43.98 | N |
| ATOM | 40861 | C8  | G A1907 | −97.273 | −12.318 | 4.956  | 1.00 | 43.98 | C |
| ATOM | 40862 | N7  | G A1907 | −97.701 | −11.084 | 4.995  | 1.00 | 43.98 | N |
| ATOM | 40863 | C5  | G A1907 | −98.942 | −11.193 | 5.609  | 1.00 | 43.98 | C |
| ATOM | 40864 | C6  | G A1907 | −99.899 | −10.202 | 5.933  | 1.00 | 43.98 | C |
| ATOM | 40865 | O6  | G A1907 | −99.820 | −8.993  | 5.718  | 1.00 | 43.98 | O |
| ATOM | 40866 | N1  | G A1907 | −101.028| −10.751 | 6.550  | 1.00 | 43.98 | N |
| ATOM | 40867 | C2  | G A1907 | −101.216| −12.090 | 6.825  | 1.00 | 43.98 | C |

TABLE 6-continued

H69 Neomycin Binding Site for Fully-Rotated Ribosome

| ATOM | 40868 | N2 | G A1907 | −102.362 | −12.444 | 7.428 | 1.00 | 43.98 | N |
|---|---|---|---|---|---|---|---|---|---|
| ATOM | 40869 | N3 | G A1907 | −100.334 | −13.023 | 6.528 | 1.00 | 43.98 | N |
| ATOM | 40870 | C4 | G A1907 | −99.234 | −12.507 | 5.931 | 1.00 | 43.98 | C |
| ATOM | 40871 | P | C A1908 | −99.500 | −16.147 | 1.131 | 1.00 | 35.91 | P |
| ATOM | 40872 | OP1 | C A1908 | −100.406 | −17.193 | 0.602 | 1.00 | 35.91 | O |
| ATOM | 40873 | OP2 | C A1908 | −98.150 | −16.020 | 0.549 | 1.00 | 35.91 | O |
| ATOM | 40874 | O5' | C A1908 | −100.215 | −14.738 | 1.099 | 1.00 | 35.91 | O |
| ATOM | 40875 | C5' | C A1908 | −101.468 | −14.582 | 0.480 | 1.00 | 35.91 | C |
| ATOM | 40876 | C4' | C A1908 | −102.581 | −14.537 | 1.491 | 1.00 | 35.91 | C |
| ATOM | 40877 | O4' | C A1908 | −102.037 | −14.307 | 2.825 | 1.00 | 35.91 | O |
| ATOM | 40878 | C3' | C A1908 | −103.580 | −13.407 | 1.289 | 1.00 | 35.91 | C |
| ATOM | 40879 | O3' | C A1908 | −104.591 | −13.730 | 0.363 | 1.00 | 35.91 | O |
| ATOM | 40880 | C2' | C A1908 | −104.070 | −13.135 | 2.694 | 1.00 | 35.91 | C |
| ATOM | 40881 | O2' | C A1908 | −104.961 | −14.154 | 3.125 | 1.00 | 35.91 | O |
| ATOM | 40882 | C1' | C A1908 | −102.758 | −13.274 | 3.454 | 1.00 | 35.91 | C |
| ATOM | 40883 | N1 | C A1908 | −101.945 | −12.053 | 3.343 | 1.00 | 35.20 | N |
| ATOM | 40884 | C2 | C A1908 | −102.453 | −10.796 | 3.662 | 1.00 | 35.20 | C |
| ATOM | 40885 | O2 | C A1908 | −103.619 | −10.707 | 4.069 | 1.00 | 35.20 | O |
| ATOM | 40886 | N3 | C A1908 | −101.638 | −9.723 | 3.517 | 1.00 | 35.20 | N |
| ATOM | 40887 | C4 | C A1908 | −100.389 | −9.890 | 3.065 | 1.00 | 35.20 | C |
| ATOM | 40888 | N4 | C A1908 | −99.588 | −8.845 | 2.932 | 1.00 | 35.20 | N |
| ATOM | 40889 | C5 | C A1908 | −99.860 | −11.147 | 2.719 | 1.00 | 35.20 | C |
| ATOM | 40890 | C6 | C A1908 | −100.672 | −12.188 | 2.866 | 1.00 | 35.20 | C |
| ATOM | 40891 | P | C A1909 | −104.213 | −13.874 | −1.194 | 1.00 | 33.41 | P |
| ATOM | 40892 | OP1 | C A1909 | −104.593 | −15.249 | −1.604 | 1.00 | 33.41 | O |
| ATOM | 40893 | OP2 | C A1909 | −102.794 | −13.433 | −1.368 | 1.00 | 33.41 | O |
| ATOM | 40894 | O5' | C A1909 | −105.166 | −12.812 | −1.874 | 1.00 | 33.41 | O |
| ATOM | 40895 | C5' | C A1909 | −104.851 | −11.438 | −1.817 | 1.00 | 33.41 | C |
| ATOM | 40896 | C4' | C A1909 | −105.818 | −10.683 | −0.951 | 1.00 | 33.41 | C |
| ATOM | 40897 | O4' | C A1909 | −105.330 | −10.657 | 0.420 | 1.00 | 33.41 | O |
| ATOM | 40898 | C3' | C A1909 | −105.994 | −9.219 | −1.330 | 1.00 | 33.41 | C |
| ATOM | 40899 | O3' | C A1909 | −106.998 | −9.029 | −2.288 | 1.00 | 33.41 | O |
| ATOM | 40900 | C2' | C A1909 | −106.274 | −8.549 | −0.011 | 1.00 | 33.41 | C |
| ATOM | 40901 | O2' | C A1909 | −107.611 | −8.791 | 0.396 | 1.00 | 33.41 | O |
| ATOM | 40902 | C1' | C A1909 | −105.321 | −9.328 | 0.890 | 1.00 | 33.41 | C |
| ATOM | 40903 | N1 | C A1909 | −103.922 | −8.821 | 0.760 | 1.00 | 33.15 | N |
| ATOM | 40904 | C2 | C A1909 | −103.596 | −7.454 | 0.808 | 1.00 | 33.15 | C |
| ATOM | 40905 | O2 | C A1909 | −104.469 | −6.613 | 1.014 | 1.00 | 33.15 | O |
| ATOM | 40906 | N3 | C A1909 | −102.318 | −7.075 | 0.644 | 1.00 | 33.15 | N |
| ATOM | 40907 | C4 | C A1909 | −101.377 | −7.995 | 0.423 | 1.00 | 33.15 | C |
| ATOM | 40908 | N4 | C A1909 | −100.110 | −7.609 | 0.256 | 1.00 | 33.15 | N |
| ATOM | 40909 | C5 | C A1909 | −101.664 | −9.383 | 0.352 | 1.00 | 33.15 | C |
| ATOM | 40910 | C6 | C A1909 | −102.937 | −9.745 | 0.512 | 1.00 | 33.15 | C |
| ATOM | 40911 | P | G A1910 | −106.609 | −8.971 | −3.844 | 1.00 | 37.29 | P |
| ATOM | 40912 | OP1 | G A1910 | −107.608 | −9.802 | −4.576 | 1.00 | 37.29 | O |
| ATOM | 40913 | OP2 | G A1910 | −105.174 | −9.324 | −3.952 | 1.00 | 37.29 | O |
| ATOM | 40914 | O5' | G A1910 | −106.819 | −7.431 | −4.181 | 1.00 | 37.29 | O |
| ATOM | 40915 | C5' | G A1910 | −107.827 | −6.699 | −3.510 | 1.00 | 37.29 | C |
| ATOM | 40916 | C4' | G A1910 | −107.428 | −5.269 | −3.273 | 1.00 | 37.29 | C |
| ATOM | 40917 | O4' | G A1910 | −106.515 | −5.162 | −2.146 | 1.00 | 37.28 | O |
| ATOM | 40918 | C3' | G A1910 | −106.674 | −4.597 | −4.383 | 1.00 | 37.28 | C |
| ATOM | 40919 | O3' | G A1910 | −107.485 | −4.285 | −5.485 | 1.00 | 37.28 | O |
| ATOM | 40920 | C2' | G A1910 | −106.096 | −3.392 | −3.662 | 1.00 | 37.28 | C |
| ATOM | 40921 | O2' | G A1910 | −107.100 | −2.432 | −3.389 | 1.00 | 37.28 | O |
| ATOM | 40922 | C1' | G A1910 | −105.674 | −4.038 | −2.342 | 1.00 | 37.29 | C |
| ATOM | 40923 | N9 | G A1910 | −104.280 | −4.492 | −2.406 | 1.00 | 36.74 | N |
| ATOM | 40924 | C8 | G A1910 | −103.758 | −5.740 | −2.573 | 1.00 | 36.74 | C |
| ATOM | 40925 | N7 | G A1910 | −102.460 | −5.721 | −2.627 | 1.00 | 36.74 | N |
| ATOM | 40926 | C5 | G A1910 | −102.111 | −4.387 | −2.513 | 1.00 | 36.74 | C |
| ATOM | 40927 | C6 | G A1910 | −100.846 | −3.733 | −2.501 | 1.00 | 36.74 | C |
| ATOM | 40928 | O6 | G A1910 | −99.706 | −4.210 | −2.601 | 1.00 | 36.74 | O |
| ATOM | 40929 | N1 | G A1910 | −101.000 | −2.353 | −2.347 | 1.00 | 36.74 | N |
| ATOM | 40930 | C2 | G A1910 | −102.207 | −1.685 | −2.223 | 1.00 | 36.74 | C |
| ATOM | 40931 | N2 | G A1910 | −102.170 | −0.349 | −2.085 | 1.00 | 36.74 | N |
| ATOM | 40932 | N3 | G A1910 | −103.381 | −2.290 | −2.232 | 1.00 | 36.74 | N |
| ATOM | 40933 | C4 | G A1910 | −103.242 | −3.624 | −2.380 | 1.00 | 36.74 | C |
| ATOM | 40934 | P | U A1911 | −106.908 | −4.492 | −6.962 | 1.00 | 41.32 | P |
| ATOM | 40935 | OP1 | U A1911 | −108.063 | −4.501 | −7.885 | 1.00 | 41.32 | O |
| ATOM | 40936 | OP2 | U A1911 | −106.012 | −5.673 | −6.925 | 1.00 | 41.32 | O |
| ATOM | 40937 | O5' | U A1911 | −106.063 | −3.167 | −7.165 | 1.00 | 41.32 | O |
| ATOM | 40938 | C5' | U A1911 | −106.529 | −1.944 | −6.624 | 1.00 | 41.32 | C |
| ATOM | 40939 | C4' | U A1911 | −105.443 | −0.914 | −6.584 | 1.00 | 41.32 | C |
| ATOM | 40940 | O4' | U A1911 | −104.510 | −1.221 | −5.528 | 1.00 | 41.32 | O |
| ATOM | 40941 | C3' | U A1911 | −104.583 | −0.831 | −7.818 | 1.00 | 41.32 | C |
| ATOM | 40942 | O3' | U A1911 | −105.202 | −0.108 | −8.848 | 1.00 | 41.32 | O |
| ATOM | 40943 | C2' | U A1911 | −103.318 | −0.180 | −7.298 | 1.00 | 41.32 | C |
| ATOM | 40944 | O2' | U A1911 | −103.486 | 1.227 | −7.187 | 1.00 | 41.32 | O |
| ATOM | 40945 | C1' | U A1911 | −103.224 | −0.772 | −5.890 | 1.00 | 41.32 | C |

TABLE 6-continued

H69 Neomycin Binding Site for Fully-Rotated Ribosome

| ATOM | 40946 | N1 | U A1911 | −102.268 | −1.909 | −5.807 | 1.00 | 41.23 | N |
|---|---|---|---|---|---|---|---|---|---|
| ATOM | 40947 | C2 | U A1911 | −100.939 | −1.553 | −5.624 | 1.00 | 41.23 | C |
| ATOM | 40948 | O2 | U A1911 | −100.552 | −0.397 | −5.566 | 1.00 | 41.23 | O |
| ATOM | 40949 | N3 | U A1911 | −100.067 | −2.604 | −5.536 | 1.00 | 41.23 | N |
| ATOM | 40950 | C4 | U A1911 | −100.378 | −3.941 | −5.600 | 1.00 | 41.23 | C |
| ATOM | 40951 | O4 | U A1911 | −99.450 | −4.734 | −5.501 | 1.00 | 41.23 | O |
| ATOM | 40952 | C5 | U A1911 | −101.768 | −4.251 | −5.775 | 1.00 | 41.23 | C |
| ATOM | 40953 | C6 | U A1911 | −102.648 | −3.242 | −5.867 | 1.00 | 41.23 | C |
| ATOM | 40954 | P | A A1912 | −104.946 | −0.526 | −10.364 | 1.00 | 28.49 | P |
| ATOM | 40955 | OP1 | A A1912 | −105.973 | 0.165 | −11.203 | 1.00 | 28.49 | O |
| ATOM | 40956 | OP2 | A A1912 | −104.874 | −2.011 | −10.392 | 1.00 | 28.49 | O |
| ATOM | 40957 | O5' | A A1912 | −103.508 | 0.089 | −10.651 | 1.00 | 28.49 | O |
| ATOM | 40958 | C5' | A A1912 | −103.253 | 1.459 | −10.428 | 1.00 | 28.49 | C |
| ATOM | 40959 | C4' | A A1912 | −102.201 | 1.975 | −11.359 | 1.00 | 28.49 | C |
| ATOM | 40960 | O4' | A A1912 | −100.904 | 1.750 | −10.791 | 1.00 | 28.49 | O |
| ATOM | 40961 | C3' | A A1912 | −102.121 | 1.313 | −12.720 | 1.00 | 28.49 | C |
| ATOM | 40962 | O3' | A A1912 | −103.097 | 1.813 | −13.629 | 1.00 | 28.49 | O |
| ATOM | 40963 | C2' | A A1912 | −100.675 | 1.588 | −13.151 | 1.00 | 28.49 | C |
| ATOM | 40964 | O2' | A A1912 | −100.578 | 2.803 | −13.874 | 1.00 | 28.49 | O |
| ATOM | 40965 | C1' | A A1912 | −99.950 | 1.760 | −11.812 | 1.00 | 28.49 | C |
| ATOM | 40966 | N9 | A A1912 | −98.962 | 0.708 | −11.550 | 1.00 | 27.91 | N |
| ATOM | 40967 | C8 | A A1912 | −98.969 | −0.642 | −11.765 | 1.00 | 27.91 | C |
| ATOM | 40968 | N7 | A A1912 | −97.855 | −1.213 | −11.374 | 1.00 | 27.91 | N |
| ATOM | 40969 | C5 | A A1912 | −97.081 | −0.176 | −10.869 | 1.00 | 27.91 | C |
| ATOM | 40970 | C6 | A A1912 | −95.802 | −0.104 | −10.297 | 1.00 | 27.91 | C |
| ATOM | 40971 | N6 | A A1912 | −94.984 | −1.143 | −10.104 | 1.00 | 27.91 | N |
| ATOM | 40972 | N1 | A A1912 | −95.362 | 1.109 | −9.925 | 1.00 | 27.91 | N |
| ATOM | 40973 | C2 | A A1912 | −96.144 | 2.168 | −10.106 | 1.00 | 27.91 | C |
| ATOM | 40974 | N3 | A A1912 | −97.354 | 2.223 | −10.628 | 1.00 | 27.91 | N |
| ATOM | 40975 | C4 | A A1912 | −97.760 | 1.006 | −10.986 | 1.00 | 27.91 | C |
| ATOM | 40976 | P | A A1913 | −103.317 | 1.105 | −15.057 | 1.00 | 66.34 | P |
| ATOM | 40977 | OP1 | A A1913 | −104.778 | 0.948 | −15.242 | 1.00 | 66.34 | O |
| ATOM | 40978 | OP2 | A A1913 | −102.463 | −0.102 | −15.082 | 1.00 | 66.34 | O |
| ATOM | 40979 | O5' | A A1913 | −102.752 | 2.179 | −16.079 | 1.00 | 66.34 | O |
| ATOM | 40980 | C5' | A A1913 | −103.582 | 3.221 | −16.571 | 1.00 | 66.34 | C |
| ATOM | 40981 | C4' | A A1913 | −103.815 | 3.087 | −18.053 | 1.00 | 66.34 | C |
| ATOM | 40982 | O4' | A A1913 | −102.818 | 3.865 | −18.761 | 1.00 | 66.34 | O |
| ATOM | 40983 | C3' | A A1913 | −103.711 | 1.660 | −18.599 | 1.00 | 66.34 | C |
| ATOM | 40984 | O3' | A A1913 | −104.674 | 1.466 | −19.643 | 1.00 | 66.34 | O |
| ATOM | 40985 | C2' | A A1913 | −102.293 | 1.611 | −19.167 | 1.00 | 66.34 | C |
| ATOM | 40986 | O2' | A A1913 | −102.082 | 0.659 | −20.196 | 1.00 | 66.34 | O |
| ATOM | 40987 | C1' | A A1913 | −102.122 | 3.033 | −19.670 | 1.00 | 66.34 | C |
| ATOM | 40988 | N9 | A A1913 | −100.735 | 3.471 | −19.715 | 1.00 | 67.09 | N |
| ATOM | 40989 | C8 | A A1913 | −99.646 | 2.711 | −20.091 | 1.00 | 67.09 | C |
| ATOM | 40990 | N7 | A A1913 | −98.520 | 3.373 | −20.051 | 1.00 | 67.09 | N |
| ATOM | 40991 | C5 | A A1913 | −98.915 | 4.639 | −19.613 | 1.00 | 67.09 | C |
| ATOM | 40992 | C6 | A A1913 | −98.165 | 5.788 | −19.369 | 1.00 | 67.09 | C |
| ATOM | 40993 | N6 | A A1913 | −96.834 | 5.774 | −19.554 | 1.00 | 67.09 | N |
| ATOM | 40994 | N1 | A A1913 | −98.847 | 6.886 | −18.939 | 1.00 | 67.08 | N |
| ATOM | 40995 | C2 | A A1913 | −100.181 | 6.816 | −18.779 | 1.00 | 67.09 | C |
| ATOM | 40996 | N3 | A A1913 | −100.997 | 5.790 | −18.980 | 1.00 | 67.09 | N |
| ATOM | 40997 | C4 | A A1913 | −100.281 | 4.725 | −19.396 | 1.00 | 67.09 | C |
| ATOM | 40998 | P | C A1914 | −105.960 | 0.510 | −19.393 | 1.00 | 64.06 | P |
| ATOM | 40999 | OP1 | C A1914 | −107.182 | 1.338 | −19.641 | 1.00 | 64.06 | O |
| ATOM | 41000 | OP2 | C A1914 | −105.784 | −0.128 | −18.050 | 1.00 | 64.06 | O |
| ATOM | 41001 | O5' | C A1914 | −105.798 | −0.595 | −20.531 | 1.00 | 64.06 | O |
| ATOM | 41002 | C5' | C A1914 | −104.513 | −1.078 | −20.891 | 1.00 | 64.06 | C |
| ATOM | 41003 | C4' | C A1914 | −104.521 | −2.567 | −21.101 | 1.00 | 64.06 | C |
| ATOM | 41004 | O4' | C A1914 | −103.630 | −2.911 | −22.195 | 1.00 | 64.06 | O |
| ATOM | 41005 | C3' | C A1914 | −104.012 | −3.413 | −19.946 | 1.00 | 64.06 | C |
| ATOM | 41006 | O3' | C A1914 | −104.963 | −3.584 | −18.905 | 1.00 | 64.06 | O |
| ATOM | 41007 | C2' | C A1914 | −103.640 | −4.707 | −20.652 | 1.00 | 64.06 | C |
| ATOM | 41008 | O2' | C A1914 | −104.803 | −5.458 | −20.967 | 1.00 | 64.06 | O |
| ATOM | 41009 | C1' | C A1914 | −103.051 | −4.176 | −21.957 | 1.00 | 64.06 | C |
| ATOM | 41010 | N1 | C A1914 | −101.568 | −4.028 | −21.902 | 1.00 | 63.15 | N |
| ATOM | 41011 | C2 | C A1914 | −100.778 | −4.976 | −22.588 | 1.00 | 63.15 | C |
| ATOM | 41012 | O2 | C A1914 | −101.322 | −5.911 | −23.202 | 1.00 | 63.15 | O |
| ATOM | 41013 | N3 | C A1914 | −99.427 | −4.874 | −22.570 | 1.00 | 63.15 | N |
| ATOM | 41014 | C4 | C A1914 | −98.845 | −3.874 | −21.911 | 1.00 | 63.15 | C |
| ATOM | 41015 | N4 | C A1914 | −97.503 | −3.826 | −21.940 | 1.00 | 63.15 | N |
| ATOM | 41016 | C5 | C A1914 | −99.622 | −2.890 | −21.209 | 1.00 | 63.15 | C |
| ATOM | 41017 | C6 | C A1914 | −100.962 | −2.998 | −21.228 | 1.00 | 63.15 | C |
| ATOM | 41018 | P | U A1915 | −104.618 | −4.540 | −17.652 | 1.00 | 50.19 | P |
| ATOM | 41019 | OP1 | U A1915 | −105.832 | −4.587 | −16.774 | 1.00 | 50.19 | O |
| ATOM | 41020 | OP2 | U A1915 | −103.337 | −4.051 | −17.075 | 1.00 | 50.19 | O |
| ATOM | 41021 | O5' | U A1915 | −104.388 | −5.960 | −18.348 | 1.00 | 50.19 | O |
| ATOM | 41022 | C5' | U A1915 | −104.003 | −7.098 | −17.588 | 1.00 | 50.19 | C |
| ATOM | 41023 | C4' | U A1915 | −103.236 | −8.090 | −18.426 | 1.00 | 50.19 | C |

TABLE 6-continued

H69 Neomycin Binding Site for Fully-Rotated Ribosome

| ATOM | 41024 | O4' | U A1915 | −102.549 | −7.397 | −19.499 | 1.00 | 50.19 | O |
| --- | --- | --- | --- | --- | --- | --- | --- | --- | --- |
| ATOM | 41025 | C3' | U A1915 | −102.133 | −8.844 | −17.704 | 1.00 | 50.19 | C |
| ATOM | 41026 | O3' | U A1915 | −102.606 | −9.956 | −16.990 | 1.00 | 50.19 | O |
| ATOM | 41027 | C2' | U A1915 | −101.181 | −9.208 | −18.827 | 1.00 | 50.19 | C |
| ATOM | 41028 | O2' | U A1915 | −101.676 | −10.310 | −19.563 | 1.00 | 50.19 | O |
| ATOM | 41029 | C1' | U A1915 | −101.268 | −7.963 | −19.701 | 1.00 | 50.19 | C |
| ATOM | 41030 | N1 | U A1915 | −100.226 | −6.943 | −19.339 | 1.00 | 50.55 | N |
| ATOM | 41031 | C2 | U A1915 | −98.869 | −7.294 | −19.304 | 1.00 | 50.55 | C |
| ATOM | 41032 | O2 | U A1915 | −98.424 | −8.407 | −19.545 | 1.00 | 50.55 | O |
| ATOM | 41033 | N3 | U A1915 | −98.014 | −6.275 | −18.956 | 1.00 | 50.55 | N |
| ATOM | 41034 | C4 | U A1915 | −98.338 | −4.969 | −18.647 | 1.00 | 50.55 | C |
| ATOM | 41035 | O4 | U A1915 | −97.440 | −4.178 | −18.354 | 1.00 | 50.55 | O |
| ATOM | 41036 | C5 | U A1915 | −99.737 | −4.670 | −18.700 | 1.00 | 50.55 | C |
| ATOM | 41037 | C6 | U A1915 | −100.601 | −5.640 | −19.034 | 1.00 | 50.55 | C |
| ATOM | 41038 | P | A A1916 | −102.792 | −9.865 | −15.403 | 1.00 | 36.99 | P |
| ATOM | 41039 | OP1 | A A1916 | −103.479 | −11.101 | −14.985 | 1.00 | 36.99 | O |
| ATOM | 41040 | OP2 | A A1916 | −103.425 | −8.556 | −15.107 | 1.00 | 36.99 | O |
| ATOM | 41041 | O5' | A A1916 | −101.303 | −9.883 | −14.867 | 1.00 | 36.99 | O |
| ATOM | 41042 | C5' | A A1916 | −100.559 | −11.079 | −14.906 | 1.00 | 36.99 | C |
| ATOM | 41043 | C4' | A A1916 | −99.103 | −10.807 | −15.088 | 1.00 | 36.99 | C |
| ATOM | 41044 | O4' | A A1916 | −98.901 | −9.886 | −16.192 | 1.00 | 36.99 | O |
| ATOM | 41045 | C3' | A A1916 | −98.419 | −10.135 | −13.926 | 1.00 | 36.99 | C |
| ATOM | 41046 | O3' | A A1916 | −98.121 | −11.031 | −12.884 | 1.00 | 36.99 | O |
| ATOM | 41047 | C2' | A A1916 | −97.196 | −9.536 | −14.586 | 1.00 | 36.99 | C |
| ATOM | 41048 | O2' | A A1916 | −96.226 | −10.531 | −14.846 | 1.00 | 36.99 | O |
| ATOM | 41049 | C1' | A A1916 | −97.791 | −9.060 | −15.911 | 1.00 | 36.99 | C |
| ATOM | 41050 | N9 | A A1916 | −98.264 | −7.682 | −15.790 | 1.00 | 37.66 | N |
| ATOM | 41051 | C8 | A A1916 | −99.537 | −7.185 | −15.847 | 1.00 | 37.66 | C |
| ATOM | 41052 | N7 | A A1916 | −99.593 | −5.893 | −15.623 | 1.00 | 37.66 | N |
| ATOM | 41053 | C5 | A A1916 | −98.273 | −5.534 | −15.375 | 1.00 | 37.66 | C |
| ATOM | 41054 | C6 | A A1916 | −97.663 | −4.307 | −15.072 | 1.00 | 37.66 | C |
| ATOM | 41055 | N6 | A A1916 | −98.330 | −3.155 | −14.956 | 1.00 | 37.66 | N |
| ATOM | 41056 | N1 | A A1916 | −96.323 | −4.318 | −14.887 | 1.00 | 37.66 | N |
| ATOM | 41057 | C2 | A A1916 | −95.652 | −5.480 | −14.999 | 1.00 | 37.66 | C |
| ATOM | 41058 | N3 | A A1916 | −96.117 | −6.696 | −15.285 | 1.00 | 37.66 | N |
| ATOM | 41059 | C4 | A A1916 | −97.447 | −6.640 | −15.463 | 1.00 | 37.66 | C |
| ATOM | 41060 | P | U A1917 | −98.719 | −10.782 | −11.417 | 1.00 | 30.02 | P |
| ATOM | 41061 | OP1 | U A1917 | −98.859 | −12.125 | −10.763 | 1.00 | 30.02 | O |
| ATOM | 41062 | OP2 | U A1917 | −99.937 | −9.918 | −11.580 | 1.00 | 30.02 | O |
| ATOM | 41063 | O5' | U A1917 | −97.558 | −9.957 | −10.706 | 1.00 | 30.02 | O |
| ATOM | 41064 | C5' | U A1917 | −96.215 | −10.394 | −10.778 | 1.00 | 30.02 | C |
| ATOM | 41065 | C4' | U A1917 | −95.278 | −9.239 | −10.936 | 1.00 | 30.02 | C |
| ATOM | 41066 | O4' | U A1917 | −95.691 | −8.425 | −12.060 | 1.00 | 30.02 | O |
| ATOM | 41067 | C3' | U A1917 | −95.233 | −8.266 | −9.783 | 1.00 | 30.02 | C |
| ATOM | 41068 | O3' | U A1917 | −94.438 | −8.723 | −8.718 | 1.00 | 30.02 | O |
| ATOM | 41069 | C2' | U A1917 | −94.687 | −7.026 | −10.442 | 1.00 | 30.02 | C |
| ATOM | 41070 | O2' | U A1917 | −93.298 | −7.156 | −10.649 | 1.00 | 30.02 | O |
| ATOM | 41071 | C1' | U A1917 | −95.382 | −7.076 | −11.800 | 1.00 | 30.02 | C |
| ATOM | 41072 | N1 | U A1917 | −96.642 | −6.277 | −11.816 | 1.00 | 30.05 | N |
| ATOM | 41073 | C2 | U A1917 | −96.542 | −4.920 | −11.520 | 1.00 | 30.05 | C |
| ATOM | 41074 | O2 | U A1917 | −95.484 | −4.363 | −11.260 | 1.00 | 30.05 | O |
| ATOM | 41075 | N3 | U A1917 | −97.723 | −4.228 | −11.530 | 1.00 | 30.05 | N |
| ATOM | 41076 | C4 | U A1917 | −98.963 | −4.721 | −11.815 | 1.00 | 30.05 | C |
| ATOM | 41077 | O4 | U A1917 | −99.905 | −3.945 | −11.790 | 1.00 | 30.05 | O |
| ATOM | 41078 | C5 | U A1917 | −99.017 | −6.114 | −12.114 | 1.00 | 30.05 | C |
| ATOM | 41079 | C6 | U A1917 | −97.881 | −6.825 | −12.105 | 1.00 | 30.05 | C |
| ATOM | 41080 | P | A A1918 | −94.870 | −8.410 | −7.211 | 1.00 | 31.13 | P |
| ATOM | 41081 | OP1 | A A1918 | −93.796 | −8.908 | −6.325 | 1.00 | 31.14 | O |
| ATOM | 41082 | OP2 | A A1918 | −96.242 | −8.926 | −7.041 | 1.00 | 31.14 | O |
| ATOM | 41083 | O5' | A A1918 | −94.897 | −6.831 | −7.176 | 1.00 | 31.13 | O |
| ATOM | 41084 | C5' | A A1918 | −93.714 | −6.074 | −7.385 | 1.00 | 31.13 | C |
| ATOM | 41085 | C4' | A A1918 | −93.982 | −4.607 | −7.217 | 1.00 | 31.13 | C |
| ATOM | 41086 | O4' | A A1918 | −95.048 | −4.223 | −8.124 | 1.00 | 31.13 | O |
| ATOM | 41087 | C3' | A A1918 | −94.443 | −4.204 | −5.830 | 1.00 | 31.14 | C |
| ATOM | 41088 | O3' | A A1918 | −93.916 | −2.927 | −5.511 | 1.00 | 31.14 | O |
| ATOM | 41089 | C2' | A A1918 | −95.959 | −4.124 | −5.973 | 1.00 | 31.14 | C |
| ATOM | 41090 | O2' | A A1918 | −96.579 | −3.244 | −5.073 | 1.00 | 31.13 | O |
| ATOM | 41091 | C1' | A A1918 | −96.115 | −3.650 | −7.403 | 1.00 | 31.14 | C |
| ATOM | 41092 | N9 | A A1918 | −97.369 | −4.056 | −8.037 | 1.00 | 31.95 | N |
| ATOM | 41093 | C8 | A A1918 | −97.713 | −5.286 | −8.508 | 1.00 | 31.95 | C |
| ATOM | 41094 | N7 | A A1918 | −98.908 | −5.329 | −9.053 | 1.00 | 31.95 | N |
| ATOM | 41095 | C5 | A A1918 | −99.393 | −4.041 | −8.939 | 1.00 | 31.95 | C |
| ATOM | 41096 | C6 | A A1918 | −100.611 | −3.431 | −9.321 | 1.00 | 31.95 | C |
| ATOM | 41097 | N6 | A A1918 | −101.636 | −4.038 | −9.923 | 1.00 | 31.95 | N |
| ATOM | 41098 | N1 | A A1918 | −100.761 | −2.120 | −9.070 | 1.00 | 31.95 | N |
| ATOM | 41099 | C2 | A A1918 | −99.753 | −1.479 | −8.463 | 1.00 | 31.95 | C |
| ATOM | 41100 | N3 | A A1918 | −98.572 | −1.949 | −8.055 | 1.00 | 31.95 | N |
| ATOM | 41101 | C4 | A A1918 | −98.445 | −3.254 | −8.323 | 1.00 | 31.95 | C |

TABLE 6-continued

H69 Neomycin Binding Site for Fully-Rotated Ribosome

| ATOM | 41102 | P   | A A1919 | −92.596  | −2.812 | −4.603 | 1.00 | 23.80 | P |
|------|-------|-----|---------|----------|--------|--------|------|-------|---|
| ATOM | 41103 | OP1 | A A1919 | −91.434  | −3.220 | −5.448 | 1.00 | 23.80 | O |
| ATOM | 41104 | OP2 | A A1919 | −92.872  | −3.558 | −3.348 | 1.00 | 23.80 | O |
| ATOM | 41105 | O5' | A A1919 | −92.522  | −1.247 | −4.291 | 1.00 | 23.80 | O |
| ATOM | 41106 | C5' | A A1919 | −91.306  | −0.622 | −3.878 | 1.00 | 23.80 | C |
| ATOM | 41107 | C4' | A A1919 | −91.191  | 0.775  | −4.441 | 1.00 | 23.80 | C |
| ATOM | 41108 | O4' | A A1919 | −91.456  | 0.723  | −5.869 | 1.00 | 23.80 | O |
| ATOM | 41109 | C3' | A A1919 | −92.191  | 1.809  | −3.915 | 1.00 | 23.80 | C |
| ATOM | 41110 | O3' | A A1919 | −91.774  | 2.445  | −2.721 | 1.00 | 23.80 | O |
| ATOM | 41111 | C2' | A A1919 | −92.298  | 2.763  | −5.091 | 1.00 | 23.80 | C |
| ATOM | 41112 | O2' | A A1919 | −91.130  | 3.567  | −5.199 | 1.00 | 23.80 | O |
| ATOM | 41113 | C1' | A A1919 | −92.297  | 1.787  | −6.248 | 1.00 | 23.80 | C |
| ATOM | 41114 | N9  | A A1919 | −93.641  | 1.250  | −6.494 | 1.00 | 23.52 | N |
| ATOM | 41115 | C8  | A A1919 | −94.017  | −0.045 | −6.750 | 1.00 | 23.52 | C |
| ATOM | 41116 | N7  | A A1919 | −95.311  | −0.190 | −6.886 | 1.00 | 23.52 | N |
| ATOM | 41117 | C5  | A A1919 | −95.807  | 1.094  | −6.697 | 1.00 | 23.52 | C |
| ATOM | 41118 | C6  | A A1919 | −97.106  | 1.616  | −6.712 | 1.00 | 23.52 | C |
| ATOM | 41119 | N6  | A A1919 | −98.209  | 0.886  | −6.937 | 1.00 | 23.52 | N |
| ATOM | 41120 | N1  | A A1919 | −97.222  | 2.941  | −6.486 | 1.00 | 23.52 | N |
| ATOM | 41121 | C2  | A A1919 | −96.132  | 3.675  | −6.273 | 1.00 | 23.52 | C |
| ATOM | 41122 | N3  | A A1919 | −94.870  | 3.294  | −6.244 | 1.00 | 23.52 | N |
| ATOM | 41123 | C4  | A A1919 | −94.782  | 1.986  | −6.457 | 1.00 | 23.52 | C |
| ATOM | 41124 | P   | C A1920 | −92.289  | 1.931  | −1.293 | 1.00 | 19.37 | P |
| ATOM | 41125 | OP1 | C A1920 | −91.485  | 2.625  | −0.268 | 1.00 | 19.37 | O |
| ATOM | 41126 | OP2 | C A1920 | −92.276  | 0.452  | −1.315 | 1.00 | 19.37 | O |
| ATOM | 41127 | O5' | C A1920 | −93.782  | 2.437  | −1.245 | 1.00 | 19.37 | O |
| ATOM | 41128 | C5' | C A1920 | −94.190  | 3.559  | −1.982 | 1.00 | 19.37 | C |
| ATOM | 41129 | C4' | C A1920 | −95.678  | 3.619  | −2.048 | 1.00 | 19.37 | C |
| ATOM | 41130 | O4' | C A1920 | −96.144  | 2.780  | −3.145 | 1.00 | 19.37 | O |
| ATOM | 41131 | C3' | C A1920 | −96.401  | 3.063  | −0.839 | 1.00 | 19.37 | C |
| ATOM | 41132 | O3' | C A1920 | −96.446  | 3.959  | 0.266  | 1.00 | 19.37 | O |
| ATOM | 41133 | C2' | C A1920 | −97.760  | 2.703  | −1.428 | 1.00 | 19.37 | C |
| ATOM | 41134 | O2' | C A1920 | −98.520  | 3.870  | −1.707 | 1.00 | 19.37 | O |
| ATOM | 41135 | C1' | C A1920 | −97.325  | 2.093  | −2.761 | 1.00 | 19.37 | C |
| ATOM | 41136 | N1  | C A1920 | −97.021  | 0.609  | −2.637 | 1.00 | 19.84 | N |
| ATOM | 41137 | C2  | C A1920 | −98.087  | −0.310 | −2.527 | 1.00 | 19.84 | C |
| ATOM | 41138 | O2  | C A1920 | −99.239  | 0.148  | −2.565 | 1.00 | 19.84 | O |
| ATOM | 41139 | N3  | C A1920 | −97.837  | −1.652 | −2.383 | 1.00 | 19.84 | N |
| ATOM | 41140 | C4  | C A1920 | −96.566  | −2.111 | −2.347 | 1.00 | 19.84 | C |
| ATOM | 41141 | N4  | C A1920 | −96.329  | −3.423 | −2.194 | 1.00 | 19.84 | N |
| ATOM | 41142 | C5  | C A1920 | −95.459  | −1.211 | −2.466 | 1.00 | 19.84 | C |
| ATOM | 41143 | C6  | C A1920 | −95.726  | 0.108  | −2.596 | 1.00 | 19.84 | C |
| ATOM | 41144 | P   | G A1921 | −96.436  | 3.384  | 1.780  | 1.00 | 18.78 | P |
| ATOM | 41145 | OP1 | G A1921 | −96.230  | 4.534  | 2.694  | 1.00 | 18.78 | O |
| ATOM | 41146 | OP2 | G A1921 | −95.478  | 2.269  | 1.817  | 1.00 | 18.78 | O |
| ATOM | 41147 | O5' | G A1921 | −97.911  | 2.840  | 1.940  | 1.00 | 18.78 | O |
| ATOM | 41148 | C5' | G A1921 | −99.002  | 3.681  | 1.620  | 1.00 | 18.78 | C |
| ATOM | 41149 | C4' | G A1921 | −100.311 | 2.969  | 1.752  | 1.00 | 18.78 | C |
| ATOM | 41150 | O4' | G A1921 | −100.514 | 2.107  | 0.610  | 1.00 | 18.78 | O |
| ATOM | 41151 | C3' | G A1921 | −100.440 | 2.031  | 2.933  | 1.00 | 18.78 | C |
| ATOM | 41152 | O3' | G A1921 | −100.716 | 2.694  | 4.146  | 1.00 | 18.78 | O |
| ATOM | 41153 | C2' | G A1921 | −101.552 | 1.112  | 2.475  | 1.00 | 18.78 | C |
| ATOM | 41154 | O2' | G A1921 | −102.806 | 1.771  | 2.517  | 1.00 | 18.78 | O |
| ATOM | 41155 | C1' | G A1921 | −101.170 | 0.926  | 1.022  | 1.00 | 18.78 | C |
| ATOM | 41156 | N9  | G A1921 | −100.251 | −0.200 | 0.862  | 1.00 | 19.32 | N |
| ATOM | 41157 | C8  | G A1921 | −98.887  | −0.187 | 0.823  | 1.00 | 19.32 | C |
| ATOM | 41158 | N7  | G A1921 | −98.383  | −1.377 | 0.681  | 1.00 | 19.32 | N |
| ATOM | 41159 | C5  | G A1921 | −99.489  | −2.193 | 0.645  | 1.00 | 19.32 | C |
| ATOM | 41160 | C6  | G A1921 | −99.580  | −3.581 | 0.507  | 1.00 | 19.32 | C |
| ATOM | 41161 | O6  | G A1921 | −98.652  | −4.381 | 0.389  | 1.00 | 19.32 | O |
| ATOM | 41162 | N1  | G A1921 | −100.900 | −4.024 | 0.514  | 1.00 | 19.32 | N |
| ATOM | 41163 | C2  | G A1921 | −102.002 | −3.225 | 0.644  | 1.00 | 19.32 | C |
| ATOM | 41164 | N2  | G A1921 | −103.189 | −3.849 | 0.632  | 1.00 | 19.32 | N |
| ATOM | 41165 | N3  | G A1921 | −101.925 | −1.914 | 0.765  | 1.00 | 19.32 | N |
| ATOM | 41166 | C4  | G A1921 | −100.648 | −1.488 | 0.758  | 1.00 | 19.32 | C |
| ATOM | 41167 | P   | G A1922 | −100.684 | 1.881  | 5.528  | 1.00 | 37.73 | P |
| ATOM | 41168 | OP1 | G A1922 | −100.369 | 2.855  | 6.593  | 1.00 | 37.73 | O |
| ATOM | 41169 | OP2 | G A1922 | −99.793  | 0.711  | 5.340  | 1.00 | 37.73 | O |
| ATOM | 41170 | O5' | G A1922 | −102.177 | 1.394  | 5.675  | 1.00 | 37.73 | O |
| ATOM | 41171 | C5' | G A1922 | −102.487 | 0.279  | 6.468  | 1.00 | 37.73 | C |
| ATOM | 41172 | C4' | G A1922 | −103.640 | −0.478 | 5.895  | 1.00 | 37.73 | C |
| ATOM | 41173 | O4' | G A1922 | −103.377 | −0.801 | 4.509  | 1.00 | 37.73 | O |
| ATOM | 41174 | C3' | G A1922 | −103.912 | −1.812 | 6.542  | 1.00 | 37.73 | C |
| ATOM | 41175 | O3' | G A1922 | −104.661 | −1.685 | 7.713  | 1.00 | 37.73 | O |
| ATOM | 41176 | C2' | G A1922 | −104.606 | −2.584 | 5.442  | 1.00 | 37.73 | C |
| ATOM | 41177 | O2' | G A1922 | −105.954 | −2.157 | 5.291  | 1.00 | 37.73 | O |
| ATOM | 41178 | C1' | G A1922 | −103.808 | −2.118 | 4.236  | 1.00 | 37.73 | C |
| ATOM | 41179 | N9  | G A1922 | −102.614 | −2.945 | 4.037  | 1.00 | 38.39 | N |

TABLE 6-continued

H69 Neomycin Binding Site for Fully-Rotated Ribosome

| ATOM | 41180 | C8 | G A1922 | −101.348 | −2.433 | 3.988 | 1.00 | 38.39 | C |
|---|---|---|---|---|---|---|---|---|---|
| ATOM | 41181 | N7 | G A1922 | −100.440 | −3.342 | 3.811 | 1.00 | 38.39 | N |
| ATOM | 41182 | C5 | G A1922 | −101.153 | −4.531 | 3.753 | 1.00 | 38.39 | C |
| ATOM | 41183 | C6 | G A1922 | −100.665 | −5.854 | 3.581 | 1.00 | 38.39 | C |
| ATOM | 41184 | O6 | G A1922 | −99.480 | −6.206 | 3.445 | 1.00 | 38.39 | O |
| ATOM | 41185 | N1 | G A1922 | −101.721 | −6.768 | 3.572 | 1.00 | 38.39 | N |
| ATOM | 41186 | C2 | G A1922 | −103.050 | −6.446 | 3.719 | 1.00 | 38.39 | C |
| ATOM | 41187 | N2 | G A1922 | −103.899 | −7.485 | 3.686 | 1.00 | 38.39 | N |
| ATOM | 41188 | N3 | G A1922 | −103.507 | −5.210 | 3.887 | 1.00 | 38.39 | N |
| ATOM | 41189 | C4 | G A1922 | −102.509 | −4.305 | 3.894 | 1.00 | 38.39 | C |
| ATOM | 41190 | P | U A1923 | −103.917 | −1.629 | 9.118 | 1.00 | 33.93 | P |
| ATOM | 41191 | OP1 | U A1923 | −104.740 | −0.762 | 10.004 | 1.00 | 33.93 | O |
| ATOM | 41192 | OP2 | U A1923 | −102.500 | −1.249 | 8.862 | 1.00 | 33.93 | O |
| ATOM | 41193 | O5' | U A1923 | −104.007 | −3.144 | 9.583 | 1.00 | 33.93 | O |
| ATOM | 41194 | C5' | U A1923 | −105.225 | −3.855 | 9.443 | 1.00 | 33.93 | C |
| ATOM | 41195 | C4' | U A1923 | −105.005 | −5.239 | 8.908 | 1.00 | 33.93 | C |
| ATOM | 41196 | O4' | U A1923 | −104.275 | −5.176 | 7.672 | 1.00 | 33.93 | O |
| ATOM | 41197 | C3' | U A1923 | −104.183 | −6.163 | 9.786 | 1.00 | 33.93 | C |
| ATOM | 41198 | O3' | U A1923 | −104.964 | −6.765 | 10.798 | 1.00 | 33.93 | O |
| ATOM | 41199 | C2' | U A1923 | −103.602 | −7.170 | 8.798 | 1.00 | 33.93 | C |
| ATOM | 41200 | O2' | U A1923 | −104.463 | −8.288 | 8.634 | 1.00 | 33.93 | O |
| ATOM | 41201 | C1' | U A1923 | −103.554 | −6.369 | 7.487 | 1.00 | 33.93 | C |
| ATOM | 41202 | N1 | U A1923 | −102.187 | −6.033 | 7.091 | 1.00 | 34.23 | N |
| ATOM | 41203 | C2 | U A1923 | −101.272 | −7.060 | 7.048 | 1.00 | 34.23 | C |
| ATOM | 41204 | O2 | U A1923 | −101.560 | −8.213 | 7.328 | 1.00 | 34.23 | O |
| ATOM | 41205 | N3 | U A1923 | −100.010 | −6.678 | 6.675 | 1.00 | 34.23 | N |
| ATOM | 41206 | C4 | U A1923 | −99.593 | −5.407 | 6.343 | 1.00 | 34.23 | C |
| ATOM | 41207 | O4 | U A1923 | −98.413 | −5.218 | 6.012 | 1.00 | 34.23 | O |
| ATOM | 41208 | C5 | U A1923 | −100.615 | −4.409 | 6.414 | 1.00 | 34.23 | C |
| ATOM | 41209 | C6 | U A1923 | −101.851 | −4.752 | 6.770 | 1.00 | 34.23 | C |
| ATOM | 41210 | P | C A1924 | −104.585 | −6.596 | 12.348 | 1.00 | 47.21 | P |
| ATOM | 41211 | OP1 | C A1924 | −105.750 | −5.976 | 13.016 | 1.00 | 47.21 | O |
| ATOM | 41212 | OP2 | C A1924 | −103.273 | −5.913 | 12.422 | 1.00 | 47.21 | O |
| ATOM | 41213 | O5' | C A1924 | −104.442 | −8.100 | 12.809 | 1.00 | 47.21 | O |
| ATOM | 41214 | C5' | C A1924 | −105.225 | −9.105 | 12.190 | 1.00 | 47.21 | C |
| ATOM | 41215 | C4' | C A1924 | −104.384 | −10.274 | 11.770 | 1.00 | 47.21 | C |
| ATOM | 41216 | O4' | C A1924 | −103.573 | −9.914 | 10.634 | 1.00 | 47.21 | O |
| ATOM | 41217 | C3' | C A1924 | −103.391 | −10.768 | 12.804 | 1.00 | 47.21 | C |
| ATOM | 41218 | O3' | C A1924 | −103.990 | −11.634 | 13.747 | 1.00 | 47.21 | O |
| ATOM | 41219 | C2' | C A1924 | −102.312 | −11.438 | 11.962 | 1.00 | 47.21 | C |
| ATOM | 41220 | O2' | C A1924 | −102.660 | −12.784 | 11.662 | 1.00 | 47.21 | O |
| ATOM | 41221 | C1' | C A1924 | −102.356 | −10.621 | 10.671 | 1.00 | 47.21 | C |
| ATOM | 41222 | N1 | C A1924 | −101.251 | −9.658 | 10.567 | 1.00 | 47.75 | N |
| ATOM | 41223 | C2 | C A1924 | −100.201 | −10.063 | 9.758 | 1.00 | 47.75 | C |
| ATOM | 41224 | O2 | C A1924 | −100.272 | −11.190 | 9.251 | 1.00 | 47.75 | O |
| ATOM | 41225 | N3 | C A1924 | −99.154 | −9.224 | 9.573 | 1.00 | 47.75 | N |
| ATOM | 41226 | C4 | C A1924 | −99.137 | −8.017 | 10.155 | 1.00 | 47.75 | C |
| ATOM | 41227 | N4 | C A1924 | −98.064 | −7.246 | 9.928 | 1.00 | 47.75 | N |
| ATOM | 41228 | C5 | C A1924 | −100.219 | −7.575 | 10.990 | 1.00 | 47.75 | C |
| ATOM | 41229 | C6 | C A1924 | −101.254 | −8.420 | 11.162 | 1.00 | 47.75 | C |
| ATOM | 41230 | P | C A1925 | −103.283 | −11.894 | 15.149 | 1.00 | 99.05 | P |
| ATOM | 41231 | OP1 | C A1925 | −103.645 | −13.272 | 15.570 | 1.00 | 99.05 | O |
| ATOM | 41232 | OP2 | C A1925 | −103.631 | −10.753 | 16.037 | 1.00 | 99.05 | O |
| ATOM | 41233 | O5' | C A1925 | −101.747 | −11.823 | 14.763 | 1.00 | 99.05 | O |
| ATOM | 41234 | C5' | C A1925 | −101.073 | −10.573 | 14.720 | 1.00 | 99.05 | C |
| ATOM | 41235 | C4' | C A1925 | −100.095 | −10.445 | 15.857 | 1.00 | 99.05 | C |
| ATOM | 41236 | O4' | C A1925 | −99.546 | −9.107 | 15.853 | 1.00 | 99.05 | O |
| ATOM | 41237 | C3' | C A1925 | −100.684 | −10.686 | 17.240 | 1.00 | 99.05 | C |
| ATOM | 41238 | O3' | C A1925 | −99.769 | −11.439 | 18.043 | 1.00 | 99.05 | O |
| ATOM | 41239 | C2' | C A1925 | −100.891 | −9.281 | 17.817 | 1.00 | 99.05 | C |
| ATOM | 41240 | O2' | C A1925 | −100.696 | −9.192 | 19.217 | 1.00 | 99.05 | O |
| ATOM | 41241 | C1' | C A1925 | −99.880 | −8.412 | 17.041 | 1.00 | 99.05 | C |
| ATOM | 41242 | N1 | C A1925 | −100.420 | −7.078 | 16.626 | 1.00 | 98.62 | N |
| ATOM | 41243 | C2 | C A1925 | −99.775 | −5.864 | 16.952 | 1.00 | 98.62 | C |
| ATOM | 41244 | O2 | C A1925 | −98.736 | −5.873 | 17.642 | 1.00 | 98.62 | O |
| ATOM | 41245 | N3 | C A1925 | −100.321 | −4.694 | 16.510 | 1.00 | 98.62 | N |
| ATOM | 41246 | C4 | C A1925 | −101.442 | −4.689 | 15.771 | 1.00 | 98.62 | C |
| ATOM | 41247 | N4 | C A1925 | −101.940 | −3.514 | 15.364 | 1.00 | 98.62 | N |
| ATOM | 41248 | C5 | C A1925 | −102.105 | −5.902 | 15.415 | 1.00 | 98.62 | C |
| ATOM | 41249 | C6 | C A1925 | −101.561 | −7.049 | 15.850 | 1.00 | 98.62 | C |
| ATOM | 41250 | P | U A1926 | −100.085 | −12.988 | 18.367 | 1.00 | 85.68 | P |
| ATOM | 41251 | OP1 | U A1926 | −100.409 | −13.654 | 17.078 | 1.00 | 85.68 | O |
| ATOM | 41252 | OP2 | U A1926 | −101.090 | −13.004 | 19.453 | 1.00 | 85.68 | O |
| ATOM | 41253 | O5' | U A1926 | −98.707 | −13.538 | 18.912 | 1.00 | 85.68 | O |
| ATOM | 41254 | C5' | U A1926 | −97.616 | −12.674 | 19.120 | 1.00 | 85.68 | C |
| ATOM | 41255 | C4' | U A1926 | −96.429 | −13.080 | 18.294 | 1.00 | 85.68 | C |
| ATOM | 41256 | O4' | U A1926 | −96.855 | −13.771 | 17.078 | 1.00 | 85.68 | O |
| ATOM | 41257 | C3' | U A1926 | −95.599 | −11.945 | 17.760 | 1.00 | 85.68 | C |

TABLE 6-continued

H69 Neomycin Binding Site for Fully-Rotated Ribosome

| ATOM | 41258 | O3' | U A1926 | −94.819 | −11.311 | 18.740 | 1.00 | 85.68 | O |
|---|---|---|---|---|---|---|---|---|---|
| ATOM | 41259 | C2' | U A1926 | −94.820 | −12.622 | 16.648 | 1.00 | 85.68 | C |
| ATOM | 41260 | O2' | U A1926 | −93.825 | −13.495 | 17.180 | 1.00 | 85.68 | O |
| ATOM | 41261 | C1' | U A1926 | −95.942 | −13.467 | 16.023 | 1.00 | 85.68 | C |
| ATOM | 41262 | N1 | U A1926 | −96.685 | −12.719 | 14.940 | 1.00 | 85.26 | N |
| ATOM | 41263 | C2 | U A1926 | −96.020 | −11.840 | 14.068 | 1.00 | 85.26 | C |
| ATOM | 41264 | O2 | U A1926 | −94.820 | −11.609 | 14.087 | 1.00 | 85.26 | O |
| ATOM | 41265 | N3 | U A1926 | −96.807 | −11.210 | 13.130 | 1.00 | 85.26 | N |
| ATOM | 41266 | C4 | U A1926 | −98.163 | −11.354 | 12.961 | 1.00 | 85.26 | C |
| ATOM | 41267 | O4 | U A1926 | −98.726 | −10.720 | 12.073 | 1.00 | 85.26 | O |
| ATOM | 41268 | C5 | U A1926 | −98.788 | −12.265 | 13.868 | 1.00 | 85.26 | C |
| ATOM | 41269 | C6 | U A1926 | −98.051 | −12.892 | 14.796 | 1.00 | 85.26 | C |
| ATOM | 41270 | P | A A1927 | −95.141 | −9.786 | 19.091 | 1.00 | 19.33 | P |
| ATOM | 41271 | OP1 | A A1927 | −95.899 | −9.774 | 20.377 | 1.00 | 19.33 | O |
| ATOM | 41272 | OP2 | A A1927 | −95.773 | −9.191 | 17.876 | 1.00 | 19.33 | O |
| ATOM | 41273 | O5' | A A1927 | −93.693 | −9.170 | 19.308 | 1.00 | 19.33 | O |
| ATOM | 41274 | C5' | A A1927 | −93.509 | −7.767 | 19.417 | 1.00 | 19.33 | C |
| ATOM | 41275 | C4' | A A1927 | −92.318 | −7.312 | 18.620 | 1.00 | 19.33 | C |
| ATOM | 41276 | O4' | A A1927 | −91.248 | −8.274 | 18.768 | 1.00 | 19.33 | O |
| ATOM | 41277 | C3' | A A1927 | −92.521 | −7.196 | 17.122 | 1.00 | 19.33 | C |
| ATOM | 41278 | O3' | A A1927 | −93.137 | −5.964 | 16.763 | 1.00 | 19.33 | O |
| ATOM | 41279 | C2' | A A1927 | −91.098 | −7.357 | 16.582 | 1.00 | 19.33 | C |
| ATOM | 41280 | O2' | A A1927 | −90.394 | −6.117 | 16.619 | 1.00 | 19.33 | O |
| ATOM | 41281 | C1' | A A1927 | −90.463 | −8.312 | 17.610 | 1.00 | 19.33 | C |
| ATOM | 41282 | N9 | A A1927 | −90.405 | −9.708 | 17.148 | 1.00 | 19.12 | N |
| ATOM | 41283 | C8 | A A1927 | −91.333 | −10.642 | 17.464 | 1.00 | 19.12 | C |
| ATOM | 41284 | N7 | A A1927 | −91.085 | −11.821 | 16.962 | 1.00 | 19.12 | N |
| ATOM | 41285 | C5 | A A1927 | −89.894 | −11.662 | 16.285 | 1.00 | 19.12 | C |
| ATOM | 41286 | C6 | A A1927 | −89.130 | −12.574 | 15.525 | 1.00 | 19.12 | C |
| ATOM | 41287 | N6 | A A1927 | −89.457 | −13.857 | 15.347 | 1.00 | 19.12 | N |
| ATOM | 41288 | N1 | A A1927 | −87.998 | −12.114 | 14.969 | 1.00 | 19.12 | N |
| ATOM | 41289 | C2 | A A1927 | −87.703 | −10.818 | 15.182 | 1.00 | 19.12 | C |
| ATOM | 41290 | N3 | A A1927 | −88.356 | −9.870 | 15.872 | 1.00 | 19.12 | N |
| ATOM | 41291 | C4 | A A1927 | −89.460 | −10.362 | 16.411 | 1.00 | 19.12 | C |
| ATOM | 41292 | P | A A1928 | −93.897 | −5.791 | 15.356 | 1.00 | 6.80 | P |
| ATOM | 41293 | OP1 | A A1928 | −94.452 | −4.431 | 15.324 | 1.00 | 6.80 | O |
| ATOM | 41294 | OP2 | A A1928 | −94.823 | −6.930 | 15.209 | 1.00 | 6.80 | O |
| ATOM | 41295 | O5' | A A1928 | −92.714 | −5.913 | 14.296 | 1.00 | 6.80 | O |
| ATOM | 41296 | C5' | A A1928 | −92.119 | −4.766 | 13.719 | 1.00 | 6.80 | C |
| ATOM | 41297 | C4' | A A1928 | −90.900 | −5.141 | 12.923 | 1.00 | 6.80 | C |
| ATOM | 41298 | O4' | A A1928 | −90.264 | −6.274 | 13.545 | 1.00 | 6.80 | O |
| ATOM | 41299 | C3' | A A1928 | −91.145 | −5.574 | 11.476 | 1.00 | 6.80 | C |
| ATOM | 41300 | O3' | A A1928 | −91.175 | −4.479 | 10.582 | 1.00 | 6.80 | O |
| ATOM | 41301 | C2' | A A1928 | −89.994 | −6.535 | 11.187 | 1.00 | 6.80 | C |
| ATOM | 41302 | O2' | A A1928 | −88.836 | −5.838 | 10.729 | 1.00 | 6.80 | O |
| ATOM | 41303 | C1' | A A1928 | −89.709 | −7.128 | 12.565 | 1.00 | 6.80 | C |
| ATOM | 41304 | N9 | A A1928 | −90.292 | −8.475 | 12.728 | 1.00 | 6.70 | N |
| ATOM | 41305 | C8 | A A1928 | −91.537 | −8.774 | 13.187 | 1.00 | 6.70 | C |
| ATOM | 41306 | N7 | A A1928 | −91.775 | −10.050 | 13.248 | 1.00 | 6.70 | N |
| ATOM | 41307 | C5 | A A1928 | −90.609 | −10.636 | 12.794 | 1.00 | 6.70 | C |
| ATOM | 41308 | C6 | A A1928 | −90.229 | −11.971 | 12.617 | 1.00 | 6.70 | C |
| ATOM | 41309 | N6 | A A1928 | −91.021 | −13.012 | 12.889 | 1.00 | 6.70 | N |
| ATOM | 41310 | N1 | A A1928 | −88.995 | −12.212 | 12.161 | 1.00 | 6.70 | N |
| ATOM | 41311 | C2 | A A1928 | −88.200 | −11.193 | 11.898 | 1.00 | 6.70 | C |
| ATOM | 41312 | N3 | A A1928 | −88.454 | −9.902 | 12.029 | 1.00 | 6.70 | N |
| ATOM | 41313 | C4 | A A1928 | −89.687 | −9.681 | 12.484 | 1.00 | 6.70 | C |
| ATOM | 41314 | P | G A1929 | −92.480 | −4.140 | 9.728 | 1.00 | 9.15 | P |
| ATOM | 41315 | OP1 | G A1929 | −92.518 | −2.677 | 9.562 | 1.00 | 9.15 | O |
| ATOM | 41316 | OP2 | G A1929 | −93.631 | −4.834 | 10.354 | 1.00 | 9.15 | O |
| ATOM | 41317 | O5' | G A1929 | −92.155 | −4.792 | 8.374 | 1.00 | 9.15 | O |
| ATOM | 41318 | C5' | G A1929 | −91.828 | −6.132 | 8.337 | 1.00 | 9.15 | C |
| ATOM | 41319 | C4' | G A1929 | −90.623 | −6.350 | 7.523 | 1.00 | 9.15 | C |
| ATOM | 41320 | O4' | G A1929 | −89.989 | −7.547 | 7.982 | 1.00 | 9.15 | O |
| ATOM | 41321 | C3' | G A1929 | −90.913 | −6.616 | 6.098 | 1.00 | 9.15 | C |
| ATOM | 41322 | O3' | G A1929 | −89.684 | −6.581 | 5.423 | 1.00 | 9.15 | O |
| ATOM | 41323 | C2' | G A1929 | −91.407 | −8.048 | 6.176 | 1.00 | 9.15 | C |
| ATOM | 41324 | O2' | G A1929 | −91.387 | −8.737 | 4.938 | 1.00 | 9.15 | O |
| ATOM | 41325 | C1' | G A1929 | −90.410 | −8.635 | 7.185 | 1.00 | 9.15 | C |
| ATOM | 41326 | N9 | G A1929 | −90.969 | −9.640 | 8.102 | 1.00 | 9.80 | N |
| ATOM | 41327 | C8 | G A1929 | −90.493 | −10.910 | 8.340 | 1.00 | 9.80 | C |
| ATOM | 41328 | N7 | G A1929 | −91.149 | −11.543 | 9.280 | 1.00 | 9.80 | N |
| ATOM | 41329 | C5 | G A1929 | −92.095 | −10.628 | 9.711 | 1.00 | 9.80 | C |
| ATOM | 41330 | C6 | G A1929 | −93.108 | −10.747 | 10.692 | 1.00 | 9.80 | C |
| ATOM | 41331 | O6 | G A1929 | −93.388 | −11.717 | 11.406 | 1.00 | 9.80 | O |
| ATOM | 41332 | N1 | G A1929 | −93.850 | −9.579 | 10.819 | 1.00 | 9.80 | N |
| ATOM | 41333 | C2 | G A1929 | −93.660 | −8.432 | 10.080 | 1.00 | 9.80 | C |
| ATOM | 41334 | N2 | G A1929 | −94.489 | −7.387 | 10.329 | 1.00 | 9.80 | N |
| ATOM | 41335 | N3 | G A1929 | −92.722 | −8.332 | 9.145 | 1.00 | 9.80 | N |

TABLE 6-continued

H69 Neomycin Binding Site for Fully-Rotated Ribosome

| ATOM | 41336 | C4 | G A1929 | −91.982 | −9.449 | 9.014 | 1.00 | 9.80 | C |
|---|---|---|---|---|---|---|---|---|---|
| ATOM | 41337 | P | G A1930 | −89.610 | −6.132 | 3.910 | 1.00 | 14.03 | P |
| ATOM | 41338 | OP1 | G A1930 | −89.368 | −4.669 | 3.916 | 1.00 | 14.03 | O |
| ATOM | 41339 | OP2 | G A1930 | −90.825 | −6.674 | 3.213 | 1.00 | 14.03 | O |
| ATOM | 41340 | O5' | G A1930 | −88.320 | −6.900 | 3.408 | 1.00 | 14.03 | O |
| ATOM | 41341 | C5' | G A1930 | −87.411 | −7.465 | 4.335 | 1.00 | 14.03 | C |
| ATOM | 41342 | C4' | G A1930 | −86.002 | −7.175 | 3.937 | 1.00 | 14.03 | C |
| ATOM | 41343 | O4' | G A1930 | −85.134 | −8.181 | 4.497 | 1.00 | 14.03 | O |
| ATOM | 41344 | C3' | G A1930 | −85.753 | −7.194 | 2.449 | 1.00 | 14.03 | C |
| ATOM | 41345 | O3' | G A1930 | −84.743 | −6.247 | 2.138 | 1.00 | 14.03 | O |
| ATOM | 41346 | C2' | G A1930 | −85.244 | −8.608 | 2.206 | 1.00 | 14.03 | C |
| ATOM | 41347 | O2' | G A1930 | −84.464 | −8.754 | 1.050 | 1.00 | 14.03 | O |
| ATOM | 41348 | C1' | G A1930 | −84.430 | −8.837 | 3.460 | 1.00 | 14.03 | C |
| ATOM | 41349 | N9 | G A1930 | −84.262 | −10.244 | 3.842 | 1.00 | 13.66 | N |
| ATOM | 41350 | C8 | G A1930 | −85.162 | −11.284 | 3.826 | 1.00 | 13.66 | C |
| ATOM | 41351 | N7 | G A1930 | −84.672 | −12.400 | 4.273 | 1.00 | 13.66 | N |
| ATOM | 41352 | C5 | G A1930 | −83.378 | −12.061 | 4.623 | 1.00 | 13.66 | C |
| ATOM | 41353 | C6 | G A1930 | −82.342 | −12.845 | 5.168 | 1.00 | 13.66 | C |
| ATOM | 41354 | O6 | G A1930 | −82.396 | −14.041 | 5.441 | 1.00 | 13.66 | O |
| ATOM | 41355 | N1 | G A1930 | −81.175 | −12.135 | 5.393 | 1.00 | 13.66 | N |
| ATOM | 41356 | C2 | G A1930 | −81.019 | −10.817 | 5.104 | 1.00 | 13.66 | C |
| ATOM | 41357 | N2 | G A1930 | −79.836 | −10.285 | 5.391 | 1.00 | 13.66 | N |
| ATOM | 41358 | N3 | G A1930 | −81.960 | −10.064 | 4.579 | 1.00 | 13.66 | N |
| ATOM | 41359 | C4 | G A1930 | −83.109 | −10.747 | 4.374 | 1.00 | 13.66 | C |
| ATOM | 41360 | P | U A1931 | −84.547 | −5.765 | 0.622 | 1.00 | 13.59 | P |
| ATOM | 41361 | OP1 | U A1931 | −85.785 | −6.128 | −0.112 | 1.00 | 13.59 | O |
| ATOM | 41362 | OP2 | U A1931 | −83.243 | −6.337 | 0.133 | 1.00 | 13.59 | O |
| ATOM | 41363 | O5' | U A1931 | −84.462 | −4.168 | 0.760 | 1.00 | 13.59 | O |
| ATOM | 41364 | C5' | U A1931 | −83.944 | −3.550 | 1.913 | 1.00 | 13.59 | C |
| ATOM | 41365 | C4' | U A1931 | −82.778 | −2.644 | 1.587 | 1.00 | 13.59 | C |
| ATOM | 41366 | O4' | U A1931 | −81.936 | −2.542 | 2.755 | 1.00 | 13.59 | O |
| ATOM | 41367 | C3' | U A1931 | −81.848 | −3.110 | 0.465 | 1.00 | 13.59 | C |
| ATOM | 41368 | O3' | U A1931 | −82.194 | −2.576 | −0.801 | 1.00 | 13.59 | O |
| ATOM | 41369 | C2' | U A1931 | −80.462 | −2.678 | 0.930 | 1.00 | 13.59 | C |
| ATOM | 41370 | O2' | U A1931 | −80.201 | −1.326 | 0.589 | 1.00 | 13.59 | O |
| ATOM | 41371 | C1' | U A1931 | −80.594 | −2.763 | 2.427 | 1.00 | 13.59 | C |
| ATOM | 41372 | N1 | U A1931 | −80.203 | −4.071 | 2.964 | 1.00 | 13.70 | N |
| ATOM | 41373 | C2 | U A1931 | −78.897 | −4.278 | 3.276 | 1.00 | 13.70 | C |
| ATOM | 41374 | O2 | U A1931 | −78.072 | −3.435 | 3.038 | 1.00 | 13.70 | O |
| ATOM | 41375 | N3 | U A1931 | −78.604 | −5.487 | 3.840 | 1.00 | 13.70 | N |
| ATOM | 41376 | C4 | U A1931 | −79.497 | −6.483 | 4.142 | 1.00 | 13.70 | C |
| ATOM | 41377 | O4 | U A1931 | −79.130 | −7.524 | 4.669 | 1.00 | 13.70 | O |
| ATOM | 41378 | C5 | U A1931 | −80.842 | −6.193 | 3.806 | 1.00 | 13.70 | C |
| ATOM | 41379 | C6 | U A1931 | −81.141 | −5.017 | 3.254 | 1.00 | 13.70 | C |
| TER | | | | | | | | | |
| END | | | | | | | | | |

TABLE 7

H69 Neomycin Binding Site for Unrotated Ribosome

| ATOM | 32464 | P | G A1515 | −31.881 | 117.606 | 101.995 | 1.00 | 7.98 | P |
|---|---|---|---|---|---|---|---|---|---|
| ATOM | 32465 | OP1 | G A1515 | −32.095 | 118.164 | 103.346 | 1.00 | 7.98 | O |
| ATOM | 32466 | OP2 | G A1515 | −31.678 | 116.145 | 101.830 | 1.00 | 7.98 | O |
| ATOM | 32467 | O5' | G A1515 | −33.029 | 118.085 | 101.036 | 1.00 | 7.98 | O |
| ATOM | 32468 | C5' | G A1515 | −33.496 | 119.407 | 101.098 | 1.00 | 7.98 | C |
| ATOM | 32469 | C4' | G A1515 | −34.575 | 119.623 | 100.099 | 1.00 | 7.98 | C |
| ATOM | 32470 | O4' | G A1515 | −34.111 | 119.230 | 98.782 | 1.00 | 7.98 | O |
| ATOM | 32471 | C3' | G A1515 | −35.806 | 118.780 | 100.296 | 1.00 | 7.98 | C |
| ATOM | 32472 | O3' | G A1515 | −36.634 | 119.265 | 101.315 | 1.00 | 7.98 | O |
| ATOM | 32473 | C2' | G A1515 | −36.436 | 118.834 | 98.931 | 1.00 | 7.98 | C |
| ATOM | 32474 | O2' | G A1515 | −37.017 | 120.101 | 98.721 | 1.00 | 7.98 | O |
| ATOM | 32475 | C1' | G A1515 | −35.201 | 118.715 | 98.039 | 1.00 | 7.98 | C |
| ATOM | 32476 | N9 | G A1515 | −34.916 | 117.309 | 97.694 | 1.00 | 8.01 | N |
| ATOM | 32477 | C8 | G A1515 | −33.970 | 116.582 | 98.350 | 1.00 | 8.01 | C |
| ATOM | 32478 | N7 | G A1515 | −33.892 | 115.363 | 97.913 | 1.00 | 8.01 | N |
| ATOM | 32479 | C5 | G A1515 | −34.853 | 115.261 | 96.929 | 1.00 | 8.01 | C |
| ATOM | 32480 | C6 | G A1515 | −35.167 | 114.127 | 96.160 | 1.00 | 8.01 | C |
| ATOM | 32481 | O6 | G A1515 | −34.624 | 112.987 | 96.223 | 1.00 | 8.01 | O |
| ATOM | 32482 | N1 | G A1515 | −36.189 | 114.455 | 95.277 | 1.00 | 8.01 | N |
| ATOM | 32483 | C2 | G A1515 | −36.789 | 115.678 | 95.166 | 1.00 | 8.01 | C |
| ATOM | 32484 | N2 | G A1515 | −37.745 | 115.775 | 94.249 | 1.00 | 8.01 | N |
| ATOM | 32485 | N3 | G A1515 | −36.498 | 116.728 | 95.892 | 1.00 | 8.01 | N |
| ATOM | 32486 | C4 | G A1515 | −35.509 | 116.452 | 96.764 | 1.00 | 8.01 | C |
| ATOM | 32487 | P | G A1516 | −37.407 | 118.244 | 102.263 | 1.00 | 3.93 | P |

TABLE 7-continued

H69 Neomycin Binding Site for Unrotated Ribosome

| ATOM | 32488 | OP1 | G A1516 | −37.954 | 119.029 | 103.387 | 1.00 | 3.93 | O |
|---|---|---|---|---|---|---|---|---|---|
| ATOM | 32489 | OP2 | G A1516 | −36.470 | 117.138 | 102.562 | 1.00 | 3.93 | O |
| ATOM | 32490 | O5' | G A1516 | −38.596 | 117.734 | 101.329 | 1.00 | 3.93 | O |
| ATOM | 32491 | C5' | G A1516 | −39.544 | 118.658 | 100.841 | 1.00 | 3.93 | C |
| ATOM | 32492 | C4' | G A1516 | −40.410 | 118.079 | 99.757 | 1.00 | 3.93 | C |
| ATOM | 32493 | O4' | G A1516 | −39.618 | 117.710 | 98.597 | 1.00 | 3.93 | O |
| ATOM | 32494 | C3' | G A1516 | −41.165 | 116.812 | 100.097 | 1.00 | 3.93 | C |
| ATOM | 32495 | O3' | G A1516 | −42.305 | 117.060 | 100.891 | 1.00 | 3.93 | O |
| ATOM | 32496 | C2' | G A1516 | −41.516 | 116.297 | 98.723 | 1.00 | 3.93 | C |
| ATOM | 32497 | O2' | G A1516 | −42.606 | 117.035 | 98.192 | 1.00 | 3.93 | O |
| ATOM | 32498 | C1' | G A1516 | −40.244 | 116.637 | 97.933 | 1.00 | 3.93 | C |
| ATOM | 32499 | N9 | G A1516 | −39.328 | 115.498 | 97.922 | 1.00 | 4.29 | N |
| ATOM | 32500 | C8 | G A1516 | −38.192 | 115.311 | 98.668 | 1.00 | 4.29 | C |
| ATOM | 32501 | N7 | G A1516 | −37.619 | 114.144 | 98.480 | 1.00 | 4.29 | N |
| ATOM | 32502 | C5 | G A1516 | −38.468 | 113.523 | 97.577 | 1.00 | 4.29 | C |
| ATOM | 32503 | C6 | G A1516 | −38.383 | 112.245 | 96.996 | 1.00 | 4.29 | C |
| ATOM | 32504 | O6 | G A1516 | −37.512 | 111.412 | 97.217 | 1.00 | 4.29 | O |
| ATOM | 32505 | N1 | G A1516 | −39.429 | 111.994 | 96.100 | 1.00 | 4.29 | N |
| ATOM | 32506 | C2 | G A1516 | −40.474 | 112.861 | 95.802 | 1.00 | 4.29 | C |
| ATOM | 32507 | N2 | G A1516 | −41.423 | 112.444 | 94.925 | 1.00 | 4.29 | N |
| ATOM | 32508 | N3 | G A1516 | −40.559 | 114.069 | 96.360 | 1.00 | 4.29 | N |
| ATOM | 32509 | C4 | G A1516 | −39.532 | 114.334 | 97.224 | 1.00 | 4.29 | C |
| ATOM | 32510 | P | G A1517 | −42.644 | 116.119 | 102.144 | 1.00 | 20.20 | P |
| ATOM | 32511 | OP1 | G A1517 | −43.899 | 116.654 | 102.769 | 1.00 | 20.20 | O |
| ATOM | 32512 | OP2 | G A1517 | −41.402 | 116.037 | 102.961 | 1.00 | 20.20 | O |
| ATOM | 32513 | O5' | G A1517 | −42.934 | 114.712 | 101.467 | 1.00 | 20.20 | O |
| ATOM | 32514 | C5' | G A1517 | −44.109 | 114.507 | 100.710 | 1.00 | 20.20 | C |
| ATOM | 32515 | C4' | G A1517 | −44.675 | 113.137 | 100.949 | 1.00 | 20.20 | C |
| ATOM | 32516 | O4' | G A1517 | −46.123 | 113.216 | 100.986 | 1.00 | 20.20 | O |
| ATOM | 32517 | C3' | G A1517 | −44.370 | 112.106 | 99.879 | 1.00 | 20.20 | C |
| ATOM | 32518 | O3' | G A1517 | −43.127 | 111.469 | 100.069 | 1.00 | 20.20 | O |
| ATOM | 32519 | C2' | G A1517 | −45.564 | 111.179 | 99.945 | 1.00 | 20.20 | C |
| ATOM | 32520 | O2' | G A1517 | −45.451 | 110.289 | 101.038 | 1.00 | 20.20 | O |
| ATOM | 32521 | C1' | G A1517 | −46.684 | 112.173 | 100.242 | 1.00 | 20.20 | C |
| ATOM | 32522 | N9 | G A1517 | −47.240 | 112.764 | 99.013 | 1.00 | 20.45 | N |
| ATOM | 32523 | C8 | G A1517 | −47.033 | 114.049 | 98.561 | 1.00 | 20.45 | C |
| ATOM | 32524 | N7 | G A1517 | −47.658 | 114.296 | 97.435 | 1.00 | 20.45 | N |
| ATOM | 32525 | C5 | G A1517 | −48.317 | 113.103 | 97.126 | 1.00 | 20.45 | C |
| ATOM | 32526 | C6 | G A1517 | −49.151 | 112.737 | 96.037 | 1.00 | 20.45 | C |
| ATOM | 32527 | O6 | G A1517 | −49.521 | 113.398 | 95.063 | 1.00 | 20.45 | O |
| ATOM | 32528 | N1 | G A1517 | −49.583 | 111.431 | 96.151 | 1.00 | 20.45 | N |
| ATOM | 32529 | C2 | G A1517 | −49.268 | 110.579 | 97.170 | 1.00 | 20.45 | C |
| ATOM | 32530 | N2 | G A1517 | −49.779 | 109.349 | 97.121 | 1.00 | 20.45 | N |
| ATOM | 32531 | N3 | G A1517 | −48.511 | 110.891 | 98.180 | 1.00 | 20.45 | N |
| ATOM | 32532 | C4 | G A1517 | −48.072 | 112.157 | 98.100 | 1.00 | 20.45 | C |
| ATOM | 32533 | P | A A1518 | −41.997 | 111.615 | 98.942 | 1.00 | 10.21 | P |
| ATOM | 32534 | OP1 | A A1518 | −40.725 | 111.069 | 99.488 | 1.00 | 10.21 | O |
| ATOM | 32535 | OP2 | A A1518 | −42.035 | 113.035 | 98.468 | 1.00 | 10.21 | O |
| ATOM | 32536 | O5' | A A1518 | −42.538 | 110.652 | 97.804 | 1.00 | 10.21 | O |
| ATOM | 32537 | C5' | A A1518 | −42.626 | 109.254 | 98.025 | 1.00 | 10.21 | C |
| ATOM | 32538 | C4' | A A1518 | −43.607 | 108.598 | 97.084 | 1.00 | 10.21 | C |
| ATOM | 32539 | O4' | A A1518 | −44.906 | 109.243 | 97.171 | 1.00 | 10.21 | O |
| ATOM | 32540 | C3' | A A1518 | −43.273 | 108.672 | 95.615 | 1.00 | 10.21 | C |
| ATOM | 32541 | O3' | A A1518 | −42.258 | 107.763 | 95.236 | 1.00 | 10.21 | O |
| ATOM | 32542 | C2' | A A1518 | −44.618 | 108.394 | 94.978 | 1.00 | 10.21 | C |
| ATOM | 32543 | O2' | A A1518 | −44.920 | 107.011 | 95.056 | 1.00 | 10.21 | O |
| ATOM | 32544 | C1' | A A1518 | −45.556 | 109.165 | 95.921 | 1.00 | 10.21 | C |
| ATOM | 32545 | N9 | A A1518 | −45.812 | 110.546 | 95.454 | 1.00 | 10.45 | N |
| ATOM | 32546 | C8 | A A1518 | −45.390 | 111.655 | 96.119 | 1.00 | 10.45 | C |
| ATOM | 32547 | N7 | A A1518 | −45.713 | 112.790 | 95.547 | 1.00 | 10.45 | N |
| ATOM | 32548 | C5 | A A1518 | −46.392 | 112.422 | 94.411 | 1.00 | 10.45 | C |
| ATOM | 32549 | C6 | A A1518 | −46.969 | 113.199 | 93.389 | 1.00 | 10.45 | C |
| ATOM | 32550 | N6 | A A1518 | −46.979 | 114.532 | 93.329 | 1.00 | 10.45 | N |
| ATOM | 32551 | N1 | A A1518 | −47.568 | 112.517 | 92.397 | 1.00 | 10.45 | N |
| ATOM | 32552 | C2 | A A1518 | −47.581 | 111.172 | 92.460 | 1.00 | 10.45 | C |
| ATOM | 32553 | N3 | A A1518 | −47.071 | 110.353 | 93.379 | 1.00 | 10.45 | N |
| ATOM | 32554 | C4 | A A1518 | −46.471 | 111.042 | 94.346 | 1.00 | 10.45 | C |
| TER | | | | | | | | | |
| ATOM | 40737 | P | G A1903 | −34.819 | 134.604 | 124.042 | 1.00 | 0.04 | P |
| ATOM | 40738 | OP1 | G A1903 | −35.213 | 134.085 | 125.364 | 1.00 | 0.04 | O |
| ATOM | 40739 | OP2 | G A1903 | −33.506 | 134.200 | 123.461 | 1.00 | 0.04 | O |
| ATOM | 40740 | O5' | G A1903 | −35.985 | 134.356 | 122.997 | 1.00 | 0.04 | O |
| ATOM | 40741 | C5' | G A1903 | −37.326 | 134.217 | 123.430 | 1.00 | 0.04 | C |
| ATOM | 40742 | C4' | G A1903 | −38.312 | 134.513 | 122.328 | 1.00 | 0.04 | C |
| ATOM | 40743 | O4' | G A1903 | −37.689 | 135.289 | 121.274 | 1.00 | 0.04 | O |
| ATOM | 40744 | C3' | G A1903 | −38.877 | 133.325 | 121.590 | 1.00 | 0.04 | C |
| ATOM | 40745 | O3' | G A1903 | −39.859 | 132.644 | 122.335 | 1.00 | 0.04 | O |
| ATOM | 40746 | C2' | G A1903 | −39.425 | 133.986 | 120.341 | 1.00 | 0.04 | C |

TABLE 7-continued

H69 Neomycin Binding Site for Unrotated Ribosome

| ATOM | 40747 | O2' | G A1903 | −40.636 | 134.646 | 120.626 | 1.00 | 0.04 O |
|------|-------|-----|---------|---------|---------|---------|------|--------|
| ATOM | 40748 | C1' | G A1903 | −38.368 | 135.045 | 120.061 | 1.00 | 0.04 C |
| ATOM | 40749 | N9 | G A1903 | −37.414 | 134.592 | 119.035 | 1.00 | 0.01 N |
| ATOM | 40750 | C8 | G A1903 | −36.064 | 134.282 | 119.063 | 1.00 | 0.01 C |
| ATOM | 40751 | N7 | G A1903 | −35.630 | 133.881 | 117.884 | 1.00 | 0.01 N |
| ATOM | 40752 | C5 | G A1903 | −36.755 | 133.917 | 117.064 | 1.00 | 0.01 C |
| ATOM | 40753 | C6 | G A1903 | −36.941 | 133.614 | 115.704 | 1.00 | 0.01 C |
| ATOM | 40754 | O6 | G A1903 | −36.138 | 133.228 | 114.878 | 1.00 | 0.01 O |
| ATOM | 40755 | N1 | G A1903 | −38.218 | 133.802 | 115.256 | 1.00 | 0.01 N |
| ATOM | 40756 | C2 | G A1903 | −39.238 | 134.231 | 116.030 | 1.00 | 0.01 C |
| ATOM | 40757 | N2 | G A1903 | −40.411 | 134.335 | 115.387 | 1.00 | 0.01 N |
| ATOM | 40758 | N3 | G A1903 | −39.110 | 134.530 | 117.320 | 1.00 | 0.01 N |
| ATOM | 40759 | C4 | G A1903 | −37.847 | 134.351 | 117.759 | 1.00 | 0.01 C |
| ATOM | 40760 | P | G A1904 | −40.245 | 131.107 | 121.998 | 1.00 | 0.68 P |
| ATOM | 40761 | OP1 | G A1904 | −41.073 | 130.609 | 123.141 | 1.00 | 0.68 O |
| ATOM | 40762 | OP2 | G A1904 | −38.979 | 130.391 | 121.662 | 1.00 | 0.68 O |
| ATOM | 40763 | O5' | G A1904 | −41.156 | 131.234 | 120.695 | 1.00 | 0.68 O |
| ATOM | 40764 | C5' | G A1904 | −42.460 | 131.780 | 120.775 | 1.00 | 0.68 C |
| ATOM | 40765 | C4' | G A1904 | −43.131 | 131.765 | 119.439 | 1.00 | 0.68 C |
| ATOM | 40766 | O4' | G A1904 | −42.329 | 132.516 | 118.487 | 1.00 | 0.68 O |
| ATOM | 40767 | C3' | G A1904 | −43.262 | 130.399 | 118.792 | 1.00 | 0.68 C |
| ATOM | 40768 | O3' | G A1904 | −44.334 | 129.633 | 119.291 | 1.00 | 0.68 O |
| ATOM | 40769 | C2' | G A1904 | −43.418 | 130.759 | 117.340 | 1.00 | 0.68 C |
| ATOM | 40770 | O2' | G A1904 | −44.721 | 131.292 | 117.119 | 1.00 | 0.68 O |
| ATOM | 40771 | C1' | G A1904 | −42.379 | 131.886 | 117.222 | 1.00 | 0.68 C |
| ATOM | 40772 | N9 | G A1904 | −41.017 | 131.365 | 116.897 | 1.00 | 0.52 N |
| ATOM | 40773 | C8 | G A1904 | −39.972 | 131.266 | 117.768 | 1.00 | 0.52 C |
| ATOM | 40774 | N7 | G A1904 | −38.878 | 130.767 | 117.255 | 1.00 | 0.52 N |
| ATOM | 40775 | C5 | G A1904 | −39.191 | 130.496 | 115.947 | 1.00 | 0.52 C |
| ATOM | 40776 | C6 | G A1904 | −38.394 | 129.941 | 114.902 | 1.00 | 0.52 C |
| ATOM | 40777 | O6 | G A1904 | −37.219 | 129.565 | 114.912 | 1.00 | 0.52 O |
| ATOM | 40778 | N1 | G A1904 | −39.078 | 129.832 | 113.721 | 1.00 | 0.52 N |
| ATOM | 40779 | C2 | G A1904 | −40.368 | 130.213 | 113.573 | 1.00 | 0.52 C |
| ATOM | 40780 | N2 | G A1904 | −40.864 | 130.044 | 112.351 | 1.00 | 0.52 N |
| ATOM | 40781 | N3 | G A1904 | −41.130 | 130.729 | 114.528 | 1.00 | 0.52 N |
| ATOM | 40782 | C4 | G A1904 | −40.493 | 130.859 | 115.709 | 1.00 | 0.52 C |
| ATOM | 40783 | P | C A1905 | −44.210 | 128.036 | 119.281 | 1.00 | 0.21 P |
| ATOM | 40784 | OP1 | C A1905 | −45.534 | 127.470 | 119.728 | 1.00 | 0.21 O |
| ATOM | 40785 | OP2 | C A1905 | −42.980 | 127.697 | 120.055 | 1.00 | 0.21 O |
| ATOM | 40786 | O5' | C A1905 | −43.971 | 127.728 | 117.727 | 1.00 | 0.21 O |
| ATOM | 40787 | C5' | C A1905 | −45.066 | 127.557 | 116.833 | 1.00 | 0.21 C |
| ATOM | 40788 | C4' | C A1905 | −44.601 | 127.423 | 115.398 | 1.00 | 0.21 C |
| ATOM | 40789 | O4' | C A1905 | −43.316 | 128.060 | 115.240 | 1.00 | 0.21 O |
| ATOM | 40790 | C3' | C A1905 | −44.408 | 126.001 | 114.888 | 1.00 | 0.21 C |
| ATOM | 40791 | O3' | C A1905 | −45.612 | 125.469 | 114.350 | 1.00 | 0.21 O |
| ATOM | 40792 | C2' | C A1905 | −43.293 | 126.130 | 113.842 | 1.00 | 0.21 C |
| ATOM | 40793 | O2' | C A1905 | −43.822 | 126.333 | 112.529 | 1.00 | 0.21 O |
| ATOM | 40794 | C1' | C A1905 | −42.550 | 127.392 | 114.273 | 1.00 | 0.21 C |
| ATOM | 40795 | N1 | C A1905 | −41.246 | 127.091 | 114.842 | 1.00 | 0.07 N |
| ATOM | 40796 | C2 | C A1905 | −40.235 | 126.639 | 113.998 | 1.00 | 0.07 C |
| ATOM | 40797 | O2 | C A1905 | −40.483 | 126.484 | 112.792 | 1.00 | 0.07 O |
| ATOM | 40798 | N3 | C A1905 | −39.021 | 126.356 | 114.496 | 1.00 | 0.07 N |
| ATOM | 40799 | C4 | C A1905 | −38.821 | 126.524 | 115.783 | 1.00 | 0.07 C |
| ATOM | 40800 | N4 | C A1905 | −37.618 | 126.230 | 116.293 | 1.00 | 0.07 N |
| ATOM | 40801 | C5 | C A1905 | −39.849 | 127.003 | 116.645 | 1.00 | 0.07 C |
| ATOM | 40802 | C6 | C A1905 | −41.046 | 127.275 | 116.150 | 1.00 | 0.07 C |
| ATOM | 40803 | P | G A1906 | −46.331 | 124.191 | 115.013 | 1.00 | 22.98 P |
| ATOM | 40804 | OP1 | G A1906 | −45.660 | 123.936 | 116.329 | 1.00 | 22.98 O |
| ATOM | 40805 | OP2 | G A1906 | −46.340 | 123.108 | 113.985 | 1.00 | 22.98 O |
| ATOM | 40806 | O5' | G A1906 | −47.808 | 124.710 | 115.255 | 1.00 | 22.98 O |
| ATOM | 40807 | C5' | G A1906 | −48.903 | 124.008 | 114.730 | 1.00 | 22.98 C |
| ATOM | 40808 | C4' | G A1906 | −50.188 | 124.644 | 115.135 | 1.00 | 22.98 C |
| ATOM | 40809 | O4' | G A1906 | −50.464 | 125.789 | 114.294 | 1.00 | 22.98 O |
| ATOM | 40810 | C3' | G A1906 | −51.405 | 123.765 | 115.007 | 1.00 | 22.98 C |
| ATOM | 40811 | O3' | G A1906 | −51.549 | 122.919 | 116.127 | 1.00 | 22.98 O |
| ATOM | 40812 | C2' | G A1906 | −52.534 | 124.770 | 114.851 | 1.00 | 22.98 C |
| ATOM | 40813 | O2' | G A1906 | −52.964 | 125.254 | 116.120 | 1.00 | 22.98 O |
| ATOM | 40814 | C1' | G A1906 | −51.841 | 125.898 | 114.064 | 1.00 | 22.98 C |
| ATOM | 40815 | N9 | G A1906 | −52.066 | 125.751 | 112.623 | 1.00 | 22.86 N |
| ATOM | 40816 | C8 | G A1906 | −51.277 | 125.085 | 111.736 | 1.00 | 22.86 C |
| ATOM | 40817 | N7 | G A1906 | −51.766 | 125.078 | 110.524 | 1.00 | 22.86 N |
| ATOM | 40818 | C5 | G A1906 | −52.963 | 125.766 | 110.627 | 1.00 | 22.86 C |
| ATOM | 40819 | C6 | G A1906 | −53.952 | 126.088 | 109.663 | 1.00 | 22.86 C |
| ATOM | 40820 | O6 | G A1906 | −53.981 | 125.834 | 108.460 | 1.00 | 22.86 O |
| ATOM | 40821 | N1 | G A1906 | −55.001 | 126.803 | 110.221 | 1.00 | 22.86 N |
| ATOM | 40822 | C2 | G A1906 | −55.090 | 127.165 | 111.536 | 1.00 | 22.86 C |
| ATOM | 40823 | N2 | G A1906 | −56.163 | 127.854 | 111.946 | 1.00 | 22.86 N |
| ATOM | 40824 | N3 | G A1906 | −54.173 | 126.866 | 112.422 | 1.00 | 22.86 N |

TABLE 7-continued

H69 Neomycin Binding Site for Unrotated Ribosome

| ATOM | 40825 | C4 | G A1906 | −53.147 | 126.176 | 111.915 | 1.00 | 22.86 | C |
|---|---|---|---|---|---|---|---|---|---|
| ATOM | 40826 | P | G A1907 | −52.488 | 121.623 | 116.062 | 1.00 | 13.06 | P |
| ATOM | 40827 | OP1 | G A1907 | −52.081 | 120.742 | 117.195 | 1.00 | 13.06 | O |
| ATOM | 40828 | OP2 | G A1907 | −52.434 | 121.083 | 114.673 | 1.00 | 13.06 | O |
| ATOM | 40829 | O5' | G A1907 | −53.913 | 122.242 | 116.328 | 1.00 | 13.06 | O |
| ATOM | 40830 | C5' | G A1907 | −54.754 | 122.498 | 115.248 | 1.00 | 13.06 | C |
| ATOM | 40831 | C4' | G A1907 | −56.004 | 123.171 | 115.672 | 1.00 | 13.06 | C |
| ATOM | 40832 | O4' | G A1907 | −56.100 | 124.427 | 114.959 | 1.00 | 13.06 | O |
| ATOM | 40833 | C3' | G A1907 | −57.281 | 122.398 | 115.332 | 1.00 | 13.06 | C |
| ATOM | 40834 | O3' | G A1907 | −57.750 | 121.598 | 116.409 | 1.00 | 13.06 | O |
| ATOM | 40835 | C2' | G A1907 | −58.255 | 123.477 | 114.882 | 1.00 | 13.06 | C |
| ATOM | 40836 | O2' | G A1907 | −58.897 | 124.074 | 116.000 | 1.00 | 13.06 | O |
| ATOM | 40837 | C1' | G A1907 | −57.305 | 124.495 | 114.248 | 1.00 | 13.06 | C |
| ATOM | 40838 | N9 | G A1907 | −56.998 | 124.191 | 112.830 | 1.00 | 13.23 | N |
| ATOM | 40839 | C8 | G A1907 | −55.754 | 123.797 | 112.378 | 1.00 | 13.23 | C |
| ATOM | 40840 | N7 | G A1907 | −55.692 | 123.603 | 111.087 | 1.00 | 13.23 | N |
| ATOM | 40841 | C5 | G A1907 | −56.972 | 123.906 | 110.639 | 1.00 | 13.23 | C |
| ATOM | 40842 | C6 | G A1907 | −57.513 | 123.868 | 109.319 | 1.00 | 13.23 | C |
| ATOM | 40843 | O6 | G A1907 | −56.971 | 123.558 | 108.236 | 1.00 | 13.23 | O |
| ATOM | 40844 | N1 | G A1907 | −58.848 | 124.247 | 109.336 | 1.00 | 13.23 | N |
| ATOM | 40845 | C2 | G A1907 | −59.569 | 124.605 | 110.446 | 1.00 | 13.23 | C |
| ATOM | 40846 | N2 | G A1907 | −60.847 | 124.944 | 110.239 | 1.00 | 13.23 | N |
| ATOM | 40847 | N3 | G A1907 | −59.085 | 124.644 | 111.670 | 1.00 | 13.23 | N |
| ATOM | 40848 | C4 | G A1907 | −57.785 | 124.285 | 111.698 | 1.00 | 13.23 | C |
| ATOM | 40849 | P | C A1908 | −58.077 | 120.042 | 116.166 | 1.00 | 22.31 | P |
| ATOM | 40850 | OP1 | C A1908 | −58.340 | 119.430 | 117.489 | 1.00 | 22.31 | O |
| ATOM | 40851 | OP2 | C A1908 | −56.981 | 119.485 | 115.328 | 1.00 | 22.31 | O |
| ATOM | 40852 | O5' | C A1908 | −59.427 | 120.100 | 115.327 | 1.00 | 22.31 | O |
| ATOM | 40853 | C5' | C A1908 | −60.560 | 120.792 | 115.830 | 1.00 | 22.31 | C |
| ATOM | 40854 | C4' | C A1908 | −61.604 | 121.008 | 114.764 | 1.00 | 22.31 | C |
| ATOM | 40855 | O4' | C A1908 | −61.160 | 122.035 | 113.841 | 1.00 | 22.31 | O |
| ATOM | 40856 | C3' | C A1908 | −61.897 | 119.813 | 113.886 | 1.00 | 22.31 | C |
| ATOM | 40857 | O3' | C A1908 | −62.824 | 118.928 | 114.465 | 1.00 | 22.31 | O |
| ATOM | 40858 | C2' | C A1908 | −62.376 | 120.449 | 112.588 | 1.00 | 22.31 | C |
| ATOM | 40859 | O2' | C A1908 | −63.716 | 120.895 | 112.696 | 1.00 | 22.31 | O |
| ATOM | 40860 | C1' | C A1908 | −61.476 | 121.667 | 112.516 | 1.00 | 22.31 | C |
| ATOM | 40861 | N1 | C A1908 | −60.223 | 121.375 | 111.800 | 1.00 | 22.46 | N |
| ATOM | 40862 | C2 | C A1908 | −60.343 | 121.151 | 110.452 | 1.00 | 22.46 | C |
| ATOM | 40863 | O2 | C A1908 | −61.493 | 121.218 | 110.015 | 1.00 | 22.46 | O |
| ATOM | 40864 | N3 | C A1908 | −59.244 | 120.879 | 109.708 | 1.00 | 22.46 | N |
| ATOM | 40865 | C4 | C A1908 | −58.049 | 120.837 | 110.296 | 1.00 | 22.46 | C |
| ATOM | 40866 | N4 | C A1908 | −56.975 | 120.568 | 109.562 | 1.00 | 22.46 | N |
| ATOM | 40867 | C5 | C A1908 | −57.895 | 121.072 | 111.687 | 1.00 | 22.46 | C |
| ATOM | 40868 | C6 | C A1908 | −58.999 | 121.331 | 112.399 | 1.00 | 22.46 | C |
| ATOM | 40869 | P | C A1909 | −62.666 | 117.352 | 114.219 | 1.00 | 18.48 | P |
| ATOM | 40870 | OP1 | C A1909 | −63.508 | 116.660 | 115.233 | 1.00 | 18.48 | O |
| ATOM | 40871 | OP2 | C A1909 | −61.196 | 117.064 | 114.187 | 1.00 | 18.48 | O |
| ATOM | 40872 | O5' | C A1909 | −63.298 | 117.159 | 112.761 | 1.00 | 18.48 | O |
| ATOM | 40873 | C5' | C A1909 | −64.625 | 117.585 | 112.492 | 1.00 | 18.48 | C |
| ATOM | 40874 | C4' | C A1909 | −64.973 | 117.446 | 111.036 | 1.00 | 18.48 | C |
| ATOM | 40875 | O4' | C A1909 | −64.289 | 118.462 | 110.249 | 1.00 | 18.48 | O |
| ATOM | 40876 | C3' | C A1909 | −64.561 | 116.145 | 110.374 | 1.00 | 18.48 | C |
| ATOM | 40877 | O3' | C A1909 | −65.413 | 115.062 | 110.684 | 1.00 | 18.48 | O |
| ATOM | 40878 | C2' | C A1909 | −64.564 | 116.533 | 108.905 | 1.00 | 18.48 | C |
| ATOM | 40879 | O2' | C A1909 | −65.892 | 116.682 | 108.420 | 1.00 | 18.48 | O |
| ATOM | 40880 | C1' | C A1909 | −63.917 | 117.910 | 108.992 | 1.00 | 18.48 | C |
| ATOM | 40881 | N1 | C A1909 | −62.463 | 117.797 | 108.961 | 1.00 | 18.22 | N |
| ATOM | 40882 | C2 | C A1909 | −61.833 | 117.441 | 107.775 | 1.00 | 18.22 | C |
| ATOM | 40883 | O2 | C A1909 | −62.546 | 117.266 | 106.784 | 1.00 | 18.22 | O |
| ATOM | 40884 | N3 | C A1909 | −60.481 | 117.310 | 107.753 | 1.00 | 18.22 | N |
| ATOM | 40885 | C4 | C A1909 | −59.784 | 117.517 | 108.876 | 1.00 | 18.22 | C |
| ATOM | 40886 | N4 | C A1909 | −58.460 | 117.390 | 108.881 | 1.00 | 18.22 | N |
| ATOM | 40887 | C5 | C A1909 | −60.419 | 117.878 | 110.097 | 1.00 | 18.22 | C |
| ATOM | 40888 | C6 | C A1909 | −61.751 | 117.991 | 110.105 | 1.00 | 18.22 | C |
| ATOM | 40889 | P | G A1910 | −64.898 | 113.559 | 110.468 | 1.00 | 17.57 | P |
| ATOM | 40890 | OP1 | G A1910 | −65.973 | 112.660 | 110.944 | 1.00 | 17.57 | O |
| ATOM | 40891 | OP2 | G A1910 | −63.549 | 113.455 | 111.092 | 1.00 | 17.57 | O |
| ATOM | 40892 | O5' | G A1910 | −64.772 | 113.464 | 108.885 | 1.00 | 17.57 | O |
| ATOM | 40893 | C5' | G A1910 | −65.931 | 113.377 | 108.081 | 1.00 | 17.57 | C |
| ATOM | 40894 | C4' | G A1910 | −65.592 | 113.385 | 106.621 | 1.00 | 17.57 | C |
| ATOM | 40895 | O4' | G A1910 | −64.610 | 114.408 | 106.359 | 1.00 | 17.57 | O |
| ATOM | 40896 | C3' | G A1910 | −64.925 | 112.141 | 106.083 | 1.00 | 17.57 | C |
| ATOM | 40897 | O3' | G A1910 | −65.806 | 111.069 | 105.891 | 1.00 | 17.57 | O |
| ATOM | 40898 | C2' | G A1910 | −64.323 | 112.650 | 104.805 | 1.00 | 17.57 | C |
| ATOM | 40899 | O2' | G A1910 | −65.339 | 112.857 | 103.839 | 1.00 | 17.57 | O |
| ATOM | 40900 | C1' | G A1910 | −63.804 | 114.007 | 105.268 | 1.00 | 17.57 | C |
| ATOM | 40901 | N9 | G A1910 | −62.390 | 113.947 | 105.701 | 1.00 | 17.29 | N |
| ATOM | 40902 | C8 | G A1910 | −61.836 | 114.163 | 106.930 | 1.00 | 17.29 | C |

TABLE 7-continued

H69 Neomycin Binding Site for Unrotated Ribosome

| ATOM | 40903 | N7 | G A1910 | −60.534 | 114.029 | 106.926 | 1.00 | 17.29 | N |
|---|---|---|---|---|---|---|---|---|---|
| ATOM | 40904 | C5 | G A1910 | −60.192 | 113.708 | 105.616 | 1.00 | 17.29 | C |
| ATOM | 40905 | C6 | G A1910 | −58.933 | 113.441 | 104.969 | 1.00 | 17.29 | C |
| ATOM | 40906 | O6 | G A1910 | −57.780 | 113.423 | 105.424 | 1.00 | 17.29 | O |
| ATOM | 40907 | N1 | G A1910 | −59.102 | 113.164 | 103.617 | 1.00 | 17.29 | N |
| ATOM | 40908 | C2 | G A1910 | −60.316 | 113.147 | 102.967 | 1.00 | 17.29 | C |
| ATOM | 40909 | N2 | G A1910 | −60.336 | 112.866 | 101.655 | 1.00 | 17.29 | N |
| ATOM | 40910 | N3 | G A1910 | −61.471 | 113.394 | 103.555 | 1.00 | 17.29 | N |
| ATOM | 40911 | C4 | G A1910 | −61.343 | 113.664 | 104.865 | 1.00 | 17.29 | C |
| ATOM | 40912 | P | U A1911 | −65.303 | 109.592 | 106.231 | 1.00 | 11.08 | P |
| ATOM | 40913 | OP1 | U A1911 | −66.489 | 108.696 | 106.169 | 1.00 | 11.08 | O |
| ATOM | 40914 | OP2 | U A1911 | −64.537 | 109.691 | 107.503 | 1.00 | 11.08 | O |
| ATOM | 40915 | O5' | U A1911 | −64.311 | 109.265 | 105.022 | 1.00 | 11.08 | O |
| ATOM | 40916 | C5' | U A1911 | −64.701 | 109.489 | 103.674 | 1.00 | 11.08 | C |
| ATOM | 40917 | C4' | U A1911 | −63.525 | 109.385 | 102.734 | 1.00 | 11.08 | C |
| ATOM | 40918 | O4' | U A1911 | −62.585 | 110.457 | 103.001 | 1.00 | 11.08 | O |
| ATOM | 40919 | C3' | U A1911 | −62.692 | 108.121 | 102.856 | 1.00 | 11.08 | C |
| ATOM | 40920 | O3' | U A1911 | −63.255 | 107.022 | 102.172 | 1.00 | 11.08 | O |
| ATOM | 40921 | C2' | U A1911 | −61.336 | 108.553 | 102.314 | 1.00 | 11.08 | C |
| ATOM | 40922 | O2' | U A1911 | −61.308 | 108.531 | 100.894 | 1.00 | 11.08 | O |
| ATOM | 40923 | C1' | U A1911 | −61.266 | 110.006 | 102.789 | 1.00 | 11.08 | C |
| ATOM | 40924 | N1 | U A1911 | −60.515 | 110.131 | 104.053 | 1.00 | 11.00 | N |
| ATOM | 40925 | C2 | U A1911 | −59.115 | 110.085 | 103.953 | 1.00 | 11.00 | C |
| ATOM | 40926 | O2 | U A1911 | −58.479 | 109.968 | 102.911 | 1.00 | 11.00 | O |
| ATOM | 40927 | N3 | U A1911 | −58.443 | 110.185 | 105.133 | 1.00 | 11.00 | N |
| ATOM | 40928 | C4 | U A1911 | −59.019 | 110.340 | 106.367 | 1.00 | 11.00 | C |
| ATOM | 40929 | O4 | U A1911 | −58.253 | 110.425 | 107.322 | 1.00 | 11.00 | O |
| ATOM | 40930 | C5 | U A1911 | −60.471 | 110.373 | 106.394 | 1.00 | 11.00 | C |
| ATOM | 40931 | C6 | U A1911 | −61.164 | 110.265 | 105.256 | 1.00 | 11.00 | C |
| ATOM | 40932 | P | A A1912 | −63.221 | 105.563 | 102.838 | 1.00 | 13.79 | P |
| ATOM | 40933 | OP1 | A A1912 | −64.413 | 104.821 | 102.339 | 1.00 | 13.79 | O |
| ATOM | 40934 | OP2 | A A1912 | −63.054 | 105.748 | 104.313 | 1.00 | 13.79 | O |
| ATOM | 40935 | O5' | A A1912 | −61.907 | 104.937 | 102.218 | 1.00 | 13.79 | O |
| ATOM | 40936 | C5' | A A1912 | −61.862 | 104.600 | 100.850 | 1.00 | 13.79 | C |
| ATOM | 40937 | C4' | A A1912 | −60.644 | 103.778 | 100.516 | 1.00 | 13.79 | C |
| ATOM | 40938 | O4' | A A1912 | −59.450 | 104.454 | 100.949 | 1.00 | 13.79 | O |
| ATOM | 40939 | C3' | A A1912 | −60.562 | 102.416 | 101.169 | 1.00 | 13.79 | C |
| ATOM | 40940 | O3' | A A1912 | −61.323 | 101.452 | 100.470 | 1.00 | 13.79 | O |
| ATOM | 40941 | C2' | A A1912 | −59.055 | 102.115 | 101.206 | 1.00 | 13.79 | C |
| ATOM | 40942 | O2' | A A1912 | −58.648 | 101.347 | 100.080 | 1.00 | 13.79 | O |
| ATOM | 40943 | C1' | A A1912 | −58.422 | 103.513 | 101.114 | 1.00 | 13.79 | C |
| ATOM | 40944 | N9 | A A1912 | −57.661 | 103.864 | 102.306 | 1.00 | 13.81 | N |
| ATOM | 40945 | C8 | A A1912 | −58.142 | 104.009 | 103.572 | 1.00 | 13.81 | C |
| ATOM | 40946 | N7 | A A1912 | −57.203 | 104.340 | 104.411 | 1.00 | 13.81 | N |
| ATOM | 40947 | C5 | A A1912 | −56.060 | 104.415 | 103.630 | 1.00 | 13.81 | C |
| ATOM | 40948 | C6 | A A1912 | −54.754 | 104.712 | 103.951 | 1.00 | 13.81 | C |
| ATOM | 40949 | N6 | A A1912 | −54.373 | 105.006 | 105.195 | 1.00 | 13.81 | N |
| ATOM | 40950 | N1 | A A1912 | −53.870 | 104.697 | 102.949 | 1.00 | 13.81 | N |
| ATOM | 40951 | C2 | A A1912 | −54.278 | 104.407 | 101.719 | 1.00 | 13.81 | C |
| ATOM | 40952 | N3 | A A1912 | −55.486 | 104.108 | 101.307 | 1.00 | 13.81 | N |
| ATOM | 40953 | C4 | A A1912 | −56.327 | 104.131 | 102.328 | 1.00 | 13.81 | C |
| ATOM | 40954 | P | A A1913 | −62.512 | 100.696 | 101.214 | 1.00 | 52.95 | P |
| ATOM | 40955 | OP1 | A A1913 | −63.758 | 101.046 | 100.505 | 1.00 | 52.95 | O |
| ATOM | 40956 | OP2 | A A1913 | −62.403 | 101.007 | 102.658 | 1.00 | 52.95 | O |
| ATOM | 40957 | O5' | A A1913 | −62.147 | 99.179 | 100.967 | 1.00 | 52.95 | O |
| ATOM | 40958 | C5' | A A1913 | −61.978 | 98.678 | 99.649 | 1.00 | 52.95 | C |
| ATOM | 40959 | C4' | A A1913 | −62.318 | 97.222 | 99.587 | 1.00 | 52.95 | C |
| ATOM | 40960 | O4' | A A1913 | −61.471 | 96.577 | 98.608 | 1.00 | 52.95 | O |
| ATOM | 40961 | C3' | A A1913 | −62.111 | 96.478 | 100.900 | 1.00 | 52.95 | C |
| ATOM | 40962 | O3' | A A1913 | −63.152 | 95.521 | 101.080 | 1.00 | 52.95 | O |
| ATOM | 40963 | C2' | A A1913 | −60.761 | 95.784 | 100.717 | 1.00 | 52.95 | C |
| ATOM | 40964 | O2' | A A1913 | −60.605 | 94.585 | 101.450 | 1.00 | 52.95 | O |
| ATOM | 40965 | C1' | A A1913 | −60.724 | 95.535 | 99.214 | 1.00 | 52.95 | C |
| ATOM | 40966 | N9 | A A1913 | −59.381 | 95.580 | 98.653 | 1.00 | 53.35 | N |
| ATOM | 40967 | C8 | A A1913 | −58.254 | 96.230 | 99.112 | 1.00 | 53.35 | C |
| ATOM | 40968 | N7 | A A1913 | −57.209 | 96.083 | 98.333 | 1.00 | 53.35 | N |
| ATOM | 40969 | C5 | A A1913 | −57.704 | 95.297 | 97.306 | 1.00 | 53.35 | C |
| ATOM | 40970 | C6 | A A1913 | −57.112 | 94.779 | 96.163 | 1.00 | 53.35 | C |
| ATOM | 40971 | N6 | A A1913 | −55.844 | 95.010 | 95.865 | 1.00 | 53.35 | N |
| ATOM | 40972 | N1 | A A1913 | −57.886 | 94.036 | 95.338 | 1.00 | 53.35 | N |
| ATOM | 40973 | C2 | A A1913 | −59.173 | 93.819 | 95.655 | 1.00 | 53.35 | C |
| ATOM | 40974 | N3 | A A1913 | −59.846 | 94.248 | 96.711 | 1.00 | 53.35 | N |
| ATOM | 40975 | C4 | A A1913 | −59.036 | 94.983 | 97.487 | 1.00 | 53.35 | C |
| ATOM | 40976 | P | C A1914 | −64.614 | 96.012 | 101.541 | 1.00 | 66.92 | P |
| ATOM | 40977 | OP1 | C A1914 | −65.572 | 94.946 | 101.149 | 1.00 | 66.92 | O |
| ATOM | 40978 | OP2 | C A1914 | −64.813 | 97.382 | 100.992 | 1.00 | 66.92 | O |
| ATOM | 40979 | O5' | C A1914 | −64.478 | 96.073 | 103.136 | 1.00 | 66.92 | O |
| ATOM | 40980 | C5' | C A1914 | −63.481 | 95.313 | 103.824 | 1.00 | 66.92 | C |

TABLE 7-continued

H69 Neomycin Binding Site for Unrotated Ribosome

| ATOM | 40981 | C4' | C A1914 | −63.972 | 94.848 | 105.176 | 1.00 | 66.92 | C |
|---|---|---|---|---|---|---|---|---|---|
| ATOM | 40982 | O4' | C A1914 | −63.129 | 93.786 | 105.682 | 1.00 | 66.92 | O |
| ATOM | 40983 | C3' | C A1914 | −63.954 | 95.876 | 106.293 | 1.00 | 66.92 | C |
| ATOM | 40984 | O3' | C A1914 | −65.032 | 96.795 | 106.213 | 1.00 | 66.92 | O |
| ATOM | 40985 | C2' | C A1914 | −63.990 | 95.003 | 107.545 | 1.00 | 66.92 | C |
| ATOM | 40986 | O2' | C A1914 | −65.323 | 94.621 | 107.856 | 1.00 | 66.92 | O |
| ATOM | 40987 | C1' | C A1914 | −63.212 | 93.756 | 107.092 | 1.00 | 66.92 | C |
| ATOM | 40988 | N1 | C A1914 | −61.839 | 93.677 | 107.676 | 1.00 | 65.84 | N |
| ATOM | 40989 | C2 | C A1914 | −60.697 | 93.544 | 106.863 | 1.00 | 65.84 | C |
| ATOM | 40990 | O2 | C A1914 | −60.808 | 93.516 | 105.625 | 1.00 | 65.84 | O |
| ATOM | 40991 | N3 | C A1914 | −59.473 | 93.459 | 107.451 | 1.00 | 65.84 | N |
| ATOM | 40992 | C4 | C A1914 | −59.341 | 93.490 | 108.781 | 1.00 | 65.84 | C |
| ATOM | 40993 | N4 | C A1914 | −58.106 | 93.407 | 109.294 | 1.00 | 65.84 | N |
| ATOM | 40994 | C5 | C A1914 | −60.483 | 93.615 | 109.630 | 1.00 | 65.84 | C |
| ATOM | 40995 | C6 | C A1914 | −61.691 | 93.697 | 109.044 | 1.00 | 65.84 | C |
| ATOM | 40996 | P | U A1915 | −64.847 | 98.301 | 106.742 | 1.00 | 39.28 | P |
| ATOM | 40997 | OP1 | U A1915 | −66.208 | 98.875 | 106.923 | 1.00 | 39.28 | O |
| ATOM | 40998 | OP2 | U A1915 | −63.899 | 98.978 | 105.806 | 1.00 | 39.28 | O |
| ATOM | 40999 | O5' | U A1915 | −64.150 | 98.082 | 108.167 | 1.00 | 39.28 | O |
| ATOM | 41000 | C5' | U A1915 | −64.923 | 97.857 | 109.342 | 1.00 | 39.28 | C |
| ATOM | 41001 | C4' | U A1915 | −64.051 | 97.713 | 110.575 | 1.00 | 39.28 | C |
| ATOM | 41002 | O4' | U A1915 | −63.158 | 96.579 | 110.423 | 1.00 | 39.28 | O |
| ATOM | 41003 | C3' | U A1915 | −63.126 | 98.877 | 110.888 | 1.00 | 39.28 | C |
| ATOM | 41004 | O3' | U A1915 | −63.774 | 99.931 | 111.572 | 1.00 | 39.28 | O |
| ATOM | 41005 | C2' | U A1915 | −62.013 | 98.219 | 111.695 | 1.00 | 39.28 | C |
| ATOM | 41006 | O2' | U A1915 | −62.397 | 98.036 | 113.042 | 1.00 | 39.28 | O |
| ATOM | 41007 | C1' | U A1915 | −61.915 | 96.854 | 111.028 | 1.00 | 39.28 | C |
| ATOM | 41008 | N1 | U A1915 | −60.870 | 96.837 | 109.987 | 1.00 | 39.93 | N |
| ATOM | 41009 | C2 | U A1915 | −59.553 | 96.781 | 110.443 | 1.00 | 39.93 | C |
| ATOM | 41010 | O2 | U A1915 | −59.248 | 96.718 | 111.640 | 1.00 | 39.93 | O |
| ATOM | 41011 | N3 | U A1915 | −58.617 | 96.798 | 109.431 | 1.00 | 39.93 | N |
| ATOM | 41012 | C4 | U A1915 | −58.869 | 96.866 | 108.072 | 1.00 | 39.93 | C |
| ATOM | 41013 | O4 | U A1915 | −57.910 | 96.863 | 107.303 | 1.00 | 39.93 | O |
| ATOM | 41014 | C5 | U A1915 | −60.250 | 96.933 | 107.682 | 1.00 | 39.93 | C |
| ATOM | 41015 | C6 | U A1915 | −61.181 | 96.921 | 108.639 | 1.00 | 39.93 | C |
| ATOM | 41016 | P | A A1916 | −62.990 | 101.299 | 111.861 | 1.00 | 40.79 | P |
| ATOM | 41017 | OP1 | A A1916 | −63.608 | 101.913 | 113.062 | 1.00 | 40.79 | O |
| ATOM | 41018 | OP2 | A A1916 | −62.979 | 102.068 | 110.589 | 1.00 | 40.79 | O |
| ATOM | 41019 | O5' | A A1916 | −61.508 | 100.800 | 112.206 | 1.00 | 40.79 | O |
| ATOM | 41020 | C5' | A A1916 | −60.962 | 100.968 | 113.508 | 1.00 | 40.79 | C |
| ATOM | 41021 | C4' | A A1916 | −59.454 | 100.912 | 113.494 | 1.00 | 40.79 | C |
| ATOM | 41022 | O4' | A A1916 | −59.011 | 99.843 | 112.627 | 1.00 | 40.79 | O |
| ATOM | 41023 | C3' | A A1916 | −58.756 | 102.135 | 112.941 | 1.00 | 40.79 | C |
| ATOM | 41024 | O3' | A A1916 | −58.643 | 103.167 | 113.875 | 1.00 | 40.79 | O |
| ATOM | 41025 | C2' | A A1916 | −57.426 | 101.592 | 112.472 | 1.00 | 40.79 | C |
| ATOM | 41026 | O2' | A A1916 | −56.547 | 101.396 | 113.564 | 1.00 | 40.79 | O |
| ATOM | 41027 | C1' | A A1916 | −57.849 | 100.241 | 111.926 | 1.00 | 40.79 | C |
| ATOM | 41028 | N9 | A A1916 | −58.191 | 100.324 | 110.505 | 1.00 | 40.80 | N |
| ATOM | 41029 | C8 | A A1916 | −59.444 | 100.378 | 109.947 | 1.00 | 40.80 | C |
| ATOM | 41030 | N7 | A A1916 | −59.451 | 100.441 | 108.641 | 1.00 | 40.80 | N |
| ATOM | 41031 | C5 | A A1916 | −58.104 | 100.429 | 108.339 | 1.00 | 40.80 | C |
| ATOM | 41032 | C6 | A A1916 | −57.446 | 100.475 | 107.115 | 1.00 | 40.80 | C |
| ATOM | 41033 | N6 | A A1916 | −58.091 | 100.544 | 105.947 | 1.00 | 40.80 | N |
| ATOM | 41034 | N1 | A A1916 | −56.095 | 100.454 | 107.160 | 1.00 | 40.80 | N |
| ATOM | 41035 | C2 | A A1916 | −55.474 | 100.386 | 108.353 | 1.00 | 40.80 | C |
| ATOM | 41036 | N3 | A A1916 | −55.994 | 100.340 | 109.576 | 1.00 | 40.80 | N |
| ATOM | 41037 | C4 | A A1916 | −57.321 | 100.361 | 109.477 | 1.00 | 40.80 | C |
| ATOM | 41038 | P | U A1917 | −59.362 | 104.553 | 113.563 | 1.00 | 18.47 | P |
| ATOM | 41039 | OP1 | U A1917 | −59.681 | 105.177 | 114.864 | 1.00 | 18.47 | O |
| ATOM | 41040 | OP2 | U A1917 | −60.476 | 104.252 | 112.608 | 1.00 | 18.47 | O |
| ATOM | 41041 | O5' | U A1917 | −58.219 | 105.381 | 112.820 | 1.00 | 18.47 | O |
| ATOM | 41042 | C5' | U A1917 | −56.958 | 105.559 | 113.430 | 1.00 | 18.47 | C |
| ATOM | 41043 | C4' | U A1917 | −55.843 | 105.202 | 112.504 | 1.00 | 18.47 | C |
| ATOM | 41044 | O4' | U A1917 | −56.155 | 103.974 | 111.813 | 1.00 | 18.47 | O |
| ATOM | 41045 | C3' | U A1917 | −55.570 | 106.188 | 111.391 | 1.00 | 18.47 | C |
| ATOM | 41046 | O3' | U A1917 | −54.811 | 107.294 | 111.827 | 1.00 | 18.47 | O |
| ATOM | 41047 | C2' | U A1917 | −54.859 | 105.328 | 110.359 | 1.00 | 18.47 | C |
| ATOM | 41048 | O2' | U A1917 | −53.498 | 105.132 | 110.711 | 1.00 | 18.47 | O |
| ATOM | 41049 | C1' | U A1917 | −55.595 | 104.000 | 110.517 | 1.00 | 18.47 | C |
| ATOM | 41050 | N1 | U A1917 | −56.680 | 103.850 | 109.529 | 1.00 | 18.57 | N |
| ATOM | 41051 | C2 | U A1917 | −56.296 | 103.875 | 108.216 | 1.00 | 18.57 | C |
| ATOM | 41052 | O2 | U A1917 | −55.141 | 104.009 | 107.861 | 1.00 | 18.57 | O |
| ATOM | 41053 | N3 | U A1917 | −57.329 | 103.735 | 107.336 | 1.00 | 18.57 | N |
| ATOM | 41054 | C4 | U A1917 | −58.667 | 103.579 | 107.612 | 1.00 | 18.57 | C |
| ATOM | 41055 | O4 | U A1917 | −59.448 | 103.474 | 106.668 | 1.00 | 18.57 | O |
| ATOM | 41056 | C5 | U A1917 | −59.000 | 103.565 | 108.999 | 1.00 | 18.57 | C |
| ATOM | 41057 | C6 | U A1917 | −58.008 | 103.699 | 109.888 | 1.00 | 18.57 | C |
| ATOM | 41058 | P | A A1918 | −55.215 | 108.775 | 111.370 | 1.00 | 15.03 | P |

TABLE 7-continued

H69 Neomycin Binding Site for Unrotated Ribosome

| ATOM | 41059 | OP1 | A A1918 | −54.284 | 109.710 | 112.047 | 1.00 | 15.03 | O |
|---|---|---|---|---|---|---|---|---|---|
| ATOM | 41060 | OP2 | A A1918 | −56.683 | 108.926 | 111.598 | 1.00 | 15.03 | O |
| ATOM | 41061 | O5' | A A1918 | −54.889 | 108.735 | 109.817 | 1.00 | 15.03 | O |
| ATOM | 41062 | C5' | A A1918 | −53.601 | 108.312 | 109.379 | 1.00 | 15.03 | C |
| ATOM | 41063 | C4' | A A1918 | −53.522 | 108.199 | 107.880 | 1.00 | 15.03 | C |
| ATOM | 41064 | O4' | A A1918 | −54.519 | 107.246 | 107.415 | 1.00 | 15.03 | O |
| ATOM | 41065 | C3' | A A1918 | −53.755 | 109.498 | 107.128 | 1.00 | 15.03 | C |
| ATOM | 41066 | O3' | A A1918 | −52.817 | 109.622 | 106.080 | 1.00 | 15.03 | O |
| ATOM | 41067 | C2' | A A1918 | −55.151 | 109.354 | 106.547 | 1.00 | 15.03 | C |
| ATOM | 41068 | O2' | A A1918 | −55.317 | 109.983 | 105.290 | 1.00 | 15.03 | O |
| ATOM | 41069 | C1' | A A1918 | −55.352 | 107.834 | 106.447 | 1.00 | 15.03 | C |
| ATOM | 41070 | N9 | A A1918 | −56.723 | 107.435 | 106.738 | 1.00 | 14.94 | N |
| ATOM | 41071 | C8 | A A1918 | −57.255 | 107.364 | 107.990 | 1.00 | 14.94 | C |
| ATOM | 41072 | N7 | A A1918 | −58.518 | 107.046 | 108.006 | 1.00 | 14.94 | N |
| ATOM | 41073 | C5 | A A1918 | −58.840 | 106.921 | 106.670 | 1.00 | 14.94 | C |
| ATOM | 41074 | C6 | A A1918 | −60.050 | 106.598 | 106.033 | 1.00 | 14.94 | C |
| ATOM | 41075 | N6 | A A1918 | −61.171 | 106.337 | 106.718 | 1.00 | 14.94 | N |
| ATOM | 41076 | N1 | A A1918 | −60.064 | 106.555 | 104.674 | 1.00 | 14.94 | N |
| ATOM | 41077 | C2 | A A1918 | −58.922 | 106.828 | 104.025 | 1.00 | 14.94 | C |
| ATOM | 41078 | N3 | A A1918 | −57.728 | 107.151 | 104.535 | 1.00 | 14.94 | N |
| ATOM | 41079 | C4 | A A1918 | −57.748 | 107.179 | 105.874 | 1.00 | 14.94 | C |
| ATOM | 41080 | P | A A1919 | −51.570 | 110.612 | 106.246 | 1.00 | 18.21 | P |
| ATOM | 41081 | OP1 | A A1919 | −50.538 | 109.875 | 107.053 | 1.00 | 18.21 | O |
| ATOM | 41082 | OP2 | A A1919 | −52.104 | 111.911 | 106.763 | 1.00 | 18.21 | O |
| ATOM | 41083 | O5' | A A1919 | −51.075 | 110.793 | 104.733 | 1.00 | 18.21 | O |
| ATOM | 41084 | C5' | A A1919 | −49.698 | 110.910 | 104.410 | 1.00 | 18.21 | C |
| ATOM | 41085 | C4' | A A1919 | −49.386 | 110.225 | 103.107 | 1.00 | 18.21 | C |
| ATOM | 41086 | O4' | A A1919 | −49.758 | 108.824 | 103.200 | 1.00 | 18.21 | O |
| ATOM | 41087 | C3' | A A1919 | −50.158 | 110.720 | 101.894 | 1.00 | 18.21 | C |
| ATOM | 41088 | O3' | A A1919 | −49.597 | 111.864 | 101.307 | 1.00 | 18.21 | O |
| ATOM | 41089 | C2' | A A1919 | −50.149 | 109.508 | 100.991 | 1.00 | 18.21 | C |
| ATOM | 41090 | O2' | A A1919 | −48.856 | 109.307 | 100.440 | 1.00 | 18.21 | O |
| ATOM | 41091 | C1' | A A1919 | −50.415 | 108.422 | 102.014 | 1.00 | 18.21 | C |
| ATOM | 41092 | N9 | A A1919 | −51.847 | 108.317 | 102.324 | 1.00 | 18.07 | N |
| ATOM | 41093 | C8 | A A1919 | −52.370 | 108.370 | 103.592 | 1.00 | 18.07 | C |
| ATOM | 41094 | N7 | A A1919 | −53.670 | 108.295 | 103.642 | 1.00 | 18.07 | N |
| ATOM | 41095 | C5 | A A1919 | −54.022 | 108.193 | 102.315 | 1.00 | 18.07 | C |
| ATOM | 41096 | C6 | A A1919 | −55.269 | 108.072 | 101.717 | 1.00 | 18.07 | C |
| ATOM | 41097 | N6 | A A1919 | −56.395 | 108.041 | 102.426 | 1.00 | 18.07 | N |
| ATOM | 41098 | N1 | A A1919 | −55.311 | 108.003 | 100.373 | 1.00 | 18.07 | N |
| ATOM | 41099 | C2 | A A1919 | −54.162 | 108.043 | 99.694 | 1.00 | 18.07 | C |
| ATOM | 41100 | N3 | A A1919 | −52.918 | 108.155 | 100.151 | 1.00 | 18.07 | N |
| ATOM | 41101 | C4 | A A1919 | −52.919 | 108.222 | 101.487 | 1.00 | 18.07 | C |
| ATOM | 41102 | P | C A1920 | −50.378 | 113.246 | 101.400 | 1.00 | 13.85 | P |
| ATOM | 41103 | OP1 | C A1920 | −49.583 | 114.235 | 100.648 | 1.00 | 13.85 | O |
| ATOM | 41104 | OP2 | C A1920 | −50.665 | 113.492 | 102.828 | 1.00 | 13.85 | O |
| ATOM | 41105 | O5' | C A1920 | −51.732 | 112.941 | 100.633 | 1.00 | 13.85 | O |
| ATOM | 41106 | C5' | C A1920 | −51.751 | 112.689 | 99.236 | 1.00 | 13.85 | C |
| ATOM | 41107 | C4' | C A1920 | −53.169 | 112.601 | 98.738 | 1.00 | 13.85 | C |
| ATOM | 41108 | O4' | C A1920 | −53.847 | 111.497 | 99.404 | 1.00 | 13.85 | O |
| ATOM | 41109 | C3' | C A1920 | −54.028 | 113.813 | 99.038 | 1.00 | 13.85 | C |
| ATOM | 41110 | O3' | C A1920 | −53.926 | 114.801 | 98.047 | 1.00 | 13.85 | O |
| ATOM | 41111 | C2' | C A1920 | −55.429 | 113.231 | 99.195 | 1.00 | 13.85 | C |
| ATOM | 41112 | O2' | C A1920 | −56.029 | 112.977 | 97.931 | 1.00 | 13.85 | O |
| ATOM | 41113 | C1' | C A1920 | −55.112 | 111.900 | 99.871 | 1.00 | 13.85 | C |
| ATOM | 41114 | N1 | C A1920 | −55.024 | 112.038 | 101.349 | 1.00 | 14.42 | N |
| ATOM | 41115 | C2 | C A1920 | −56.108 | 112.548 | 102.080 | 1.00 | 14.42 | C |
| ATOM | 41116 | O2 | C A1920 | −57.128 | 112.854 | 101.452 | 1.00 | 14.42 | O |
| ATOM | 41117 | N3 | C A1920 | −56.010 | 112.699 | 103.438 | 1.00 | 14.42 | N |
| ATOM | 41118 | C4 | C A1920 | −54.869 | 112.349 | 104.069 | 1.00 | 14.42 | C |
| ATOM | 41119 | N4 | C A1920 | −54.789 | 112.501 | 105.400 | 1.00 | 14.42 | N |
| ATOM | 41120 | C5 | C A1920 | −53.754 | 111.812 | 103.334 | 1.00 | 14.42 | C |
| ATOM | 41121 | C6 | C A1920 | −53.866 | 111.685 | 101.997 | 1.00 | 14.42 | C |
| ATOM | 41122 | P | G A1921 | −53.726 | 116.329 | 98.472 | 1.00 | 15.45 | P |
| ATOM | 41123 | OP1 | G A1921 | −53.165 | 117.033 | 97.283 | 1.00 | 15.45 | O |
| ATOM | 41124 | OP2 | G A1921 | −52.967 | 116.347 | 99.758 | 1.00 | 15.45 | O |
| ATOM | 41125 | O5' | G A1921 | −55.210 | 116.804 | 98.723 | 1.00 | 15.45 | O |
| ATOM | 41126 | C5' | G A1921 | −56.168 | 116.637 | 97.714 | 1.00 | 15.45 | C |
| ATOM | 41127 | C4' | G A1921 | −57.535 | 116.564 | 98.281 | 1.00 | 15.45 | C |
| ATOM | 41128 | O4' | G A1921 | −57.567 | 115.626 | 99.389 | 1.00 | 15.45 | O |
| ATOM | 41129 | C3' | G A1921 | −58.053 | 117.841 | 98.886 | 1.00 | 15.45 | C |
| ATOM | 41130 | O3' | G A1921 | −58.430 | 118.798 | 97.911 | 1.00 | 15.45 | O |
| ATOM | 41131 | C2' | G A1921 | −59.195 | 117.323 | 99.753 | 1.00 | 15.45 | C |
| ATOM | 41132 | O2' | G A1921 | −60.346 | 117.013 | 98.981 | 1.00 | 15.45 | O |
| ATOM | 41133 | C1' | G A1921 | −58.589 | 116.015 | 100.281 | 1.00 | 15.45 | C |
| ATOM | 41134 | N9 | G A1921 | −58.016 | 116.201 | 101.613 | 1.00 | 15.48 | N |
| ATOM | 41135 | C8 | G A1921 | −56.729 | 116.255 | 102.059 | 1.00 | 15.48 | C |
| ATOM | 41136 | N7 | G A1921 | −56.683 | 116.492 | 103.349 | 1.00 | 15.48 | N |

TABLE 7-continued

H69 Neomycin Binding Site for Unrotated Ribosome

| ATOM | 41137 | C5 | G A1921 | −58.008 | 116.601 | 103.739 | 1.00 | 15.48 | C |
|------|-------|------|---------|---------|---------|---------|------|-------|---|
| ATOM | 41138 | C6 | G A1921 | −58.605 | 116.844 | 104.989 | 1.00 | 15.48 | C |
| ATOM | 41139 | O6 | G A1921 | −58.040 | 117.014 | 106.064 | 1.00 | 15.48 | O |
| ATOM | 41140 | N1 | G A1921 | −59.991 | 116.876 | 104.931 | 1.00 | 15.48 | N |
| ATOM | 41141 | C2 | G A1921 | −60.712 | 116.691 | 103.792 | 1.00 | 15.48 | C |
| ATOM | 41142 | N2 | G A1921 | −62.042 | 116.748 | 103.895 | 1.00 | 15.48 | N |
| ATOM | 41143 | N3 | G A1921 | −60.172 | 116.464 | 102.619 | 1.00 | 15.48 | N |
| ATOM | 41144 | C4 | G A1921 | −58.830 | 116.432 | 102.677 | 1.00 | 15.48 | C |
| ATOM | 41145 | P | G A1922 | −58.188 | 120.379 | 98.166 | 1.00 | 22.26 | P |
| ATOM | 41146 | OP1 | G A1922 | −58.232 | 121.061 | 96.833 | 1.00 | 22.26 | O |
| ATOM | 41147 | OP2 | G A1922 | −56.962 | 120.522 | 99.006 | 1.00 | 22.26 | O |
| ATOM | 41148 | O5' | G A1922 | −59.459 | 120.772 | 99.011 | 1.00 | 22.26 | O |
| ATOM | 41149 | C5' | G A1922 | −60.729 | 120.253 | 98.687 | 1.00 | 22.26 | C |
| ATOM | 41150 | C4' | G A1922 | −61.662 | 120.463 | 99.821 | 1.00 | 22.26 | C |
| ATOM | 41151 | O4' | G A1922 | −61.374 | 119.496 | 100.862 | 1.00 | 22.26 | O |
| ATOM | 41152 | C3' | G A1922 | −61.523 | 121.799 | 100.524 | 1.00 | 22.26 | C |
| ATOM | 41153 | O3' | G A1922 | −62.172 | 122.851 | 99.841 | 1.00 | 22.26 | O |
| ATOM | 41154 | C2' | G A1922 | −62.113 | 121.502 | 101.888 | 1.00 | 22.26 | C |
| ATOM | 41155 | O2' | G A1922 | −63.539 | 121.492 | 101.829 | 1.00 | 22.26 | O |
| ATOM | 41156 | C1' | G A1922 | −61.614 | 120.072 | 102.123 | 1.00 | 22.26 | C |
| ATOM | 41157 | N9 | G A1922 | −60.368 | 120.037 | 102.904 | 1.00 | 21.71 | N |
| ATOM | 41158 | C8 | G A1922 | −59.077 | 119.846 | 102.487 | 1.00 | 21.71 | C |
| ATOM | 41159 | N7 | G A1922 | −58.214 | 119.880 | 103.472 | 1.00 | 21.71 | N |
| ATOM | 41160 | C5 | G A1922 | −58.999 | 120.115 | 104.594 | 1.00 | 21.71 | C |
| ATOM | 41161 | C6 | G A1922 | −58.660 | 120.257 | 105.962 | 1.00 | 21.71 | C |
| ATOM | 41162 | O6 | G A1922 | −57.541 | 120.213 | 106.482 | 1.00 | 21.71 | O |
| ATOM | 41163 | N1 | G A1922 | −59.777 | 120.478 | 106.759 | 1.00 | 21.71 | N |
| ATOM | 41164 | C2 | G A1922 | −61.064 | 120.564 | 106.304 | 1.00 | 21.71 | C |
| ATOM | 41165 | N2 | G A1922 | −62.033 | 120.793 | 107.206 | 1.00 | 21.71 | N |
| ATOM | 41166 | N3 | G A1922 | −61.381 | 120.437 | 105.030 | 1.00 | 21.71 | N |
| ATOM | 41167 | C4 | G A1922 | −60.317 | 120.211 | 104.249 | 1.00 | 21.71 | C |
| ATOM | 41168 | P | U A1923 | −61.367 | 124.177 | 99.427 | 1.00 | 15.44 | P |
| ATOM | 41169 | OP1 | U A1923 | −62.103 | 124.790 | 98.303 | 1.00 | 15.44 | O |
| ATOM | 41170 | OP2 | U A1923 | −59.953 | 123.800 | 99.217 | 1.00 | 15.44 | O |
| ATOM | 41171 | O5' | U A1923 | −61.492 | 125.085 | 100.727 | 1.00 | 15.44 | O |
| ATOM | 41172 | C5' | U A1923 | −62.764 | 125.452 | 101.239 | 1.00 | 15.44 | C |
| ATOM | 41173 | C4' | U A1923 | −62.754 | 125.551 | 102.748 | 1.00 | 15.44 | C |
| ATOM | 41174 | O4' | U A1923 | −62.186 | 124.344 | 103.329 | 1.00 | 15.44 | O |
| ATOM | 41175 | C3' | U A1923 | −61.913 | 126.670 | 103.354 | 1.00 | 15.44 | C |
| ATOM | 41176 | O3' | U A1923 | −62.541 | 127.935 | 103.282 | 1.00 | 15.44 | O |
| ATOM | 41177 | C2' | U A1923 | −61.693 | 126.178 | 104.781 | 1.00 | 15.44 | C |
| ATOM | 41178 | O2' | U A1923 | −62.806 | 126.479 | 105.604 | 1.00 | 15.44 | O |
| ATOM | 41179 | C1' | U A1923 | −61.617 | 124.654 | 104.585 | 1.00 | 15.44 | C |
| ATOM | 41180 | N1 | U A1923 | −60.218 | 124.166 | 104.638 | 1.00 | 16.02 | N |
| ATOM | 41181 | C2 | U A1923 | −59.879 | 123.670 | 105.878 | 1.00 | 16.02 | C |
| ATOM | 41182 | O2 | U A1923 | −60.695 | 123.600 | 106.798 | 1.00 | 16.02 | O |
| ATOM | 41183 | N3 | U A1923 | −58.574 | 123.250 | 106.008 | 1.00 | 16.02 | N |
| ATOM | 41184 | C4 | U A1923 | −57.581 | 123.279 | 105.056 | 1.00 | 16.02 | C |
| ATOM | 41185 | O4 | U A1923 | −56.462 | 122.846 | 105.370 | 1.00 | 16.02 | O |
| ATOM | 41186 | C5 | U A1923 | −58.002 | 123.832 | 103.796 | 1.00 | 16.02 | C |
| ATOM | 41187 | C6 | U A1923 | −59.274 | 124.249 | 103.635 | 1.00 | 16.02 | C |
| ATOM | 41188 | P | C A1924 | −61.704 | 129.278 | 103.562 | 1.00 | 19.15 | P |
| ATOM | 41189 | OP1 | C A1924 | −62.594 | 130.418 | 103.220 | 1.00 | 19.15 | O |
| ATOM | 41190 | OP2 | C A1924 | −60.410 | 129.152 | 102.853 | 1.00 | 19.15 | O |
| ATOM | 41191 | O5' | C A1924 | −61.462 | 129.230 | 105.139 | 1.00 | 19.15 | O |
| ATOM | 41192 | C5' | C A1924 | −62.532 | 129.440 | 106.040 | 1.00 | 19.15 | C |
| ATOM | 41193 | C4' | C A1924 | −62.045 | 129.566 | 107.457 | 1.00 | 19.15 | C |
| ATOM | 41194 | O4' | C A1924 | −61.628 | 128.271 | 107.957 | 1.00 | 19.15 | O |
| ATOM | 41195 | C3' | C A1924 | −60.828 | 130.435 | 107.673 | 1.00 | 19.15 | C |
| ATOM | 41196 | O3' | C A1924 | −61.139 | 131.799 | 107.710 | 1.00 | 19.15 | O |
| ATOM | 41197 | C2' | C A1924 | −60.301 | 129.912 | 108.990 | 1.00 | 19.15 | C |
| ATOM | 41198 | O2' | C A1924 | −61.130 | 130.337 | 110.057 | 1.00 | 19.15 | O |
| ATOM | 41199 | C1' | C A1924 | −60.512 | 128.424 | 108.804 | 1.00 | 19.15 | C |
| ATOM | 41200 | N1 | C A1924 | −59.359 | 127.778 | 108.167 | 1.00 | 18.80 | N |
| ATOM | 41201 | C2 | C A1924 | −58.264 | 127.499 | 108.968 | 1.00 | 18.80 | C |
| ATOM | 41202 | O2 | C A1924 | −58.333 | 127.843 | 110.152 | 1.00 | 18.80 | O |
| ATOM | 41203 | N3 | C A1924 | −57.190 | 126.882 | 108.425 | 1.00 | 18.80 | N |
| ATOM | 41204 | C4 | C A1924 | −57.208 | 126.546 | 107.134 | 1.00 | 18.80 | C |
| ATOM | 41205 | N4 | C A1924 | −56.132 | 125.939 | 106.638 | 1.00 | 18.80 | N |
| ATOM | 41206 | C5 | C A1924 | −58.328 | 126.817 | 106.290 | 1.00 | 18.80 | C |
| ATOM | 41207 | C6 | C A1924 | −59.373 | 127.435 | 106.844 | 1.00 | 18.80 | C |
| ATOM | 41208 | P | C A1925 | −60.072 | 132.865 | 107.204 | 1.00 | 14.22 | P |
| ATOM | 41209 | OP1 | C A1925 | −60.667 | 134.209 | 107.423 | 1.00 | 14.22 | O |
| ATOM | 41210 | OP2 | C A1925 | −59.687 | 132.466 | 105.831 | 1.00 | 14.22 | O |
| ATOM | 41211 | O5' | C A1925 | −58.854 | 132.637 | 108.204 | 1.00 | 14.22 | O |
| ATOM | 41212 | C5' | C A1925 | −59.006 | 132.921 | 109.583 | 1.00 | 14.22 | C |
| ATOM | 41213 | C4' | C A1925 | −57.781 | 132.549 | 110.374 | 1.00 | 14.22 | C |
| ATOM | 41214 | O4' | C A1925 | −57.538 | 131.126 | 110.283 | 1.00 | 14.22 | O |

TABLE 7-continued

H69 Neomycin Binding Site for Unrotated Ribosome

| ATOM | 41215 | C3' | C A1925 | −56.481 | 133.171 | 109.914 | 1.00 | 14.22 | C |
|---|---|---|---|---|---|---|---|---|---|
| ATOM | 41216 | O3' | C A1925 | −56.332 | 134.504 | 110.351 | 1.00 | 14.22 | O |
| ATOM | 41217 | C2' | C A1925 | −55.464 | 132.223 | 110.499 | 1.00 | 14.22 | C |
| ATOM | 41218 | O2' | C A1925 | −55.350 | 132.411 | 111.901 | 1.00 | 14.22 | O |
| ATOM | 41219 | C1' | C A1925 | −56.155 | 130.890 | 110.238 | 1.00 | 14.22 | C |
| ATOM | 41220 | N1 | C A1925 | −55.833 | 130.374 | 108.908 | 1.00 | 14.59 | N |
| ATOM | 41221 | C2 | C A1925 | −54.641 | 129.678 | 108.756 | 1.00 | 14.59 | C |
| ATOM | 41222 | O2 | C A1925 | −53.954 | 129.522 | 109.767 | 1.00 | 14.59 | O |
| ATOM | 41223 | N3 | C A1925 | −54.275 | 129.188 | 107.544 | 1.00 | 14.59 | N |
| ATOM | 41224 | C4 | C A1925 | −55.084 | 129.393 | 106.490 | 1.00 | 14.59 | C |
| ATOM | 41225 | N4 | C A1925 | −54.695 | 128.898 | 105.294 | 1.00 | 14.59 | N |
| ATOM | 41226 | C5 | C A1925 | −56.324 | 130.120 | 106.620 | 1.00 | 14.59 | C |
| ATOM | 41227 | C6 | C A1925 | −56.653 | 130.592 | 107.839 | 1.00 | 14.59 | C |
| ATOM | 41228 | P | U A1926 | −55.180 | 135.426 | 109.735 | 1.00 | 30.05 | P |
| ATOM | 41229 | OP1 | U A1926 | −55.658 | 136.829 | 109.765 | 1.00 | 30.05 | O |
| ATOM | 41230 | OP2 | U A1926 | −54.790 | 134.829 | 108.425 | 1.00 | 30.05 | O |
| ATOM | 41231 | O5' | U A1926 | −54.021 | 135.238 | 110.785 | 1.00 | 30.05 | O |
| ATOM | 41232 | C5' | U A1926 | −52.703 | 135.533 | 110.425 | 1.00 | 30.05 | C |
| ATOM | 41233 | C4' | U A1926 | −51.762 | 134.501 | 110.947 | 1.00 | 30.05 | C |
| ATOM | 41234 | O4' | U A1926 | −52.233 | 133.171 | 110.619 | 1.00 | 30.05 | O |
| ATOM | 41235 | C3' | U A1926 | −50.377 | 134.532 | 110.362 | 1.00 | 30.05 | C |
| ATOM | 41236 | O3' | U A1926 | −49.606 | 135.599 | 110.865 | 1.00 | 30.05 | O |
| ATOM | 41237 | C2' | U A1926 | −49.874 | 133.154 | 110.712 | 1.00 | 30.05 | C |
| ATOM | 41238 | O2' | U A1926 | −49.625 | 133.058 | 112.107 | 1.00 | 30.05 | O |
| ATOM | 41239 | C1' | U A1926 | −51.119 | 132.331 | 110.387 | 1.00 | 30.05 | C |
| ATOM | 41240 | N1 | U A1926 | −51.157 | 131.906 | 108.976 | 1.00 | 30.24 | N |
| ATOM | 41241 | C2 | U A1926 | −50.074 | 131.318 | 108.350 | 1.00 | 30.24 | C |
| ATOM | 41242 | O2 | U A1926 | −48.999 | 131.089 | 108.848 | 1.00 | 30.24 | O |
| ATOM | 41243 | N3 | U A1926 | −50.284 | 130.995 | 107.051 | 1.00 | 30.24 | N |
| ATOM | 41244 | C4 | U A1926 | −51.438 | 131.188 | 106.331 | 1.00 | 30.24 | C |
| ATOM | 41245 | O4 | U A1926 | −51.468 | 130.834 | 105.152 | 1.00 | 30.24 | O |
| ATOM | 41246 | C5 | U A1926 | −52.516 | 131.791 | 107.033 | 1.00 | 30.24 | C |
| ATOM | 41247 | C6 | U A1926 | −52.331 | 132.118 | 108.303 | 1.00 | 30.24 | C |
| ATOM | 41248 | P | A A1927 | −49.933 | 137.083 | 110.347 | 1.00 | 11.68 | P |
| ATOM | 41249 | OP1 | A A1927 | −50.521 | 137.843 | 111.490 | 1.00 | 11.68 | O |
| ATOM | 41250 | OP2 | A A1927 | −50.739 | 136.918 | 109.106 | 1.00 | 11.68 | O |
| ATOM | 41251 | O5' | A A1927 | −48.485 | 137.648 | 109.980 | 1.00 | 11.68 | O |
| ATOM | 41252 | C5' | A A1927 | −47.960 | 137.503 | 108.665 | 1.00 | 11.68 | C |
| ATOM | 41253 | C4' | A A1927 | −46.591 | 136.860 | 108.664 | 1.00 | 11.68 | C |
| ATOM | 41254 | O4' | A A1927 | −45.944 | 137.057 | 109.932 | 1.00 | 11.68 | O |
| ATOM | 41255 | C3' | A A1927 | −46.553 | 135.358 | 108.469 | 1.00 | 11.68 | C |
| ATOM | 41256 | O3' | A A1927 | −46.689 | 134.991 | 107.123 | 1.00 | 11.68 | O |
| ATOM | 41257 | C2' | A A1927 | −45.207 | 134.974 | 109.057 | 1.00 | 11.68 | C |
| ATOM | 41258 | O2' | A A1927 | −44.151 | 135.210 | 108.120 | 1.00 | 11.68 | O |
| ATOM | 41259 | C1' | A A1927 | −45.082 | 135.971 | 110.201 | 1.00 | 11.68 | C |
| ATOM | 41260 | N9 | A A1927 | −45.450 | 135.413 | 111.507 | 1.00 | 11.46 | N |
| ATOM | 41261 | C8 | A A1927 | −46.647 | 135.641 | 112.104 | 1.00 | 11.46 | C |
| ATOM | 41262 | N7 | A A1927 | −46.730 | 135.142 | 113.305 | 1.00 | 11.46 | N |
| ATOM | 41263 | C5 | A A1927 | −45.495 | 134.561 | 113.512 | 1.00 | 11.46 | C |
| ATOM | 41264 | C6 | A A1927 | −44.974 | 133.860 | 114.612 | 1.00 | 11.46 | C |
| ATOM | 41265 | N6 | A A1927 | −45.697 | 133.645 | 115.712 | 1.00 | 11.46 | N |
| ATOM | 41266 | N1 | A A1927 | −43.702 | 133.391 | 114.546 | 1.00 | 11.46 | N |
| ATOM | 41267 | C2 | A A1927 | −43.022 | 133.651 | 113.423 | 1.00 | 11.46 | C |
| ATOM | 41268 | N3 | A A1927 | −43.425 | 134.300 | 112.327 | 1.00 | 11.46 | N |
| ATOM | 41269 | C4 | A A1927 | −44.683 | 134.738 | 112.424 | 1.00 | 11.46 | C |
| ATOM | 41270 | P | A A1928 | −47.798 | 133.927 | 106.706 | 1.00 | 9.61 | P |
| ATOM | 41271 | OP1 | A A1928 | −48.017 | 134.087 | 105.251 | 1.00 | 9.61 | O |
| ATOM | 41272 | OP2 | A A1928 | −48.955 | 134.116 | 107.631 | 1.00 | 9.61 | O |
| ATOM | 41273 | O5' | A A1928 | −47.067 | 132.532 | 106.996 | 1.00 | 9.61 | O |
| ATOM | 41274 | C5' | A A1928 | −45.886 | 132.178 | 106.287 | 1.00 | 9.61 | C |
| ATOM | 41275 | C4' | A A1928 | −44.957 | 131.314 | 107.111 | 1.00 | 9.61 | C |
| ATOM | 41276 | O4' | A A1928 | −44.628 | 131.969 | 108.360 | 1.00 | 9.61 | O |
| ATOM | 41277 | C3' | A A1928 | −45.496 | 129.958 | 107.537 | 1.00 | 9.61 | C |
| ATOM | 41278 | O3' | A A1928 | −45.400 | 128.984 | 106.516 | 1.00 | 9.61 | O |
| ATOM | 41279 | C2' | A A1928 | −44.647 | 129.628 | 108.753 | 1.00 | 9.61 | C |
| ATOM | 41280 | O2' | A A1928 | −43.390 | 129.099 | 108.366 | 1.00 | 9.61 | O |
| ATOM | 41281 | C1' | A A1928 | −44.432 | 131.002 | 109.371 | 1.00 | 9.61 | C |
| ATOM | 41282 | N9 | A A1928 | −45.385 | 131.253 | 110.453 | 1.00 | 9.14 | N |
| ATOM | 41283 | C8 | A A1928 | −46.650 | 131.728 | 110.322 | 1.00 | 9.14 | C |
| ATOM | 41284 | N7 | A A1928 | −47.268 | 131.842 | 111.462 | 1.00 | 9.14 | N |
| ATOM | 41285 | C5 | A A1928 | −46.352 | 131.408 | 112.392 | 1.00 | 9.14 | C |
| ATOM | 41286 | C6 | A A1928 | −46.429 | 131.280 | 113.781 | 1.00 | 9.14 | C |
| ATOM | 41287 | N6 | A A1928 | −47.561 | 131.613 | 114.415 | 1.00 | 9.14 | N |
| ATOM | 41288 | N1 | A A1928 | −45.326 | 130.795 | 114.456 | 1.00 | 9.14 | N |
| ATOM | 41289 | C2 | A A1928 | −44.229 | 130.446 | 113.761 | 1.00 | 9.14 | C |
| ATOM | 41290 | N3 | A A1928 | −44.055 | 130.522 | 112.430 | 1.00 | 9.14 | N |
| ATOM | 41291 | C4 | A A1928 | −45.167 | 131.024 | 111.795 | 1.00 | 9.14 | C |
| ATOM | 41292 | P | G A1929 | −46.705 | 128.158 | 106.070 | 1.00 | 23.81 | P |

TABLE 7-continued

H69 Neomycin Binding Site for Unrotated Ribosome

| ATOM | 41293 | OP1 | G | A1929 | −46.216 | 126.936 | 105.362 | 1.00 | 23.81 | O |
|---|---|---|---|---|---|---|---|---|---|---|
| ATOM | 41294 | OP2 | G | A1929 | −47.597 | 129.115 | 105.346 | 1.00 | 23.81 | O |
| ATOM | 41295 | O5' | G | A1929 | −47.372 | 127.754 | 107.466 | 1.00 | 23.81 | O |
| ATOM | 41296 | C5' | G | A1929 | −47.526 | 126.386 | 107.845 | 1.00 | 23.81 | C |
| ATOM | 41297 | C4' | G | A1929 | −46.609 | 126.004 | 108.989 | 1.00 | 23.81 | C |
| ATOM | 41298 | O4' | G | A1929 | −46.616 | 127.053 | 109.996 | 1.00 | 23.81 | O |
| ATOM | 41299 | C3' | G | A1929 | −47.002 | 124.738 | 109.724 | 1.00 | 23.81 | C |
| ATOM | 41300 | O3' | G | A1929 | −45.847 | 124.141 | 110.261 | 1.00 | 23.81 | O |
| ATOM | 41301 | C2' | G | A1929 | −47.846 | 125.261 | 110.856 | 1.00 | 23.81 | C |
| ATOM | 41302 | O2' | G | A1929 | −47.945 | 124.390 | 111.955 | 1.00 | 23.81 | O |
| ATOM | 41303 | C1' | G | A1929 | −47.096 | 126.534 | 111.217 | 1.00 | 23.81 | C |
| ATOM | 41304 | N9 | G | A1929 | −47.952 | 127.533 | 111.841 | 1.00 | 23.23 | N |
| ATOM | 41305 | C8 | G | A1929 | −47.826 | 128.131 | 113.061 | 1.00 | 23.23 | C |
| ATOM | 41306 | N7 | G | A1929 | −48.821 | 128.925 | 113.318 | 1.00 | 23.23 | N |
| ATOM | 41307 | C5 | G | A1929 | −49.657 | 128.810 | 112.216 | 1.00 | 23.23 | C |
| ATOM | 41308 | C6 | G | A1929 | −50.889 | 129.430 | 111.904 | 1.00 | 23.23 | C |
| ATOM | 41309 | O6 | G | A1929 | −51.544 | 130.240 | 112.567 | 1.00 | 23.23 | O |
| ATOM | 41310 | N1 | G | A1929 | −51.370 | 129.040 | 110.669 | 1.00 | 23.23 | N |
| ATOM | 41311 | C2 | G | A1929 | −50.762 | 128.165 | 109.833 | 1.00 | 23.23 | C |
| ATOM | 41312 | N2 | G | A1929 | −51.396 | 127.921 | 108.687 | 1.00 | 23.23 | N |
| ATOM | 41313 | N3 | G | A1929 | −49.624 | 127.571 | 110.102 | 1.00 | 23.23 | N |
| ATOM | 41314 | C4 | G | A1929 | −49.134 | 127.944 | 111.302 | 1.00 | 23.23 | C |
| ATOM | 41315 | P | G | A1930 | −44.794 | 123.454 | 109.288 | 1.00 | 15.78 | P |
| ATOM | 41316 | OP1 | G | A1930 | −44.061 | 124.570 | 108.592 | 1.00 | 15.78 | O |
| ATOM | 41317 | OP2 | G | A1930 | −45.524 | 122.430 | 108.477 | 1.00 | 15.78 | O |
| ATOM | 41318 | O5' | G | A1930 | −43.842 | 122.728 | 110.306 | 1.00 | 15.78 | O |
| ATOM | 41319 | C5' | G | A1930 | −42.827 | 123.445 | 110.976 | 1.00 | 15.78 | C |
| ATOM | 41320 | C4' | G | A1930 | −41.830 | 122.506 | 111.544 | 1.00 | 15.78 | C |
| ATOM | 41321 | O4' | G | A1930 | −41.384 | 123.018 | 112.822 | 1.00 | 15.78 | O |
| ATOM | 41322 | C3' | G | A1930 | −42.384 | 121.113 | 111.827 | 1.00 | 15.78 | C |
| ATOM | 41323 | O3' | G | A1930 | −41.349 | 120.148 | 111.661 | 1.00 | 15.78 | O |
| ATOM | 41324 | C2' | G | A1930 | −42.753 | 121.213 | 113.293 | 1.00 | 15.78 | C |
| ATOM | 41325 | O2' | G | A1930 | −42.869 | 119.978 | 113.951 | 1.00 | 15.78 | O |
| ATOM | 41326 | C1' | G | A1930 | −41.568 | 122.018 | 113.789 | 1.00 | 15.78 | C |
| ATOM | 41327 | N9 | G | A1930 | −41.737 | 122.649 | 115.078 | 1.00 | 14.92 | N |
| ATOM | 41328 | C8 | G | A1930 | −42.851 | 123.023 | 115.766 | 1.00 | 14.92 | C |
| ATOM | 41329 | N7 | G | A1930 | −42.541 | 123.553 | 116.913 | 1.00 | 14.92 | N |
| ATOM | 41330 | C5 | G | A1930 | −41.141 | 123.501 | 116.954 | 1.00 | 14.92 | C |
| ATOM | 41331 | C6 | G | A1930 | −40.206 | 123.927 | 117.925 | 1.00 | 14.92 | C |
| ATOM | 41332 | O6 | G | A1930 | −40.456 | 124.460 | 119.006 | 1.00 | 14.92 | O |
| ATOM | 41333 | N1 | G | A1930 | −38.889 | 123.703 | 117.550 | 1.00 | 14.92 | N |
| ATOM | 41334 | C2 | G | A1930 | −38.523 | 123.142 | 116.376 | 1.00 | 14.92 | C |
| ATOM | 41335 | N2 | G | A1930 | −37.222 | 123.010 | 116.179 | 1.00 | 14.92 | N |
| ATOM | 41336 | N3 | G | A1930 | −39.365 | 122.743 | 115.459 | 1.00 | 14.92 | N |
| ATOM | 41337 | C4 | G | A1930 | −40.642 | 122.948 | 115.820 | 1.00 | 14.92 | C |
| ATOM | 41338 | P | U | A1931 | −41.710 | 118.593 | 111.605 | 1.00 | 20.12 | P |
| ATOM | 41339 | OP1 | U | A1931 | −42.990 | 118.465 | 110.881 | 1.00 | 20.12 | O |
| ATOM | 41340 | OP2 | U | A1931 | −41.632 | 118.084 | 112.977 | 1.00 | 20.12 | O |
| ATOM | 41341 | O5' | U | A1931 | −40.526 | 117.988 | 110.724 | 1.00 | 20.12 | O |
| ATOM | 41342 | C5' | U | A1931 | −40.642 | 117.903 | 109.314 | 1.00 | 20.12 | C |
| ATOM | 41343 | C4' | U | A1931 | −39.405 | 118.415 | 108.615 | 1.00 | 20.12 | C |
| ATOM | 41344 | O4' | U | A1931 | −39.127 | 119.776 | 109.011 | 1.00 | 20.12 | O |
| ATOM | 41345 | C3' | U | A1931 | −38.103 | 117.689 | 108.911 | 1.00 | 20.12 | C |
| ATOM | 41346 | O3' | U | A1931 | −37.987 | 116.478 | 108.217 | 1.00 | 20.12 | O |
| ATOM | 41347 | C2' | U | A1931 | −37.068 | 118.703 | 108.485 | 1.00 | 20.12 | C |
| ATOM | 41348 | O2' | U | A1931 | −36.926 | 118.705 | 107.071 | 1.00 | 20.12 | O |
| ATOM | 41349 | C1' | U | A1931 | −37.734 | 120.011 | 108.902 | 1.00 | 20.12 | C |
| ATOM | 41350 | N1 | U | A1931 | −37.208 | 120.525 | 110.197 | 1.00 | 20.00 | N |
| ATOM | 41351 | C2 | U | A1931 | −35.807 | 120.615 | 110.367 | 1.00 | 20.00 | C |
| ATOM | 41352 | O2 | U | A1931 | −34.940 | 120.268 | 109.566 | 1.00 | 20.00 | O |
| ATOM | 41353 | N3 | U | A1931 | −35.429 | 121.128 | 111.575 | 1.00 | 20.00 | N |
| ATOM | 41354 | C4 | U | A1931 | −36.252 | 121.561 | 112.583 | 1.00 | 20.00 | C |
| ATOM | 41355 | O4 | U | A1931 | −35.739 | 121.996 | 113.605 | 1.00 | 20.00 | O |
| ATOM | 41356 | C5 | U | A1931 | −37.654 | 121.441 | 112.336 | 1.00 | 20.00 | C |
| ATOM | 41357 | C6 | U | A1931 | −38.081 | 120.941 | 111.179 | 1.00 | 20.00 | C |
| TER | | | | | | | | | | |
| END | | | | | | | | | | |

TABLE 8

H69 Neomycin Binding Site for Intermediate-Rotated Ribosome

| ATOM | 48797 | P | G | A1515 | −75.974 | 5.456 | 3.358 | 1.00 | 86.56 | P |
|---|---|---|---|---|---|---|---|---|---|---|
| ATOM | 48798 | OP1 | G | A1515 | −75.617 | 4.050 | 3.662 | 1.00 | 86.56 | O |
| ATOM | 48799 | OP2 | G | A1515 | −76.170 | 5.852 | 1.942 | 1.00 | 86.56 | O |

TABLE 8-continued

H69 Neomycin Binding Site for Intermediate-Rotated Ribosome

| ATOM | 48800 | O5' | G | A1515 | −77.235 | 5.896 | 4.223 | 1.00 | 86.56 | O |
|---|---|---|---|---|---|---|---|---|---|---|
| ATOM | 48801 | C5' | G | A1515 | −78.538 | 5.476 | 3.865 | 1.00 | 86.56 | C |
| ATOM | 48802 | C4' | G | A1515 | −79.598 | 6.372 | 4.449 | 1.00 | 86.56 | C |
| ATOM | 48803 | O4' | G | A1515 | −79.192 | 7.763 | 4.344 | 1.00 | 86.56 | O |
| ATOM | 48804 | C1' | G | A1515 | −80.318 | 8.574 | 4.069 | 1.00 | 86.56 | C |
| ATOM | 48805 | N9 | G | A1515 | −80.130 | 9.194 | 2.744 | 1.00 | 102.19 | N |
| ATOM | 48806 | C4 | G | A1515 | −81.026 | 9.974 | 2.051 | 1.00 | 102.19 | C |
| ATOM | 48807 | N3 | G | A1515 | −82.267 | 10.320 | 2.452 | 1.00 | 102.19 | N |
| ATOM | 48808 | C2 | G | A1515 | −82.883 | 11.075 | 1.556 | 1.00 | 102.19 | C |
| ATOM | 48809 | N2 | G | A1515 | −84.132 | 11.510 | 1.797 | 1.00 | 102.19 | N |
| ATOM | 48810 | N1 | G | A1515 | −82.322 | 11.461 | 0.362 | 1.00 | 102.19 | N |
| ATOM | 48811 | C6 | G | A1515 | −81.048 | 11.115 | −0.070 | 1.00 | 102.19 | C |
| ATOM | 48812 | O6 | G | A1515 | −80.632 | 11.508 | −1.164 | 1.00 | 102.19 | O |
| ATOM | 48813 | C5 | G | A1515 | −80.383 | 10.306 | 0.879 | 1.00 | 102.19 | C |
| ATOM | 48814 | N7 | G | A1515 | −79.114 | 9.757 | 0.830 | 1.00 | 102.19 | N |
| ATOM | 48815 | C8 | G | A1515 | −79.009 | 9.108 | 1.953 | 1.00 | 102.19 | C |
| ATOM | 48816 | C2' | G | A1515 | −81.552 | 7.674 | 4.109 | 1.00 | 86.56 | C |
| ATOM | 48817 | O2' | G | A1515 | −82.068 | 7.664 | 5.432 | 1.00 | 86.56 | O |
| ATOM | 48818 | C3' | G | A1515 | −80.943 | 6.329 | 3.751 | 1.00 | 86.56 | C |
| ATOM | 48819 | O3' | G | A1515 | −81.726 | 5.220 | 4.140 | 1.00 | 86.56 | O |
| ATOM | 48831 | P | G | A1516 | −81.762 | 3.900 | 3.228 | 1.00 | 74.90 | P |
| ATOM | 48832 | OP1 | G | A1516 | −81.772 | 2.736 | 4.146 | 1.00 | 74.90 | O |
| ATOM | 48833 | OP2 | G | A1516 | −80.664 | 4.014 | 2.235 | 1.00 | 74.90 | O |
| ATOM | 48834 | O5' | G | A1516 | −83.166 | 4.027 | 2.501 | 1.00 | 74.90 | O |
| ATOM | 48835 | C5' | G | A1516 | −84.358 | 4.103 | 3.261 | 1.00 | 74.90 | C |
| ATOM | 48836 | C4' | G | A1516 | −85.241 | 5.234 | 2.806 | 1.00 | 74.90 | C |
| ATOM | 48837 | O4' | G | A1516 | −84.463 | 6.443 | 2.620 | 1.00 | 74.90 | O |
| ATOM | 48838 | C1' | G | A1516 | −85.101 | 7.263 | 1.660 | 1.00 | 74.90 | C |
| ATOM | 48839 | N9 | G | A1516 | −84.128 | 7.628 | 0.609 | 1.00 | 126.22 | N |
| ATOM | 48840 | C4 | G | A1516 | −84.429 | 8.309 | −0.545 | 1.00 | 126.22 | C |
| ATOM | 48841 | N3 | G | A1516 | −85.656 | 8.735 | −0.903 | 1.00 | 126.22 | N |
| ATOM | 48842 | C2 | G | A1516 | −85.647 | 9.350 | −2.071 | 1.00 | 126.22 | C |
| ATOM | 48843 | N2 | G | A1516 | −86.799 | 9.831 | −2.563 | 1.00 | 126.22 | N |
| ATOM | 48844 | N1 | G | A1516 | −84.520 | 9.541 | −2.830 | 1.00 | 126.22 | N |
| ATOM | 48845 | C6 | G | A1516 | −83.242 | 9.113 | −2.480 | 1.00 | 126.22 | C |
| ATOM | 48846 | O6 | G | A1516 | −82.293 | 9.339 | −3.240 | 1.00 | 126.22 | O |
| ATOM | 48847 | C5 | G | A1516 | −83.241 | 8.445 | −1.226 | 1.00 | 126.22 | C |
| ATOM | 48848 | N7 | G | A1516 | −82.204 | 7.866 | −0.508 | 1.00 | 126.22 | N |
| ATOM | 48849 | C8 | G | A1516 | −82.776 | 7.399 | 0.570 | 1.00 | 126.22 | C |
| ATOM | 48850 | C2' | G | A1516 | −86.298 | 6.481 | 1.100 | 1.00 | 74.90 | C |
| ATOM | 48851 | O2' | G | A1516 | −87.473 | 6.894 | 1.783 | 1.00 | 74.90 | O |
| ATOM | 48852 | C3' | G | A1516 | −85.929 | 5.050 | 1.469 | 1.00 | 74.90 | C |
| ATOM | 48853 | O3' | G | A1516 | −87.037 | 4.170 | 1.536 | 1.00 | 74.90 | O |
| ATOM | 48865 | P | G | A1517 | −86.971 | 2.734 | 0.819 | 1.00 | 77.49 | P |
| ATOM | 48866 | OP1 | G | A1517 | −88.091 | 1.925 | 1.356 | 1.00 | 77.49 | O |
| ATOM | 48867 | OP2 | G | A1517 | −85.585 | 2.228 | 0.975 | 1.00 | 77.49 | O |
| ATOM | 48868 | O5' | G | A1517 | −87.246 | 3.095 | −0.704 | 1.00 | 77.49 | O |
| ATOM | 48869 | C5' | G | A1517 | −88.193 | 4.092 | −1.043 | 1.00 | 77.49 | C |
| ATOM | 48870 | C4' | G | A1517 | −88.783 | 3.861 | −2.410 | 1.00 | 77.49 | C |
| ATOM | 48871 | O4' | G | A1517 | −90.198 | 3.570 | −2.276 | 1.00 | 77.49 | O |
| ATOM | 48872 | C1' | G | A1517 | −90.927 | 4.204 | −3.300 | 1.00 | 77.49 | C |
| ATOM | 48873 | N9 | G | A1517 | −91.823 | 5.200 | −2.680 | 1.00 | 92.53 | N |
| ATOM | 48874 | C4 | G | A1517 | −92.819 | 5.937 | −3.279 | 1.00 | 92.53 | C |
| ATOM | 48875 | N3 | G | A1517 | −93.162 | 5.909 | −4.583 | 1.00 | 92.53 | N |
| ATOM | 48876 | C2 | G | A1517 | −94.155 | 6.741 | −4.853 | 1.00 | 92.53 | C |
| ATOM | 48877 | N2 | G | A1517 | −94.621 | 6.835 | −6.107 | 1.00 | 92.53 | N |
| ATOM | 48878 | N1 | G | A1517 | −94.764 | 7.540 | −3.918 | 1.00 | 92.53 | N |
| ATOM | 48879 | C6 | G | A1517 | −94.428 | 7.587 | −2.571 | 1.00 | 92.53 | C |
| ATOM | 48880 | O6 | G | A1517 | −95.042 | 8.342 | −1.809 | 1.00 | 92.53 | O |
| ATOM | 48881 | C5 | G | A1517 | −93.365 | 6.700 | −2.269 | 1.00 | 92.53 | C |
| ATOM | 48882 | N7 | G | A1517 | −92.738 | 6.447 | −1.059 | 1.00 | 92.53 | N |
| ATOM | 48883 | C8 | G | A1517 | −91.837 | 5.551 | −1.349 | 1.00 | 92.53 | C |
| ATOM | 48884 | C2' | G | A1517 | −89.930 | 4.833 | −4.264 | 1.00 | 77.49 | C |
| ATOM | 48885 | O2' | G | A1517 | −89.639 | 3.896 | −5.292 | 1.00 | 77.49 | O |
| ATOM | 48886 | C3' | G | A1517 | −88.719 | 5.046 | −3.364 | 1.00 | 77.49 | C |
| ATOM | 48887 | O3' | G | A1517 | −87.493 | 5.113 | −4.072 | 1.00 | 77.49 | O |
| ATOM | 48899 | P | A | A1518 | −86.457 | 6.308 | −3.792 | 1.00 | 74.99 | P |
| ATOM | 48900 | OP1 | A | A1518 | −85.146 | 5.887 | −4.341 | 1.00 | 74.99 | O |
| ATOM | 48901 | OP2 | A | A1518 | −86.552 | 6.635 | −2.356 | 1.00 | 74.99 | O |
| ATOM | 48902 | O5' | A | A1518 | −87.050 | 7.500 | −4.661 | 1.00 | 74.99 | O |
| ATOM | 48903 | C5' | A | A1518 | −87.174 | 7.376 | −6.068 | 1.00 | 74.99 | C |
| ATOM | 48904 | C4' | A | A1518 | −88.306 | 8.212 | −6.603 | 1.00 | 74.99 | C |
| ATOM | 48905 | O4' | A | A1518 | −89.564 | 7.780 | −6.023 | 1.00 | 74.99 | O |
| ATOM | 48906 | C1' | A | A1518 | −90.431 | 8.884 | −5.879 | 1.00 | 74.99 | C |
| ATOM | 48907 | N9 | A | A1518 | −90.766 | 9.036 | −4.450 | 1.00 | 69.86 | N |
| ATOM | 48908 | C4 | A | A1518 | −91.863 | 9.689 | −3.946 | 1.00 | 69.86 | C |
| ATOM | 48909 | N3 | A | A1518 | −92.834 | 10.301 | −4.642 | 1.00 | 69.86 | N |
| ATOM | 48910 | C2 | A | A1518 | −93.742 | 10.828 | −3.824 | 1.00 | 69.86 | C |

TABLE 8-continued

H69 Neomycin Binding Site for Intermediate-Rotated Ribosome

| ATOM | 48911 | N1 | A | A1518 | −93.785 | 10.813 | −2.485 | 1.00 | 69.86 | N |
|---|---|---|---|---|---|---|---|---|---|---|
| ATOM | 48912 | C6 | A | A1518 | −92.791 | 10.191 | −1.814 | 1.00 | 69.86 | C |
| ATOM | 48913 | N6 | A | A1518 | −92.841 | 10.173 | −0.480 | 1.00 | 69.86 | N |
| ATOM | 48914 | C5 | A | A1518 | −91.769 | 9.588 | −2.570 | 1.00 | 69.86 | C |
| ATOM | 48915 | N7 | A | A1518 | −90.629 | 8.884 | −2.207 | 1.00 | 69.86 | N |
| ATOM | 48916 | C8 | A | A1518 | −90.070 | 8.581 | −3.355 | 1.00 | 69.86 | C |
| ATOM | 48917 | C2' | A | A1518 | −89.704 | 10.115 | −6.430 | 1.00 | 74.99 | C |
| ATOM | 48918 | O2' | A | A1518 | −90.051 | 10.288 | −7.798 | 1.00 | 74.99 | O |
| ATOM | 48919 | C3' | A | A1518 | −88.249 | 9.695 | −6.285 | 1.00 | 74.99 | C |
| ATOM | 48920 | O3' | A | A1518 | −87.364 | 10.402 | −7.136 | 1.00 | 74.99 | O |
| TER | | | | | | | | | | |
| ATOM | A11M5 | P | G | C1903 | −76.679 | −18.653 | 17.908 | 1.00 | 59.96 | P |
| ATOM | A11M6 | OP1 | G | C1903 | −77.065 | −20.028 | 17.506 | 1.00 | 59.96 | O |
| ATOM | A11M7 | OP2 | G | C1903 | −75.411 | −18.088 | 17.385 | 1.00 | 59.96 | O |
| ATOM | A11M8 | O5' | G | C1903 | −77.876 | −17.643 | 17.627 | 1.00 | 59.96 | O |
| ATOM | A11M9 | C5' | G | C1903 | −78.973 | −18.009 | 16.806 | 1.00 | 59.96 | C |
| ATOM | A11MA | C4' | G | C1903 | −80.265 | −17.456 | 17.344 | 1.00 | 59.96 | C |
| ATOM | A11MB | O4' | G | C1903 | −79.987 | −16.435 | 18.341 | 1.00 | 59.96 | O |
| ATOM | A11MC | C1' | G | C1903 | −80.957 | −15.413 | 18.267 | 1.00 | 59.96 | C |
| ATOM | A11MD | N9 | G | C1903 | −80.282 | −14.153 | 17.900 | 1.00 | 57.44 | N |
| ATOM | A11ME | C4 | G | C1903 | −80.886 | −12.946 | 17.653 | 1.00 | 57.44 | C |
| ATOM | A11MF | N3 | G | C1903 | −82.210 | −12.703 | 17.702 | 1.00 | 57.44 | N |
| ATOM | A11MG | C2 | G | C1903 | −82.494 | −11.446 | 17.411 | 1.00 | 57.44 | C |
| ATOM | A11MH | N2 | G | C1903 | −83.775 | −11.048 | 17.418 | 1.00 | 57.44 | N |
| ATOM | A11MI | N1 | G | C1903 | −81.548 | −10.498 | 17.098 | 1.00 | 57.44 | N |
| ATOM | A11MJ | C6 | G | C1903 | −80.177 | −10.727 | 17.042 | 1.00 | 57.44 | C |
| ATOM | A11MK | O6 | G | C1903 | −79.408 | −9.804 | 16.750 | 1.00 | 57.44 | O |
| ATOM | A11ML | C5 | G | C1903 | −79.861 | −12.075 | 17.351 | 1.00 | 57.44 | C |
| ATOM | A11MM | N7 | G | C1903 | −78.634 | −12.718 | 17.409 | 1.00 | 57.44 | N |
| ATOM | A11MN | C8 | G | C1903 | −78.932 | −13.945 | 17.737 | 1.00 | 57.44 | C |
| ATOM | A11MO | C2' | G | C1903 | −81.990 | −15.837 | 17.222 | 1.00 | 59.96 | C |
| ATOM | A11MP | O2' | G | C1903 | −83.022 | −16.563 | 17.872 | 1.00 | 59.96 | O |
| ATOM | A11MQ | C3' | G | C1903 | −81.157 | −16.751 | 16.337 | 1.00 | 59.96 | C |
| ATOM | A11MR | O3' | G | C1903 | −81.927 | −17.652 | 15.560 | 1.00 | 59.96 | O |
| ATOM | A11N3 | P | G | C1904 | −82.022 | −17.478 | 13.964 | 1.00 | 55.65 | P |
| ATOM | A11N4 | OP1 | G | C1904 | −82.374 | −18.805 | 13.402 | 1.00 | 55.65 | O |
| ATOM | A11N5 | OP2 | G | C1904 | −80.768 | −16.825 | 13.513 | 1.00 | 55.65 | O |
| ATOM | A11N6 | O5' | G | C1904 | −83.245 | −16.477 | 13.793 | 1.00 | 55.65 | O |
| ATOM | A11N7 | C5' | G | C1904 | −84.532 | −16.806 | 14.292 | 1.00 | 55.65 | C |
| ATOM | A11N8 | C4' | G | C1904 | −85.449 | −15.610 | 14.284 | 1.00 | 55.65 | C |
| ATOM | A11N9 | O4' | G | C1904 | −84.935 | −14.594 | 15.186 | 1.00 | 55.65 | O |
| ATOM | A11NA | C1' | G | C1904 | −85.187 | −13.309 | 14.657 | 1.00 | 55.65 | C |
| ATOM | A11NB | N9 | G | C1904 | −83.893 | −12.657 | 14.376 | 1.00 | 66.38 | N |
| ATOM | A11NC | C4 | G | C1904 | −83.697 | −11.356 | 13.975 | 1.00 | 66.38 | C |
| ATOM | A11ND | N3 | G | C1904 | −84.654 | −10.427 | 13.770 | 1.00 | 66.38 | N |
| ATOM | A11NE | C2 | G | C1904 | −84.147 | −9.265 | 13.391 | 1.00 | 66.38 | C |
| ATOM | A11NF | N2 | G | C1904 | −84.963 | −8.231 | 13.144 | 1.00 | 66.38 | N |
| ATOM | A11NG | N1 | G | C1904 | −82.806 | −9.032 | 13.225 | 1.00 | 66.38 | N |
| ATOM | A11NH | C6 | G | C1904 | −81.804 | −9.973 | 13.430 | 1.00 | 66.38 | C |
| ATOM | A11NI | O6 | G | C1904 | −80.621 | −9.665 | 13.253 | 1.00 | 66.38 | O |
| ATOM | A11NJ | C5 | G | C1904 | −82.333 | −11.223 | 13.836 | 1.00 | 66.38 | C |
| ATOM | A11NK | N7 | G | C1904 | −81.683 | −12.409 | 14.138 | 1.00 | 66.38 | N |
| ATOM | A11NL | C8 | G | C1904 | −82.646 | −13.229 | 14.449 | 1.00 | 66.38 | C |
| ATOM | A11NM | C2' | G | C1904 | −86.017 | −13.491 | 13.390 | 1.00 | 55.65 | C |
| ATOM | A11NN | O2' | G | C1904 | −87.393 | −13.472 | 13.740 | 1.00 | 55.65 | O |
| ATOM | A11NO | C3' | G | C1904 | −85.585 | −14.882 | 12.954 | 1.00 | 55.65 | C |
| ATOM | A11NP | O3' | G | C1904 | −86.492 | −15.509 | 12.065 | 1.00 | 55.65 | O |
| ATOM | A11O1 | P | C | C1905 | −86.064 | −15.792 | 10.540 | 1.00 | 64.97 | P |
| ATOM | A11O2 | OP1 | C | C1905 | −87.067 | −16.724 | 9.974 | 1.00 | 64.97 | O |
| ATOM | A11O3 | OP2 | C | C1905 | −84.638 | −16.202 | 10.552 | 1.00 | 64.97 | O |
| ATOM | A11O4 | O5' | C | C1905 | −86.209 | −14.361 | 9.858 | 1.00 | 64.97 | O |
| ATOM | A11O5 | C5' | C | C1905 | −87.469 | −13.713 | 9.784 | 1.00 | 64.97 | C |
| ATOM | A11O6 | C4' | C | C1905 | −87.320 | −12.215 | 9.707 | 1.00 | 64.97 | C |
| ATOM | A11O7 | O4' | C | C1905 | −86.285 | −11.776 | 10.617 | 1.00 | 64.97 | O |
| ATOM | A11O8 | C1' | C | C1905 | −85.660 | −10.616 | 10.119 | 1.00 | 64.97 | C |
| ATOM | A11O9 | N1 | C | C1905 | −84.194 | −10.836 | 10.074 | 1.00 | 64.02 | N |
| ATOM | A11OA | C6 | C | C1905 | −83.631 | −12.085 | 10.082 | 1.00 | 64.02 | C |
| ATOM | A11OB | C2 | C | C1905 | −83.370 | −9.709 | 10.046 | 1.00 | 64.02 | C |
| ATOM | A11OC | O2 | C | C1905 | −83.890 | −8.584 | 10.044 | 1.00 | 64.02 | O |
| ATOM | A11OD | N3 | C | C1905 | −82.026 | −9.862 | 10.014 | 1.00 | 64.02 | N |
| ATOM | A11OE | C4 | C | C1905 | −81.491 | −11.080 | 10.016 | 1.00 | 64.02 | C |
| ATOM | A11OF | N4 | C | C1905 | −80.161 | −11.186 | 9.984 | 1.00 | 64.02 | N |
| ATOM | A11OG | C5 | C | C1905 | −82.302 | −12.249 | 10.052 | 1.00 | 64.02 | C |
| ATOM | A11OH | C2' | C | C1905 | −86.252 | −10.316 | 8.737 | 1.00 | 64.97 | C |
| ATOM | A11OI | O2' | C | C1905 | −87.233 | −9.298 | 8.874 | 1.00 | 64.97 | O |
| ATOM | A11OJ | C3' | C | C1905 | −86.895 | −11.648 | 8.361 | 1.00 | 64.97 | C |
| ATOM | A11OK | O3' | C | C1905 | −87.985 | −11.509 | 7.463 | 1.00 | 64.97 | O |
| ATOM | A11OW | P | G | C1906 | −88.145 | −12.490 | 6.200 | 1.00 | 96.23 | P |

TABLE 8-continued

H69 Neomycin Binding Site for Intermediate-Rotated Ribosome

| ATOM | A11OX | OP1 | G | C1906 | −87.207 | −13.622 | 6.396 | 1.00 | 96.23 | O |
|---|---|---|---|---|---|---|---|---|---|---|
| ATOM | A11OY | OP2 | G | C1906 | −88.011 | −11.656 | 4.981 | 1.00 | 96.23 | O |
| ATOM | A11OZ | O5' | G | C1906 | −89.646 | −13.005 | 6.339 | 1.00 | 96.23 | O |
| ATOM | A11P0 | C5' | G | C1906 | −90.638 | −12.211 | 6.977 | 1.00 | 96.23 | C |
| ATOM | A11P1 | C4' | G | C1906 | −91.918 | −12.985 | 7.171 | 1.00 | 96.23 | C |
| ATOM | A11P2 | O4' | G | C1906 | −92.676 | −12.415 | 8.271 | 1.00 | 96.23 | O |
| ATOM | A11P3 | C1' | G | C1906 | −94.060 | −12.519 | 8.009 | 1.00 | 96.23 | C |
| ATOM | A11P4 | N9 | G | C1906 | −94.624 | −11.158 | 7.937 | 1.00 | 78.74 | N |
| ATOM | A11P5 | C4 | G | C1906 | −95.933 | −10.797 | 8.146 | 1.00 | 78.74 | C |
| ATOM | A11P6 | N3 | G | C1906 | −96.945 | −11.632 | 8.464 | 1.00 | 78.74 | N |
| ATOM | A11P7 | C2 | G | C1906 | −98.090 | −10.987 | 8.606 | 1.00 | 78.74 | C |
| ATOM | A11P8 | N2 | G | C1906 | −99.200 | −11.672 | 8.919 | 1.00 | 78.74 | N |
| ATOM | A11P9 | N1 | G | C1906 | −98.229 | −9.629 | 8.447 | 1.00 | 78.74 | N |
| ATOM | A11PA | C6 | G | C1906 | −97.203 | −8.751 | 8.121 | 1.00 | 78.74 | C |
| ATOM | A11PB | O6 | G | C1906 | −97.440 | −7.543 | 8.003 | 1.00 | 78.74 | O |
| ATOM | A11PC | C5 | G | C1906 | −95.967 | −9.430 | 7.966 | 1.00 | 78.74 | C |
| ATOM | A11PD | N7 | G | C1906 | −94.708 | −8.942 | 7.646 | 1.00 | 78.74 | N |
| ATOM | A11PE | C8 | G | C1906 | −93.946 | −10.001 | 7.640 | 1.00 | 78.74 | C |
| ATOM | A11PF | C2' | G | C1906 | −94.225 | −13.276 | 6.692 | 1.00 | 96.23 | C |
| ATOM | A11PG | O2' | G | C1906 | −94.360 | −14.662 | 6.982 | 1.00 | 96.23 | O |
| ATOM | A11PH | C3' | G | C1906 | −92.897 | −12.976 | 6.004 | 1.00 | 96.23 | C |
| ATOM | A11PI | O3' | G | C1906 | −92.537 | −13.892 | 4.973 | 1.00 | 96.23 | O |
| ATOM | A11PU | P | G | C1907 | −93.655 | −14.707 | 4.144 | 1.00 | 102.68 | P |
| ATOM | A11PV | OP1 | G | C1907 | −94.126 | −15.810 | 5.017 | 1.00 | 102.68 | O |
| ATOM | A11PW | OP2 | G | C1907 | −93.056 | −15.048 | 2.830 | 1.00 | 102.68 | O |
| ATOM | A11PX | O5' | G | C1907 | −94.819 | −13.642 | 3.942 | 1.00 | 102.68 | O |
| ATOM | A11PY | C5' | G | C1907 | −95.987 | −13.972 | 3.204 | 1.00 | 102.68 | C |
| ATOM | A11PZ | C4' | G | C1907 | −97.106 | −14.434 | 4.106 | 1.00 | 102.68 | C |
| ATOM | A11Q0 | O4' | G | C1907 | −97.072 | −13.687 | 5.351 | 1.00 | 102.68 | O |
| ATOM | A11Q1 | C1' | G | C1907 | −98.378 | −13.339 | 5.749 | 1.00 | 102.68 | C |
| ATOM | A11Q2 | N9 | G | C1907 | −98.520 | −11.878 | 5.614 | 1.00 | 85.50 | N |
| ATOM | A11Q3 | C4 | G | C1907 | −99.632 | −11.104 | 5.848 | 1.00 | 85.50 | C |
| ATOM | A11Q4 | N3 | G | C1907 | −100.845 | −11.533 | 6.253 | 1.00 | 85.50 | N |
| ATOM | A11Q5 | C2 | G | C1907 | −101.704 | −10.533 | 6.384 | 1.00 | 85.50 | C |
| ATOM | A11Q6 | N2 | G | C1907 | −102.961 | −10.779 | 6.779 | 1.00 | 85.50 | N |
| ATOM | A11Q7 | N1 | G | C1907 | −101.397 | −9.218 | 6.138 | 1.00 | 85.50 | N |
| ATOM | A11Q8 | C6 | G | C1907 | −100.154 | −8.757 | 5.721 | 1.00 | 85.50 | C |
| ATOM | A11Q9 | O6 | G | C1907 | −99.967 | −7.552 | 5.523 | 1.00 | 85.50 | O |
| ATOM | A11QA | C5 | G | C1907 | −99.227 | −9.815 | 5.575 | 1.00 | 85.50 | C |
| ATOM | A11QB | N7 | G | C1907 | −97.899 | −9.772 | 5.183 | 1.00 | 85.50 | N |
| ATOM | A11QC | C8 | G | C1907 | −97.522 | −11.016 | 5.222 | 1.00 | 85.50 | C |
| ATOM | A11QD | C2' | G | C1907 | −99.344 | −14.095 | 4.843 | 1.00 | 102.68 | C |
| ATOM | A11QE | O2' | G | C1907 | −99.597 | −15.371 | 5.415 | 1.00 | 102.68 | O |
| ATOM | A11QF | C3' | G | C1907 | −98.518 | −14.223 | 3.573 | 1.00 | 102.68 | C |
| ATOM | A11QG | O3' | G | C1907 | −98.946 | −15.268 | 2.716 | 1.00 | 102.68 | O |
| ATOM | A11QS | P | C | C1908 | −99.370 | −14.952 | 1.199 | 1.00 | 90.49 | P |
| ATOM | A11QT | OP1 | C | C1908 | −99.405 | −16.249 | 0.478 | 1.00 | 90.49 | O |
| ATOM | A11QU | OP2 | C | C1908 | −98.467 | −13.885 | 0.702 | 1.00 | 90.49 | O |
| ATOM | A11QV | O5' | C | C1908 | −100.847 | −14.382 | 1.357 | 1.00 | 90.49 | O |
| ATOM | A11QW | C5' | C | C1908 | −101.877 | −15.180 | 1.918 | 1.00 | 90.49 | C |
| ATOM | A11QX | C4' | C | C1908 | −102.995 | −14.335 | 2.473 | 1.00 | 90.49 | C |
| ATOM | A11QY | O4' | C | C1908 | −102.482 | −13.431 | 3.489 | 1.00 | 90.49 | O |
| ATOM | A11QZ | C1' | C | C1908 | −103.218 | −12.224 | 3.469 | 1.00 | 90.49 | C |
| ATOM | A11R0 | N1 | C | C1908 | −102.299 | −11.102 | 3.156 | 1.00 | 79.94 | N |
| ATOM | A11R1 | C6 | C | C1908 | −101.011 | −11.299 | 2.730 | 1.00 | 79.94 | C |
| ATOM | A11R2 | C2 | C | C1908 | −102.787 | −9.801 | 3.311 | 1.00 | 79.94 | C |
| ATOM | A11R3 | O2 | C | C1908 | −103.955 | −9.638 | 3.697 | 1.00 | 79.94 | O |
| ATOM | A11R4 | N3 | C | C1908 | −101.984 | −8.749 | 3.034 | 1.00 | 79.94 | N |
| ATOM | A11R5 | C4 | C | C1908 | −100.734 | −8.953 | 2.619 | 1.00 | 79.94 | C |
| ATOM | A11R6 | N4 | C | C1908 | −99.976 | −7.886 | 2.360 | 1.00 | 79.94 | N |
| ATOM | A11R7 | C5 | C | C1908 | −100.206 | −10.264 | 2.454 | 1.00 | 79.94 | C |
| ATOM | A11R8 | C2' | C | C1908 | −104.316 | −12.377 | 2.414 | 1.00 | 90.49 | C |
| ATOM | A11R9 | O2' | C | C1908 | −105.476 | −12.900 | 3.047 | 1.00 | 90.49 | O |
| ATOM | A11RA | C3' | C | C1908 | −103.687 | −13.407 | 1.489 | 1.00 | 90.49 | C |
| ATOM | A11RB | O3' | C | C1908 | −104.620 | −14.077 | 0.656 | 1.00 | 90.49 | O |
| ATOM | A11RN | P | C | C1909 | −104.615 | −13.829 | −0.935 | 1.00 | 97.60 | P |
| ATOM | A11RO | OP1 | C | C1909 | −105.274 | −15.002 | −1.562 | 1.00 | 97.60 | O |
| ATOM | A11RP | OP2 | C | C1909 | −103.223 | −13.501 | −1.329 | 1.00 | 97.60 | O |
| ATOM | A11RQ | O5' | C | C1909 | −105.538 | −12.544 | −1.093 | 1.00 | 97.60 | O |
| ATOM | A11RR | C5' | C | C1909 | −106.874 | −12.542 | −0.614 | 1.00 | 97.60 | C |
| ATOM | A11RS | C4' | C | C1909 | −107.414 | −11.141 | −0.490 | 1.00 | 97.60 | C |
| ATOM | A11RT | O4' | C | C1909 | −106.609 | −10.380 | 0.449 | 1.00 | 97.60 | O |
| ATOM | A11RU | C1' | C | C1909 | −106.557 | −9.026 | 0.050 | 1.00 | 97.60 | C |
| ATOM | A11RV | N1 | C | C1909 | −105.140 | −8.645 | −0.176 | 1.00 | 95.16 | N |
| ATOM | A11RW | C6 | C | C1909 | −104.137 | −9.574 | −0.279 | 1.00 | 95.16 | C |
| ATOM | A11RX | C2 | C | C1909 | −104.836 | −7.284 | −0.282 | 1.00 | 95.16 | C |
| ATOM | A11RY | O2 | C | C1909 | −105.753 | −6.456 | −0.186 | 1.00 | 95.16 | O |
| ATOM | A11RZ | N3 | C | C1909 | −103.555 | −6.898 | −0.486 | 1.00 | 95.16 | N |

TABLE 8-continued

H69 Neomycin Binding Site for Intermediate-Rotated Ribosome

| ATOM | A11S0 | C4 | C | C1909 | −102.590 | −7.811 | −0.585 | 1.00 | 95.16 | C |
|---|---|---|---|---|---|---|---|---|---|---|
| ATOM | A11S1 | N4 | C | C1909 | −101.340 | −7.390 | −0.789 | 1.00 | 95.16 | N |
| ATOM | A11S2 | C5 | C | C1909 | −102.866 | −9.203 | −0.481 | 1.00 | 95.16 | C |
| ATOM | A11S3 | C2' | C | C1909 | −107.400 | −8.882 | −1.218 | 1.00 | 97.60 | C |
| ATOM | A11S4 | O2' | C | C1909 | −108.715 | −8.492 | −0.850 | 1.00 | 97.60 | O |
| ATOM | A11S5 | C3' | C | C1909 | −107.383 | −10.307 | −1.757 | 1.00 | 97.60 | C |
| ATOM | A11S6 | O3' | C | C1909 | −108.455 | −10.600 | −2.636 | 1.00 | 97.60 | O |
| ATOM | A11SI | P | G | C1910 | −108.248 | −10.478 | −4.223 | 1.00 | 96.71 | P |
| ATOM | A11SJ | OP1 | G | C1910 | −109.593 | −10.316 | −4.828 | 1.00 | 96.71 | O |
| ATOM | A11SK | OP2 | G | C1910 | −107.409 | −11.627 | −4.647 | 1.00 | 96.71 | O |
| ATOM | A11SL | O5' | G | C1910 | −107.422 | −9.126 | −4.359 | 1.00 | 96.71 | O |
| ATOM | A11SM | C5' | G | C1910 | −107.638 | −8.237 | −5.443 | 1.00 | 96.71 | C |
| ATOM | A11SN | C4' | G | C1910 | −107.890 | −6.834 | −4.959 | 1.00 | 96.71 | C |
| ATOM | A11SO | O4' | G | C1910 | −107.198 | −6.620 | −3.700 | 1.00 | 96.70 | O |
| ATOM | A11SP | C1' | G | C1910 | −106.651 | −5.325 | −3.657 | 1.00 | 96.71 | C |
| ATOM | A11SQ | N9 | G | C1910 | −105.182 | −5.448 | −3.622 | 1.00 | 106.21 | N |
| ATOM | A11SR | C4 | G | C1910 | −104.255 | −4.436 | −3.616 | 1.00 | 106.21 | C |
| ATOM | A11SS | N3 | G | C1910 | −104.516 | −3.114 | −3.657 | 1.00 | 106.21 | N |
| ATOM | A11ST | C2 | G | C1910 | −103.407 | −2.394 | −3.644 | 1.00 | 106.21 | C |
| ATOM | A11SU | N2 | G | C1910 | −103.488 | −1.055 | −3.679 | 1.00 | 106.21 | N |
| ATOM | A11SV | N1 | G | C1910 | −102.144 | −2.932 | −3.600 | 1.00 | 106.21 | N |
| ATOM | A11SW | C6 | G | C1910 | −101.855 | −4.291 | −3.561 | 1.00 | 106.21 | C |
| ATOM | A11SX | O6 | G | C1910 | −100.682 | −4.679 | −3.519 | 1.00 | 106.21 | O |
| ATOM | A11SY | C5 | G | C1910 | −103.033 | −5.072 | −3.571 | 1.00 | 106.21 | C |
| ATOM | A11SZ | N7 | G | C1910 | −103.183 | −6.449 | −3.543 | 1.00 | 106.21 | N |
| ATOM | A11T0 | C8 | G | C1910 | −104.473 | −6.625 | −3.572 | 1.00 | 106.21 | C |
| ATOM | A11T1 | C2' | G | C1910 | −107.139 | −4.576 | −4.897 | 1.00 | 96.70 | C |
| ATOM | A11T2 | O2' | G | C1910 | −108.351 | −3.911 | −4.576 | 1.00 | 96.70 | O |
| ATOM | A11T3 | C3' | G | C1910 | −107.386 | −5.723 | −5.865 | 1.00 | 96.70 | C |
| ATOM | A11T4 | O3' | G | C1910 | −108.303 | −5.410 | −6.899 | 1.00 | 96.70 | O |
| ATOM | A11TG | P | U | C1911 | −107.815 | −5.339 | −8.427 | 1.00 | 111.47 | P |
| ATOM | A11TH | OP1 | U | C1911 | −109.025 | −5.462 | −9.276 | 1.00 | 111.47 | O |
| ATOM | A11TI | OP2 | U | C1911 | −106.727 | −6.335 | −8.590 | 1.00 | 111.47 | O |
| ATOM | A11TJ | O5' | U | C1911 | −107.224 | −3.867 | −8.538 | 1.00 | 111.47 | O |
| ATOM | A11TK | C5' | U | C1911 | −107.947 | −2.750 | −8.040 | 1.00 | 111.47 | C |
| ATOM | A11TL | C4' | U | C1911 | −107.068 | −1.533 | −7.908 | 1.00 | 111.47 | C |
| ATOM | A11TM | O4' | U | C1911 | −106.198 | −1.669 | −6.754 | 1.00 | 111.47 | O |
| ATOM | A11TN | C1' | U | C1911 | −104.959 | −1.040 | −7.010 | 1.00 | 111.47 | C |
| ATOM | A11TO | N1 | U | C1911 | −103.884 | −2.059 | −6.934 | 1.00 | 107.82 | N |
| ATOM | A11TP | C6 | U | C1911 | −104.111 | −3.380 | −7.243 | 1.00 | 107.82 | C |
| ATOM | A11TQ | C2 | U | C1911 | −102.629 | −1.635 | −6.542 | 1.00 | 107.82 | C |
| ATOM | A11TR | O2 | U | C1911 | −102.375 | −0.479 | −6.255 | 1.00 | 107.82 | O |
| ATOM | A11TS | N3 | U | C1911 | −101.676 | −2.620 | −6.486 | 1.00 | 107.82 | N |
| ATOM | A11TT | C4 | U | C1911 | −101.841 | −3.955 | −6.782 | 1.00 | 107.82 | C |
| ATOM | A11TU | O4 | U | C1911 | −100.882 | −4.721 | −6.685 | 1.00 | 107.82 | O |
| ATOM | A11TV | C5 | U | C1911 | −103.164 | −4.321 | −7.183 | 1.00 | 107.82 | C |
| ATOM | A11TW | C2' | U | C1911 | −105.048 | −0.400 | −8.398 | 1.00 | 111.47 | C |
| ATOM | A11TX | O2' | U | C1911 | −105.506 | 0.938 | −8.249 | 1.00 | 111.47 | O |
| ATOM | A11TY | C3' | U | C1911 | −106.108 | −1.271 | −9.056 | 1.00 | 111.47 | C |
| ATOM | A11TZ | O3' | U | C1911 | −106.737 | −0.666 | −10.173 | 1.00 | 111.47 | O |
| ATOM | A11UA | P | A | C1912 | −106.485 | −1.236 | −11.657 | 1.00 | 87.86 | P |
| ATOM | A11UB | OP1 | A | C1912 | −106.258 | −2.698 | −11.538 | 1.00 | 87.86 | O |
| ATOM | A11UC | OP2 | A | C1912 | −107.606 | −0.758 | −12.504 | 1.00 | 87.86 | O |
| ATOM | A11UD | O5' | A | C1912 | −105.135 | −0.511 | −12.083 | 1.00 | 87.86 | O |
| ATOM | A11UE | C5' | A | C1912 | −104.994 | 0.895 | −11.953 | 1.00 | 87.86 | C |
| ATOM | A11UF | C4' | A | C1912 | −104.151 | 1.477 | −13.059 | 1.00 | 87.86 | C |
| ATOM | A11UG | O4' | A | C1912 | −102.766 | 1.527 | −12.647 | 1.00 | 87.86 | O |
| ATOM | A11UH | C1' | A | C1912 | −101.924 | 1.388 | −13.766 | 1.00 | 87.86 | C |
| ATOM | A11UI | N9 | A | C1912 | −100.952 | 0.310 | −13.498 | 1.00 | 101.33 | N |
| ATOM | A11UJ | C4 | A | C1912 | −99.807 | 0.497 | −12.762 | 1.00 | 101.33 | C |
| ATOM | A11UK | N3 | A | C1912 | −99.397 | 1.644 | −12.194 | 1.00 | 101.33 | N |
| ATOM | A11UL | C2 | A | C1912 | −98.243 | 1.471 | −11.559 | 1.00 | 101.33 | C |
| ATOM | A11UM | N1 | A | C1912 | −97.507 | 0.363 | −11.435 | 1.00 | 101.33 | N |
| ATOM | A11UN | C6 | A | C1912 | −97.945 | −0.774 | −12.016 | 1.00 | 101.33 | C |
| ATOM | A11UO | N6 | A | C1912 | −97.199 | −1.873 | −11.883 | 1.00 | 101.33 | N |
| ATOM | A11UP | C5 | A | C1912 | −99.162 | −0.724 | −12.724 | 1.00 | 101.33 | C |
| ATOM | A11UQ | N7 | A | C1912 | −99.893 | −1.674 | −13.426 | 1.00 | 101.33 | N |
| ATOM | A11UR | C8 | A | C1912 | −100.943 | −1.016 | −13.863 | 1.00 | 101.33 | C |
| ATOM | A11US | C2' | A | C1912 | −102.800 | 1.116 | −14.997 | 1.00 | 87.86 | C |
| ATOM | A11UT | O2' | A | C1912 | −102.934 | 2.322 | −15.734 | 1.00 | 87.86 | O |
| ATOM | A11UU | C3' | A | C1912 | −104.133 | 0.707 | −14.371 | 1.00 | 87.86 | C |
| ATOM | A11UV | O3' | A | C1912 | −105.255 | 1.009 | −15.185 | 1.00 | 87.86 | O |
| ATOM | A11V7 | P | A | C1913 | −105.782 | −0.039 | −16.281 | 1.00 | 141.29 | P |
| ATOM | A11V8 | OP1 | A | C1913 | −104.715 | −1.051 | −16.471 | 1.00 | 141.29 | O |
| ATOM | A11V9 | OP2 | A | C1913 | −107.125 | −0.492 | −15.842 | 1.00 | 141.29 | O |
| ATOM | A11VA | O5' | A | C1913 | −105.915 | 0.859 | −17.590 | 1.00 | 141.29 | O |
| ATOM | A11VB | C5' | A | C1913 | −106.630 | 2.087 | −17.564 | 1.00 | 141.29 | C |
| ATOM | A11VC | C4' | A | C1913 | −106.259 | 2.972 | −18.733 | 1.00 | 141.29 | C |

TABLE 8-continued

H69 Neomycin Binding Site for Intermediate-Rotated Ribosome

| ATOM | A11VD | O4' | A | C1913 | −104.878 | 3.403 | −18.608 | 1.00 | 141.29 | O |
|---|---|---|---|---|---|---|---|---|---|---|
| ATOM | A11VE | C1' | A | C1913 | −104.321 | 3.587 | −19.898 | 1.00 | 141.29 | C |
| ATOM | A11VF | N9 | A | C1913 | −103.114 | 2.740 | −20.030 | 1.00 | 263.81 | N |
| ATOM | A11VG | C4 | A | C1913 | −102.970 | 1.391 | −19.780 | 1.00 | 263.81 | C |
| ATOM | A11VH | N3 | A | C1913 | −103.894 | 0.529 | −19.331 | 1.00 | 263.81 | N |
| ATOM | A11VI | C2 | A | C1913 | −103.406 | −0.696 | −19.198 | 1.00 | 263.81 | C |
| ATOM | A11VJ | N1 | A | C1913 | −102.172 | −1.136 | −19.442 | 1.00 | 263.80 | N |
| ATOM | A11VK | C6 | A | C1913 | −101.256 | −0.255 | −19.889 | 1.00 | 263.81 | C |
| ATOM | A11VL | N6 | A | C1913 | −100.027 | −0.709 | −20.129 | 1.00 | 263.81 | N |
| ATOM | A11VM | C5 | A | C1913 | −101.654 | 1.083 | −20.074 | 1.00 | 263.81 | C |
| ATOM | A11VN | N7 | A | C1913 | −100.974 | 2.210 | −20.510 | 1.00 | 263.81 | N |
| ATOM | A11VO | C8 | A | C1913 | −101.880 | 3.156 | −20.468 | 1.00 | 263.81 | C |
| ATOM | A11VP | C2' | A | C1913 | −105.395 | 3.231 | −20.924 | 1.00 | 141.29 | C |
| ATOM | A11VQ | O2' | A | C1913 | −106.069 | 4.423 | −21.306 | 1.00 | 141.29 | O |
| ATOM | A11VR | C3' | A | C1913 | −106.309 | 2.327 | −20.105 | 1.00 | 141.29 | C |
| ATOM | A11VS | O3' | A | C1913 | −107.617 | 2.205 | −20.626 | 1.00 | 141.29 | O |
| ATOM | A11W4 | P | C | C1914 | −108.084 | 0.831 | −21.319 | 1.00 | 227.50 | P |
| ATOM | A11W5 | OP1 | C | C1914 | −109.108 | 1.179 | −22.332 | 1.00 | 227.50 | O |
| ATOM | A11W6 | OP2 | C | C1914 | −108.452 | −0.104 | −20.229 | 1.00 | 227.50 | O |
| ATOM | A11W7 | O5' | C | C1914 | −106.753 | 0.324 | −22.045 | 1.00 | 227.50 | O |
| ATOM | A11W8 | C5' | C | C1914 | −105.940 | −0.699 | −21.475 | 1.00 | 227.50 | C |
| ATOM | A11W9 | C4' | C | C1914 | −106.107 | −2.010 | −22.202 | 1.00 | 227.50 | C |
| ATOM | A11WA | O4' | C | C1914 | −105.219 | −2.057 | −23.351 | 1.00 | 227.50 | O |
| ATOM | A11WB | C1' | C | C1914 | −104.865 | −3.399 | −23.620 | 1.00 | 227.50 | C |
| ATOM | A11WC | N1 | C | C1914 | −103.382 | −3.522 | −23.661 | 1.00 | 124.89 | N |
| ATOM | A11WD | C6 | C | C1914 | −102.509 | −2.517 | −23.320 | 1.00 | 124.89 | C |
| ATOM | A11WE | C2 | C | C1914 | −102.881 | −4.748 | −24.109 | 1.00 | 124.89 | C |
| ATOM | A11WF | O2 | C | C1914 | −103.679 | −5.645 | −24.418 | 1.00 | 124.89 | O |
| ATOM | A11WG | N3 | C | C1914 | −101.547 | −4.943 | −24.188 | 1.00 | 124.89 | N |
| ATOM | A11WH | C4 | C | C1914 | −100.708 | −3.969 | −23.849 | 1.00 | 124.89 | C |
| ATOM | A11WI | N4 | C | C1914 | −99.401 | −4.220 | −23.950 | 1.00 | 124.89 | N |
| ATOM | A11WJ | C5 | C | C1914 | −101.180 | −2.702 | −23.397 | 1.00 | 124.89 | C |
| ATOM | A11WK | C2' | C | C1914 | −105.495 | −4.278 | −22.533 | 1.00 | 227.50 | C |
| ATOM | A11WL | O2' | C | C1914 | −106.722 | −4.802 | −23.027 | 1.00 | 227.50 | O |
| ATOM | A11WM | C3' | C | C1914 | −105.744 | −3.264 | −21.423 | 1.00 | 227.50 | C |
| ATOM | A11WN | O3' | C | C1914 | −106.752 | −3.661 | −20.509 | 1.00 | 227.50 | O |
| ATOM | A11WZ | P | U | C1915 | −106.355 | −4.438 | −19.159 | 1.00 | 143.42 | P |
| ATOM | A11X0 | OP1 | U | C1915 | −107.601 | −5.025 | −18.612 | 1.00 | 143.42 | O |
| ATOM | A11X1 | OP2 | U | C1915 | −105.584 | −3.489 | −18.318 | 1.00 | 143.42 | O |
| ATOM | A11X2 | O5' | U | C1915 | −105.398 | −5.597 | −19.684 | 1.00 | 143.42 | O |
| ATOM | A11X3 | C5' | U | C1915 | −105.924 | −6.845 | −20.111 | 1.00 | 143.42 | C |
| ATOM | A11X4 | C4' | U | C1915 | −104.832 | −7.868 | −20.315 | 1.00 | 143.42 | C |
| ATOM | A11X5 | O4' | U | C1915 | −103.846 | −7.363 | −21.250 | 1.00 | 143.42 | O |
| ATOM | A11X6 | C1' | U | C1915 | −102.572 | −7.886 | −20.932 | 1.00 | 143.42 | C |
| ATOM | A11X7 | N1 | U | C1915 | −101.635 | −6.761 | −20.696 | 1.00 | 169.91 | N |
| ATOM | A11X8 | C6 | U | C1915 | −102.068 | −5.509 | −20.325 | 1.00 | 169.91 | C |
| ATOM | A11X9 | C2 | U | C1915 | −100.286 | −7.018 | −20.860 | 1.00 | 169.91 | C |
| ATOM | A11XA | O2 | U | C1915 | −99.851 | −8.108 | −21.186 | 1.00 | 169.91 | O |
| ATOM | A11XB | N3 | U | C1915 | −99.458 | −5.950 | −20.629 | 1.00 | 169.91 | N |
| ATOM | A11XC | C4 | U | C1915 | −99.833 | −4.676 | −20.257 | 1.00 | 169.91 | C |
| ATOM | A11XD | O4 | U | C1915 | −98.971 | −3.817 | −20.084 | 1.00 | 169.91 | O |
| ATOM | A11XE | C5 | U | C1915 | −101.241 | −4.484 | −20.106 | 1.00 | 169.91 | C |
| ATOM | A11XF | C2' | U | C1915 | −102.728 | −8.775 | −19.696 | 1.00 | 143.42 | C |
| ATOM | A11XG | O2' | U | C1915 | −102.891 | −10.121 | −20.119 | 1.00 | 143.42 | O |
| ATOM | A11XH | C3' | U | C1915 | −104.017 | −8.233 | −19.085 | 1.00 | 143.42 | C |
| ATOM | A11XI | O3' | U | C1915 | −104.683 | −9.158 | −18.241 | 1.00 | 143.42 | O |
| ATOM | A11XT | P | A | C1916 | −104.077 | −9.532 | −16.800 | 1.00 | 104.25 | P |
| ATOM | A11XU | OP1 | A | C1916 | −104.986 | −10.534 | −16.192 | 1.00 | 104.25 | O |
| ATOM | A11XV | OP2 | A | C1916 | −103.841 | −8.257 | −16.078 | 1.00 | 104.25 | O |
| ATOM | A11XW | O5' | A | C1916 | −102.689 | −10.215 | −17.172 | 1.00 | 104.25 | O |
| ATOM | A11XX | C5' | A | C1916 | −101.891 | −10.838 | −16.180 | 1.00 | 104.25 | C |
| ATOM | A11XY | C4' | A | C1916 | −100.423 | −10.720 | −16.499 | 1.00 | 104.25 | C |
| ATOM | A11XZ | O4' | A | C1916 | −100.238 | −9.814 | −17.623 | 1.00 | 104.25 | O |
| ATOM | A11Y0 | C1' | A | C1916 | −99.091 | −9.016 | −17.416 | 1.00 | 104.25 | C |
| ATOM | A11Y1 | N9 | A | C1916 | −99.531 | −7.620 | −17.225 | 1.00 | 118.95 | N |
| ATOM | A11Y2 | C4 | A | C1916 | −98.757 | −6.485 | −17.189 | 1.00 | 118.95 | C |
| ATOM | A11Y3 | N3 | A | C1916 | −97.426 | −6.385 | −17.334 | 1.00 | 118.95 | N |
| ATOM | A11Y4 | C2 | A | C1916 | −97.042 | −5.114 | −17.244 | 1.00 | 118.95 | C |
| ATOM | A11Y5 | N1 | A | C1916 | −97.775 | −4.010 | −17.039 | 1.00 | 118.95 | N |
| ATOM | A11Y6 | C6 | A | C1916 | −99.112 | −4.147 | −16.897 | 1.00 | 118.95 | C |
| ATOM | A11Y7 | N6 | A | C1916 | −99.873 | −3.068 | −16.690 | 1.00 | 118.95 | N |
| ATOM | A11Y8 | C5 | A | C1916 | −99.641 | −5.443 | −16.974 | 1.00 | 118.95 | C |
| ATOM | A11Y9 | N7 | A | C1916 | −100.941 | −5.906 | −16.869 | 1.00 | 118.95 | N |
| ATOM | A11YA | C8 | A | C1916 | −100.818 | −7.198 | −17.021 | 1.00 | 118.95 | C |
| ATOM | A11YB | C2' | A | C1916 | −98.381 | −9.555 | −16.180 | 1.00 | 104.25 | C |
| ATOM | A11YC | O2' | A | C1916 | −97.482 | −10.579 | −16.582 | 1.00 | 104.25 | O |
| ATOM | A11YD | C3' | A | C1916 | −99.551 | −10.134 | −15.400 | 1.00 | 104.25 | C |
| ATOM | A11YE | O3' | A | C1916 | −99.173 | −11.090 | −14.424 | 1.00 | 104.25 | O |

TABLE 8-continued

H69 Neomycin Binding Site for Intermediate-Rotated Ribosome

| ATOM | A11YQ | P | U | C1917 | −99.700 | −10.963 | −12.909 | 1.00 | 94.66 | P |
|------|-------|-----|---|-------|----------|---------|---------|------|-------|---|
| ATOM | A11YR | OP1 | U | C1917 | −99.673 | −12.325 | −12.323 | 1.00 | 94.66 | O |
| ATOM | A11YS | OP2 | U | C1917 | −100.992 | −10.232 | −12.951 | 1.00 | 94.66 | O |
| ATOM | A11YT | O5' | U | C1917 | −98.587 | −10.056 | −12.221 | 1.00 | 94.66 | O |
| ATOM | A11YU | C5' | U | C1917 | −97.217 | −10.428 | −12.258 | 1.00 | 94.66 | C |
| ATOM | A11YV | C4' | U | C1917 | −96.320 | −9.229 | −12.435 | 1.00 | 94.66 | C |
| ATOM | A11YW | O4' | U | C1917 | −96.683 | −8.514 | −13.646 | 1.00 | 94.66 | O |
| ATOM | A11YX | C1' | U | C1917 | −96.487 | −7.126 | −13.463 | 1.00 | 94.66 | C |
| ATOM | A11YY | N1 | U | C1917 | −97.792 | −6.430 | −13.606 | 1.00 | 97.62 | N |
| ATOM | A11YZ | C6 | U | C1917 | −98.995 | −7.095 | −13.659 | 1.00 | 97.62 | C |
| ATOM | A11Z0 | C2 | U | C1917 | −97.753 | −5.052 | −13.696 | 1.00 | 97.62 | C |
| ATOM | A11Z1 | O2 | U | C1917 | −96.713 | −4.418 | −13.654 | 1.00 | 97.62 | O |
| ATOM | A11Z2 | N3 | U | C1917 | −98.974 | −4.440 | −13.830 | 1.00 | 97.62 | N |
| ATOM | A11Z3 | C4 | U | C1917 | −100.208 | −5.050 | −13.889 | 1.00 | 97.62 | C |
| ATOM | A11Z4 | O4 | U | C1917 | −101.222 | −4.362 | −14.012 | 1.00 | 97.62 | O |
| ATOM | A11Z5 | C5 | U | C1917 | −100.172 | −6.476 | −13.792 | 1.00 | 97.62 | C |
| ATOM | A11Z6 | C2' | U | C1917 | −95.881 | −6.930 | −12.076 | 1.00 | 94.66 | C |
| ATOM | A11Z7 | O2' | U | C1917 | −94.464 | −6.967 | −12.198 | 1.00 | 94.66 | O |
| ATOM | A11Z8 | C3' | U | C1917 | −96.403 | −8.165 | −11.355 | 1.00 | 94.66 | C |
| ATOM | A11Z9 | O3' | U | C1917 | −95.677 | −8.499 | −10.186 | 1.00 | 94.66 | O |
| ATOM | A11ZK | P | A | C1918 | −96.359 | −8.323 | −8.741 | 1.00 | 79.74 | P |
| ATOM | A11ZL | OP1 | A | C1918 | −95.370 | −8.774 | −7.732 | 1.00 | 79.75 | O |
| ATOM | A11ZM | OP2 | A | C1918 | −97.683 | −8.994 | −8.794 | 1.00 | 79.75 | O |
| ATOM | A11ZN | O5' | A | C1918 | −96.554 | −6.751 | −8.639 | 1.00 | 79.74 | O |
| ATOM | A11ZO | C5' | A | C1918 | −95.451 | −5.871 | −8.810 | 1.00 | 79.74 | C |
| ATOM | A11ZP | C4' | A | C1918 | −95.851 | −4.436 | −8.605 | 1.00 | 79.74 | C |
| ATOM | A11ZQ | O4' | A | C1918 | −96.839 | −4.068 | −9.607 | 1.00 | 79.74 | O |
| ATOM | A11ZR | C1' | A | C1918 | −97.972 | −3.502 | −8.982 | 1.00 | 79.75 | C |
| ATOM | A11ZS | N9 | A | C1918 | −99.163 | −3.895 | −9.739 | 1.00 | 105.75 | N |
| ATOM | A11ZT | C4 | A | C1918 | −100.289 | −3.136 | −9.948 | 1.00 | 105.75 | C |
| ATOM | A11ZU | N3 | A | C1918 | −100.529 | −1.889 | −9.510 | 1.00 | 105.75 | N |
| ATOM | A11ZV | C2 | A | C1918 | −101.731 | −1.475 | −9.907 | 1.00 | 105.75 | C |
| ATOM | A11ZW | N1 | A | C1918 | −102.654 | −2.117 | −10.634 | 1.00 | 105.75 | N |
| ATOM | A11ZX | C6 | A | C1918 | −102.385 | −3.370 | −11.056 | 1.00 | 105.75 | C |
| ATOM | A11ZY | N6 | A | C1918 | −103.304 | −4.011 | −11.782 | 1.00 | 105.75 | N |
| ATOM | A11ZZ | C5 | A | C1918 | −101.141 | −3.923 | −10.701 | 1.00 | 105.75 | C |
| ATOM | A1200 | N7 | A | C1918 | −100.562 | −5.156 | −10.963 | 1.00 | 105.75 | N |
| ATOM | A1201 | C8 | A | C1918 | −99.394 | −5.089 | −10.372 | 1.00 | 105.75 | C |
| ATOM | A1202 | C2' | A | C1918 | −97.967 | −4.015 | −7.547 | 1.00 | 79.75 | C |
| ATOM | A1203 | O2' | A | C1918 | −98.681 | −3.155 | −6.687 | 1.00 | 79.74 | O |
| ATOM | A1204 | C3' | A | C1918 | −96.473 | −4.128 | −7.245 | 1.00 | 79.75 | C |
| ATOM | A1205 | O3' | A | C1918 | −95.970 | −2.890 | −6.753 | 1.00 | 79.75 | O |
| ATOM | A120H | P | A | C1919 | −94.589 | −2.863 | −5.928 | 1.00 | 82.74 | P |
| ATOM | A120I | OP1 | A | C1919 | −93.590 | −3.619 | −6.722 | 1.00 | 82.74 | O |
| ATOM | A120J | OP2 | A | C1919 | −94.894 | −3.317 | −4.550 | 1.00 | 82.74 | O |
| ATOM | A120K | O5' | A | C1919 | −94.215 | −1.319 | −5.917 | 1.00 | 82.74 | O |
| ATOM | A120L | C5' | A | C1919 | −92.866 | −0.889 | −5.815 | 1.00 | 82.74 | C |
| ATOM | A120M | C4' | A | C1919 | −92.746 | 0.576 | −6.134 | 1.00 | 82.74 | C |
| ATOM | A120N | O4' | A | C1919 | −93.107 | 0.796 | −7.527 | 1.00 | 82.74 | O |
| ATOM | A120O | C1' | A | C1919 | −93.947 | 1.920 | −7.641 | 1.00 | 82.74 | C |
| ATOM | A120P | N9 | A | C1919 | −95.304 | 1.440 | −7.970 | 1.00 | 96.93 | N |
| ATOM | A120Q | C4 | A | C1919 | −96.499 | 2.123 | −7.937 | 1.00 | 96.93 | C |
| ATOM | A120R | N3 | A | C1919 | −96.718 | 3.401 | −7.587 | 1.00 | 96.93 | N |
| ATOM | A120S | C2 | A | C1919 | −98.012 | 3.704 | −7.675 | 1.00 | 96.93 | C |
| ATOM | A120T | N1 | A | C1919 | −99.042 | 2.932 | −8.046 | 1.00 | 96.93 | N |
| ATOM | A120U | C6 | A | C1919 | −98.790 | 1.653 | −8.391 | 1.00 | 96.93 | C |
| ATOM | A120V | N6 | A | C1919 | −99.806 | 0.873 | −8.763 | 1.00 | 96.93 | N |
| ATOM | A120W | C5 | A | C1919 | −97.460 | 1.211 | −8.338 | 1.00 | 96.93 | C |
| ATOM | A120X | N7 | A | C1919 | −96.892 | −0.017 | −8.624 | 1.00 | 96.93 | N |
| ATOM | A120Y | C8 | A | C1919 | −95.619 | 0.170 | −8.392 | 1.00 | 96.93 | C |
| ATOM | A120Z | C2' | A | C1919 | −93.905 | 2.651 | −6.303 | 1.00 | 82.74 | C |
| ATOM | A1210 | O2' | A | C1919 | −92.792 | 3.534 | −6.304 | 1.00 | 82.74 | O |
| ATOM | A1211 | C3' | A | C1919 | −93.677 | 1.492 | −5.347 | 1.00 | 82.74 | C |
| ATOM | A1212 | O3' | A | C1919 | −93.142 | 1.877 | −4.092 | 1.00 | 82.74 | O |
| ATOM | A121E | P | C | C1920 | −94.102 | 2.023 | −2.812 | 1.00 | 71.50 | P |
| ATOM | A121F | OP1 | C | C1920 | −94.344 | 0.655 | −2.289 | 1.00 | 71.50 | O |
| ATOM | A121G | OP2 | C | C1920 | −93.487 | 3.030 | −1.914 | 1.00 | 71.50 | O |
| ATOM | A121H | O5' | C | C1920 | −95.440 | 2.603 | −3.443 | 1.00 | 71.50 | O |
| ATOM | A121I | C5' | C | C1920 | −95.937 | 3.878 | −3.076 | 1.00 | 71.50 | C |
| ATOM | A121J | C4' | C | C1920 | −97.426 | 3.964 | −3.292 | 1.00 | 71.50 | C |
| ATOM | A121K | O4' | C | C1920 | −97.800 | 3.180 | −4.458 | 1.00 | 71.50 | O |
| ATOM | A121L | C1' | C | C1920 | −99.057 | 2.570 | −4.249 | 1.00 | 71.50 | C |
| ATOM | A121M | N1 | C | C1920 | −98.883 | 1.097 | −4.281 | 1.00 | 99.59 | N |
| ATOM | A121N | C6 | C | C1920 | −97.654 | 0.499 | −4.381 | 1.00 | 99.59 | C |
| ATOM | A121O | C2 | C | C1920 | −100.029 | 0.301 | −4.221 | 1.00 | 99.59 | C |
| ATOM | A121P | O2 | C | C1920 | −101.137 | 0.849 | −4.135 | 1.00 | 99.59 | O |
| ATOM | A121Q | N3 | C | C1920 | −99.908 | −1.046 | −4.247 | 1.00 | 99.59 | N |
| ATOM | A121R | C4 | C | C1920 | −98.702 | −1.606 | −4.333 | 1.00 | 99.59 | C |

TABLE 8-continued

H69 Neomycin Binding Site for Intermediate-Rotated Ribosome

| ATOM | A121S | N4 | C | C1920 | −98.608 | −2.935 | −4.367 | 1.00 | 99.59 | N |
|---|---|---|---|---|---|---|---|---|---|---|
| ATOM | A121T | C5 | C | C1920 | −97.520 | −0.830 | −4.409 | 1.00 | 99.59 | C |
| ATOM | A121U | C2' | C | C1920 | −99.584 | 3.058 | −2.897 | 1.00 | 71.50 | C |
| ATOM | A121V | O2' | C | C1920 | −100.378 | 4.218 | −3.103 | 1.00 | 71.50 | O |
| ATOM | A121W | C3' | C | C1920 | −98.290 | 3.403 | −2.175 | 1.00 | 71.50 | C |
| ATOM | A121X | O3' | C | C1920 | −98.460 | 4.317 | −1.104 | 1.00 | 71.50 | O |
| ATOM | A1229 | P | G | C1921 | −98.648 | 3.781 | 0.397 | 1.00 | 93.18 | P |
| ATOM | A122A | OP1 | G | C1921 | −97.734 | 2.625 | 0.571 | 1.00 | 93.18 | O |
| ATOM | A122B | OP2 | G | C1921 | −98.500 | 4.948 | 1.299 | 1.00 | 93.18 | O |
| ATOM | A122C | O5' | G | C1921 | −100.157 | 3.283 | 0.402 | 1.00 | 93.18 | O |
| ATOM | A122D | C5' | G | C1921 | −101.216 | 4.169 | 0.075 | 1.00 | 93.18 | C |
| ATOM | A122E | C4' | G | C1921 | −102.526 | 3.438 | −0.056 | 1.00 | 93.18 | C |
| ATOM | A122F | O4' | G | C1921 | −102.447 | 2.459 | −1.126 | 1.00 | 93.18 | O |
| ATOM | A122G | C1' | G | C1921 | −103.255 | 1.342 | −0.810 | 1.00 | 93.18 | C |
| ATOM | A122H | N9 | G | C1921 | −102.404 | 0.139 | −0.756 | 1.00 | 85.51 | N |
| ATOM | A122I | C4 | G | C1921 | −102.859 | −1.157 | −0.708 | 1.00 | 85.51 | C |
| ATOM | A122J | N3 | G | C1921 | −104.152 | −1.543 | −0.719 | 1.00 | 85.51 | N |
| ATOM | A122K | C2 | G | C1921 | −104.277 | −2.859 | −0.669 | 1.00 | 85.51 | C |
| ATOM | A122L | N2 | G | C1921 | −105.500 | −3.412 | −0.674 | 1.00 | 85.51 | N |
| ATOM | A122M | N1 | G | C1921 | −103.215 | −3.728 | −0.617 | 1.00 | 85.51 | N |
| ATOM | A122N | C6 | G | C1921 | −101.877 | −3.351 | −0.603 | 1.00 | 85.51 | C |
| ATOM | A122O | O6 | G | C1921 | −100.998 | −4.219 | −0.558 | 1.00 | 85.51 | O |
| ATOM | A122P | C5 | G | C1921 | −101.727 | −1.941 | −0.657 | 1.00 | 85.51 | C |
| ATOM | A122Q | N7 | G | C1921 | −100.583 | −1.156 | −0.664 | 1.00 | 85.51 | N |
| ATOM | A122R | C8 | G | C1921 | −101.032 | 0.069 | −0.720 | 1.00 | 85.51 | C |
| ATOM | A122S | C2' | G | C1921 | −103.924 | 1.624 | 0.533 | 1.00 | 93.18 | C |
| ATOM | A122T | O2' | G | C1921 | −105.188 | 2.226 | 0.294 | 1.00 | 93.18 | O |
| ATOM | A122U | C3' | G | C1921 | −102.952 | 2.618 | 1.147 | 1.00 | 93.18 | C |
| ATOM | A122V | O3' | G | C1921 | −103.512 | 3.404 | 2.183 | 1.00 | 93.18 | O |
| ATOM | A1237 | P | G | C1922 | −103.338 | 2.961 | 3.719 | 1.00 | 85.73 | P |
| ATOM | A1238 | OP1 | G | C1922 | −103.763 | 4.109 | 4.554 | 1.00 | 85.73 | O |
| ATOM | A1239 | OP2 | G | C1922 | −101.957 | 2.440 | 3.874 | 1.00 | 85.73 | O |
| ATOM | A123A | O5' | G | C1922 | −104.384 | 1.772 | 3.860 | 1.00 | 85.73 | O |
| ATOM | A123B | C5' | G | C1922 | −105.752 | 1.964 | 3.533 | 1.00 | 85.73 | C |
| ATOM | A123C | C4' | G | C1922 | −106.469 | 0.650 | 3.351 | 1.00 | 85.73 | C |
| ATOM | A123D | O4' | G | C1922 | −105.811 | −0.136 | 2.323 | 1.00 | 85.73 | O |
| ATOM | A123E | C1' | G | C1922 | −105.905 | −1.512 | 2.638 | 1.00 | 85.73 | C |
| ATOM | A123F | N9 | G | C1922 | −104.542 | −2.057 | 2.796 | 1.00 | 120.70 | N |
| ATOM | A123G | C4 | G | C1922 | −104.196 | −3.390 | 2.823 | 1.00 | 120.70 | C |
| ATOM | A123H | N3 | G | C1922 | −105.038 | −4.437 | 2.694 | 1.00 | 120.70 | N |
| ATOM | A123I | C2 | G | C1922 | −104.404 | −5.598 | 2.754 | 1.00 | 120.70 | C |
| ATOM | A123J | N2 | G | C1922 | −105.096 | −6.742 | 2.644 | 1.00 | 120.70 | N |
| ATOM | A123K | N1 | G | C1922 | −103.048 | −5.723 | 2.928 | 1.00 | 120.70 | N |
| ATOM | A123L | C6 | G | C1922 | −102.163 | −4.661 | 3.063 | 1.00 | 120.70 | C |
| ATOM | A123M | O6 | G | C1922 | −100.957 | −4.885 | 3.217 | 1.00 | 120.70 | O |
| ATOM | A123N | C5 | G | C1922 | −102.829 | −3.410 | 3.000 | 1.00 | 120.70 | C |
| ATOM | A123O | N7 | G | C1922 | −102.324 | −2.122 | 3.090 | 1.00 | 120.70 | N |
| ATOM | A123P | C8 | G | C1922 | −103.372 | −1.355 | 2.968 | 1.00 | 120.70 | C |
| ATOM | A123Q | C2' | G | C1922 | −106.719 | −1.634 | 3.922 | 1.00 | 85.73 | C |
| ATOM | A123R | O2' | G | C1922 | −108.086 | −1.808 | 3.582 | 1.00 | 85.73 | O |
| ATOM | A123S | C3' | G | C1922 | −106.484 | −0.270 | 4.558 | 1.00 | 85.73 | C |
| ATOM | A123T | O3' | G | C1922 | −107.457 | 0.093 | 5.520 | 1.00 | 85.73 | O |
| ATOM | A1245 | P | U | C1923 | −107.087 | 0.072 | 7.082 | 1.00 | 93.79 | P |
| ATOM | A1246 | OP1 | U | C1923 | −108.367 | 0.090 | 7.833 | 1.00 | 93.79 | O |
| ATOM | A1247 | OP2 | U | C1923 | −106.108 | 1.162 | 7.316 | 1.00 | 93.79 | O |
| ATOM | A1248 | O5' | U | C1923 | −106.373 | −1.340 | 7.249 | 1.00 | 93.79 | O |
| ATOM | A1249 | C5' | U | C1923 | −106.811 | −2.281 | 8.217 | 1.00 | 93.79 | C |
| ATOM | A124A | C4' | U | C1923 | −106.981 | −3.650 | 7.612 | 1.00 | 93.79 | C |
| ATOM | A124B | O4' | U | C1923 | −106.258 | −3.723 | 6.357 | 1.00 | 93.79 | O |
| ATOM | A124C | C1' | U | C1923 | −105.649 | −4.985 | 6.216 | 1.00 | 93.79 | C |
| ATOM | A124D | N1 | U | C1923 | −104.176 | −4.797 | 6.216 | 1.00 | 127.15 | N |
| ATOM | A124E | C6 | U | C1923 | −103.601 | −3.559 | 6.427 | 1.00 | 127.15 | C |
| ATOM | A124F | C2 | U | C1923 | −103.386 | −5.901 | 5.964 | 1.00 | 127.15 | C |
| ATOM | A124G | O2 | U | C1923 | −103.838 | −7.016 | 5.765 | 1.00 | 127.15 | O |
| ATOM | A124H | N3 | U | C1923 | −102.039 | −5.654 | 5.969 | 1.00 | 127.15 | N |
| ATOM | A124I | C4 | U | C1923 | −101.402 | −4.450 | 6.181 | 1.00 | 127.15 | C |
| ATOM | A124J | O4 | U | C1923 | −100.171 | −4.397 | 6.149 | 1.00 | 127.15 | O |
| ATOM | A124K | C5 | U | C1923 | −102.281 | −3.351 | 6.423 | 1.00 | 127.15 | C |
| ATOM | A124L | C2' | U | C1923 | −106.126 | −5.857 | 7.377 | 1.00 | 93.79 | C |
| ATOM | A124M | O2' | U | C1923 | −107.307 | −6.538 | 6.976 | 1.00 | 93.79 | O |
| ATOM | A124N | C3' | U | C1923 | −106.435 | −4.806 | 8.432 | 1.00 | 93.79 | C |
| ATOM | A124O | O3' | U | C1923 | −107.346 | −5.244 | 9.422 | 1.00 | 93.79 | O |
| ATOM | A124Z | P | C | C1924 | −107.003 | −5.068 | 10.982 | 1.00 | 116.36 | P |
| ATOM | A1250 | OP1 | C | C1924 | −108.293 | −4.922 | 11.699 | 1.00 | 116.36 | O |
| ATOM | A1251 | OP2 | C | C1924 | −105.996 | −3.984 | 11.096 | 1.00 | 116.36 | O |
| ATOM | A1252 | O5' | C | C1924 | −106.338 | −6.463 | 11.345 | 1.00 | 116.36 | O |
| ATOM | A1253 | C5' | C | C1924 | −106.956 | −7.683 | 10.967 | 1.00 | 116.36 | C |
| ATOM | A1254 | C4' | C | C1924 | −105.978 | −8.826 | 10.993 | 1.00 | 116.36 | C |

TABLE 8-continued

H69 Neomycin Binding Site for Intermediate-Rotated Ribosome

| ATOM | A1255 | O4' | C | C1924 | −105.175 | −8.820 | 9.784 | 1.00 | 116.36 | O |
|---|---|---|---|---|---|---|---|---|---|---|
| ATOM | A1256 | C1' | C | C1924 | −103.877 | −9.300 | 10.067 | 1.00 | 116.36 | C |
| ATOM | A1257 | N1 | C | C1924 | −102.887 | −8.252 | 9.709 | 1.00 | 91.52 | N |
| ATOM | A1258 | C6 | C | C1924 | −103.230 | −6.939 | 9.506 | 1.00 | 91.52 | C |
| ATOM | A1259 | C2 | C | C1924 | −101.552 | −8.641 | 9.577 | 1.00 | 91.52 | C |
| ATOM | A125A | O2 | C | C1924 | −101.255 | −9.830 | 9.763 | 1.00 | 91.52 | O |
| ATOM | A125B | N3 | C | C1924 | −100.611 | −7.725 | 9.251 | 1.00 | 91.52 | N |
| ATOM | A125C | C4 | C | C1924 | −100.952 | −6.452 | 9.055 | 1.00 | 91.52 | C |
| ATOM | A125D | N4 | C | C1924 | −99.981 | −5.589 | 8.738 | 1.00 | 91.52 | N |
| ATOM | A125E | C5 | C | C1924 | −102.305 | −6.020 | 9.182 | 1.00 | 91.52 | C |
| ATOM | A125F | C2' | C | C1924 | −103.827 | −9.656 | 11.555 | 1.00 | 116.36 | C |
| ATOM | A125G | O2' | C | C1924 | −104.119 | −11.038 | 11.705 | 1.00 | 116.36 | O |
| ATOM | A125H | C3' | C | C1924 | −104.952 | −8.797 | 12.114 | 1.00 | 116.36 | C |
| ATOM | A125I | O3' | C | C1924 | −105.470 | −9.262 | 13.346 | 1.00 | 116.36 | O |
| ATOM | A125U | P | C | C1925 | −104.585 | −9.163 | 14.682 | 1.00 | 90.13 | P |
| ATOM | A125V | OP1 | C | C1925 | −105.492 | −9.418 | 15.827 | 1.00 | 90.13 | O |
| ATOM | A125W | OP2 | C | C1925 | −103.850 | −7.875 | 14.627 | 1.00 | 90.13 | O |
| ATOM | A125X | O5' | C | C1925 | −103.569 | −10.375 | 14.516 | 1.00 | 90.13 | O |
| ATOM | A125Y | C5' | C | C1925 | −102.460 | −10.516 | 15.386 | 1.00 | 90.13 | C |
| ATOM | A125Z | C4' | C | C1925 | −101.294 | −11.168 | 14.687 | 1.00 | 90.13 | C |
| ATOM | A1260 | O4' | C | C1925 | −101.269 | −10.757 | 13.294 | 1.00 | 90.13 | O |
| ATOM | A1261 | C1' | C | C1925 | −99.938 | −10.547 | 12.877 | 1.00 | 90.13 | C |
| ATOM | A1262 | N1 | C | C1925 | −99.757 | −9.101 | 12.611 | 1.00 | 79.97 | N |
| ATOM | A1263 | C6 | C | C1925 | −100.626 | −8.155 | 13.093 | 1.00 | 79.97 | C |
| ATOM | A1264 | C2 | C | C1925 | −98.653 | −8.707 | 11.859 | 1.00 | 79.97 | C |
| ATOM | A1265 | O2 | C | C1925 | −97.874 | −9.572 | 11.435 | 1.00 | 79.97 | O |
| ATOM | A1266 | N3 | C | C1925 | −98.452 | −7.393 | 11.604 | 1.00 | 79.97 | N |
| ATOM | A1267 | C4 | C | C1925 | −99.302 | −6.482 | 12.072 | 1.00 | 79.97 | C |
| ATOM | A1268 | N4 | C | C1925 | −99.067 | −5.199 | 11.794 | 1.00 | 79.97 | N |
| ATOM | A1269 | C5 | C | C1925 | −100.438 | −6.850 | 12.846 | 1.00 | 79.97 | C |
| ATOM | A126A | C2' | C | C1925 | −99.028 | −11.034 | 13.999 | 1.00 | 90.13 | C |
| ATOM | A126B | O2' | C | C1925 | −98.765 | −12.418 | 13.816 | 1.00 | 90.13 | O |
| ATOM | A126C | C3' | C | C1925 | −99.915 | −10.801 | 15.216 | 1.00 | 90.13 | C |
| ATOM | A126D | O3' | C | C1925 | −99.536 | −11.558 | 16.354 | 1.00 | 90.13 | O |
| ATOM | A126P | P | U | C1926 | −99.850 | −11.017 | 17.838 | 1.00 | 110.07 | P |
| ATOM | A126Q | OP1 | U | C1926 | −100.305 | −12.177 | 18.639 | 1.00 | 110.07 | O |
| ATOM | A126R | OP2 | U | C1926 | −100.751 | −9.846 | 17.702 | 1.00 | 110.07 | O |
| ATOM | A126S | O5' | U | C1926 | −98.422 | −10.538 | 18.344 | 1.00 | 110.07 | O |
| ATOM | A126T | C5' | U | C1926 | −97.767 | −9.458 | 17.708 | 1.00 | 110.07 | C |
| ATOM | A126U | C4' | U | C1926 | −96.544 | −9.914 | 16.952 | 1.00 | 110.07 | C |
| ATOM | A126V | O4' | U | C1926 | −96.702 | −9.557 | 15.557 | 1.00 | 110.07 | O |
| ATOM | A126W | C1' | U | C1926 | −95.498 | −9.068 | 15.028 | 1.00 | 110.07 | C |
| ATOM | A126X | N1 | U | C1926 | −95.698 | −7.648 | 14.647 | 1.00 | 89.96 | N |
| ATOM | A126Y | C6 | U | C1926 | −96.778 | −6.906 | 15.078 | 1.00 | 89.96 | C |
| ATOM | A126Z | C2 | U | C1926 | −94.755 | −7.100 | 13.808 | 1.00 | 89.96 | C |
| ATOM | A1270 | O2 | U | C1926 | −93.801 | −7.742 | 13.414 | 1.00 | 89.96 | O |
| ATOM | A1271 | N3 | U | C1926 | −94.969 | −5.789 | 13.466 | 1.00 | 89.96 | N |
| ATOM | A1272 | C4 | U | C1926 | −96.021 | −4.990 | 13.867 | 1.00 | 89.96 | C |
| ATOM | A1273 | O4 | U | C1926 | −96.082 | −3.823 | 13.477 | 1.00 | 89.96 | O |
| ATOM | A1274 | C5 | U | C1926 | −96.967 | −5.629 | 14.730 | 1.00 | 89.96 | C |
| ATOM | A1275 | C2' | U | C1926 | −94.413 | −9.239 | 16.086 | 1.00 | 110.07 | C |
| ATOM | A1276 | O2' | U | C1926 | −93.734 | −10.469 | 15.864 | 1.00 | 110.07 | O |
| ATOM | A1277 | C3' | U | C1926 | −95.219 | −9.288 | 17.382 | 1.00 | 110.07 | C |
| ATOM | A1278 | O3' | U | C1926 | −94.574 | −10.025 | 18.406 | 1.00 | 110.07 | O |
| ATOM | A127J | P | A | C1927 | −94.770 | −9.646 | 19.957 | 1.00 | 87.96 | P |
| ATOM | A127K | OP1 | A | C1927 | −94.740 | −10.918 | 20.721 | 1.00 | 87.96 | O |
| ATOM | A127L | OP2 | A | C1927 | −95.971 | −8.788 | 20.057 | 1.00 | 87.96 | O |
| ATOM | A127M | O5' | A | C1927 | −93.467 | −8.788 | 20.278 | 1.00 | 87.96 | O |
| ATOM | A127N | C5' | A | C1927 | −93.485 | −7.369 | 20.209 | 1.00 | 87.96 | C |
| ATOM | A127O | C4' | A | C1927 | −92.143 | −6.823 | 19.788 | 1.00 | 87.96 | C |
| ATOM | A127P | O4' | A | C1927 | −91.116 | −7.797 | 20.088 | 1.00 | 87.96 | O |
| ATOM | A127Q | C1' | A | C1927 | −90.116 | −7.777 | 19.098 | 1.00 | 87.96 | C |
| ATOM | A127R | N9 | A | C1927 | −90.000 | −9.135 | 18.523 | 1.00 | 70.80 | N |
| ATOM | A127S | C4 | A | C1927 | −88.972 | −9.623 | 17.750 | 1.00 | 70.80 | C |
| ATOM | A127T | N3 | A | C1927 | −87.885 | −8.962 | 17.330 | 1.00 | 70.80 | N |
| ATOM | A127U | C2 | A | C1927 | −87.109 | −9.745 | 16.587 | 1.00 | 70.80 | C |
| ATOM | A127V | N1 | A | C1927 | −87.282 | −11.024 | 16.241 | 1.00 | 70.80 | N |
| ATOM | A127W | C6 | A | C1927 | −88.380 | −11.667 | 16.682 | 1.00 | 70.80 | C |
| ATOM | A127X | N6 | A | C1927 | −88.548 | −12.944 | 16.333 | 1.00 | 70.80 | N |
| ATOM | A127Y | C5 | A | C1927 | −89.284 | −10.941 | 17.475 | 1.00 | 70.80 | C |
| ATOM | A127Z | N7 | A | C1927 | −90.481 | −11.295 | 18.070 | 1.00 | 70.80 | N |
| ATOM | A1280 | C8 | A | C1927 | −90.859 | −10.199 | 18.683 | 1.00 | 70.80 | C |
| ATOM | A1281 | C2' | A | C1927 | −90.489 | −6.720 | 18.059 | 1.00 | 87.96 | C |
| ATOM | A1282 | O2' | A | C1927 | −89.771 | −5.523 | 18.331 | 1.00 | 87.96 | O |
| ATOM | A1283 | C3' | A | C1927 | −91.984 | −6.528 | 18.303 | 1.00 | 87.96 | C |
| ATOM | A1284 | O3' | A | C1927 | −92.444 | −5.231 | 17.958 | 1.00 | 87.96 | O |
| ATOM | A128G | P | A | C1928 | −93.676 | −5.041 | 16.945 | 1.00 | 70.25 | P |
| ATOM | A128H | OP1 | A | C1928 | −94.137 | −3.638 | 17.078 | 1.00 | 70.25 | O |

TABLE 8-continued

H69 Neomycin Binding Site for Intermediate-Rotated Ribosome

| ATOM | A128I | OP2 | A | C1928 | −94.639 | −6.130 | 17.215 | 1.00 | 70.25 | O |
|---|---|---|---|---|---|---|---|---|---|---|
| ATOM | A128J | O5' | A | C1928 | −92.998 | −5.255 | 15.521 | 1.00 | 70.25 | O |
| ATOM | A128K | C5' | A | C1928 | −92.479 | −4.155 | 14.796 | 1.00 | 70.25 | C |
| ATOM | A128L | C4' | A | C1928 | −91.247 | −4.528 | 14.006 | 1.00 | 70.25 | C |
| ATOM | A128M | O4' | A | C1928 | −90.354 | −5.344 | 14.820 | 1.00 | 70.25 | O |
| ATOM | A128N | C1' | A | C1928 | −89.670 | −6.269 | 13.979 | 1.00 | 70.25 | C |
| ATOM | A128O | N9 | A | C1928 | −90.117 | −7.634 | 14.311 | 1.00 | 59.11 | N |
| ATOM | A128P | C4 | A | C1928 | −89.505 | −8.789 | 13.892 | 1.00 | 59.11 | C |
| ATOM | A128Q | N3 | A | C1928 | −88.367 | −8.892 | 13.189 | 1.00 | 59.11 | N |
| ATOM | A128R | C2 | A | C1928 | −88.053 | −10.169 | 12.990 | 1.00 | 59.11 | C |
| ATOM | A128S | N1 | A | C1928 | −88.697 | −11.273 | 13.383 | 1.00 | 59.11 | N |
| ATOM | A128T | C6 | A | C1928 | −89.840 | −11.135 | 14.084 | 1.00 | 59.11 | C |
| ATOM | A128U | N6 | A | C1928 | −90.481 | −12.238 | 14.478 | 1.00 | 59.11 | N |
| ATOM | A128V | C5 | A | C1928 | −90.279 | −9.830 | 14.366 | 1.00 | 59.11 | C |
| ATOM | A128W | N7 | A | C1928 | −91.383 | −9.345 | 15.048 | 1.00 | 59.11 | N |
| ATOM | A128X | C8 | A | C1928 | −91.250 | −8.044 | 14.966 | 1.00 | 59.11 | C |
| ATOM | A128Y | C2' | A | C1928 | −90.052 | −5.923 | 12.548 | 1.00 | 70.25 | C |
| ATOM | A128Z | O2' | A | C1928 | −89.193 | −4.890 | 12.085 | 1.00 | 70.25 | O |
| ATOM | A1290 | C3' | A | C1928 | −91.461 | −5.406 | 12.787 | 1.00 | 70.25 | C |
| ATOM | A1291 | O3' | A | C1928 | −92.073 | −4.765 | 11.674 | 1.00 | 70.25 | O |
| ATOM | A129D | P | G | C1929 | −91.583 | −3.330 | 11.139 | 1.00 | 85.66 | P |
| ATOM | A129E | OP1 | G | C1929 | −92.590 | −2.334 | 11.584 | 1.00 | 85.66 | O |
| ATOM | A129F | OP2 | G | C1929 | −90.174 | −3.152 | 11.557 | 1.00 | 85.66 | O |
| ATOM | A129G | O5' | G | C1929 | −91.657 | −3.503 | 9.554 | 1.00 | 85.66 | O |
| ATOM | A129H | C5' | G | C1929 | −91.978 | −4.760 | 8.953 | 1.00 | 85.66 | C |
| ATOM | A129I | C4' | G | C1929 | −90.750 | −5.619 | 8.754 | 1.00 | 85.66 | C |
| ATOM | A129J | O4' | G | C1929 | −90.704 | −6.646 | 9.784 | 1.00 | 85.66 | O |
| ATOM | A129K | C1' | G | C1929 | −90.576 | −7.916 | 9.175 | 1.00 | 85.66 | C |
| ATOM | A129L | N9 | G | C1929 | −91.242 | −8.914 | 10.014 | 1.00 | 94.85 | N |
| ATOM | A129M | C4 | G | C1929 | −92.549 | −8.923 | 10.423 | 1.00 | 94.85 | C |
| ATOM | A129N | N3 | G | C1929 | −93.462 | −7.980 | 10.131 | 1.00 | 94.85 | N |
| ATOM | A129O | C2 | G | C1929 | −94.634 | −8.258 | 10.670 | 1.00 | 94.85 | C |
| ATOM | A129P | N2 | G | C1929 | −95.651 | −7.411 | 10.473 | 1.00 | 94.85 | N |
| ATOM | A129Q | N1 | G | C1929 | −94.891 | −9.369 | 11.438 | 1.00 | 94.85 | N |
| ATOM | A129R | C6 | G | C1929 | −93.958 | −10.352 | 11.751 | 1.00 | 94.85 | C |
| ATOM | A129S | O6 | G | C1929 | −94.289 | −11.316 | 12.449 | 1.00 | 94.85 | O |
| ATOM | A129T | C5 | G | C1929 | −92.693 | −10.068 | 11.176 | 1.00 | 94.85 | C |
| ATOM | A129U | N7 | G | C1929 | −91.500 | −10.771 | 11.234 | 1.00 | 94.85 | N |
| ATOM | A129V | C8 | G | C1929 | −90.673 | −10.051 | 10.529 | 1.00 | 94.85 | C |
| ATOM | A129W | C2' | G | C1929 | −91.179 | −7.756 | 7.788 | 1.00 | 85.66 | C |
| ATOM | A129X | O2' | G | C1929 | −90.760 | −8.781 | 6.913 | 1.00 | 85.66 | O |
| ATOM | A129Y | C3' | G | C1929 | −90.682 | −6.366 | 7.419 | 1.00 | 85.66 | C |
| ATOM | A129Z | O3' | G | C1929 | −89.325 | −6.454 | 6.995 | 1.00 | 85.66 | O |
| ATOM | A12AB | P | G | C1930 | −88.636 | −5.235 | 6.217 | 1.00 | 81.43 | P |
| ATOM | A12AC | OP1 | G | C1930 | −88.069 | −4.326 | 7.243 | 1.00 | 81.43 | O |
| ATOM | A12AD | OP2 | G | C1930 | −89.640 | −4.700 | 5.267 | 1.00 | 81.43 | O |
| ATOM | A12AE | O5' | G | C1930 | −87.462 | −5.951 | 5.418 | 1.00 | 81.43 | O |
| ATOM | A12AF | C5' | G | C1930 | −86.500 | −6.755 | 6.094 | 1.00 | 81.43 | C |
| ATOM | A12AG | C4' | G | C1930 | −85.165 | −6.726 | 5.394 | 1.00 | 81.43 | C |
| ATOM | A12AH | O4' | G | C1930 | −84.313 | −7.775 | 5.937 | 1.00 | 81.43 | O |
| ATOM | A12AI | C1' | G | C1930 | −83.857 | −8.599 | 4.882 | 1.00 | 81.43 | C |
| ATOM | A12AJ | N9 | G | C1930 | −83.693 | −9.963 | 5.387 | 1.00 | 75.46 | N |
| ATOM | A12AK | C4 | G | C1930 | −82.546 | −10.427 | 5.973 | 1.00 | 75.46 | C |
| ATOM | A12AL | N3 | G | C1930 | −81.428 | −9.702 | 6.167 | 1.00 | 75.46 | N |
| ATOM | A12AM | C2 | G | C1930 | −80.483 | −10.408 | 6.755 | 1.00 | 75.46 | C |
| ATOM | A12AN | N2 | G | C1930 | −79.304 | −9.829 | 7.021 | 1.00 | 75.46 | N |
| ATOM | A12AO | N1 | G | C1930 | −80.625 | −11.723 | 7.122 | 1.00 | 75.46 | N |
| ATOM | A12AP | C6 | G | C1930 | −81.771 | −12.488 | 6.928 | 1.00 | 75.46 | C |
| ATOM | A12AQ | O6 | G | C1930 | −81.791 | −13.667 | 7.300 | 1.00 | 75.46 | O |
| ATOM | A12AR | C5 | G | C1930 | −82.797 | −11.739 | 6.296 | 1.00 | 75.46 | C |
| ATOM | A12AS | N7 | G | C1930 | −84.083 | −12.097 | 5.918 | 1.00 | 75.46 | N |
| ATOM | A12AT | C8 | G | C1930 | −84.578 | −11.013 | 5.381 | 1.00 | 75.46 | C |
| ATOM | A12AU | C2' | G | C1930 | −84.893 | −8.452 | 3.777 | 1.00 | 81.43 | C |
| ATOM | A12AV | O2' | G | C1930 | −84.389 | −8.859 | 2.524 | 1.00 | 81.43 | O |
| ATOM | A12AW | C3' | G | C1930 | −85.217 | −6.966 | 3.886 | 1.00 | 81.43 | C |
| ATOM | A12AX | O3' | G | C1930 | −84.192 | −6.201 | 3.251 | 1.00 | 81.43 | O |
| ATOM | A12B9 | P | U | C1931 | −84.240 | −5.933 | 1.668 | 1.00 | 64.85 | P |
| ATOM | A12BA | OP1 | U | C1931 | −85.571 | −6.376 | 1.192 | 1.00 | 64.85 | O |
| ATOM | A12BB | OP2 | U | C1931 | −83.030 | −6.565 | 1.086 | 1.00 | 64.85 | O |
| ATOM | A12BC | O5' | U | C1931 | −84.129 | −4.343 | 1.552 | 1.00 | 64.85 | O |
| ATOM | A12BD | C5' | U | C1931 | −84.175 | −3.499 | 2.697 | 1.00 | 64.85 | C |
| ATOM | A12BE | C4' | U | C1931 | −82.990 | −2.569 | 2.742 | 1.00 | 64.85 | C |
| ATOM | A12BF | O4' | U | C1931 | −82.378 | −2.614 | 4.058 | 1.00 | 64.85 | O |
| ATOM | A12BG | C1' | U | C1931 | −80.974 | −2.553 | 3.947 | 1.00 | 64.85 | C |
| ATOM | A12BH | N1 | U | C1931 | −80.406 | −3.830 | 4.444 | 1.00 | 66.05 | N |
| ATOM | A12BI | C6 | U | C1931 | −81.207 | −4.895 | 4.804 | 1.00 | 66.05 | C |
| ATOM | A12BJ | C2 | U | C1931 | −79.033 | −3.910 | 4.561 | 1.00 | 66.05 | C |
| ATOM | A12BK | O2 | U | C1931 | −78.284 | −2.997 | 4.261 | 1.00 | 66.05 | O |

TABLE 8-continued

H69 Neomycin Binding Site for Intermediate-Rotated Ribosome

| ATOM | A12BL | N3 | U | C1931 | −78.562 | −5.106 | 5.031 | 1.00 | 66.05 | N |
|---|---|---|---|---|---|---|---|---|---|---|
| ATOM | A12BM | C4 | U | C1931 | −79.305 | −6.207 | 5.401 | 1.00 | 66.05 | C |
| ATOM | A12BN | O4 | U | C1931 | −78.739 | −7.219 | 5.809 | 1.00 | 66.05 | O |
| ATOM | A12BO | C5 | U | C1931 | −80.718 | −6.051 | 5.262 | 1.00 | 66.05 | C |
| ATOM | A12BP | C2' | U | C1931 | −80.636 | −2.305 | 2.478 | 1.00 | 64.85 | C |
| ATOM | A12BQ | O2' | U | C1931 | −80.550 | −0.904 | 2.259 | 1.00 | 64.85 | O |
| ATOM | A12BR | C3' | U | C1931 | −81.852 | −2.893 | 1.780 | 1.00 | 64.85 | C |
| ATOM | A12BS | O3' | U | C1931 | −82.070 | −2.366 | 0.481 | 1.00 | 64.85 | O |
| TER | | | | | | | | | | |
| ATOM | A84BU | C1 | NMY | 12905 | −95.087 | −4.167 | 4.519 | 1.00 | 232.49 | C |
| ATOM | A84BV | O1 | NMY | 12905 | −96.233 | −4.750 | 3.927 | 1.00 | 232.49 | O |
| ATOM | A84BW | C2 | NMY | 12905 | −94.531 | −5.207 | 5.500 | 1.00 | 232.49 | C |
| ATOM | A84BX | N2 | NMY | 12905 | −94.072 | −6.376 | 4.798 | 1.00 | 232.49 | N |
| ATOM | A84BY | C3 | NMY | 12905 | −95.527 | −5.611 | 6.500 | 1.00 | 232.49 | C |
| ATOM | A84BZ | O3 | NMY | 12905 | −94.763 | −6.232 | 7.502 | 1.00 | 232.49 | O |
| ATOM | A84C0 | C4 | NMY | 12905 | −96.233 | −4.486 | 7.052 | 1.00 | 232.49 | C |
| ATOM | A84C1 | O4 | NMY | 12905 | −97.190 | −4.620 | 8.089 | 1.00 | 232.49 | O |
| ATOM | A84C2 | C5 | NMY | 12905 | −96.134 | −3.119 | 6.420 | 1.00 | 232.49 | C |
| ATOM | A84C3 | O5 | NMY | 12905 | −95.336 | −2.955 | 5.148 | 1.00 | 232.49 | O |
| ATOM | A84C4 | C6 | NMY | 12905 | −96.532 | −1.894 | 7.215 | 1.00 | 232.49 | C |
| ATOM | A84C5 | N6 | NMY | 12905 | −95.547 | −0.814 | 7.324 | 1.00 | 232.49 | N |
| ATOM | A84C6 | C7 | NMY | 12905 | −97.960 | −3.496 | 0.219 | 1.00 | 232.49 | C |
| ATOM | A84C7 | N7 | NMY | 12905 | −98.173 | −2.589 | −0.916 | 1.00 | 232.49 | N |
| ATOM | A84C8 | C8 | NMY | 12905 | −98.695 | −3.224 | 1.511 | 1.00 | 232.49 | C |
| ATOM | A84C9 | C9 | NMY | 12905 | −98.154 | −4.055 | 2.687 | 1.00 | 232.49 | C |
| ATOM | A84CA | N9 | NMY | 12905 | −98.692 | −3.584 | 3.931 | 1.00 | 232.49 | N |
| ATOM | A84CB | C10 | NMY | 12905 | −96.623 | −4.050 | 2.755 | 1.00 | 232.49 | C |
| ATOM | A84CC | C11 | NMY | 12905 | −95.941 | −4.603 | 1.533 | 1.00 | 232.49 | C |
| ATOM | A84CD | O11 | NMY | 12905 | −94.705 | −3.954 | 1.346 | 1.00 | 232.49 | O |
| ATOM | A84CE | C12 | NMY | 12905 | −96.762 | −4.454 | 0.230 | 1.00 | 232.49 | C |
| ATOM | A84CF | O12 | NMY | 12905 | −96.588 | −5.326 | −0.806 | 1.00 | 232.49 | O |
| ATOM | A84CG | C13 | NMY | 12905 | −93.780 | −4.747 | 0.614 | 1.00 | 232.49 | C |
| ATOM | A84CH | C14 | NMY | 12905 | −92.906 | −3.918 | −0.246 | 1.00 | 232.49 | C |
| ATOM | A84CI | O14 | NMY | 12905 | −92.743 | −4.635 | −1.406 | 1.00 | 232.49 | O |
| ATOM | A84CJ | C15 | NMY | 12905 | −91.683 | −3.790 | 0.476 | 1.00 | 232.49 | C |
| ATOM | A84CK | C16 | NMY | 12905 | −91.692 | −4.853 | 1.517 | 1.00 | 232.49 | C |
| ATOM | A84CL | O16 | NMY | 12905 | −92.902 | −5.527 | 1.439 | 1.00 | 232.49 | O |
| ATOM | A84CM | C17 | NMY | 12905 | −91.528 | −4.318 | 2.918 | 1.00 | 232.49 | C |
| ATOM | A84CN | O17 | NMY | 12905 | −91.733 | −5.183 | 3.946 | 1.00 | 232.49 | O |
| ATOM | A84CO | C18 | NMY | 12905 | −89.713 | −2.865 | −0.463 | 1.00 | 232.49 | C |
| ATOM | A84CP | O18 | NMY | 12905 | −90.639 | −3.951 | −0.471 | 1.00 | 232.49 | O |
| ATOM | A84CQ | C19 | NMY | 12905 | −90.162 | −1.430 | −0.648 | 1.00 | 232.49 | C |
| ATOM | A84CR | N19 | NMY | 12905 | −87.542 | −4.535 | −2.804 | 1.00 | 232.49 | N |
| ATOM | A84CS | C20 | NMY | 12905 | −89.341 | −0.689 | −1.527 | 1.00 | 232.49 | C |
| ATOM | A84CT | O20 | NMY | 12905 | −89.536 | 0.701 | −1.232 | 1.00 | 232.49 | O |
| ATOM | A84CU | C21 | NMY | 12905 | −87.915 | −1.010 | −1.322 | 1.00 | 232.49 | C |
| ATOM | A84CV | O21 | NMY | 12905 | −86.929 | 0.006 | −1.297 | 1.00 | 232.49 | O |
| ATOM | A84CW | C22 | NMY | 12905 | −87.469 | −2.463 | −1.348 | 1.00 | 232.49 | C |
| ATOM | A84CX | O22 | NMY | 12905 | −88.258 | −3.238 | −0.502 | 1.00 | 232.49 | O |
| ATOM | A84CY | C23 | NMY | 12905 | −87.473 | −3.094 | −2.737 | 1.00 | 232.49 | C |
| ATOM | A84CZ | N23 | NMY | 12905 | −91.491 | −1.413 | −1.254 | 1.00 | 232.49 | N |
| END | | | | | | | | | | |

TABLE 9

H69 Neomycin Binding Site for Unrotated Ribosome

| ATOM | A420H | P | G | E1515 | −32.433 | 114.986 | 100.787 | 1.00 | 64.61 | P |
|---|---|---|---|---|---|---|---|---|---|---|
| ATOM | A420I | OP1 | G | E1515 | −32.585 | 115.515 | 102.164 | 1.00 | 64.61 | O |
| ATOM | A420J | OP2 | G | E1515 | −32.068 | 113.560 | 100.608 | 1.00 | 64.61 | O |
| ATOM | A420K | O5' | G | E1515 | −33.730 | 115.326 | 99.932 | 1.00 | 64.61 | O |
| ATOM | A420L | C5' | G | E1515 | −34.372 | 116.582 | 100.063 | 1.00 | 64.61 | C |
| ATOM | A420M | C4' | G | E1515 | −35.385 | 116.813 | 98.972 | 1.00 | 64.61 | C |
| ATOM | A420N | O4' | G | E1515 | −34.809 | 116.509 | 97.674 | 1.00 | 64.61 | O |
| ATOM | A420O | C1' | G | E1515 | −35.813 | 115.999 | 96.817 | 1.00 | 64.61 | C |
| ATOM | A420P | N9 | G | E1515 | −35.455 | 114.620 | 96.439 | 1.00 | 93.72 | N |
| ATOM | A420Q | C4 | G | E1515 | −36.177 | 113.821 | 95.588 | 1.00 | 93.72 | C |
| ATOM | A420R | N3 | G | E1515 | −37.315 | 114.161 | 94.948 | 1.00 | 93.72 | N |
| ATOM | A420S | C2 | G | E1515 | −37.771 | 113.177 | 94.191 | 1.00 | 93.72 | C |
| ATOM | A420T | N2 | G | E1515 | −38.899 | 113.349 | 93.483 | 1.00 | 93.72 | N |
| ATOM | A420U | N1 | G | E1515 | −37.158 | 111.955 | 94.075 | 1.00 | 93.72 | N |
| ATOM | A420V | C6 | G | E1515 | −35.988 | 111.587 | 94.728 | 1.00 | 93.72 | C |
| ATOM | A420W | O6 | G | E1515 | −35.507 | 110.463 | 94.563 | 1.00 | 93.72 | O |
| ATOM | A420X | C5 | G | E1515 | −35.490 | 112.631 | 95.540 | 1.00 | 93.72 | C |
| ATOM | A420Y | N7 | G | E1515 | −34.363 | 112.670 | 96.344 | 1.00 | 93.72 | N |

TABLE 9-continued

H69 Neomycin Binding Site for Unrotated Ribosome

| ATOM | A420Z | C8 | G | E1515 | −34.385 | 113.865 | 96.860 | 1.00 | 93.72 | C |
|---|---|---|---|---|---|---|---|---|---|---|
| ATOM | A4210 | C2' | G | E1515 | −37.133 | 116.046 | 97.587 | 1.00 | 64.61 | C |
| ATOM | A4211 | O2' | G | E1515 | −37.758 | 117.299 | 97.345 | 1.00 | 64.61 | O |
| ATOM | A4212 | C3' | G | E1515 | −36.632 | 115.952 | 99.019 | 1.00 | 64.61 | C |
| ATOM | A4213 | O3' | G | E1515 | −37.566 | 116.396 | 99.983 | 1.00 | 64.61 | O |
| ATOM | A421F | P | G | E1516 | −37.979 | 115.445 | 101.210 | 1.00 | 83.64 | P |
| ATOM | A421G | OP1 | G | E1516 | −38.308 | 116.328 | 102.354 | 1.00 | 83.64 | O |
| ATOM | A421H | OP2 | G | E1516 | −36.904 | 114.436 | 101.375 | 1.00 | 83.64 | O |
| ATOM | A421I | O5' | G | E1516 | −39.298 | 114.748 | 100.672 | 1.00 | 83.64 | O |
| ATOM | A421J | C5' | G | E1516 | −40.435 | 115.528 | 100.360 | 1.00 | 83.64 | C |
| ATOM | A421K | C4' | G | E1516 | −41.017 | 115.163 | 99.023 | 1.00 | 83.64 | C |
| ATOM | A421L | O4' | G | E1516 | −39.966 | 114.817 | 98.086 | 1.00 | 83.64 | O |
| ATOM | A421M | C1' | G | E1516 | −40.476 | 113.920 | 97.117 | 1.00 | 83.64 | C |
| ATOM | A421N | N9 | G | E1516 | −39.614 | 112.722 | 97.060 | 1.00 | 95.24 | N |
| ATOM | A421O | C4 | G | E1516 | −39.911 | 111.570 | 96.370 | 1.00 | 95.24 | C |
| ATOM | A421P | N3 | G | E1516 | −41.033 | 111.351 | 95.655 | 1.00 | 95.24 | N |
| ATOM | A421Q | C2 | G | E1516 | −41.055 | 110.149 | 95.110 | 1.00 | 95.24 | C |
| ATOM | A421R | N2 | G | E1516 | −42.110 | 109.781 | 94.366 | 1.00 | 95.24 | N |
| ATOM | A421S | N1 | G | E1516 | −40.043 | 109.231 | 95.247 | 1.00 | 95.24 | N |
| ATOM | A421T | C6 | G | E1516 | −38.875 | 109.434 | 95.977 | 1.00 | 95.24 | C |
| ATOM | A421U | O6 | G | E1516 | −38.029 | 108.535 | 96.034 | 1.00 | 95.24 | O |
| ATOM | A421V | C5 | G | E1516 | −38.845 | 110.723 | 96.573 | 1.00 | 95.24 | C |
| ATOM | A421W | N7 | G | E1516 | −37.886 | 111.333 | 97.371 | 1.00 | 95.24 | N |
| ATOM | A421X | C8 | G | E1516 | −38.381 | 112.514 | 97.633 | 1.00 | 95.24 | C |
| ATOM | A421Y | C2' | G | E1516 | −41.919 | 113.578 | 97.517 | 1.00 | 83.64 | C |
| ATOM | A421Z | O2' | G | E1516 | −42.803 | 114.408 | 96.779 | 1.00 | 83.64 | O |
| ATOM | A4220 | C3' | G | E1516 | −41.923 | 113.948 | 98.993 | 1.00 | 83.64 | C |
| ATOM | A4221 | O3' | G | E1516 | −43.212 | 114.204 | 99.521 | 1.00 | 83.64 | O |
| ATOM | A422D | P | G | E1517 | −43.683 | 113.489 | 100.880 | 1.00 | 79.55 | P |
| ATOM | A422E | OP1 | G | E1517 | −44.894 | 114.203 | 101.356 | 1.00 | 79.55 | O |
| ATOM | A422F | OP2 | G | E1517 | −42.501 | 113.420 | 101.772 | 1.00 | 79.55 | O |
| ATOM | A422G | O5' | G | E1517 | −44.074 | 112.028 | 100.393 | 1.00 | 79.55 | O |
| ATOM | A422H | C5' | G | E1517 | −45.072 | 111.841 | 99.403 | 1.00 | 79.55 | C |
| ATOM | A422I | C4' | G | E1517 | −45.759 | 110.505 | 99.551 | 1.00 | 79.55 | C |
| ATOM | A422J | O4' | G | E1517 | −47.191 | 110.688 | 99.426 | 1.00 | 79.55 | O |
| ATOM | A422K | C1' | G | E1517 | −47.756 | 109.610 | 98.712 | 1.00 | 79.55 | C |
| ATOM | A422L | N9 | G | E1517 | −48.347 | 110.140 | 97.467 | 1.00 | 95.87 | N |
| ATOM | A422M | C4 | G | E1517 | −49.170 | 109.483 | 96.581 | 1.00 | 95.87 | C |
| ATOM | A422N | N3 | G | E1517 | −49.595 | 108.208 | 96.680 | 1.00 | 95.87 | N |
| ATOM | A422O | C2 | G | E1517 | −50.375 | 107.866 | 95.668 | 1.00 | 95.87 | C |
| ATOM | A422P | N2 | G | E1517 | −50.886 | 106.628 | 95.613 | 1.00 | 95.87 | N |
| ATOM | A422Q | N1 | G | E1517 | −50.713 | 108.708 | 94.637 | 1.00 | 95.87 | N |
| ATOM | A422R | C6 | G | E1517 | −50.287 | 110.025 | 94.513 | 1.00 | 95.87 | C |
| ATOM | A422S | O6 | G | E1517 | −50.648 | 110.704 | 93.543 | 1.00 | 95.87 | O |
| ATOM | A422T | C5 | G | E1517 | −49.449 | 110.404 | 95.593 | 1.00 | 95.87 | C |
| ATOM | A422U | N7 | G | E1517 | −48.820 | 111.614 | 95.849 | 1.00 | 95.87 | N |
| ATOM | A422V | C8 | G | E1517 | −48.181 | 111.411 | 96.967 | 1.00 | 95.87 | C |
| ATOM | A422W | C2' | G | E1517 | −46.658 | 108.593 | 98.446 | 1.00 | 79.55 | C |
| ATOM | A422X | O2' | G | E1517 | −46.657 | 107.636 | 99.496 | 1.00 | 79.55 | O |
| ATOM | A422Y | C3' | G | E1517 | −45.406 | 109.462 | 98.501 | 1.00 | 79.55 | C |
| ATOM | A422Z | O3' | G | E1517 | −44.230 | 108.740 | 98.814 | 1.00 | 79.55 | O |
| ATOM | A423B | P | A | E1518 | −42.948 | 108.828 | 97.853 | 1.00 | 57.08 | P |
| ATOM | A423C | OP1 | A | E1518 | −41.810 | 108.216 | 98.582 | 1.00 | 57.08 | O |
| ATOM | A423D | OP2 | A | E1518 | −42.835 | 110.234 | 97.414 | 1.00 | 57.08 | O |
| ATOM | A423E | O5' | A | E1518 | −43.364 | 107.907 | 96.623 | 1.00 | 57.08 | O |
| ATOM | A423F | C5' | A | E1518 | −43.642 | 106.529 | 96.812 | 1.00 | 57.08 | C |
| ATOM | A423G | C4' | A | E1518 | −44.650 | 106.021 | 95.813 | 1.00 | 57.08 | C |
| ATOM | A423H | O4' | A | E1518 | −45.868 | 106.803 | 95.891 | 1.00 | 57.08 | O |
| ATOM | A423I | C1' | A | E1518 | −46.473 | 106.877 | 94.617 | 1.00 | 57.08 | C |
| ATOM | A423J | N9 | A | E1518 | −46.585 | 108.292 | 94.221 | 1.00 | 81.47 | N |
| ATOM | A423K | C4 | A | E1518 | −47.383 | 108.760 | 93.210 | 1.00 | 81.47 | C |
| ATOM | A423L | N3 | A | E1518 | −48.192 | 108.035 | 92.423 | 1.00 | 81.47 | N |
| ATOM | A423M | C2 | A | E1518 | −48.822 | 108.818 | 91.552 | 1.00 | 81.47 | C |
| ATOM | A423N | N1 | A | E1518 | −48.740 | 110.146 | 91.392 | 1.00 | 81.47 | N |
| ATOM | A423O | C6 | A | E1518 | −47.916 | 110.847 | 92.203 | 1.00 | 81.47 | C |
| ATOM | A423P | N6 | A | E1518 | −47.835 | 112.170 | 92.041 | 1.00 | 81.47 | N |
| ATOM | A423Q | C5 | A | E1518 | −47.189 | 110.128 | 93.171 | 1.00 | 81.47 | C |
| ATOM | A423R | N7 | A | E1518 | −46.277 | 110.517 | 94.142 | 1.00 | 81.47 | N |
| ATOM | A423S | C8 | A | E1518 | −45.947 | 109.394 | 94.734 | 1.00 | 81.47 | C |
| ATOM | A423T | C2' | A | E1518 | −45.602 | 106.080 | 93.648 | 1.00 | 57.08 | C |
| ATOM | A423U | O2' | A | E1518 | −46.099 | 104.755 | 93.583 | 1.00 | 57.08 | O |
| ATOM | A423V | C3' | A | E1518 | −44.253 | 106.120 | 94.353 | 1.00 | 57.08 | C |
| ATOM | A423W | O3' | A | E1518 | −43.370 | 105.089 | 93.952 | 1.00 | 57.08 | O |
| TER | | | | | | | | | | |
| ATOM | A676E | P | G | G1903 | −35.400 | 131.852 | 122.787 | 1.00 | 74.00 | P |
| ATOM | A676F | OP1 | G | G1903 | −36.024 | 131.508 | 124.089 | 1.00 | 74.00 | O |
| ATOM | A676G | OP2 | G | G1903 | −34.071 | 131.280 | 122.460 | 1.00 | 74.00 | O |
| ATOM | A676H | O5' | G | G1903 | −36.420 | 131.561 | 121.599 | 1.00 | 74.00 | O |

TABLE 9-continued

H69 Neomycin Binding Site for Unrotated Ribosome

| ATOM | A676I | C5' | G | G1903 | −37.693 | 130.982 | 121.843 | 1.00 | 74.00 | C |
|---|---|---|---|---|---|---|---|---|---|---|
| ATOM | A676J | C4' | G | G1903 | −38.746 | 131.586 | 120.952 | 1.00 | 74.00 | C |
| ATOM | A676K | O4' | G | G1903 | −38.117 | 132.461 | 119.981 | 1.00 | 74.00 | O |
| ATOM | A676L | C1' | G | G1903 | −38.817 | 132.413 | 118.760 | 1.00 | 74.00 | C |
| ATOM | A676M | N9 | G | G1903 | −37.892 | 131.949 | 117.706 | 1.00 | 72.55 | N |
| ATOM | A676N | C4 | G | G1903 | −38.213 | 131.642 | 116.407 | 1.00 | 72.55 | C |
| ATOM | A676O | N3 | G | G1903 | −39.445 | 131.693 | 115.865 | 1.00 | 72.55 | N |
| ATOM | A676P | C2 | G | G1903 | −39.447 | 131.332 | 114.596 | 1.00 | 72.55 | C |
| ATOM | A676Q | N2 | G | G1903 | −40.608 | 131.333 | 113.926 | 1.00 | 72.55 | N |
| ATOM | A676R | N1 | G | G1903 | −38.321 | 130.948 | 113.906 | 1.00 | 72.55 | N |
| ATOM | A676S | C6 | G | G1903 | −37.038 | 130.887 | 114.445 | 1.00 | 72.55 | C |
| ATOM | A676T | O6 | G | G1903 | −36.088 | 130.529 | 113.739 | 1.00 | 72.55 | O |
| ATOM | A676U | C5 | G | G1903 | −37.026 | 131.273 | 115.810 | 1.00 | 72.55 | C |
| ATOM | A676V | N7 | G | G1903 | −35.975 | 131.354 | 116.710 | 1.00 | 72.55 | N |
| ATOM | A676W | C8 | G | G1903 | −36.533 | 131.761 | 117.817 | 1.00 | 72.55 | C |
| ATOM | A676X | C2' | G | G1903 | −40.011 | 131.475 | 118.945 | 1.00 | 74.00 | C |
| ATOM | A676Y | O2' | G | G1903 | −41.144 | 132.249 | 119.307 | 1.00 | 74.00 | O |
| ATOM | A676Z | C3' | G | G1903 | −39.549 | 130.608 | 120.108 | 1.00 | 74.00 | C |
| ATOM | A677O | O3' | G | G1903 | −40.617 | 130.011 | 120.831 | 1.00 | 74.00 | O |
| ATOM | A677C | P | G | G1904 | −40.936 | 128.438 | 120.683 | 1.00 | 70.78 | P |
| ATOM | A677D | OP1 | G | G1904 | −41.613 | 128.013 | 121.933 | 1.00 | 70.78 | O |
| ATOM | A677E | OP2 | G | G1904 | −39.675 | 127.763 | 120.294 | 1.00 | 70.78 | O |
| ATOM | A677F | O5' | G | G1904 | −41.966 | 128.397 | 119.472 | 1.00 | 70.78 | O |
| ATOM | A677G | C5' | G | G1904 | −43.168 | 129.152 | 119.505 | 1.00 | 70.78 | C |
| ATOM | A677H | C4' | G | G1904 | −43.857 | 129.147 | 118.164 | 1.00 | 70.78 | C |
| ATOM | A677I | O4' | G | G1904 | −43.059 | 129.891 | 117.203 | 1.00 | 70.78 | O |
| ATOM | A677J | C1' | G | G1904 | −43.103 | 129.257 | 115.943 | 1.00 | 70.78 | C |
| ATOM | A677K | N9 | G | G1904 | −41.753 | 128.748 | 115.635 | 1.00 | 49.07 | N |
| ATOM | A677L | C4 | G | G1904 | −41.288 | 128.235 | 114.445 | 1.00 | 49.07 | C |
| ATOM | A677M | N3 | G | G1904 | −41.978 | 128.099 | 113.292 | 1.00 | 49.07 | N |
| ATOM | A677N | C2 | G | G1904 | −41.239 | 127.572 | 112.326 | 1.00 | 49.07 | C |
| ATOM | A677O | N2 | G | G1904 | −41.766 | 127.367 | 111.109 | 1.00 | 49.07 | N |
| ATOM | A677P | N1 | G | G1904 | −39.925 | 127.209 | 112.478 | 1.00 | 49.07 | N |
| ATOM | A677Q | C6 | G | G1904 | −39.196 | 127.341 | 113.653 | 1.00 | 49.07 | C |
| ATOM | A677R | O6 | G | G1904 | −38.014 | 126.984 | 113.696 | 1.00 | 49.07 | O |
| ATOM | A677S | C5 | G | G1904 | −39.974 | 127.901 | 114.692 | 1.00 | 49.07 | C |
| ATOM | A677T | N7 | G | G1904 | −39.616 | 128.188 | 115.997 | 1.00 | 49.07 | N |
| ATOM | A677U | C8 | G | G1904 | −40.701 | 128.684 | 116.515 | 1.00 | 49.07 | C |
| ATOM | A677V | C2' | G | G1904 | −44.125 | 128.128 | 116.037 | 1.00 | 70.78 | C |
| ATOM | A677W | O2' | G | G1904 | −45.405 | 128.646 | 115.707 | 1.00 | 70.78 | O |
| ATOM | A677X | C3' | G | G1904 | −44.043 | 127.781 | 117.515 | 1.00 | 70.78 | C |
| ATOM | A677Y | O3' | G | G1904 | −45.176 | 127.082 | 118.002 | 1.00 | 70.78 | O |
| ATOM | A678A | P | C | G1905 | −45.138 | 125.480 | 118.153 | 1.00 | 73.26 | P |
| ATOM | A678B | OP1 | C | G1905 | −46.412 | 125.072 | 118.791 | 1.00 | 73.26 | O |
| ATOM | A678C | OP2 | C | G1905 | −43.861 | 125.132 | 118.825 | 1.00 | 73.26 | O |
| ATOM | A678D | O5' | C | G1905 | −45.107 | 124.983 | 116.641 | 1.00 | 73.26 | O |
| ATOM | A678E | C5' | C | G1905 | −46.168 | 125.291 | 115.749 | 1.00 | 73.26 | C |
| ATOM | A678F | C4' | C | G1905 | −45.816 | 124.931 | 114.328 | 1.00 | 73.26 | C |
| ATOM | A678G | O4' | C | G1905 | −44.543 | 125.519 | 113.980 | 1.00 | 73.26 | O |
| ATOM | A678H | C1' | C | G1905 | −43.846 | 124.692 | 113.083 | 1.00 | 73.26 | C |
| ATOM | A678I | N1 | C | G1905 | −42.483 | 124.446 | 113.623 | 1.00 | 58.02 | N |
| ATOM | A678J | C6 | C | G1905 | −42.107 | 124.859 | 114.877 | 1.00 | 58.02 | C |
| ATOM | A678K | C2 | C | G1905 | −41.542 | 123.838 | 112.794 | 1.00 | 58.02 | C |
| ATOM | A678L | O2 | C | G1905 | −41.886 | 123.486 | 111.658 | 1.00 | 58.02 | O |
| ATOM | A678M | N3 | C | G1905 | −40.285 | 123.625 | 113.247 | 1.00 | 58.02 | N |
| ATOM | A678N | C4 | C | G1905 | −39.938 | 124.013 | 114.472 | 1.00 | 58.02 | C |
| ATOM | A678O | N4 | C | G1905 | −38.691 | 123.793 | 114.889 | 1.00 | 58.02 | N |
| ATOM | A678P | C5 | C | G1905 | −40.865 | 124.654 | 115.336 | 1.00 | 58.02 | C |
| ATOM | A678Q | C2' | C | G1905 | −44.656 | 123.404 | 112.884 | 1.00 | 73.26 | C |
| ATOM | A678R | O2' | C | G1905 | −45.330 | 123.464 | 111.632 | 1.00 | 73.26 | O |
| ATOM | A678S | C3' | C | G1905 | −45.650 | 123.444 | 114.045 | 1.00 | 73.26 | C |
| ATOM | A678T | O3' | C | G1905 | −46.890 | 122.816 | 113.751 | 1.00 | 73.26 | O |
| ATOM | A6795 | P | G | G1906 | −47.085 | 121.238 | 113.975 | 1.00 | 86.11 | P |
| ATOM | A6796 | OP1 | G | G1906 | −46.313 | 120.870 | 115.186 | 1.00 | 86.11 | O |
| ATOM | A6797 | OP2 | G | G1906 | −46.757 | 120.572 | 112.691 | 1.00 | 86.11 | O |
| ATOM | A6798 | O5' | G | G1906 | −48.648 | 121.111 | 114.272 | 1.00 | 86.11 | O |
| ATOM | A6799 | C5' | G | G1906 | −49.611 | 121.312 | 113.245 | 1.00 | 86.11 | C |
| ATOM | A679A | C4' | G | G1906 | −50.768 | 122.155 | 113.729 | 1.00 | 86.11 | C |
| ATOM | A679B | O4' | G | G1906 | −50.940 | 123.304 | 112.851 | 1.00 | 86.11 | O |
| ATOM | A679C | C1' | G | G1906 | −52.320 | 123.569 | 112.676 | 1.00 | 86.11 | C |
| ATOM | A679D | N9 | G | G1906 | −52.684 | 123.232 | 111.291 | 1.00 | 72.55 | N |
| ATOM | A679E | C4 | G | G1906 | −53.858 | 123.526 | 110.643 | 1.00 | 72.55 | C |
| ATOM | A679F | N3 | G | G1906 | −54.895 | 124.226 | 111.148 | 1.00 | 72.55 | N |
| ATOM | A679G | C2 | G | G1906 | −55.873 | 124.356 | 110.268 | 1.00 | 72.55 | C |
| ATOM | A679H | N2 | G | G1906 | −56.989 | 125.024 | 110.599 | 1.00 | 72.55 | N |
| ATOM | A679I | N1 | G | G1906 | −55.830 | 123.838 | 108.999 | 1.00 | 72.55 | N |
| ATOM | A679J | C6 | G | G1906 | −54.776 | 123.115 | 108.458 | 1.00 | 72.55 | C |
| ATOM | A679K | O6 | G | G1906 | −54.843 | 122.693 | 107.299 | 1.00 | 72.55 | O |

TABLE 9-continued

H69 Neomycin Binding Site for Unrotated Ribosome

| ATOM | A679L | C5 | G | G1906 | −53.721 | 122.966 | 109.391 | 1.00 | 72.55 | C |
|---|---|---|---|---|---|---|---|---|---|---|
| ATOM | A679M | N7 | G | G1906 | −52.496 | 122.325 | 109.262 | 1.00 | 72.55 | N |
| ATOM | A679N | C8 | G | G1906 | −51.926 | 122.502 | 110.420 | 1.00 | 72.55 | C |
| ATOM | A679O | C2' | G | G1906 | −53.067 | 122.691 | 113.665 | 1.00 | 86.11 | C |
| ATOM | A679P | O2' | G | G1906 | −53.107 | 123.357 | 114.919 | 1.00 | 86.11 | O |
| ATOM | A679Q | C3' | G | G1906 | −52.139 | 121.491 | 113.716 | 1.00 | 86.11 | C |
| ATOM | A679R | O3' | G | G1906 | −52.373 | 120.635 | 114.816 | 1.00 | 86.11 | O |
| ATOM | A67A3 | P | G | G1907 | −53.423 | 119.426 | 114.673 | 1.00 | 88.28 | P |
| ATOM | A67A4 | OP1 | G | G1907 | −53.600 | 118.840 | 116.023 | 1.00 | 88.28 | O |
| ATOM | A67A5 | OP2 | G | G1907 | −52.937 | 118.555 | 113.575 | 1.00 | 88.28 | O |
| ATOM | A67A6 | O5' | G | G1907 | −54.759 | 120.167 | 114.225 | 1.00 | 88.28 | O |
| ATOM | A67A7 | C5' | G | G1907 | −55.480 | 120.981 | 115.136 | 1.00 | 88.28 | C |
| ATOM | A67A8 | C4' | G | G1907 | −56.890 | 121.232 | 114.667 | 1.00 | 88.28 | C |
| ATOM | A67A9 | O4' | G | G1907 | −56.892 | 122.091 | 113.497 | 1.00 | 88.28 | O |
| ATOM | A67AA | C1' | G | G1907 | −58.027 | 121.799 | 112.703 | 1.00 | 88.28 | C |
| ATOM | A67AB | N9 | G | G1907 | −57.584 | 121.439 | 111.343 | 1.00 | 87.88 | N |
| ATOM | A67AC | C4 | G | G1907 | −58.377 | 121.474 | 110.223 | 1.00 | 87.88 | C |
| ATOM | A67AD | N3 | G | G1907 | −59.670 | 121.857 | 110.190 | 1.00 | 87.88 | N |
| ATOM | A67AE | C2 | G | G1907 | −60.175 | 121.792 | 108.971 | 1.00 | 87.88 | C |
| ATOM | A67AF | N2 | G | G1907 | −61.453 | 122.142 | 108.762 | 1.00 | 87.88 | N |
| ATOM | A67AG | N1 | G | G1907 | −59.462 | 121.387 | 107.872 | 1.00 | 87.88 | N |
| ATOM | A67AH | C6 | G | G1907 | −58.129 | 120.988 | 107.880 | 1.00 | 87.88 | C |
| ATOM | A67AI | O6 | G | G1907 | −57.588 | 120.640 | 106.823 | 1.00 | 87.88 | O |
| ATOM | A67AJ | C5 | G | G1907 | −57.576 | 121.051 | 109.186 | 1.00 | 87.88 | C |
| ATOM | A67AK | N7 | G | G1907 | −56.301 | 120.749 | 109.648 | 1.00 | 87.88 | N |
| ATOM | A67AL | C8 | G | G1907 | −56.353 | 120.991 | 110.931 | 1.00 | 87.88 | C |
| ATOM | A67AM | C2' | G | G1907 | −58.779 | 120.650 | 113.378 | 1.00 | 88.28 | C |
| ATOM | A67AN | O2' | G | G1907 | −59.792 | 121.197 | 114.211 | 1.00 | 88.28 | O |
| ATOM | A67AO | C3' | G | G1907 | −57.670 | 120.017 | 114.208 | 1.00 | 88.28 | C |
| ATOM | A67AP | O3' | G | G1907 | −58.137 | 119.221 | 115.280 | 1.00 | 88.28 | O |
| ATOM | A67B1 | P | C | G1908 | −58.845 | 117.812 | 114.984 | 1.00 | 68.10 | P |
| ATOM | A67B2 | OP1 | C | G1908 | −58.845 | 117.047 | 116.255 | 1.00 | 68.10 | O |
| ATOM | A67B3 | OP2 | C | G1908 | −58.177 | 117.224 | 113.798 | 1.00 | 68.10 | O |
| ATOM | A67B4 | O5' | C | G1908 | −60.328 | 118.242 | 114.612 | 1.00 | 68.10 | O |
| ATOM | A67B5 | C5' | C | G1908 | −61.303 | 117.274 | 114.276 | 1.00 | 68.10 | C |
| ATOM | A67B6 | C4' | C | G1908 | −62.390 | 117.863 | 113.420 | 1.00 | 68.10 | C |
| ATOM | A67B7 | O4' | C | G1908 | −61.859 | 118.975 | 112.647 | 1.00 | 68.10 | O |
| ATOM | A67B8 | C1' | C | G1908 | −62.377 | 118.942 | 111.337 | 1.00 | 68.10 | C |
| ATOM | A67B9 | N1 | C | G1908 | −61.271 | 118.596 | 110.409 | 1.00 | 64.93 | N |
| ATOM | A67BA | C6 | C | G1908 | −60.058 | 118.171 | 110.888 | 1.00 | 64.93 | C |
| ATOM | A67BB | C2 | C | G1908 | −61.463 | 118.727 | 109.032 | 1.00 | 64.93 | C |
| ATOM | A67BC | O2 | C | G1908 | −62.563 | 119.113 | 108.616 | 1.00 | 64.93 | O |
| ATOM | A67BD | N3 | C | G1908 | −60.450 | 118.421 | 108.186 | 1.00 | 64.93 | N |
| ATOM | A67BE | C4 | C | G1908 | −59.280 | 118.005 | 108.672 | 1.00 | 64.93 | C |
| ATOM | A67BF | N4 | C | G1908 | −58.299 | 117.714 | 107.821 | 1.00 | 64.93 | N |
| ATOM | A67BG | C5 | C | G1908 | −59.050 | 117.868 | 110.064 | 1.00 | 64.93 | C |
| ATOM | A67BH | C2' | C | G1908 | −63.491 | 117.901 | 111.321 | 1.00 | 68.10 | C |
| ATOM | A67BI | O2' | C | G1908 | −64.696 | 118.529 | 111.740 | 1.00 | 68.10 | O |
| ATOM | A67BJ | C3' | C | G1908 | −62.986 | 116.933 | 112.378 | 1.00 | 68.10 | C |
| ATOM | A67BK | O3' | C | G1908 | −63.989 | 116.084 | 112.911 | 1.00 | 68.10 | O |
| ATOM | A67BW | P | C | G1909 | −63.895 | 114.492 | 112.709 | 1.00 | 116.78 | P |
| ATOM | A67BX | OP1 | C | G1909 | −64.729 | 113.868 | 113.765 | 1.00 | 116.78 | O |
| ATOM | A67BY | OP2 | C | G1909 | −62.455 | 114.137 | 112.635 | 1.00 | 116.78 | O |
| ATOM | A67BZ | O5' | C | G1909 | −64.578 | 114.283 | 111.290 | 1.00 | 116.78 | O |
| ATOM | A67C0 | C5' | C | G1909 | −65.852 | 114.839 | 111.009 | 1.00 | 116.78 | C |
| ATOM | A67C1 | C4' | C | G1909 | −66.095 | 114.946 | 109.528 | 1.00 | 116.78 | C |
| ATOM | A67C2 | O4' | C | G1909 | −65.228 | 115.958 | 108.947 | 1.00 | 116.78 | O |
| ATOM | A67C3 | C1' | C | G1909 | −64.869 | 115.576 | 107.633 | 1.00 | 116.78 | C |
| ATOM | A67C4 | N1 | C | G1909 | −63.398 | 115.397 | 107.572 | 1.00 | 73.62 | N |
| ATOM | A67C5 | C6 | C | G1909 | −62.612 | 115.314 | 108.693 | 1.00 | 73.62 | C |
| ATOM | A67C6 | C2 | C | G1909 | −62.813 | 115.299 | 106.309 | 1.00 | 73.62 | C |
| ATOM | A67C7 | O2 | C | G1909 | −63.538 | 115.371 | 105.308 | 1.00 | 73.62 | O |
| ATOM | A67C8 | N3 | C | G1909 | −61.477 | 115.127 | 106.200 | 1.00 | 73.62 | N |
| ATOM | A67C9 | C4 | C | G1909 | −60.722 | 115.050 | 107.294 | 1.00 | 73.62 | C |
| ATOM | A67CA | N4 | C | G1909 | −59.409 | 114.882 | 107.139 | 1.00 | 73.62 | N |
| ATOM | A67CB | C5 | C | G1909 | −61.285 | 115.145 | 108.598 | 1.00 | 73.62 | C |
| ATOM | A67CC | C2' | C | G1909 | −65.611 | 114.276 | 107.320 | 1.00 | 116.78 | C |
| ATOM | A67CD | O2' | C | G1909 | −66.870 | 114.593 | 106.738 | 1.00 | 116.78 | O |
| ATOM | A67CE | C3' | C | G1909 | −65.785 | 113.704 | 108.716 | 1.00 | 116.78 | C |
| ATOM | A67CF | O3' | C | G1909 | −66.793 | 112.716 | 108.815 | 1.00 | 116.78 | O |
| ATOM | A67CR | P | G | G1910 | −66.400 | 111.158 | 108.868 | 1.00 | 107.42 | P |
| ATOM | A67CS | OP1 | G | G1910 | −67.527 | 110.446 | 109.517 | 1.00 | 107.42 | O |
| ATOM | A67CT | OP2 | G | G1910 | −65.050 | 111.060 | 109.478 | 1.00 | 107.42 | O |
| ATOM | A67CU | O5' | G | G1910 | −66.328 | 110.769 | 107.331 | 1.00 | 107.42 | O |
| ATOM | A67CV | C5' | G | G1910 | −67.397 | 111.084 | 106.455 | 1.00 | 107.42 | C |
| ATOM | A67CW | C4' | G | G1910 | −66.975 | 111.001 | 105.013 | 1.00 | 107.42 | C |
| ATOM | A67CX | O4' | G | G1910 | −65.979 | 112.020 | 104.727 | 1.00 | 107.42 | O |
| ATOM | A67CY | C1' | G | G1910 | −65.073 | 111.536 | 103.755 | 1.00 | 107.42 | C |

TABLE 9-continued

H69 Neomycin Binding Site for Unrotated Ribosome

| ATOM | A67CZ | N9 | G | G1910 | −63.727 | 111.477 | 104.349 | 1.00 | 63.82 | N |
|---|---|---|---|---|---|---|---|---|---|---|
| ATOM | A67D0 | C4 | G | G1910 | −62.576 | 111.277 | 103.633 | 1.00 | 63.82 | C |
| ATOM | A67D1 | N3 | G | G1910 | −62.501 | 111.139 | 102.294 | 1.00 | 63.82 | N |
| ATOM | A67D2 | C2 | G | G1910 | −61.258 | 110.971 | 101.884 | 1.00 | 63.82 | C |
| ATOM | A67D3 | N2 | G | G1910 | −61.012 | 110.820 | 100.574 | 1.00 | 63.82 | N |
| ATOM | A67D4 | N1 | G | G1910 | −60.175 | 110.942 | 102.728 | 1.00 | 63.82 | N |
| ATOM | A67D5 | C6 | G | G1910 | −60.233 | 111.078 | 104.113 | 1.00 | 63.82 | C |
| ATOM | A67D6 | O6 | G | G1910 | −59.195 | 111.040 | 104.781 | 1.00 | 63.82 | O |
| ATOM | A67D7 | C5 | G | G1910 | −61.564 | 111.263 | 104.564 | 1.00 | 63.82 | C |
| ATOM | A67D8 | N7 | G | G1910 | −62.070 | 111.438 | 105.846 | 1.00 | 63.82 | N |
| ATOM | A67D9 | C8 | G | G1910 | −63.359 | 111.553 | 105.671 | 1.00 | 63.82 | C |
| ATOM | A67DA | C2' | G | G1910 | −65.557 | 110.151 | 103.335 | 1.00 | 107.42 | C |
| ATOM | A67DB | O2' | G | G1910 | −66.453 | 110.295 | 102.244 | 1.00 | 107.42 | O |
| ATOM | A67DC | C3' | G | G1910 | −66.292 | 109.714 | 104.589 | 1.00 | 107.42 | C |
| ATOM | A67DD | O3' | G | G1910 | −67.192 | 108.642 | 104.384 | 1.00 | 107.42 | O |
| ATOM | A67DP | P | U | G1911 | −66.743 | 107.137 | 104.731 | 1.00 | 103.54 | P |
| ATOM | A67DQ | OP1 | U | G1911 | −67.950 | 106.284 | 104.617 | 1.00 | 103.54 | O |
| ATOM | A67DR | OP2 | U | G1911 | −66.022 | 107.182 | 106.028 | 1.00 | 103.54 | O |
| ATOM | A67DS | O5' | U | G1911 | −65.724 | 106.795 | 103.557 | 1.00 | 103.54 | O |
| ATOM | A67DT | C5' | U | G1911 | −66.099 | 106.945 | 102.195 | 1.00 | 103.54 | C |
| ATOM | A67DU | C4' | U | G1911 | −64.907 | 106.858 | 101.273 | 1.00 | 103.54 | C |
| ATOM | A67DV | O4' | U | G1911 | −63.970 | 107.928 | 101.564 | 1.00 | 103.54 | O |
| ATOM | A67DW | C1' | U | G1911 | −62.647 | 107.485 | 101.334 | 1.00 | 103.54 | C |
| ATOM | A67DX | N1 | U | G1911 | −61.879 | 107.593 | 102.604 | 1.00 | 96.63 | N |
| ATOM | A67DY | C6 | U | G1911 | −62.487 | 107.646 | 103.840 | 1.00 | 96.63 | C |
| ATOM | A67DZ | C2 | U | G1911 | −60.501 | 107.643 | 102.501 | 1.00 | 96.63 | C |
| ATOM | A67E0 | O2 | U | G1911 | −59.914 | 107.601 | 101.435 | 1.00 | 96.63 | O |
| ATOM | A67E1 | N3 | U | G1911 | −59.826 | 107.741 | 103.692 | 1.00 | 96.63 | N |
| ATOM | A67E2 | C4 | U | G1911 | −60.375 | 107.795 | 104.955 | 1.00 | 96.63 | C |
| ATOM | A67E3 | O4 | U | G1911 | −59.638 | 107.882 | 105.939 | 1.00 | 96.63 | O |
| ATOM | A67E4 | C5 | U | G1911 | −61.805 | 107.741 | 104.988 | 1.00 | 96.63 | C |
| ATOM | A67E5 | C2' | U | G1911 | −62.725 | 106.042 | 100.827 | 1.00 | 103.54 | C |
| ATOM | A67E6 | O2' | U | G1911 | −62.741 | 106.050 | 99.404 | 1.00 | 103.54 | O |
| ATOM | A67E7 | C3' | U | G1911 | −64.069 | 105.596 | 101.387 | 1.00 | 103.54 | C |
| ATOM | A67E8 | O3' | U | G1911 | −64.640 | 104.497 | 100.697 | 1.00 | 103.54 | O |
| ATOM | A67EJ | P | A | G1912 | −64.665 | 103.035 | 101.365 | 1.00 | 71.84 | P |
| ATOM | A67EK | OP1 | A | G1912 | −64.679 | 103.219 | 102.837 | 1.00 | 71.84 | O |
| ATOM | A67EL | OP2 | A | G1912 | −65.779 | 102.288 | 100.732 | 1.00 | 71.84 | O |
| ATOM | A67EM | O5' | A | G1912 | −63.271 | 102.419 | 100.905 | 1.00 | 71.84 | O |
| ATOM | A67EN | C5' | A | G1912 | −62.873 | 102.467 | 99.542 | 1.00 | 71.84 | C |
| ATOM | A67EO | C4' | A | G1912 | −61.864 | 101.395 | 99.209 | 1.00 | 71.84 | C |
| ATOM | A67EP | O4' | A | G1912 | −60.529 | 101.854 | 99.516 | 1.00 | 71.84 | O |
| ATOM | A67EQ | C1' | A | G1912 | −59.698 | 100.744 | 99.766 | 1.00 | 71.84 | C |
| ATOM | A67ER | N9 | A | G1912 | −58.922 | 100.983 | 101.000 | 1.00 | 73.35 | N |
| ATOM | A67ES | C4 | A | G1912 | −57.646 | 101.489 | 101.023 | 1.00 | 73.35 | C |
| ATOM | A67ET | N3 | A | G1912 | −56.907 | 101.850 | 99.962 | 1.00 | 73.35 | N |
| ATOM | A67EU | C2 | A | G1912 | −55.717 | 102.299 | 100.346 | 1.00 | 73.35 | C |
| ATOM | A67EV | N1 | A | G1912 | −55.215 | 102.419 | 101.580 | 1.00 | 73.35 | N |
| ATOM | A67EW | C6 | A | G1912 | −55.981 | 102.047 | 102.628 | 1.00 | 73.35 | C |
| ATOM | A67EX | N6 | A | G1912 | −55.470 | 102.172 | 103.856 | 1.00 | 73.35 | N |
| ATOM | A67EY | C5 | A | G1912 | −57.271 | 101.551 | 102.351 | 1.00 | 73.35 | C |
| ATOM | A67EZ | N7 | A | G1912 | −58.299 | 101.090 | 103.161 | 1.00 | 73.35 | N |
| ATOM | A67F0 | C8 | A | G1912 | −59.252 | 100.764 | 102.316 | 1.00 | 73.35 | C |
| ATOM | A67F1 | C2' | A | G1912 | −60.584 | 99.492 | 99.855 | 1.00 | 71.84 | C |
| ATOM | A67F2 | O2' | A | G1912 | −60.451 | 98.740 | 98.655 | 1.00 | 71.84 | O |
| ATOM | A67F3 | C3' | A | G1912 | −61.985 | 100.088 | 99.977 | 1.00 | 71.84 | C |
| ATOM | A67F4 | O3' | A | G1912 | −63.002 | 99.245 | 99.462 | 1.00 | 71.84 | O |
| ATOM | A67FG | P | A | G1913 | −64.048 | 98.540 | 100.455 | 1.00 | 137.65 | P |
| ATOM | A67FH | OP1 | A | G1913 | −63.284 | 98.088 | 101.642 | 1.00 | 137.65 | O |
| ATOM | A67FI | OP2 | A | G1913 | −65.169 | 99.489 | 100.650 | 1.00 | 137.65 | O |
| ATOM | A67FJ | O5' | A | G1913 | −64.547 | 97.280 | 99.615 | 1.00 | 137.65 | O |
| ATOM | A67FK | C5' | A | G1913 | −63.651 | 96.537 | 98.793 | 1.00 | 137.65 | C |
| ATOM | A67FL | C4' | A | G1913 | −63.509 | 95.111 | 99.266 | 1.00 | 137.65 | C |
| ATOM | A67FM | O4' | A | G1913 | −62.917 | 94.310 | 98.200 | 1.00 | 137.65 | O |
| ATOM | A67FN | C1' | A | G1913 | −61.714 | 93.731 | 98.670 | 1.00 | 137.65 | C |
| ATOM | A67FO | N9 | A | G1913 | −60.764 | 93.660 | 97.569 | 1.00 | 496.26 | N |
| ATOM | A67FP | C4 | A | G1913 | −60.992 | 93.285 | 96.273 | 1.00 | 496.26 | C |
| ATOM | A67FQ | N3 | A | G1913 | −62.139 | 92.924 | 95.678 | 1.00 | 496.26 | N |
| ATOM | A67FR | C2 | A | G1913 | −61.934 | 92.649 | 94.392 | 1.00 | 496.26 | C |
| ATOM | A67FS | N1 | A | G1913 | −60.792 | 92.695 | 93.688 | 1.00 | 496.26 | N |
| ATOM | A67FT | C6 | A | G1913 | −59.660 | 93.067 | 94.336 | 1.00 | 496.26 | C |
| ATOM | A67FU | N6 | A | G1913 | −58.450 | 93.160 | 93.776 | 1.00 | 496.26 | N |
| ATOM | A67FV | C5 | A | G1913 | −59.756 | 93.382 | 95.681 | 1.00 | 496.26 | C |
| ATOM | A67FW | N7 | A | G1913 | −58.769 | 93.784 | 96.556 | 1.00 | 496.26 | N |
| ATOM | A67FX | C8 | A | G1913 | −59.424 | 93.931 | 97.668 | 1.00 | 496.26 | C |
| ATOM | A67FY | C2' | A | G1913 | −61.262 | 94.628 | 99.809 | 1.00 | 137.65 | C |
| ATOM | A67FZ | O2' | A | G1913 | −60.285 | 94.014 | 100.623 | 1.00 | 137.65 | O |
| ATOM | A67G0 | C3' | A | G1913 | −62.598 | 94.918 | 100.478 | 1.00 | 137.65 | C |

TABLE 9-continued

H69 Neomycin Binding Site for Unrotated Ribosome

| ATOM | A67G1 | O3' | A | G1913 | −63.036 | 93.773 | 101.212 | 1.00 | 137.65 | O |
|---|---|---|---|---|---|---|---|---|---|---|
| ATOM | A67GD | P | C | G1914 | −62.121 | 93.141 | 102.371 | 1.00 | 224.95 | P |
| ATOM | A67GE | OP1 | C | G1914 | −61.510 | 91.907 | 101.820 | 1.00 | 224.95 | O |
| ATOM | A67GF | OP2 | C | G1914 | −61.230 | 94.218 | 102.863 | 1.00 | 224.95 | O |
| ATOM | A67GG | O5' | C | G1914 | −63.185 | 92.765 | 103.483 | 1.00 | 224.95 | O |
| ATOM | A67GH | C5' | C | G1914 | −64.438 | 92.211 | 103.124 | 1.00 | 224.95 | C |
| ATOM | A67GI | C4' | C | G1914 | −65.087 | 91.531 | 104.295 | 1.00 | 224.95 | C |
| ATOM | A67GJ | O4' | C | G1914 | −64.335 | 90.341 | 104.646 | 1.00 | 224.95 | O |
| ATOM | A67GK | C1' | C | G1914 | −64.322 | 90.171 | 106.046 | 1.00 | 224.95 | C |
| ATOM | A67GL | N1 | C | G1914 | −62.915 | 90.261 | 106.538 | 1.00 | 81.16 | N |
| ATOM | A67GM | C6 | C | G1914 | −62.723 | 90.146 | 107.891 | 1.00 | 81.16 | C |
| ATOM | A67GN | C2 | C | G1914 | −61.786 | 90.426 | 105.703 | 1.00 | 81.16 | C |
| ATOM | A67GO | O2 | C | G1914 | −61.876 | 90.533 | 104.472 | 1.00 | 81.16 | O |
| ATOM | A67GP | N3 | C | G1914 | −60.555 | 90.487 | 106.261 | 1.00 | 81.16 | N |
| ATOM | A67GQ | C4 | C | G1914 | −60.399 | 90.380 | 107.578 | 1.00 | 81.16 | C |
| ATOM | A67GR | N4 | C | G1914 | −59.163 | 90.442 | 108.073 | 1.00 | 81.16 | N |
| ATOM | A67GS | C5 | C | G1914 | −61.508 | 90.203 | 108.447 | 1.00 | 81.16 | C |
| ATOM | A67GT | C2' | C | G1914 | −65.216 | 91.257 | 106.647 | 1.00 | 224.95 | C |
| ATOM | A67GU | O2' | C | G1914 | −66.539 | 90.752 | 106.750 | 1.00 | 224.95 | O |
| ATOM | A67GV | C3' | C | G1914 | −65.129 | 92.338 | 105.582 | 1.00 | 224.95 | C |
| ATOM | A67GW | O3' | C | G1914 | −66.202 | 93.265 | 105.618 | 1.00 | 224.95 | O |
| ATOM | A67H8 | P | U | G1915 | −65.932 | 94.835 | 105.381 | 1.00 | 121.80 | P |
| ATOM | A67H9 | OP1 | U | G1915 | −67.215 | 95.436 | 104.942 | 1.00 | 121.80 | O |
| ATOM | A67HA | OP2 | U | G1915 | −64.751 | 94.948 | 104.489 | 1.00 | 121.80 | O |
| ATOM | A67HB | O5' | U | G1915 | −65.559 | 95.359 | 106.839 | 1.00 | 121.80 | O |
| ATOM | A67HC | C5' | U | G1915 | −66.250 | 94.892 | 107.989 | 1.00 | 121.80 | C |
| ATOM | A67HD | C4' | U | G1915 | −65.312 | 94.687 | 109.155 | 1.00 | 121.80 | C |
| ATOM | A67HE | O4' | U | G1915 | −64.344 | 93.652 | 108.836 | 1.00 | 121.80 | O |
| ATOM | A67HF | C1' | U | G1915 | −63.104 | 93.946 | 109.446 | 1.00 | 121.80 | C |
| ATOM | A67HG | N1 | U | G1915 | −62.076 | 94.105 | 108.388 | 1.00 | 72.93 | N |
| ATOM | A67HH | C6 | U | G1915 | −62.401 | 94.387 | 107.081 | 1.00 | 72.93 | C |
| ATOM | A67HI | C2 | U | G1915 | −60.752 | 93.993 | 108.768 | 1.00 | 72.93 | C |
| ATOM | A67HJ | O2 | U | G1915 | −60.407 | 93.754 | 109.911 | 1.00 | 72.93 | O |
| ATOM | A67HK | N3 | U | G1915 | −59.839 | 94.165 | 107.757 | 1.00 | 72.93 | N |
| ATOM | A67HL | C4 | U | G1915 | −60.109 | 94.439 | 106.432 | 1.00 | 72.93 | C |
| ATOM | A67HM | O4 | U | G1915 | −59.183 | 94.570 | 105.633 | 1.00 | 72.93 | O |
| ATOM | A67HN | C5 | U | G1915 | −61.496 | 94.550 | 106.114 | 1.00 | 72.93 | C |
| ATOM | A67HO | C2' | U | G1915 | −63.282 | 95.230 | 110.256 | 1.00 | 121.80 | C |
| ATOM | A67HP | O2' | U | G1915 | −63.618 | 94.896 | 111.596 | 1.00 | 121.80 | O |
| ATOM | A67HQ | C3' | U | G1915 | −64.458 | 95.883 | 109.545 | 1.00 | 121.80 | C |
| ATOM | A67HR | O3' | U | G1915 | −65.153 | 96.825 | 110.345 | 1.00 | 121.80 | O |
| ATOM | A67I2 | P | A | G1916 | −64.984 | 98.402 | 110.077 | 1.00 | 91.53 | P |
| ATOM | A67I3 | OP1 | A | G1916 | −65.945 | 99.100 | 110.964 | 1.00 | 91.53 | O |
| ATOM | A67I4 | OP2 | A | G1916 | −65.085 | 98.612 | 108.612 | 1.00 | 91.53 | O |
| ATOM | A67I5 | O5' | A | G1916 | −63.495 | 98.690 | 110.563 | 1.00 | 91.53 | O |
| ATOM | A67I6 | C5' | A | G1916 | −63.113 | 98.480 | 111.914 | 1.00 | 91.53 | C |
| ATOM | A67I7 | C4' | A | G1916 | −61.611 | 98.403 | 112.060 | 1.00 | 91.53 | C |
| ATOM | A67I8 | O4' | A | G1916 | −61.105 | 97.271 | 111.303 | 1.00 | 91.53 | O |
| ATOM | A67I9 | C1' | A | G1916 | −59.860 | 97.594 | 110.720 | 1.00 | 91.53 | C |
| ATOM | A67IA | N9 | A | G1916 | −60.011 | 97.582 | 109.250 | 1.00 | 100.55 | N |
| ATOM | A67IB | C4 | A | G1916 | −59.002 | 97.570 | 108.311 | 1.00 | 100.55 | C |
| ATOM | A67IC | N3 | A | G1916 | −57.674 | 97.539 | 108.521 | 1.00 | 100.55 | N |
| ATOM | A67ID | C2 | A | G1916 | −57.013 | 97.525 | 107.365 | 1.00 | 100.55 | C |
| ATOM | A67IE | N1 | A | G1916 | −57.491 | 97.537 | 106.111 | 1.00 | 100.55 | N |
| ATOM | A67IF | C6 | A | G1916 | −58.831 | 97.568 | 105.934 | 1.00 | 100.55 | C |
| ATOM | A67IG | N6 | A | G1916 | −59.343 | 97.583 | 104.699 | 1.00 | 100.55 | N |
| ATOM | A67IH | C5 | A | G1916 | −59.636 | 97.586 | 107.082 | 1.00 | 100.55 | C |
| ATOM | A67II | N7 | A | G1916 | −61.010 | 97.618 | 107.230 | 1.00 | 100.55 | N |
| ATOM | A67IJ | C8 | A | G1916 | −61.179 | 97.621 | 108.526 | 1.00 | 100.55 | C |
| ATOM | A67IK | C2' | A | G1916 | −59.460 | 98.971 | 111.233 | 1.00 | 91.53 | C |
| ATOM | A67IL | O2' | A | G1916 | −58.703 | 98.814 | 112.425 | 1.00 | 91.53 | O |
| ATOM | A67IM | C3' | A | G1916 | −60.821 | 99.591 | 111.529 | 1.00 | 91.53 | C |
| ATOM | A67IN | O3' | A | G1916 | −60.766 | 100.675 | 112.444 | 1.00 | 91.53 | O |
| ATOM | A67IZ | P | U | G1917 | −61.129 | 102.171 | 111.970 | 1.00 | 86.96 | P |
| ATOM | A67J0 | OP1 | U | G1917 | −61.457 | 102.946 | 113.190 | 1.00 | 86.96 | O |
| ATOM | A67J1 | OP2 | U | G1917 | −62.154 | 102.060 | 110.902 | 1.00 | 86.96 | O |
| ATOM | A67J2 | O5' | U | G1917 | −59.756 | 102.693 | 111.351 | 1.00 | 86.96 | O |
| ATOM | A67J3 | C5' | U | G1917 | −58.591 | 102.816 | 112.156 | 1.00 | 86.96 | C |
| ATOM | A67J4 | C4' | U | G1917 | −57.340 | 102.464 | 111.385 | 1.00 | 86.96 | C |
| ATOM | A67J5 | O4' | U | G1917 | −57.544 | 101.223 | 110.662 | 1.00 | 86.96 | O |
| ATOM | A67J6 | C1' | U | G1917 | −56.855 | 101.262 | 109.428 | 1.00 | 86.96 | C |
| ATOM | A67J7 | N1 | U | G1917 | −57.840 | 101.145 | 108.318 | 1.00 | 56.93 | N |
| ATOM | A67J8 | C6 | U | G1917 | −59.205 | 101.188 | 108.502 | 1.00 | 56.93 | C |
| ATOM | A67J9 | C2 | U | G1917 | −57.320 | 100.967 | 107.050 | 1.00 | 56.93 | C |
| ATOM | A67JA | O2 | U | G1917 | −56.121 | 100.919 | 106.830 | 1.00 | 56.93 | O |
| ATOM | A67JB | N3 | U | G1917 | −58.249 | 100.855 | 106.044 | 1.00 | 56.93 | N |
| ATOM | A67JC | C4 | U | G1917 | −59.621 | 100.892 | 106.170 | 1.00 | 56.93 | C |
| ATOM | A67JD | O4 | U | G1917 | −60.335 | 100.775 | 105.174 | 1.00 | 56.93 | O |

TABLE 9-continued

H69 Neomycin Binding Site for Unrotated Ribosome

| ATOM | A67JE | C5 | U | G1917 | −60.090 | 101.072 | 107.507 | 1.00 | 56.93 | C |
|---|---|---|---|---|---|---|---|---|---|---|
| ATOM | A67JF | C2' | U | G1917 | −56.080 | 102.575 | 109.378 | 1.00 | 86.96 | C |
| ATOM | A67JG | O2' | U | G1917 | −54.782 | 102.353 | 109.920 | 1.00 | 86.96 | O |
| ATOM | A67JH | C3' | U | G1917 | −56.915 | 103.448 | 110.304 | 1.00 | 86.96 | C |
| ATOM | A67JI | O3' | U | G1917 | −56.216 | 104.567 | 110.814 | 1.00 | 86.96 | O |
| ATOM | A67JT | P | A | G1918 | −56.422 | 106.014 | 110.149 | 1.00 | 77.15 | P |
| ATOM | A67JU | OP1 | A | G1918 | −55.338 | 106.886 | 110.661 | 1.00 | 77.15 | O |
| ATOM | A67JV | OP2 | A | G1918 | −57.833 | 106.411 | 110.390 | 1.00 | 77.15 | O |
| ATOM | A67JW | O5' | A | G1918 | −56.197 | 105.726 | 108.602 | 1.00 | 77.15 | O |
| ATOM | A67JX | C5' | A | G1918 | −54.895 | 105.472 | 108.088 | 1.00 | 77.15 | C |
| ATOM | A67JY | C4' | A | G1918 | −54.890 | 105.417 | 106.582 | 1.00 | 77.15 | C |
| ATOM | A67JZ | O4' | A | G1918 | −55.918 | 104.490 | 106.136 | 1.00 | 77.15 | O |
| ATOM | A67K0 | C1' | A | G1918 | −56.754 | 105.117 | 105.184 | 1.00 | 77.15 | C |
| ATOM | A67K1 | N9 | A | G1918 | −58.120 | 104.623 | 105.368 | 1.00 | 70.62 | N |
| ATOM | A67K2 | C4 | A | G1918 | −59.022 | 104.329 | 104.375 | 1.00 | 70.62 | C |
| ATOM | A67K3 | N3 | A | G1918 | −58.835 | 104.421 | 103.049 | 1.00 | 70.62 | N |
| ATOM | A67K4 | C2 | A | G1918 | −59.932 | 104.048 | 102.393 | 1.00 | 70.62 | C |
| ATOM | A67K5 | N1 | A | G1918 | −61.109 | 103.631 | 102.877 | 1.00 | 70.62 | N |
| ATOM | A67K6 | C6 | A | G1918 | −61.265 | 103.555 | 104.215 | 1.00 | 70.62 | C |
| ATOM | A67K7 | N6 | A | G1918 | −62.436 | 103.139 | 104.702 | 1.00 | 70.62 | N |
| ATOM | A67K8 | C5 | A | G1918 | −60.174 | 103.922 | 105.021 | 1.00 | 70.62 | C |
| ATOM | A67K9 | N7 | A | G1918 | −60.005 | 103.958 | 106.397 | 1.00 | 70.62 | N |
| ATOM | A67KA | C8 | A | G1918 | −58.774 | 104.383 | 106.550 | 1.00 | 70.62 | C |
| ATOM | A67KB | C2' | A | G1918 | −56.617 | 106.617 | 105.418 | 1.00 | 77.15 | C |
| ATOM | A67KC | O2' | A | G1918 | −56.933 | 107.355 | 104.256 | 1.00 | 77.15 | O |
| ATOM | A67KD | C3' | A | G1918 | −55.168 | 106.747 | 105.882 | 1.00 | 77.15 | C |
| ATOM | A67KE | O3' | A | G1918 | −54.304 | 106.899 | 104.759 | 1.00 | 77.15 | O |
| ATOM | A67KQ | P | A | G1919 | −52.939 | 107.735 | 104.908 | 1.00 | 76.58 | P |
| ATOM | A67KR | OP1 | A | G1919 | −51.997 | 106.895 | 105.689 | 1.00 | 76.58 | O |
| ATOM | A67KS | OP2 | A | G1919 | −53.303 | 109.074 | 105.434 | 1.00 | 76.58 | O |
| ATOM | A67KT | O5' | A | G1919 | −52.433 | 107.867 | 103.406 | 1.00 | 76.58 | O |
| ATOM | A67KU | C5' | A | G1919 | −51.059 | 108.080 | 103.113 | 1.00 | 76.58 | C |
| ATOM | A67KV | C4' | A | G1919 | −50.668 | 107.406 | 101.826 | 1.00 | 76.58 | C |
| ATOM | A67KW | O4' | A | G1919 | −51.141 | 106.029 | 101.839 | 1.00 | 76.58 | O |
| ATOM | A67KX | C1' | A | G1919 | −51.695 | 105.696 | 100.586 | 1.00 | 76.58 | C |
| ATOM | A67KY | N9 | A | G1919 | −53.159 | 105.609 | 100.746 | 1.00 | 55.65 | N |
| ATOM | A67KZ | C4 | A | G1919 | −54.118 | 105.573 | 99.762 | 1.00 | 55.65 | C |
| ATOM | A67L0 | N3 | A | G1919 | −53.937 | 105.600 | 98.433 | 1.00 | 55.65 | N |
| ATOM | A67L1 | C2 | A | G1919 | −55.104 | 105.552 | 97.797 | 1.00 | 55.65 | C |
| ATOM | A67L2 | N1 | A | G1919 | −56.345 | 105.480 | 98.296 | 1.00 | 55.65 | N |
| ATOM | A67L3 | C6 | A | G1919 | −56.494 | 105.455 | 99.638 | 1.00 | 55.65 | C |
| ATOM | A67L4 | N6 | A | G1919 | −57.722 | 105.387 | 100.159 | 1.00 | 55.65 | N |
| ATOM | A67L5 | C5 | A | G1919 | −55.331 | 105.505 | 100.423 | 1.00 | 55.65 | C |
| ATOM | A67L6 | N7 | A | G1919 | −55.146 | 105.496 | 101.795 | 1.00 | 55.65 | N |
| ATOM | A67L7 | C8 | A | G1919 | −53.846 | 105.561 | 101.932 | 1.00 | 55.65 | C |
| ATOM | A67L8 | C2' | A | G1919 | −51.300 | 106.805 | 99.621 | 1.00 | 76.58 | C |
| ATOM | A67L9 | O2' | A | G1919 | −49.999 | 106.527 | 99.123 | 1.00 | 76.58 | O |
| ATOM | A67LA | C3' | A | G1919 | −51.276 | 107.997 | 100.560 | 1.00 | 76.58 | C |
| ATOM | A67LB | O3' | A | G1919 | −50.549 | 109.103 | 100.057 | 1.00 | 76.58 | O |
| ATOM | A67LN | P | C | G1920 | −51.199 | 110.573 | 100.040 | 1.00 | 62.49 | P |
| ATOM | A67LO | OP1 | C | G1920 | −50.354 | 111.412 | 99.156 | 1.00 | 62.49 | O |
| ATOM | A67LP | OP2 | C | G1920 | −51.382 | 110.988 | 101.451 | 1.00 | 62.49 | O |
| ATOM | A67LQ | O5' | C | G1920 | −52.614 | 110.330 | 99.361 | 1.00 | 62.49 | O |
| ATOM | A67LR | C5' | C | G1920 | −52.720 | 109.856 | 98.029 | 1.00 | 62.49 | C |
| ATOM | A67LS | C4' | C | G1920 | −54.160 | 109.749 | 97.602 | 1.00 | 62.49 | C |
| ATOM | A67LT | O4' | C | G1920 | −54.830 | 108.717 | 98.380 | 1.00 | 62.49 | O |
| ATOM | A67LU | C1' | C | G1920 | −56.146 | 109.124 | 98.689 | 1.00 | 62.49 | C |
| ATOM | A67LV | N1 | C | G1920 | −56.240 | 109.339 | 100.152 | 1.00 | 114.54 | N |
| ATOM | A67LW | C6 | C | G1920 | −55.136 | 109.326 | 100.960 | 1.00 | 114.54 | C |
| ATOM | A67LX | C2 | C | G1920 | −57.498 | 109.562 | 100.713 | 1.00 | 114.54 | C |
| ATOM | A67LY | O2 | C | G1920 | −58.490 | 109.572 | 99.969 | 1.00 | 114.54 | O |
| ATOM | A67LZ | N3 | C | G1920 | −57.603 | 109.767 | 102.048 | 1.00 | 114.54 | N |
| ATOM | A67M0 | C4 | C | G1920 | −56.513 | 109.756 | 102.817 | 1.00 | 114.54 | C |
| ATOM | A67M1 | N4 | C | G1920 | −56.642 | 109.952 | 104.130 | 1.00 | 114.54 | N |
| ATOM | A67M2 | C5 | C | G1920 | −55.223 | 109.524 | 102.277 | 1.00 | 114.54 | C |
| ATOM | A67M3 | C2' | C | G1920 | −56.413 | 110.409 | 97.908 | 1.00 | 62.49 | C |
| ATOM | A67M4 | O2' | C | G1920 | −56.890 | 110.059 | 96.616 | 1.00 | 62.49 | O |
| ATOM | A67M5 | C3' | C | G1920 | −55.011 | 110.988 | 97.833 | 1.00 | 62.49 | C |
| ATOM | A67M6 | O3' | C | G1920 | −54.844 | 111.972 | 96.825 | 1.00 | 62.49 | O |
| ATOM | A67MI | P | G | G1921 | −54.720 | 113.529 | 97.220 | 1.00 | 67.45 | P |
| ATOM | A67MJ | OP1 | G | G1921 | −54.045 | 114.212 | 96.090 | 1.00 | 67.45 | O |
| ATOM | A67MK | OP2 | G | G1921 | −54.099 | 113.599 | 98.566 | 1.00 | 67.45 | O |
| ATOM | A67ML | O5' | G | G1921 | −56.238 | 113.990 | 97.299 | 1.00 | 67.45 | O |
| ATOM | A67MM | C5' | G | G1921 | −57.083 | 113.893 | 96.165 | 1.00 | 67.45 | C |
| ATOM | A67MN | C4' | G | G1921 | −58.536 | 113.983 | 96.549 | 1.00 | 67.45 | C |
| ATOM | A67MO | O4' | G | G1921 | −58.859 | 112.968 | 97.539 | 1.00 | 67.45 | O |
| ATOM | A67MP | C1' | G | G1921 | −59.853 | 113.463 | 98.417 | 1.00 | 67.45 | C |
| ATOM | A67MQ | N9 | G | G1921 | −59.302 | 113.496 | 99.784 | 1.00 | 72.72 | N |

TABLE 9-continued

H69 Neomycin Binding Site for Unrotated Ribosome

| ATOM | A67MR | C4 | G | G1921 | −60.006 | 113.735 | 100.942 | 1.00 | 72.72 | C |
|------|-------|-----|---|-------|---------|---------|---------|------|-------|---|
| ATOM | A67MS | N3 | G | G1921 | −61.332 | 113.962 | 101.036 | 1.00 | 72.72 | N |
| ATOM | A67MT | C2 | G | G1921 | −61.715 | 114.152 | 102.289 | 1.00 | 72.72 | C |
| ATOM | A67MU | N2 | G | G1921 | −63.008 | 114.392 | 102.560 | 1.00 | 72.72 | N |
| ATOM | A67MV | N1 | G | G1921 | −60.864 | 114.120 | 103.366 | 1.00 | 72.72 | N |
| ATOM | A67MW | C6 | G | G1921 | −59.495 | 113.892 | 103.293 | 1.00 | 72.72 | C |
| ATOM | A67MX | O6 | G | G1921 | −58.819 | 113.880 | 104.330 | 1.00 | 72.72 | O |
| ATOM | A67MY | C5 | G | G1921 | −59.074 | 113.682 | 101.954 | 1.00 | 72.72 | C |
| ATOM | A67MZ | N7 | G | G1921 | −57.812 | 113.421 | 101.442 | 1.00 | 72.72 | N |
| ATOM | A67N0 | C8 | G | G1921 | −57.992 | 113.324 | 100.157 | 1.00 | 72.72 | C |
| ATOM | A67N1 | C2' | G | G1921 | −60.238 | 114.859 | 97.929 | 1.00 | 67.45 | C |
| ATOM | A67N2 | O2' | G | G1921 | −61.320 | 114.738 | 97.017 | 1.00 | 67.45 | O |
| ATOM | A67N3 | C3' | G | G1921 | −58.964 | 115.276 | 97.212 | 1.00 | 67.45 | C |
| ATOM | A67N4 | O3' | G | G1921 | −59.137 | 116.339 | 96.293 | 1.00 | 67.45 | O |
| ATOM | A67NG | P | G | G1922 | −58.745 | 117.841 | 96.711 | 1.00 | 81.77 | P |
| ATOM | A67NH | OP1 | G | G1922 | −58.661 | 118.635 | 95.461 | 1.00 | 81.77 | O |
| ATOM | A67NI | OP2 | G | G1922 | −57.548 | 117.759 | 97.585 | 1.00 | 81.77 | O |
| ATOM | A67NJ | O5' | G | G1922 | −60.005 | 118.303 | 97.558 | 1.00 | 81.77 | O |
| ATOM | A67NK | C5' | G | G1922 | −61.318 | 118.141 | 97.049 | 1.00 | 81.77 | C |
| ATOM | A67NL | C4' | G | G1922 | −62.351 | 118.301 | 98.127 | 1.00 | 81.77 | C |
| ATOM | A67NM | O4' | G | G1922 | −62.198 | 117.257 | 99.122 | 1.00 | 81.77 | O |
| ATOM | A67NN | C1' | G | G1922 | −62.561 | 117.749 | 100.394 | 1.00 | 81.77 | C |
| ATOM | A67NO | N9 | G | G1922 | −61.407 | 117.616 | 101.302 | 1.00 | 90.75 | N |
| ATOM | A67NP | C4 | G | G1922 | −61.455 | 117.738 | 102.667 | 1.00 | 90.75 | C |
| ATOM | A67NQ | N3 | G | G1922 | −62.559 | 117.992 | 103.400 | 1.00 | 90.75 | N |
| ATOM | A67NR | C2 | G | G1922 | −62.292 | 118.051 | 104.694 | 1.00 | 90.75 | C |
| ATOM | A67NS | N2 | G | G1922 | −63.282 | 118.295 | 105.567 | 1.00 | 90.75 | N |
| ATOM | A67NT | N1 | G | G1922 | −61.039 | 117.874 | 105.226 | 1.00 | 90.75 | N |
| ATOM | A67NU | C6 | G | G1922 | −59.893 | 117.612 | 104.485 | 1.00 | 90.75 | C |
| ATOM | A67NV | O6 | G | G1922 | −58.815 | 117.470 | 105.063 | 1.00 | 90.75 | O |
| ATOM | A67NW | C5 | G | G1922 | −60.162 | 117.547 | 103.096 | 1.00 | 90.75 | C |
| ATOM | A67NX | N7 | G | G1922 | −59.314 | 117.311 | 102.022 | 1.00 | 90.75 | N |
| ATOM | A67NY | C8 | G | G1922 | −60.096 | 117.363 | 100.978 | 1.00 | 90.75 | C |
| ATOM | A67NZ | C2' | G | G1922 | −62.987 | 119.208 | 100.224 | 1.00 | 81.77 | C |
| ATOM | A67O0 | O2' | G | G1922 | −64.397 | 119.255 | 100.064 | 1.00 | 81.77 | O |
| ATOM | A67O1 | C3' | G | G1922 | −62.276 | 119.585 | 98.933 | 1.00 | 81.77 | C |
| ATOM | A67O2 | O3' | G | G1922 | −62.854 | 120.689 | 98.259 | 1.00 | 81.77 | O |
| ATOM | A67OE | P | U | G1923 | −62.010 | 122.040 | 98.038 | 1.00 | 83.59 | P |
| ATOM | A67OF | OP1 | U | G1923 | −62.627 | 122.759 | 96.899 | 1.00 | 83.59 | O |
| ATOM | A67OG | OP2 | U | G1923 | −60.578 | 121.658 | 97.948 | 1.00 | 83.59 | O |
| ATOM | A67OH | O5' | U | G1923 | −62.271 | 122.841 | 99.386 | 1.00 | 83.59 | O |
| ATOM | A67OI | C5' | U | G1923 | −63.587 | 123.009 | 99.890 | 1.00 | 83.59 | C |
| ATOM | A67OJ | C4' | U | G1923 | −63.583 | 123.209 | 101.384 | 1.00 | 83.59 | C |
| ATOM | A67OK | O4' | U | G1923 | −63.167 | 121.988 | 102.044 | 1.00 | 83.59 | O |
| ATOM | A67OL | C1' | U | G1923 | −62.484 | 122.298 | 103.240 | 1.00 | 83.59 | C |
| ATOM | A67OM | N1 | U | G1923 | −61.135 | 121.681 | 103.195 | 1.00 | 81.85 | N |
| ATOM | A67ON | C6 | U | G1923 | −60.390 | 121.627 | 102.037 | 1.00 | 81.85 | C |
| ATOM | A67OO | C2 | U | G1923 | −60.622 | 121.174 | 104.375 | 1.00 | 81.85 | C |
| ATOM | A67OP | O2 | U | G1923 | −61.229 | 121.195 | 105.431 | 1.00 | 81.85 | O |
| ATOM | A67OQ | N3 | U | G1923 | −59.368 | 120.626 | 104.282 | 1.00 | 81.85 | N |
| ATOM | A67OR | C4 | U | G1923 | −58.580 | 120.538 | 103.155 | 1.00 | 81.85 | C |
| ATOM | A67OS | O4 | U | G1923 | −57.468 | 120.015 | 103.235 | 1.00 | 81.85 | O |
| ATOM | A67OT | C5 | U | G1923 | −59.167 | 121.088 | 101.972 | 1.00 | 81.85 | C |
| ATOM | A67OU | C2' | U | G1923 | −62.411 | 123.823 | 103.355 | 1.00 | 83.59 | C |
| ATOM | A67OV | O2' | U | G1923 | −63.468 | 124.282 | 104.185 | 1.00 | 83.59 | O |
| ATOM | A67OW | C3' | U | G1923 | −62.623 | 124.260 | 101.911 | 1.00 | 83.59 | C |
| ATOM | A67OX | O3' | U | G1923 | −63.132 | 125.575 | 101.784 | 1.00 | 83.59 | O |
| ATOM | A67P8 | P | C | G1924 | −62.143 | 126.838 | 101.845 | 1.00 | 78.08 | P |
| ATOM | A67P9 | OP1 | C | G1924 | −62.902 | 128.009 | 101.346 | 1.00 | 78.08 | O |
| ATOM | A67PA | OP2 | C | G1924 | −60.889 | 126.453 | 101.151 | 1.00 | 78.08 | O |
| ATOM | A67PB | O5' | C | G1924 | −61.876 | 126.994 | 103.401 | 1.00 | 78.08 | O |
| ATOM | A67PC | C5' | C | G1924 | −62.945 | 127.225 | 104.301 | 1.00 | 78.08 | C |
| ATOM | A67PD | C4' | C | G1924 | −62.520 | 127.021 | 105.730 | 1.00 | 78.08 | C |
| ATOM | A67PE | O4' | C | G1924 | −62.046 | 125.662 | 105.934 | 1.00 | 78.08 | O |
| ATOM | A67PF | C1' | C | G1924 | −61.051 | 125.658 | 106.944 | 1.00 | 78.08 | C |
| ATOM | A67PG | N1 | C | G1924 | −59.793 | 125.128 | 106.376 | 1.00 | 91.84 | N |
| ATOM | A67PH | C6 | C | G1924 | −59.506 | 125.229 | 105.046 | 1.00 | 91.84 | C |
| ATOM | A67PI | C2 | C | G1924 | −58.869 | 124.540 | 107.238 | 1.00 | 91.84 | C |
| ATOM | A67PJ | O2 | C | G1924 | −59.125 | 124.462 | 108.448 | 1.00 | 91.84 | O |
| ATOM | A67PK | N3 | C | G1924 | −57.707 | 124.058 | 106.737 | 1.00 | 91.84 | N |
| ATOM | A67PL | C4 | C | G1924 | −57.448 | 124.154 | 105.433 | 1.00 | 91.84 | C |
| ATOM | A67PM | N4 | C | G1924 | −56.296 | 123.672 | 104.965 | 1.00 | 91.84 | N |
| ATOM | A67PN | C5 | C | G1924 | −58.367 | 124.756 | 104.535 | 1.00 | 91.84 | C |
| ATOM | A67PO | C2' | C | G1924 | −60.888 | 127.099 | 107.427 | 1.00 | 78.08 | C |
| ATOM | A67PP | O2' | C | G1924 | −61.767 | 127.311 | 108.523 | 1.00 | 78.08 | O |
| ATOM | A67PQ | C3' | C | G1924 | −61.353 | 127.864 | 106.199 | 1.00 | 78.08 | C |
| ATOM | A67PR | O3' | C | G1924 | −61.706 | 129.211 | 106.452 | 1.00 | 78.08 | O |
| ATOM | A67Q3 | P | C | G1925 | −60.840 | 130.402 | 105.806 | 1.00 | 70.20 | P |

TABLE 9-continued

H69 Neomycin Binding Site for Unrotated Ribosome

| ATOM | A67Q4 | OP1 | C | G1925 | −61.675 | 131.628 | 105.858 | 1.00 | 70.20 | O |
|---|---|---|---|---|---|---|---|---|---|---|
| ATOM | A67Q5 | OP2 | C | G1925 | −60.350 | 129.928 | 104.487 | 1.00 | 70.20 | O |
| ATOM | A67Q6 | O5' | C | G1925 | −59.625 | 130.532 | 106.820 | 1.00 | 70.20 | O |
| ATOM | A67Q7 | C5' | C | G1925 | −59.860 | 130.745 | 108.201 | 1.00 | 70.20 | C |
| ATOM | A67Q8 | C4' | C | G1925 | −58.697 | 130.285 | 109.039 | 1.00 | 70.20 | C |
| ATOM | A67Q9 | O4' | C | G1925 | −58.458 | 128.869 | 108.835 | 1.00 | 70.20 | O |
| ATOM | A67QA | C1' | C | G1925 | −57.083 | 128.592 | 109.018 | 1.00 | 70.20 | C |
| ATOM | A67QB | N1 | C | G1925 | −56.551 | 127.949 | 107.795 | 1.00 | 103.35 | N |
| ATOM | A67QC | C6 | C | G1925 | −57.215 | 127.905 | 106.597 | 1.00 | 103.35 | C |
| ATOM | A67QD | C2 | C | G1925 | −55.287 | 127.374 | 107.909 | 1.00 | 103.35 | C |
| ATOM | A67QE | O2 | C | G1925 | −54.710 | 127.433 | 109.004 | 1.00 | 103.35 | O |
| ATOM | A67QF | N3 | C | G1925 | −54.722 | 126.771 | 106.840 | 1.00 | 103.35 | N |
| ATOM | A67QG | C4 | C | G1925 | −55.370 | 126.727 | 105.680 | 1.00 | 103.35 | C |
| ATOM | A67QH | N4 | C | G1925 | −54.762 | 126.118 | 104.658 | 1.00 | 103.35 | N |
| ATOM | A67QI | C5 | C | G1925 | −56.664 | 127.308 | 105.527 | 1.00 | 103.35 | C |
| ATOM | A67QJ | C2' | C | G1925 | −56.380 | 129.919 | 109.319 | 1.00 | 70.20 | C |
| ATOM | A67QK | O2' | C | G1925 | −56.285 | 130.074 | 110.728 | 1.00 | 70.20 | O |
| ATOM | A67QL | C3' | C | G1925 | −57.359 | 130.920 | 108.724 | 1.00 | 70.20 | C |
| ATOM | A67QM | O3' | C | G1925 | −57.234 | 132.227 | 109.249 | 1.00 | 70.20 | O |
| ATOM | A67QY | P | U | G1926 | −56.055 | 133.188 | 108.741 | 1.00 | 84.21 | P |
| ATOM | A67QZ | OP1 | U | G1926 | −56.371 | 134.559 | 109.216 | 1.00 | 84.21 | O |
| ATOM | A67R0 | OP2 | U | G1926 | −55.896 | 132.957 | 107.284 | 1.00 | 84.21 | O |
| ATOM | A67R1 | O5' | U | G1926 | −54.789 | 132.625 | 109.519 | 1.00 | 84.21 | O |
| ATOM | A67R2 | C5' | U | G1926 | −53.486 | 133.078 | 109.208 | 1.00 | 84.21 | C |
| ATOM | A67R3 | C4' | U | G1926 | −52.439 | 132.101 | 109.668 | 1.00 | 84.21 | C |
| ATOM | A67R4 | O4' | U | G1926 | −52.855 | 130.747 | 109.347 | 1.00 | 84.21 | O |
| ATOM | A67R5 | C1' | U | G1926 | −51.727 | 129.973 | 108.994 | 1.00 | 84.21 | C |
| ATOM | A67R6 | N1 | U | G1926 | −51.867 | 129.539 | 107.582 | 1.00 | 85.16 | N |
| ATOM | A67R7 | C6 | U | G1926 | −52.811 | 130.073 | 106.731 | 1.00 | 85.16 | C |
| ATOM | A67R8 | C2 | U | G1926 | −50.998 | 128.558 | 107.145 | 1.00 | 85.16 | C |
| ATOM | A67R9 | O2 | U | G1926 | −50.148 | 128.057 | 107.858 | 1.00 | 85.16 | O |
| ATOM | A67RA | N3 | U | G1926 | −51.155 | 128.183 | 105.836 | 1.00 | 85.16 | N |
| ATOM | A67RB | C4 | U | G1926 | −52.075 | 128.676 | 104.936 | 1.00 | 85.16 | C |
| ATOM | A67RC | O4 | U | G1926 | −52.095 | 128.235 | 103.787 | 1.00 | 85.16 | O |
| ATOM | A67RD | C5 | U | G1926 | −52.942 | 129.687 | 105.457 | 1.00 | 85.16 | C |
| ATOM | A67RE | C2' | U | G1926 | −50.491 | 130.841 | 109.208 | 1.00 | 84.21 | C |
| ATOM | A67RF | O2' | U | G1926 | −50.040 | 130.665 | 110.543 | 1.00 | 84.21 | O |
| ATOM | A67RG | C3' | U | G1926 | −51.075 | 132.231 | 109.013 | 1.00 | 84.21 | C |
| ATOM | A67RH | O3' | U | G1926 | −50.286 | 133.264 | 109.572 | 1.00 | 84.21 | O |
| ATOM | A67RS | P | A | G1927 | −50.481 | 134.787 | 109.094 | 1.00 | 73.22 | P |
| ATOM | A67RT | OP1 | A | G1927 | −50.771 | 135.590 | 110.307 | 1.00 | 73.22 | O |
| ATOM | A67RU | OP2 | A | G1927 | −51.473 | 134.782 | 107.992 | 1.00 | 73.22 | O |
| ATOM | A67RV | O5' | A | G1927 | −49.042 | 135.164 | 108.525 | 1.00 | 73.22 | O |
| ATOM | A67RW | C5' | A | G1927 | −48.663 | 134.805 | 107.204 | 1.00 | 73.22 | C |
| ATOM | A67RX | C4' | A | G1927 | −47.295 | 134.169 | 107.175 | 1.00 | 73.22 | C |
| ATOM | A67RY | O4' | A | G1927 | −46.596 | 134.449 | 108.412 | 1.00 | 73.22 | O |
| ATOM | A67RZ | C1' | A | G1927 | −45.786 | 133.354 | 108.774 | 1.00 | 73.22 | C |
| ATOM | A67S0 | N9 | A | G1927 | −46.187 | 132.903 | 110.122 | 1.00 | 68.40 | N |
| ATOM | A67S1 | C4 | A | G1927 | −45.471 | 132.108 | 110.986 | 1.00 | 68.40 | C |
| ATOM | A67S2 | N3 | A | G1927 | −44.268 | 131.549 | 110.784 | 1.00 | 68.40 | N |
| ATOM | A67S3 | C2 | A | G1927 | −43.894 | 130.831 | 111.843 | 1.00 | 68.40 | C |
| ATOM | A67S4 | N1 | A | G1927 | −44.538 | 130.624 | 112.998 | 1.00 | 68.40 | N |
| ATOM | A67S5 | C6 | A | G1927 | −45.746 | 131.198 | 113.172 | 1.00 | 68.40 | C |
| ATOM | A67S6 | N6 | A | G1927 | −46.395 | 130.997 | 114.321 | 1.00 | 68.40 | N |
| ATOM | A67S7 | C5 | A | G1927 | −46.250 | 131.982 | 112.122 | 1.00 | 68.40 | C |
| ATOM | A67S8 | N7 | A | G1927 | −47.431 | 132.691 | 111.990 | 1.00 | 68.40 | N |
| ATOM | A67S9 | C8 | A | G1927 | −47.340 | 133.222 | 110.796 | 1.00 | 68.40 | C |
| ATOM | A67SA | C2' | A | G1927 | −45.956 | 132.265 | 107.712 | 1.00 | 73.22 | C |
| ATOM | A67SB | O2' | A | G1927 | −44.881 | 132.343 | 106.783 | 1.00 | 73.22 | O |
| ATOM | A67SC | C3' | A | G1927 | −47.278 | 132.653 | 107.054 | 1.00 | 73.22 | C |
| ATOM | A67SD | O3' | A | G1927 | −47.383 | 132.223 | 105.707 | 1.00 | 73.22 | O |
| ATOM | A67SP | P | A | G1928 | −48.556 | 131.225 | 105.246 | 1.00 | 69.37 | P |
| ATOM | A67SQ | OP1 | A | G1928 | −48.845 | 131.523 | 103.823 | 1.00 | 69.37 | O |
| ATOM | A67SR | OP2 | A | G1928 | −49.655 | 131.341 | 106.232 | 1.00 | 69.37 | O |
| ATOM | A67SS | O5' | A | G1928 | −47.861 | 129.801 | 105.366 | 1.00 | 69.37 | O |
| ATOM | A67ST | C5' | A | G1928 | −46.650 | 129.529 | 104.680 | 1.00 | 69.37 | C |
| ATOM | A67SU | C4' | A | G1928 | −45.703 | 128.714 | 105.522 | 1.00 | 69.37 | C |
| ATOM | A67SV | O4' | A | G1928 | −45.408 | 129.411 | 106.761 | 1.00 | 69.37 | O |
| ATOM | A67SW | C1' | A | G1928 | −45.187 | 128.470 | 107.794 | 1.00 | 69.37 | C |
| ATOM | A67SX | N9 | A | G1928 | −46.187 | 128.687 | 108.856 | 1.00 | 68.06 | N |
| ATOM | A67SY | C4 | A | G1928 | −46.010 | 128.425 | 110.191 | 1.00 | 68.06 | C |
| ATOM | A67SZ | N3 | A | G1928 | −44.905 | 127.947 | 110.783 | 1.00 | 68.06 | N |
| ATOM | A67T0 | C2 | A | G1928 | −45.095 | 127.824 | 112.093 | 1.00 | 68.06 | C |
| ATOM | A67T1 | N1 | A | G1928 | −46.176 | 128.106 | 112.830 | 1.00 | 68.06 | N |
| ATOM | A67T2 | C6 | A | G1928 | −47.271 | 128.586 | 112.205 | 1.00 | 68.06 | C |
| ATOM | A67T3 | N6 | A | G1928 | −48.351 | 128.868 | 112.937 | 1.00 | 68.06 | N |
| ATOM | A67T4 | C5 | A | G1928 | −47.198 | 128.760 | 110.813 | 1.00 | 68.06 | C |
| ATOM | A67T5 | N7 | A | G1928 | −48.117 | 129.220 | 109.886 | 1.00 | 68.06 | N |

TABLE 9-continued

H69 Neomycin Binding Site for Unrotated Ribosome

| ATOM | A67T6 | C8 | A | G1928 | −47.475 | 129.154 | 108.744 | 1.00 | 68.06 | C |
|---|---|---|---|---|---|---|---|---|---|---|
| ATOM | A67T7 | C2' | A | G1928 | −45.311 | 127.078 | 107.177 | 1.00 | 69.37 | C |
| ATOM | A67T8 | O2' | A | G1928 | −44.026 | 126.647 | 106.746 | 1.00 | 69.37 | O |
| ATOM | A67T9 | C3' | A | G1928 | −46.217 | 127.367 | 105.989 | 1.00 | 69.37 | C |
| ATOM | A67TA | O3' | A | G1928 | −46.179 | 126.376 | 104.980 | 1.00 | 69.37 | O |
| ATOM | A67TM | P | G | G1929 | −47.428 | 125.385 | 104.781 | 1.00 | 75.01 | P |
| ATOM | A67TN | OP1 | G | G1929 | −47.145 | 124.563 | 103.582 | 1.00 | 75.01 | O |
| ATOM | A67TO | OP2 | G | G1929 | −48.658 | 126.216 | 104.803 | 1.00 | 75.01 | O |
| ATOM | A67TP | O5' | G | G1929 | −47.362 | 124.480 | 106.086 | 1.00 | 75.01 | O |
| ATOM | A67TQ | C5' | G | G1929 | −46.142 | 123.864 | 106.476 | 1.00 | 75.01 | C |
| ATOM | A67TR | C4' | G | G1929 | −46.251 | 123.191 | 107.819 | 1.00 | 75.01 | C |
| ATOM | A67TS | O4' | G | G1929 | −46.728 | 124.140 | 108.815 | 1.00 | 75.01 | O |
| ATOM | A67TT | C1' | G | G1929 | −47.763 | 123.532 | 109.554 | 1.00 | 75.01 | C |
| ATOM | A67TU | N9 | G | G1929 | −48.629 | 124.565 | 110.132 | 1.00 | 75.35 | N |
| ATOM | A67TV | C4 | G | G1929 | −49.870 | 125.032 | 109.755 | 1.00 | 75.35 | C |
| ATOM | A67TW | N3 | G | G1929 | −50.593 | 124.631 | 108.694 | 1.00 | 75.35 | N |
| ATOM | A67TX | C2 | G | G1929 | −51.740 | 125.273 | 108.602 | 1.00 | 75.35 | C |
| ATOM | A67TY | N2 | G | G1929 | −52.566 | 124.979 | 107.589 | 1.00 | 75.35 | N |
| ATOM | A67TZ | N1 | G | G1929 | −52.155 | 126.236 | 109.487 | 1.00 | 75.35 | N |
| ATOM | A67U0 | C6 | G | G1929 | −51.435 | 126.668 | 110.592 | 1.00 | 75.35 | C |
| ATOM | A67U1 | O6 | G | G1929 | −51.895 | 127.543 | 111.335 | 1.00 | 75.35 | O |
| ATOM | A67U2 | C5 | G | G1929 | −50.200 | 125.986 | 110.698 | 1.00 | 75.35 | C |
| ATOM | A67U3 | N7 | G | G1929 | −49.201 | 126.120 | 111.646 | 1.00 | 75.35 | N |
| ATOM | A67U4 | C8 | G | G1929 | −48.302 | 125.260 | 111.270 | 1.00 | 75.35 | C |
| ATOM | A67U5 | C2' | G | G1929 | −48.435 | 122.587 | 108.567 | 1.00 | 75.01 | C |
| ATOM | A67U6 | O2' | G | G1929 | −49.248 | 121.637 | 109.222 | 1.00 | 75.01 | O |
| ATOM | A67U7 | C3' | G | G1929 | −47.216 | 121.999 | 107.875 | 1.00 | 75.01 | C |
| ATOM | A67U8 | O3' | G | G1929 | −46.659 | 120.982 | 108.697 | 1.00 | 75.01 | O |
| ATOM | A67UK | P | G | G1930 | −45.500 | 120.025 | 108.142 | 1.00 | 79.14 | P |
| ATOM | A67UL | OP1 | G | G1930 | −44.708 | 120.808 | 107.160 | 1.00 | 79.14 | O |
| ATOM | A67UM | OP2 | G | G1930 | −46.149 | 118.771 | 107.692 | 1.00 | 79.14 | O |
| ATOM | A67UN | O5' | G | G1930 | −44.635 | 119.749 | 109.447 | 1.00 | 79.14 | O |
| ATOM | A67UO | C5' | G | G1930 | −43.395 | 120.411 | 109.675 | 1.00 | 79.14 | C |
| ATOM | A67UP | C4' | G | G1930 | −42.381 | 119.481 | 110.290 | 1.00 | 79.14 | C |
| ATOM | A67UQ | O4' | G | G1930 | −41.837 | 120.090 | 111.498 | 1.00 | 79.14 | O |
| ATOM | A67UR | C1' | G | G1930 | −41.958 | 119.176 | 112.567 | 1.00 | 79.14 | C |
| ATOM | A67US | N9 | G | G1930 | −42.096 | 119.918 | 113.821 | 1.00 | 65.34 | N |
| ATOM | A67UT | C4 | G | G1930 | −41.031 | 120.378 | 114.542 | 1.00 | 65.34 | C |
| ATOM | A67UU | N3 | G | G1930 | −39.747 | 120.223 | 114.178 | 1.00 | 65.34 | N |
| ATOM | A67UV | C2 | G | G1930 | −38.929 | 120.768 | 115.052 | 1.00 | 65.34 | C |
| ATOM | A67UW | N2 | G | G1930 | −37.614 | 120.699 | 114.824 | 1.00 | 65.34 | N |
| ATOM | A67UX | N1 | G | G1930 | −39.340 | 121.413 | 116.195 | 1.00 | 65.34 | N |
| ATOM | A67UY | C6 | G | G1930 | −40.667 | 121.583 | 116.586 | 1.00 | 65.34 | C |
| ATOM | A67UZ | O6 | G | G1930 | −40.925 | 122.183 | 117.636 | 1.00 | 65.34 | O |
| ATOM | A67V0 | C5 | G | G1930 | −41.560 | 120.998 | 115.650 | 1.00 | 65.34 | C |
| ATOM | A67V1 | N7 | G | G1930 | −42.947 | 120.920 | 115.627 | 1.00 | 65.34 | N |
| ATOM | A67V2 | C8 | G | G1930 | −43.221 | 120.268 | 114.526 | 1.00 | 65.34 | C |
| ATOM | A67V3 | C2' | G | G1930 | −43.149 | 118.299 | 112.214 | 1.00 | 79.14 | C |
| ATOM | A67V4 | O2' | G | G1930 | −43.164 | 117.103 | 112.962 | 1.00 | 79.14 | O |
| ATOM | A67V5 | C3' | G | G1930 | −42.926 | 118.115 | 110.720 | 1.00 | 79.14 | C |
| ATOM | A67V6 | O3' | G | G1930 | −41.934 | 117.114 | 110.504 | 1.00 | 79.14 | O |
| ATOM | A67VI | P | U | G1931 | −42.362 | 115.620 | 110.091 | 1.00 | 95.44 | P |
| ATOM | A67VJ | OP1 | U | G1931 | −43.842 | 115.557 | 110.146 | 1.00 | 95.44 | O |
| ATOM | A67VK | OP2 | U | G1931 | −41.580 | 114.694 | 110.945 | 1.00 | 95.44 | O |
| ATOM | A67VL | O5' | U | G1931 | −41.876 | 115.499 | 108.576 | 1.00 | 95.44 | O |
| ATOM | A67VM | C5' | U | G1931 | −41.531 | 116.644 | 107.804 | 1.00 | 95.44 | C |
| ATOM | A67VN | C4' | U | G1931 | −40.245 | 116.425 | 107.054 | 1.00 | 95.44 | C |
| ATOM | A67VO | O4' | U | G1931 | −39.402 | 117.603 | 107.160 | 1.00 | 95.44 | O |
| ATOM | A67VP | C1' | U | G1931 | −38.047 | 117.223 | 107.272 | 1.00 | 95.44 | C |
| ATOM | A67VQ | N1 | U | G1931 | −37.539 | 117.663 | 108.595 | 1.00 | 85.53 | N |
| ATOM | A67VR | C6 | U | G1931 | −38.387 | 118.032 | 109.619 | 1.00 | 85.53 | C |
| ATOM | A67VS | C2 | U | G1931 | −36.169 | 117.694 | 108.770 | 1.00 | 85.53 | C |
| ATOM | A67VT | O2 | U | G1931 | −35.383 | 117.379 | 107.894 | 1.00 | 85.53 | O |
| ATOM | A67VU | N3 | U | G1931 | −35.749 | 118.108 | 110.008 | 1.00 | 85.53 | N |
| ATOM | A67VV | C4 | U | G1931 | −36.544 | 118.487 | 111.069 | 1.00 | 85.53 | C |
| ATOM | A67VW | O4 | U | G1931 | −36.025 | 118.836 | 112.128 | 1.00 | 85.53 | O |
| ATOM | A67VX | C5 | U | G1931 | −37.950 | 118.431 | 110.818 | 1.00 | 85.53 | C |
| ATOM | A67VY | C2' | U | G1931 | −37.979 | 115.705 | 107.111 | 1.00 | 95.44 | C |
| ATOM | A67VZ | O2' | U | G1931 | −37.782 | 115.399 | 105.738 | 1.00 | 95.44 | O |
| ATOM | A67W0 | C3' | U | G1931 | −39.369 | 115.291 | 107.568 | 1.00 | 95.44 | C |
| ATOM | A67W1 | O3' | U | G1931 | −39.777 | 114.024 | 107.084 | 1.00 | 95.44 | O |
| TER | | | | | | | | | | |
| ATOM | A88BI | C1 | NMY | N2905 | −52.949 | 118.562 | 103.968 | 0.77 | 92.97 | C |
| ATOM | A88BJ | O1 | NMY | N2905 | −54.161 | 118.135 | 104.561 | 0.77 | 92.97 | O |
| ATOM | A88BK | C2 | NMY | N2905 | −52.426 | 119.752 | 104.791 | 0.77 | 92.97 | C |
| ATOM | A88BL | N2 | NMY | N2905 | −52.473 | 119.418 | 106.186 | 0.77 | 92.97 | N |
| ATOM | A88BM | C3 | NMY | N2905 | −53.198 | 120.986 | 104.611 | 0.77 | 92.97 | C |
| ATOM | A88BN | O3 | NMY | N2905 | −52.453 | 121.996 | 105.253 | 0.77 | 92.97 | O |

TABLE 9-continued

H69 Neomycin Binding Site for Unrotated Ribosome

| ATOM | A88BO | C4 | NMY N2905 | −53.381 | 121.347 | 103.242 | 0.77 | 92.97 | C |
|---|---|---|---|---|---|---|---|---|---|
| ATOM | A88BP | O4 | NMY N2905 | −54.435 | 122.280 | 103.139 | 0.77 | 92.97 | O |
| ATOM | A88BQ | C5 | NMY N2905 | −53.764 | 120.175 | 102.380 | 0.77 | 92.97 | C |
| ATOM | A88BR | O5 | NMY N2905 | −53.071 | 118.856 | 102.616 | 0.77 | 92.97 | O |
| ATOM | A88BS | C6 | NMY N2905 | −54.564 | 120.406 | 101.114 | 0.77 | 92.97 | C |
| ATOM | A88BT | N6 | NMY N2905 | −55.382 | 121.622 | 101.028 | 0.77 | 92.97 | N |
| ATOM | A88BU | C7 | NMY N2905 | −55.891 | 114.385 | 103.460 | 0.77 | 92.97 | C |
| ATOM | A88BV | N7 | NMY N2905 | −55.877 | 113.133 | 102.690 | 0.77 | 92.97 | N |
| ATOM | A88BW | C8 | NMY N2905 | −56.357 | 115.659 | 102.788 | 0.77 | 92.97 | C |
| ATOM | A88BX | C9 | NMY N2905 | −55.969 | 116.906 | 103.599 | 0.77 | 92.97 | C |
| ATOM | A88BY | N9 | NMY N2905 | −56.182 | 118.116 | 102.864 | 0.77 | 92.97 | N |
| ATOM | A88BZ | C10 | NMY N2905 | −54.516 | 116.858 | 104.054 | 0.77 | 92.97 | C |
| ATOM | A88C0 | C11 | NMY N2905 | −54.255 | 115.752 | 105.031 | 0.77 | 92.97 | C |
| ATOM | A88C1 | O11 | NMY N2905 | −52.910 | 115.367 | 104.953 | 0.77 | 92.97 | O |
| ATOM | A88C2 | C12 | NMY N2905 | −55.097 | 114.486 | 104.767 | 0.77 | 92.97 | C |
| ATOM | A88C3 | O12 | NMY N2905 | −55.308 | 113.574 | 105.759 | 0.77 | 92.97 | O |
| ATOM | A88C4 | C13 | NMY N2905 | −52.251 | 115.505 | 106.199 | 0.77 | 92.97 | C |
| ATOM | A88C5 | C14 | NMY N2905 | −51.065 | 114.624 | 106.245 | 0.77 | 92.97 | C |
| ATOM | A88C6 | O14 | NMY N2905 | −50.999 | 114.167 | 107.537 | 0.77 | 92.97 | O |
| ATOM | A88C7 | C15 | NMY N2905 | −49.996 | 115.502 | 105.921 | 0.77 | 92.97 | C |
| ATOM | A88C8 | C16 | NMY N2905 | −50.398 | 116.771 | 106.577 | 0.77 | 92.97 | C |
| ATOM | A88C9 | O16 | NMY N2905 | −51.782 | 116.839 | 106.466 | 0.77 | 92.97 | O |
| ATOM | A88CA | C17 | NMY N2905 | −49.774 | 118.012 | 105.983 | 0.77 | 92.97 | C |
| ATOM | A88CB | O17 | NMY N2905 | −50.028 | 119.199 | 106.600 | 0.77 | 92.97 | O |
| ATOM | A88CC | C18 | NMY N2905 | −48.048 | 114.253 | 105.483 | 0.77 | 92.97 | C |
| ATOM | A88CD | O18 | NMY N2905 | −48.807 | 114.958 | 106.462 | 0.77 | 92.97 | O |
| ATOM | A88CE | C19 | NMY N2905 | −48.682 | 113.160 | 104.640 | 0.77 | 92.97 | C |
| ATOM | A88CF | N19 | NMY N2905 | −45.843 | 113.148 | 107.725 | 0.77 | 92.97 | N |
| ATOM | A88CG | C20 | NMY N2905 | −47.801 | 112.336 | 103.890 | 0.77 | 92.97 | C |
| ATOM | A88CH | O20 | NMY N2905 | −48.193 | 112.474 | 102.516 | 0.77 | 92.97 | O |
| ATOM | A88CI | C21 | NMY N2905 | −46.371 | 112.703 | 103.976 | 0.77 | 92.97 | C |
| ATOM | A88CJ | O21 | NMY N2905 | −45.464 | 112.248 | 102.993 | 0.77 | 92.97 | O |
| ATOM | A88CK | C22 | NMY N2905 | −45.802 | 113.378 | 105.214 | 0.77 | 92.97 | C |
| ATOM | A88CL | O22 | NMY N2905 | −46.568 | 114.487 | 105.541 | 0.77 | 92.97 | O |
| ATOM | A88CM | C23 | NMY N2905 | −45.672 | 112.489 | 106.449 | 0.77 | 92.97 | C |
| ATOM | A88CN | N23 | NMY N2905 | −49.383 | 112.238 | 105.534 | 0.77 | 92.97 | N |
| TER | | | | | | | | | |
| END | | | | | | | | | |

We claim:

1. A method to identify a compound that interferes with ribosomal function which comprises (a) surface-immobilizing a ribosome having a FRET pair sensitive to transitioning between low FRET and high FRET states under translation competent conditions, wherein said FRET pair comprises a first fluorophore attached to a ribosomal protein of said ribosome and a second fluorophore attached a ribosomal protein of said ribosome;

(b) adding a test compound to said ribosome; and (c) monitoring or detecting changes in FRET states using smFRET imaging techniques to identify a test compound capable of (i) stabilizing said ribosome in an intermediate FRET state, (ii) changing said ribosome's distribution into or out of an intermediate FRET state, or (iii) changing said ribosome's rate of transition into or out of an intermediate FRET state.

2. The method of claim 1, wherein said first fluorophore is attached to ribosomal protein L1 and said second fluorophore is attached to ribosomal protein S13.

3. The method of claim 2, wherein the fluorophore attached to L1 is at (T202C) L1 and the fluorophore attached to S13 is at or near the amino terminus of S13.

4. The method of claim 1, wherein said compound is identified as a candidate antibiotic when said test compound
   (i) stabilizes said ribosome in an intermediate FRET state or in a high FRET state,
   (ii) increases said ribosome's distribution in intermediate or high FRET states,
   (iii) increases said ribosome's rate of transition into intermediate or high FRET states, or
   (iv) abolishes FRET.

5. The method of claim 1, wherein said intermediate FRET state comprises the P/pe tRNA binding state.

6. The method of claim 1, wherein said FRET pair consists of a donor-acceptor fluorophore pair or a donor-quencher fluorophore pair.

7. The method of claim 1, wherein said first fluorophore is attached to a ribosomal protein in a large ribosomal subunit and said second fluorophore is attached to a ribosomal protein in a small ribosomal subunit.

* * * * *

UNITED STATES PATENT AND TRADEMARK OFFICE
CERTIFICATE OF CORRECTION

PATENT NO. : 9,441,263 B2
APPLICATION NO. : 14/111947
DATED : September 13, 2016
INVENTOR(S) : Scott C. Blanchard et al.

Page 1 of 1

It is certified that error appears in the above-identified patent and that said Letters Patent is hereby corrected as shown below:

Column 1, Line 12 should read:
GOVERNMENT FUNDING
This invention was made with Government support under Grant Number CA092584, DC012026, GM007739, GM065050, & GM079238 awarded by the National Institutes of Health and grant number DE-AC03-76SF00098 awarded by the Department of Energy. The Government has certain rights in the invention.

Signed and Sealed this
Twelfth Day of December, 2017

Joseph Matal
*Performing the Functions and Duties of the
Under Secretary of Commerce for Intellectual Property and
Director of the United States Patent and Trademark Office*

SEQUENCE LISTING

<160> NUMBER OF SEQ ID NOS: 1

<210> SEQ ID NO 1
<211> LENGTH: 24
<212> TYPE: RNA
<213> ORGANISM: Artificial Sequence
<220> FEATURE:
<223> OTHER INFORMATION: synthetic oligonucleotide (ribosomal mRNA
      initiator)

<400> SEQUENCE: 1
ggcaaggagg uaaaauucua caaa                                           24